United States Patent
Okano et al.

(10) Patent No.: US 8,455,500 B2
(45) Date of Patent: Jun. 4, 2013

(54) 3-HYDROXY-5-ARYLISOXAZOLE DERIVATIVE

(75) Inventors: Akihiro Okano, Tokyo (JP); Munetaka Ohkouchi, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/504,749

(22) PCT Filed: Oct. 29, 2010

(86) PCT No.: PCT/JP2010/069380
§ 371 (c)(1),
(2), (4) Date: Apr. 27, 2012

(87) PCT Pub. No.: WO2011/052756
PCT Pub. Date: May 5, 2011

(65) Prior Publication Data
US 2012/0220772 A1  Aug. 30, 2012

(30) Foreign Application Priority Data

Oct. 30, 2009 (JP) .................................. 2009-251493
Dec. 10, 2009 (JP) .................................. 2009-281014

(51) Int. Cl.
| | | |
|---|---|---|
| A61K 31/505 | (2006.01) | |
| A61K 31/4427 | (2006.01) | |
| A61K 31/42 | (2006.01) | |
| C07D 413/02 | (2006.01) | |
| C07D 413/00 | (2006.01) | |
| C07D 261/06 | (2006.01) | |
| C07D 239/24 | (2006.01) | |

(52) U.S. Cl.
USPC ........... 514/256; 514/340; 514/378; 544/333; 546/272.1; 548/247

(58) Field of Classification Search
USPC ........ 514/256, 340, 378; 544/333; 546/272.1; 548/247
See application file for complete search history.

(56) References Cited

U.S. PATENT DOCUMENTS

| 5,153,210 A | 10/1992 | Ainsworth et al. |
| 2006/0258722 A1 | 11/2006 | Yasuma et al. |
| 2009/0186909 A1 | 7/2009 | Negoro et al. |
| 2010/0130599 A1 | 5/2010 | Coty et al. |
| 2010/0267775 A1 | 10/2010 | Negoro et al. |
| 2011/0065739 A1 | 3/2011 | Ishikawa et al. |

FOREIGN PATENT DOCUMENTS

| JP | 62-175458 A | 8/1987 |
| WO | WO 00/42029 A1 | 7/2000 |
| WO | WO 2004/041266 A1 | 5/2004 |
| WO | WO 2005/035551 A2 | 4/2005 |
| WO | WO 2005/086661 A2 | 9/2005 |
| WO | WO 2007/123225 A1 | 11/2007 |
| WO | WO 2008/001931 A2 | 1/2008 |
| WO | WO 2008/030520 A1 | 3/2008 |
| WO | WO 2008/033931 A1 | 3/2008 |
| WO | WO 2008/066131 A1 | 6/2008 |
| WO | WO 2009/054390 A1 | 4/2009 |
| WO | WO 2009/054423 A1 | 4/2009 |
| WO | WO 2009/147990 A1 | 12/2009 |
| WO | WO 2011/052756 A1 | 5/2011 |
| WO | WO 2011/078371 A1 | 6/2011 |
| WO | WO 2012/046869 A1 | 4/2012 |

OTHER PUBLICATIONS

Chiasson et al., "Acarbose Treatment and the Risk of Cardiovascular Disease and Hypertension in Patients with Impaired Glucose Tolerance: The STOP-NIDDM Trial," JAMA (2003) vol. 290, No. 4, pp. 486-494.
Itoh et al., "Free fatty acids regulate insulin secretion from beta cells through GPR40," Nature (Mar. 13, 2003), vol. 422, pp. 173-176.
Kotarsky et al., "A human cell surface receptor activated by free fatty acids and thiazolidinedione drugs," Biochem, Biophys. Res. Com. (2003), vol. 301, pp. 406-410.

*Primary Examiner* — Samantha Shterengarts
(74) *Attorney, Agent, or Firm* — Birch, Stewart, Kolasch and Birch, LLP

(57) ABSTRACT

[Problem]
To provide a GPR40 activating agent having, as an active ingredient, a novel compound having a GPR40 agonist action, a salt of the compound, a solvate of the salt or the compound, or the like, particularly, an insulin secretagogue and a prophylactic and/or therapeutic agent against diabetes, obesity, or other diseases.
[Means of Solving the Problem]
A compound of Formula (I):

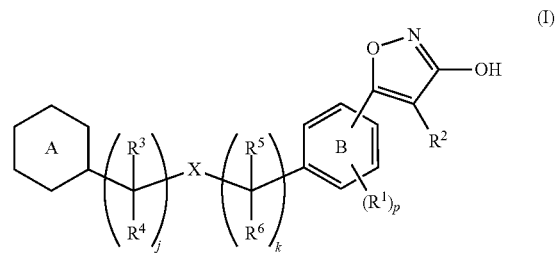

(where p is 0 to 4; j is 0 to 3; k is 0 to 2; a ring A is a specific cyclic group; a ring B is a benzene ring, a pyridine ring, or a pyrimidine ring; X is —$CH_2$—, O, —$S(O)_i$— (i is 0 to 2), or —$NR^7$—; $R^1$ to $R^6$ are specific groups),
a salt of the compound, or a solvate of the salt or the compound.

3 Claims, No Drawings

3-HYDROXY-5-ARYLISOXAZOLE DERIVATIVE

TECHNICAL FIELD

The present invention relates to a compound for modulationg the functions of G protein-coupled receptor 40 (GPR40). In particular, the present invention relates to a 3-hydroxy-5-arylisoxazole compound of Formula (I), a salt of the compound, a solvate of the compound or the salt, a pharmaceutical composition containing the compound as an active ingredient, prophylactic and/or therapeutic agents against GPR40-involving diseases, especially diabetes, and an insulin secretagogues.

BACKGROUND ART

Diabetes is categorized into Type 1 diabetes (insulin-dependent diabetes) and Type 2 diabetes (non-insulin-dependent diabetes), and borderline type diabetes (glucose tolerance disorders) has also attracted attention as a pre-diabetic condition in recent years. Type 1 diabetes is characterized by a partial or complete inability to produce insulin, which is a blood glucose regulating hormone. Type 2 diabetes is characterized by induced peripheral insulin resistance and impaired insulin secretion. Borderline type diabetes is a pathological condition exhibiting impaired glucose tolerance (IGT) or impaired fasting glucose (IFG), associated with a risk of developing Type 2 diabetes or diabetes complications.

Diabetes is caused by several predisposing factors. It is a disease characterized by high glucose levels in blood plasma in fasting and postprandial states or during an oral glucose tolerance test or by chronic hyperglycemia, in general. Controlling chronic hyperglycemia is essential in clinical management and treatment of diabetes. In particular, reduced insulin secretion from beta cells of the pancreas can induce an abrupt increase in postprandial blood glucose levels in Type 2 diabetes or borderline type diabetes. An international large-scale clinical trial has revealed that it is essential to control postprandial hyperglycemia in impaired glucose tolerance for suppressing the development and progress of not only diabetes but also hypertension and cardiovascular diseases (JAMA, 290, 486-494 (2003) (Non-Patent Document 1)). On the basis of these findings, the International Diabetes Federation published new guidelines for diabetes treatment (postprandial blood glucose control guidelines) in 2007, which recommend control of postprandial blood glucose levels as essential for Type 1 and 2 diabetic patients to alleviate diabetes and reduce risk of complications. As a practical step, an increased administration of an alpha-glucosidase inhibitor (voglibose) that is a drug for alleviating excessive postprandial blood glucose levels associated with diabetes, has been approved in Japan as a prophylactic agent against diabetes, aiming to "inhibit the development of Type 2 diabetes from impaired glucose tolerance". As described above, there has been increasing awareness of the needs of nonpharmacological and pharmacological treatments against diabetes and borderline type diabetes, targeting the control of postprandial blood glucose levels in recent years.

Diabetes is treated mainly through diet regulation and exercise. When these fail to alleviate symptoms, pharmacological treatment is needed. Various types of drugs are available as prophylactic or therapeutic agents against diabetes. Among them, examples of insulin secretagogues include sulfonylurea agents (e.g., glibenclamide, glimepiride) and rapid-acting insulin secretagogues (e.g., mitiglinide), all of which stimulate beta cells of the pancreas so as to accelerate insulin secretion. These drugs are, however, known for their ineffectiveness (primary failure, secondary failure) and side effects such as induced hypoglycemic effects. Analogs (e.g., exenatide, liraglutide) of glucagon-like peptide-1 (GLP-1), which are hormones accelerating glucose-responsive insulin secretion in beta cells of the pancreas, have become available as novel insulin secretagogues, but they are administered by injection and known for their side effects of transient gastrointestinal tract disorders. Other examples of insulin secretagogues include dipeptidyl peptidase IV (DPP-IV) inhibitors (e.g., sitagliptin, vildagliptin), which inhibit the degradation of intrinsic GLP-1, but they are known for their side effects of epipharyngitis, headache, and infections. Alpha-glucosidase inhibitors (e.g., acarbose, voglibose) inhibit the degradation and digestion of carbohydrate and thus limit an abrupt increase in postprandial blood glucose levels, but they need to be taken immediately before meals and are known for their side effects such as distension and diarrhea and serious liver disorders. Biguanides (e.g., metformin, buformin) are insulin resistance improving agents enhancing insulin sensitivity and thereby alleviating hyperglycemia, but are known to potentially induce side effects such as lactic acidosis, nausea, and vomiting. Thiazolidinedione derivatives (e.g., pioglitazone, rosiglitazone) are peroxisome proliferator-activated receptor (PPAR) gamma agonists. The derivatives increase insulin sensitivity in adipose tissue, the liver, and skeletal muscles and thereby alleviate chronic hyperglycemia, but are known to be prone to cause edema, weight gain, and serious side effects of liver disorders. Side effects of these drugs do not always occur, but remain as a major obstacle to high satisfaction with treatment. Therefore, the demand has been increasing for insulin secretagogues, particularly orally administrable insulin secretagogues, entailing few problems and side effects caused by conventional prophylactic and therapeutic agents as described above and inhibiting postprandial hyperglycemia without inducing hypoglycemia.

Fatty acid plays an important role in insulin use in the liver and skeletal muscles, glucose-responsive insulin secretion from the pancreas, and inflammation associated with fat accumulation in adipose tissue. A strong correlation is known between increased levels of fatty acid in blood plasma and the development of diabetes, metabolic syndrome, obesity, and adiposity.

GPR40, one of the G-protein-coupled receptors, is categorized in the free fatty acid receptor (FFAR) family and activated by $C_{6-22}$ saturated or unsaturated fatty acid. It is reported that high expression of GPR40 is observed in beta cells of the pancreas where the receptor is involved in insulin secretion caused by fatty acid (Nature, 422, 173-176 (2003) (Non-Patent Document 2)). Non-fatty-acid low-molecular-weight compounds having a GPR40 agonist action have been found in recent years, and it is reported that thiazolidinediones, which are insulin sensitivity improving agents, and MEDICA 16, which is a hypolipidemic agent, also exhibit agonist actions (Biochem. Biophys. Res. Comm., 301, 406-410 (2003) (Non-Patent Document 3)).

In the pancreatic islets of Langerhans isolated from GPR40 knockout mice, the glucose-responsive insulin secretagogue action of fatty acid is lower than the case with normal mice. Accordingly, substances having a GPR40 agonist action like fatty acid are expected to have the effect of inhibiting postprandial hyperglycemia based on the glucose-responsive insulin secretagogue action in the pancreas. Therefore, substances having a GPR40 agonist action are considered to be effective as prophylactic and therapeutic agents against diabetes or borderline type diabetes.

Studies have been progressed on compounds having a GPR40 activating action as insulin secretagogues or therapeutic agents against diabetes. Technologies related to compounds having a GPR40 agonist action are disclosed, for example, in WO 2004/041266 pamphlet (Patent Document 1), WO 2005/086661 pamphlet (Patent Document 2), WO 2007/123225 pamphlet (Patent Document 3), WO 2008/001931 pamphlet (Patent Document 4), WO 2009/054390 pamphlet (Patent Document 5), and WO 2009/054423 pamphlet (Patent Document 6). These documents, however, do not disclose or suggest any compounds having a 3-hydroxy-5-arylisoxazolyl group.

A technique related to a compound having a 3-hydroxy-5-arylisoxazolyl group is disclosed in WO 2008/066131 pamphlet (Patent Document 7) and WO 2009/147990 pamphlet (Patent Document 8). The compound disclosed in Patent Documents 7 and 8, however, are compounds having a G protein-coupled receptor 120 (GPR120) agonist action.

In the development of drugs, various strict criteria must be met in terms of absorption, distribution, metabolism, excretion, and other factors as well as targeted pharmacological actions. There are various things to consider, for example, interaction with other drugs, desensitization or durability, digestive tract absorption after oral administration, speed to reach the small intestine, absorption speed and first pass effect, organ barriers, protein binding, drug metabolizing enzyme induction or inhibition, excretion route and clearance in the body, and application methods (application sites, methods, purposes). It is difficult to find a drug that meets all the criteria.

Several compounds are reported to have a GPR40 agonist action, but none of them has been marketed so far. Such agonists could also involve the above-mentioned general issues in the development phase of drugs. More specifically, they have problems in usefulness and safety, such as low metabolism stability and difficulty in systemic exposure by oral administration, unfavorable pharmacokinetic effects including absorption and persistence properties, and an activity of inhibiting the human ether-a-go-go related gene (hERG) channel, possibly resulting in arrhythmia. Therefore, required is a compound that solves these problems as much as possible and still has high efficacy.

In addition, required as a GPR40 agonist is a compound with fewer problems or side effects as described above than the aforementioned conventional drugs that have been used to prevent or treat diabetes (particularly Type 2 diabetes or borderline type diabetes).

RELATED-ART DOCUMENTS

Patent Documents

Patent Document 1: WO 2004/041266 pamphlet
Patent Document 2: WO 2005/086661 pamphlet
Patent Document 3: WO 2007/123225 pamphlet
Patent Document 4: WO 2008/001931 pamphlet
Patent Document 5: WO 2009/054390 pamphlet
Patent Document 6: WO 2009/054423 pamphlet
Patent Document 7: WO 2008/066131 pamphlet
Patent Document 8: WO 2009/147990 pamphlet Non-Patent Documents Non-Patent Document 1: JAMA, 290, 486-494 (2003)
Non-Patent Document 2: Nature, 422, 173-176 (2003)
Non-Patent Document 3: Biochem. Biophys. Res. Comm., 301, 406-410 (2003)

SUMMARY OF THE INVENTION

Problem to be Solved by the Invention

In view of such medical circumstances related to diabetes, prophylactic and therapeutic drugs are required that accelerate insulin secretion, particularly glucose-responsive insulin secretion, through activation of GPR40, and thus exhibit the action of lowering blood glucose levels, particularly inhibiting postprandial hyperglycemia.

Particularly required are orally administrable GPR40 activating agents, insulin secretagogues, prophylactic and/or therapeutic agents against GPR40-involving diseases (particularly prophylactic and/or therapeutic agents against diabetes or obesity) all of which have high safety, excellent efficacy, and high selectivity with respect to other members of the FFAR family or similar receptors.

In particular, there are issues to be addressed as problems with the conventional techniques described above. More specifically, there are the following issues to be addressed with prophylactic and therapeutic agents against diabetes: ineffectiveness (primary failure, secondary failure) and side effects such as induced hypoglycemic effects caused by sulfonylurea agents and rapid-acting insulin secretagogues; transient gastrointestinal tract disorders caused by GLP-1 analogs; side effects of epipharyngitis, headache, and infections caused by DPP-IV inhibitors; side effects such as distension and diarrhea and serious liver disorders caused by alpha-glucosidase inhibitors; side effects such as lactic acidosis, nausea, and vomiting caused by biguanides; edema, weight gain, and serious liver disorders caused by thiazolidinedione derivatives; and so on. Other issues to be addressed include solubility, improvement in metabolism stability, enhancement of absorption properties, improvement in pharmacokinetic effects, reduction in the activity of inhibiting hERG, and reduction in the activity of inducing or inhibiting drug metabolizing enzymes (e.g., cytochrome P450). Consequently, there are the needs for insulin secretagogues and prophylactic and/or therapeutic agents against GPR40-involving diseases (particularly prophylactic and/or therapeutic agents against diabetes or obesity) all of which solve at least one of the issues, are orally administrable to mammals including human beings, and are clinically usable in particular.

Means for Solving the Problem

As a result of assiduous research for solving the above problems by obtaining a compound having high safety and/or excellent efficacy and modulationg the functions of GPR40, the inventors of the present invention have found that a 3-hydroxy-5-arylisoxazole derivative of Formula (I) has a GPR40 agonist action. The compound of the present invention has an excellent glucose-responsive insulin secretagogue action and has a strong hyperglycemia-inhibiting action during glucose load.

Effects of Invention

The present invention provides: a 3-hydroxy-5-arylisoxazole compound of Formula (I), a salt of the compound, or a solvate of the compound or the salt; and a pharmaceutical composition, characterized by containing as an active ingredient, the compound, a pharmaceutically acceptable salt of the compound, or a solvate of the compound or the pharmaceutically acceptable salt.

The compound of the present invention is a compound having a GPR40 agonist action, or a compound having an action of lowering a blood glucose level, particularly an action of inhibiting postprandial hyperglycemia, by activating GPR40 to accelerate an insulin secretion, particularly a glucose-responsive insulin secretion. The pharmaceutical composition containing the compound of the present invention as an active ingredient can be orally administered and is expected as an insulin secretagogues or a prophylactic agent and/or a therapeutic agent for a GPR40-involving disease, particularly diabetes (particularly Type 2 diabetes or borderline type diabetes) or obesity and adiposity.

The group of the compounds of the present invention has at least one of characteristics such as having advantageous solubility, having high metabolism stability, having excellent oral absorption properties, and having a small activity of inhibiting the hERG channel, and thus is highly useful.

MODES FOR CARRYING OUT THE INVENTION

The present invention provides: a 3-hydroxy-5-arylisoxazole compound of Formula (I) shown in the following aspects, a salt of the compound, or a solvate of the compound or the salt; and a pharmaceutical composition or GPR40 activating agent, characterized by containing the compound, the salt, or the solvate as an active ingredient.

[Aspects of the Present Invention]

[1] A first aspect of the present invention is a compound of Formula (I):

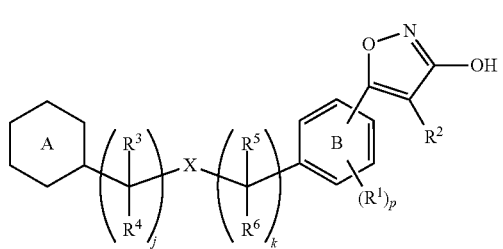

(where p is an integer of 0 to 4; j is an integer of 0 to 3; k is an integer of 0 to 2;

a ring B is a benzene ring, a pyridine ring, or a pyrimidine ring;

X is —$CH_2$—, an oxygen atom, —$S(O)_i$— (i is an integer of 0 to 2) or —$NR^7$— (with a proviso that X is not —$CH_2$— when a ring A is Formula (A) mentioned below);

$R^1$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a group: —$S(O)_iR^a$ (i is an integer of 0 to 2) or a group: —$NR^bR^c$;

$R^2$ is a group arbitrarily selected from a hydrogen atom, a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

$R^3$, $R^4$, $R^5$, $R^6$, and $R^7$ are independently a group arbitrarily selected from a hydrogen atom, a $C_{1-6}$ alkyl group, a halogenated $C_{1-6}$ alkyl group, a $C_{2-6}$ alkenyl group or a $C_{2-6}$ alkynyl group;

a ring A is Formula (A):

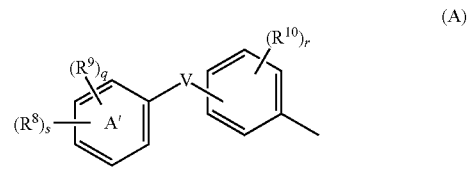

(where q and r are independently an integer of 0 to 4; s is an integer of 1 to 2; a ring A' is a benzene ring, a pyridine ring, or a pyrimidine ring; V is a single bond or an oxygen atom;

$R^8$s are independently a group arbitrarily selected from a $C_{1-6}$ alkoxy group which is substituted with 1 to 5 substituent(s) L, a $C_{2-6}$ alkenyloxy group which is substituted with 1 to 5 substituent(s) L, a $C_{2-6}$ alkynyloxy group which is substituted with 1 to 5 substituent(s) L, or non-aromatic heterocyclic oxy;

the substituents L are independently a group arbitrarily selected from a halogen atom, —OH, a $C_{1-6}$ alkoxy group, a non-aromatic heterocyclic group (the heterocyclic group is optionally substituted with —OH or a $C_{1-6}$ alkyl group), a group: —$S(O)_iR^a$ (i is an integer of 0 to 2), a group: —$CO_2R^f$, a group: —$SO_2NR^dR^e$, a group: —$CONR^dR^e$, or a group: —$NR^bR^c$;

$R^9$ and $R^{10}$ are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI); or a ring A is Formula (AA):

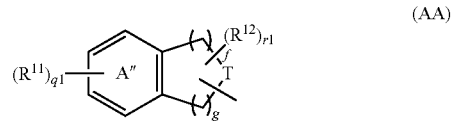

(where f is an integer of 0 to 2; g is an integer of 1 to 4; q1 is an integer of 0 to 4; r1 is an integer of 0 to 2;

a ring A" is a benzene ring, or a pyridine ring;

T is —$CH_2$—, an oxygen atom, —$S(O)_i$— (i is an integer of 0 to 2) or —$NR^7$—;

$R^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —S(O)$_i$R$^a$ (i is an integer of 0 to 2), or a group: —NR$^b$R$^c$;

R$^{12}$s are independently a group arbitrarily selected from a halogen atom, —OH, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, a C$_{2-6}$ alkynyl group which is optionally substituted with 1 to 5 substituent(s) RI, a C$_{1-6}$ alkoxy group which is optionally substituted with 1 to 5 substituent(s) RI, —SH, a group: —S(O)$_i$R$^a$ (i is an integer of 0 to 2), or a group: —NR$^b$R$^c$);

the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$) or non-aromatic heterocyclic oxy;

the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$);

the above-mentioned substituent R$^a$ is a group arbitrarily selected from a C$_{1-6}$ alkyl group or a halogenated C$_{1-6}$ alkyl group;

the above-mentioned substituents R$^b$ and R$^c$ are independently a group arbitrarily selected from a hydrogen atom, a C$_{1-6}$ alkyl group, a halogenated C$_{1-6}$ alkyl group, a C$_{2-6}$ alkenyl group, a C$_{2-6}$ alkynyl group, a C$_{2-7}$ alkanoyl group, a C$_{1-6}$ alkylsulfonyl group, an arylcarbonyl group, or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a C$_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents R$^{b1}$ and R$^{c1}$ are independently a group arbitrarily selected from a hydrogen atom, a C$_{1-6}$ alkyl group, a C$_{2-7}$ alkanoyl group or a C$_{1-6}$ alkylsulfonyl group, the above-mentioned substituents R$^d$, R$^e$ and R$^f$ are independently a group arbitrarily selected from a hydrogen atom or a C$_{1-6}$ alkyl group), a salt of the compound, or a solvate of the salt or the compound.

[1a] An aspect [1a] which is another aspect of the first aspect of the present invention is
a compound of Formula (Ia):

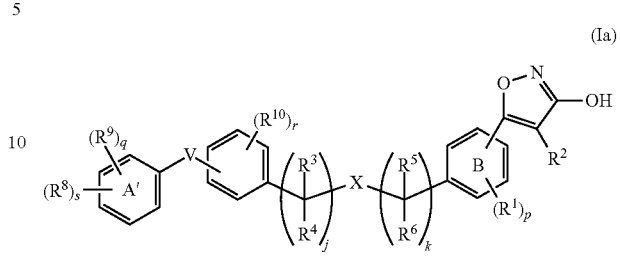

(Ia)

(where s is an integer of 1 to 2; q, r and p are independently an integer of 0 to 4; j is an integer of 0 to 3; k is an integer of 0 to 2;

a ring A' is a benzene ring, a pyridine ring, or a pyrimidine ring;

a ring B is a benzene ring, a pyridine ring, or a pyrimidine ring;

X is an oxygen atom, —S(O)$_i$— (i is an integer of 0 to 2) or —NR$^7$—;

V is a single bond or an oxygen atom;

R$^8$s are independently a group arbitrarily selected from a C$_{1-6}$ alkoxy group which is substituted with 1 to 5 substituent(s) L, a C$_{2-6}$ alkenyloxy group which is substituted with 1 to 5 substituent(s) L, a C$_{2-6}$ alkynyloxy group which is substituted with 1 to 5 substituent(s) L, or non-aromatic heterocyclic oxy;

the substituents L are independently a group arbitrarily selected from a halogen atom, —OH, a C$_{1-6}$ alkoxy group, a non-aromatic heterocyclic group (the heterocyclic group is optionally substituted with —OH or a C$_{1-6}$ alkyl group), a group: —S(O)$_i$R$^a$ (i is an integer of 0 to 2), a group: —CO$_2$R$^f$, a group: —SO$_2$NR$^d$R$^e$, a group: —CONR$^d$R$^e$ or a group: —NR$^b$R$^c$;

R$^9$ and R$^{10}$ are independently a group arbitrarily selected from a halogen atom, a C$_{1-6}$ alkyl group which is optionally substituted with 1 to 5 substituent(s) RI, a C$_{2-6}$ alkenyl group which is optionally substituted with 1 to 5 substituent(s) RI, or a C$_{2-6}$ alkynyl group which is optionally substituted with 1 to 5 substituent(s) RI;

R$^1$s are independently a group arbitrarily selected from a halogen atom, —OH, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, a C$_{2-6}$ alkynyl group which is optionally substituted with 1 to 5 substituent(s) RI, a C$_{1-6}$ alkoxy group which is optionally substituted with 1 to 5 substituent(s) RI, —SH, a group: —S(O)$_i$R$^a$ (i is an integer of 0 to 2) or a group: —NR$^b$R$^c$;

R$^2$ is a group arbitrarily selected from a hydrogen atom, a halogen atom, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, or a C$_{2-6}$ alkynyl group which is optionally substituted with 1 to 5 substituent(s) RI;

R$^3$, R$^4$, R$^5$, R$^6$, and R$^7$ are independently a group arbitrarily selected from a hydrogen atom, a C$_{1-6}$ alkyl group, a halogenated C$_{1-6}$ alkyl group, a C$_{2-6}$ alkenyl group or a C$_{2-6}$ alkynyl group;

the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$) or a non-aromatic heterocyclic oxy group; the above-mentioned substituents RII are the same as or different from each other and are each a group arbitrarily selected from the above-mentioned substituent RI, or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s) or 1 to 5 group(s): —NR$^{b1}$R$^{c1}$);

the above-mentioned substituent R$^a$ is a group arbitrarily selected from a $C_{1-6}$ alkyl group or a halogenated $C_{1-6}$ alkyl group;

the above-mentioned substituents R$^f$, R$^d$ and R$^e$ are independently a group arbitrarily selected from a hydrogen atom or a $C_{1-6}$ alkyl group;

the above-mentioned substituents R$^b$ and R$^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents R$^{b1}$ and R$^{c1}$ are independently a group arbitrarily selected from a hydrogen atom, a $C_{1-6}$ alkyl group, a $C_{2-7}$ alkanoyl group or a $C_{1-6}$ alkylsulfonyl group), a salt of the compound, or a solvate of the salt or the compound.

In the compound of Formula (Ia), preferably,
s is an integer of 1 to 2; q, r and p are independently an integer of 0 to 4; j is an integer of 1 to 3; k is an integer of 0 to 2;
a ring A' is a benzene ring, a pyridine ring, or a pyrimidine ring;
a ring B is a benzene ring or a pyridine ring;
X is an oxygen atom, a sulfur atom, or —NR$^7$—; V is a single bond or an oxygen atom;
R$^8$s are independently a group arbitrarily selected from a $C_{1-6}$ alkoxy group which is substituted with 1 to 5 substituent(s) L, a $C_{2-6}$ alkenyloxy group which is substituted with 1 to 5 substituent(s) L, a $C_{2-6}$ alkynyloxy group which is substituted with 1 to 5 substituent(s) L, or a non-aromatic heterocyclic oxy group;
the substituents L are independently a group arbitrarily selected from a halogen atom, —OH, a $C_{1-6}$ alkoxy group, a non-aromatic heterocyclic group (the heterocyclic group is optionally substituted with —OH or a $C_{1-6}$ alkyl group), a group: —S(O)$_i$R$^a$ (i is an integer of 0 to 2), a group: —CO$_2$R$^f$, a group: —SO$_2$NR$^d$R$^e$, a group: —CONR$^d$R$^e$ or a group: —NR$^b$R$^c$;
R$^a$ is a group arbitrarily selected from a $C_{1-6}$ alkyl group or a halogenated $C_{1-6}$ alkyl group;
R$^f$, R$^d$, and R$^e$ are a group arbitrarily selected from a hydrogen atom or a $C_{1-6}$ alkyl group;
R$^b$ and R$^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom selected from an oxygen atom or a sulfur atom, or with a carbonyl group;

R$^9$, R$^{10}$, and R$^1$ are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

the substituents RI are the same as or different from each other and are each a group arbitrarily selected from a halogen atom, —OH, cyano, a $C_{1-6}$ alkoxy group, or a halogenated $C_{1-6}$ alkoxy group;

R$^2$ is a group arbitrarily selected from a hydrogen atom, a halogen atom, or a cyano group;

R$^3$, R$^4$, R$^5$, R$^6$, and a R$^7$ are independently a group arbitrarily selected from a hydrogen atom, a $C_{1-6}$ alkyl group, a halogenated $C_{1-6}$ alkyl group, a $C_{2-6}$ alkenyl group, or a $C_{2-6}$ alkynyl group;

[1b] An aspect [1b] which is another aspect of the first aspect of the present invention is
a compound of Formula (Ib):

(Ib)

(where f is an integer of 0 to 2; g is an integer of 1 to 4; q1 and p are independently an integer of 0 to 4; j is an integer of 0 to 3; r1 and k are independently an integer of 0 to 2;
a ring A" is a benzene ring or a pyridine ring;
a ring B is a benzene ring, a pyridine ring, or a pyrimidine ring;
X and T are independently —CH$_2$—, an oxygen atom, —S(O)$_i$— (i is an integer of 0 to 2) or —NR$^7$—;
R$^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —S(O)$_i$R$^a$ (i is an integer of 0 to 2), or a group: —NR$^b$R$^c$ group;

R$^1$ and R$^{12}$ are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a group: —S(O)$_i$R$^a$ (i is an integer of 0 to 2), or a group: —NR$^b$R$^c$;

R$^2$ is a group arbitrarily selected from a hydrogen atom, a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

R$^3$, R$^4$, R$^5$, R$^6$, and R$^7$ are independently a group arbitrarily selected from a hydrogen atom, a $C_{1-6}$ alkyl group, a halogenated $C_{1-6}$ alkyl group, a $C_{2-6}$ alkenyl group or a $C_{2-6}$ alkynyl group;

the above-mentioned substituents RI are the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$) or a non-aromatic heterocyclic oxy group; the above-mentioned substituents MI are the same as or different from each other and are each a group arbitrarily selected from the above-mentioned substituent RI, or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s) or 1 to 5 group(s): —NR$^{b1}$R$^{c1}$);

the above-mentioned substituent R$^a$ is a group arbitrarily selected from a $C_{1-6}$ alkyl group or a halogenated $C_{1-6}$ alkyl group;

the above-mentioned substituents R$^b$ and R$^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents R$^{b1}$ and R$^{c1}$ are independently a group arbitrarily selected from a hydrogen atom, a $C_{1-6}$ alkyl group, a $C_{2-7}$ alkanoyl group or a $C_{1-6}$ alkylsulfonyl group;

the above-mentioned substituents R$^d$ and R$^e$ are independently a group arbitrarily selected from a hydrogen atom or a $C_{1-6}$ alkyl group), a salt of the compound, or a solvate of the salt or the compound.

In the compound of Formula (Ib), preferably,
f is an integer of 0 to 2; g is an integer of 1 to 4; q1 and p are independently an integer of 0 to 4; r1, j, and k are independently an integer of 0 to 2;

a ring A" and a ring B are independently a benzene ring or a pyridine ring;

X and T are independently —CH$_2$—, an oxygen atom, —S(O)$_i$— (i is an integer of 0 to 2) or —NR$^7$—;

R$^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —S(O)$_i$R$^a$ (i is an integer of 0 to 2), or a group: —NR$^b$R$^c$;

R$^a$ is a group arbitrarily selected from a $C_{1-6}$ alkyl group or a halogenated $C_{1-6}$ alkyl group;

R$^b$ and R$^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

R$^1$ and R$^{12}$ are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a group: —S(O)$_i$R$^a$ (i is an integer of 0 to 2, and R$^a$ is the same as defined as R$^a$ above), or a group: —NR$^b$R$^c$ (R$^b$ and R$^c$ are the same as defined as R$^b$ and R$^c$ above);

R$^2$ is a group arbitrarily selected from a hydrogen atom, a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

R$^3$, R$^4$, R$^5$, R$^6$, and R$^7$ are independently a group arbitrarily selected from a hydrogen atom, a $C_{1-6}$ alkyl group, a halogenated $C_{1-6}$ alkyl group, a $C_{2-6}$ alkenyl group or a $C_{2-6}$ alkynyl group;

the above-mentioned substituents RI are the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s): —S(O)$_i$R$^a$ (i is an integer of 0 to 2, and R$^a$ is the same as defined as R$^a$ above), 1 to 5 group(s): —SO$_2$NR$^d$R$^e$, or 1 to 5 group(s): —CONR$^d$R$^e$ (R$^d$ and R$^e$ are the same as defined as $R^d$ and $R^e$ above), or 1 to 5 group(s): —$NR^{b1}R^{c1}$) or a non-aromatic heterocyclic oxy;

the above-mentioned substituents RII are the same as or different from each other and are each a group arbitrarily selected from the above-mentioned substituent RI, or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s) or 1 to 5 group(s): —$NR^{b1}R^{c1}$);

the above-mentioned substituents $R^{b1}$ and $R^{c1}$ are independently a group arbitrarily selected from a hydrogen atom, a $C_{1-6}$ alkyl group, a $C_{2-7}$ alkanoyl group or a $C_{1-6}$ alkylsulfonyl group;

Each group in Formulae (I), (Ia), and (Ib) according to Aspect [1], [1a], and [1b] are specifically described below.

In the explanation of the compound according to the present invention, for example, "$C_{1-6}$" indicates that the number of constituent carbon atoms, which is the number of carbon atoms in a linear, branched, or cyclic group unless otherwise indicated, is 1 to 6. The number of constituent carbon atoms includes the total number of carbon atoms in a group having a linear or branched group substituted with a cyclic group or a cyclic group substituted with a linear or branched group. Therefore, as for an acyclic group, "$C_{1-6}$" means a "linear or branched chain with the number of constituent carbon atoms of 1 to 6". As for a cyclic group, "$C_{1-6}$" means a "cyclic group with the number of ring-constituting carbon atoms of 1 to 6". As for a group having an acyclic group and a cyclic group, "$C_{1-6}$" means a "group with the total number of carbon atoms of 1 to 6".

The "alkyl group" is a linear, branched, or cyclic alkyl group. Examples of the "$C_{1-6}$ alkyl" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, 1-cyclopropylethyl, 2-cyclopropylethyl, 2-cyclobutylethyl, 2-methylcyclopropyl, and the like.

The "alkenyl group" is a linear, branched, or cyclic alkenyl group. Examples of the "$C_{2-6}$ alkenyl" include vinyl, allyl, isopropenyl, 2-methylallyl, butenyl, pentenyl, hexenyl, 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, 2,5-cyclohexadien-1-yl, and the like.

The "alkynyl group" is a linear, branched, or cyclic alkynyl group. Examples of the "$C_{2-6}$ alkynyl" include ethynyl, 1-propynyl, 2-propynyl, butynyl, pentynyl, hexynyl, and the like.

The "alkoxy group" is a linear, branched, or cyclic alkoxy group and comprehensively a group of R'O— (as for the $C_{1-6}$ alkoxy, R' is the $C_{1-6}$ alkyl listed above). Examples of the "$C_{1-6}$ alkoxy" include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, cyclopropyloxy, cyclobutyloxy, cyclopentyloxy, cyclohexyloxy, cyclopropylmethoxy, 1-cyclopropylethoxy, 2-cyclopropylethoxy, cyclobutylmethoxy, 2-cyclobutylethoxy, cyclopentylmethoxy, 2-methylcyclopropyloxy, and the like.

The "alkenyloxy group" is denoting a linear, branched, or cyclic alkenyloxy group and comprehensively a group of R'''O— (as for the $C_{2-6}$ alkenyloxy, R''' is the $C_{2-6}$ alkenyl listed above). Examples of the "$C_{2-6}$ alkenyloxy" include vinyloxy, allyloxy, isopropenyloxy, 2-methylallyloxy, butenyloxy, 3-methyl-3-butenyloxy, pentenyloxy, hexenyloxy, and the like.

The "alkynyloxy group" is denoting a linear, branched, or cyclic alkynyloxy group, and comprehensively a group of R'''O— (as for the $C_{2-6}$ alkenyloxy, R''' is the $C_{2-6}$ alkenyl listed above). Examples of the "$C_{2-6}$ alkynyl" include ethynyloxy, 1-propynyloxy, 2-propynyloxy, butynyloxy, pentynyloxy, hexynyloxy, and the like.

Examples of the "aryl group" include a monocyclic or ring-fused $C_{6-14}$ aryl group, for example, phenyl, 1-naphthyl, 2-naphthyl, anthryl, phenanthryl, acenaphthyl, and the like, or fused aryl which is partly hydrogenated such as (1-, 2-, 4-, or 5-)indanyl, indenyl, tetrahydronaphthyl, and the like. The aryl group which is partly hydrogenated means a monovalent group obtained by removing any hydrogen atom from a fused ring which is partly hydrogenated, and the hydrogen atom to be removed is optionally a hydrogen atom in an aromatic ring moiety or a hydrogen atom in a hydrogenated moiety of the fused ring. For example, tetrahydronaphthyl includes 1,2,3,4-tetrahydronaphthalene (-1-yl, -2-yl, -3-yl, -4-yl, -5-yl, -6-yl, -7-yl, -8-yl), and the like.

Examples of the "heterocyclic group" include a heteroaryl group, and a saturated or unsaturated non-aromatic heterocyclic group. The term "cyclic" used for these groups means a monovalent group obtained by removing any hydrogen atom from a ring having a 3- to 14-membered, preferably a 3- to 12-membered, monocyclic ring or fused ring containing, in addition to carbon atoms, at least one (preferably 1 to 4) heteroatom(s) arbitrarily selected from N, O, and S.

The "heteroaryl group" can be monocyclic or ring-fused, and the monocyclic heteroaryl group preferably has 5 to 7 ring members and includes, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, 1,4-oxazepinyl, and the like.

The ring-fused heteroaryl group preferably has 8 to 12 ring members and includes a monovalent group obtained by removing any hydrogen atom from a fused ring formed by fusing the 5- to 7-membered heterocyclic ring and a monocyclic aryl group (a benzene ring, for example) or a monocyclic heteroaryl group, and the like. The hydrogen atom is optionally removed from any of the fused rings.

Specifically, indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, and the like are mentioned.

In addition, a ring-fused heteroaryl group, etc. which is partly hydrogenated, such as indolinyl, dihydrobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl is mentioned. The ring-fused heteroaryl group, etc. which is partly hydrogenated is preferably one having 8 to 12 ring members, namely a monovalent group obtained by removing any hydrogen atom from a ring which is partly hydrogenated in the fused ring formed by fusing the 5- to 7-membered heterocyclic ring and a monocyclic aryl group (a benzene ring, for example) or a monocyclic heteroaryl group. The hydrogen atom to be removed is optionally a hydrogen atom in the aryl group or in the heterocyclic moiety or a hydrogen atom in the hydrogenated moiety. In the case of tetrahydroquinolyl, examples of the partially hydrogenated ring-fused heteroaryl group include 5,6,7,8-tetrahydroquinolyl and 1,2,3,4-tetrahydroquinolyl. Depending on the position in these groups from which the hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" include a 3- to 8-membered saturated or unsaturated non-aromatic heterocyclic group, for example, aziridinyl, azetidinyl, oxiranyl, oxetanyl, thietanyl, pyrrolidinyl, tetrahydrofuryl, thiolanyl, pyrazolinyl, pyrazolidinyl, piperidinyl, tetrahydropyranyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, oxepanyl, tetrahydrothiopyranyl, 1,1-dioxidetetrahydro-2H-thiopyran-4-yl, and the like, and the "non-aromatic heterocyclic group" means a monovalent group obtained by removing any hydrogen atom from the ring.

Examples of the "non-aromatic heterocyclic group which is optionally substituted with —OH or a $C_{1-6}$ alkyl group" include, in addition to the groups mentioned as the "non-aromatic heterocyclic group", a group in which the cyclic group is substituted with —OH or the "$C_{1-6}$ alkyl group" at any position. For example, methylaziridinyl, methylazetidinyl, methyloxiranyl, methyloxetanyl, methylthietanyl, methylpyrrolidinyl, methyltetrahydrofuryl, methylthiolanyl, methylpyrazolinyl, methylpyrazolidinyl, methylpiperidinyl, methyltetrahydropyranyl, methylpiperazinyl, methyloxazolinyl, methylisoxazolinyl, methyloxazolidinyl, methylisoxazolidinyl, methylthiazolinyl, methylisothiazolinyl, methylthiazolidinyl, methylisothiazolidinyl, methyloxadiazolinyl, methyloxadiazolidinyl, methylmorpholinyl, methylthiomorpholinyl, methylquinuclidinyl, methyloxepanyl, 4-hydroxy-1,1-dioxidetetrahydro-2H-thiopyran-4-yl, and the like are mentioned.

The "aralkyl group" is a group in which a linear or branched alkyl group of the "$C_{1-6}$ alkyl" is substituted with the "aryl group", and examples of the "aralkyl group" include benzyl, phenethyl, 3-phenylpropyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, 1,2,3,4-tetrahydronaphthalen-2-ylmethyl, and the like.

The "heteroarylalkyl group" is a group in which a linear or branched alkyl group of the "$C_{1-6}$ alkyl" is substituted with the "heteroaryl group", and examples of the "heteroarylalkyl group" include those substituted with the "monocyclic heteroaryl group", such as pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3-thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, 6H-1,3,4-thiadiazinylmethyl, 1,4-diazepinylmethyl, 1,4-oxazepinylmethyl, and the like, and those substituted with the "ring-fused heteroaryl group", such as indolylmethyl, isoindolylmethyl, benzofuranylmethyl, isobenzofuranylmethyl, benzothienylmethyl, isobenzothienylmethyl, benzoxazolylmethyl, 1,2-benzisoxazolylmethyl, benzothiazolylmethyl, 1,2-benzisothiazolylmethyl, 1H-benzimidazolylmethyl, 1H-indazolylmethyl, 1H-benzotriazolylmethyl, 2,1,3-benzothiadiazinylmethyl, chromenylmethyl, isochromenylmethyl, 4H-1,4-benzoxazinylmethyl, 4H-1,4-benzothiazinylmethyl, quinolylmethyl, isoquinolylmethyl, cinnolinylmethyl, quinazolinylmethyl, quinoxalinylmethyl, phthalazinylmethyl, benzoxazepinylmethyl, benzoazepinylmethyl, benzodiazepinylmethyl, naphthyridinylmethyl, purinylmethyl, pteridinylmethyl, carbazolylmethyl, carbolinylmethyl, acridinylmethyl, phenoxazinylmethyl, phenothiazinylmethyl, phenazinylmethyl, phenoxathiinylmethyl, thianthrenylmethyl, phenanthridinylmethyl, phenanthrolinylmethyl, indolizinylmethyl, thieno[3,2-c]pyridylmethyl, thiazolo[5,4-c]pyridylmethyl, pyrrolo[1,2-b]pyridazinylmethyl, pyrazolo[1,5-a]pyridylmethyl, imidazo[1,2-a]pyridylmethyl, imidazo[1,5-a]pyridylmethyl, imidazo[1,2-b]pyridazinylmethyl, imidazo[1,5-a]pyrimidinylmethyl, 1,2,4-triazolo[4,3-a]pyridylmethyl, 1,2,4-triazolo[4,3-b]pyridazinylmethyl, 1H-pyrazolo[3,4-b]pyridylmethyl, 1,2,4-triazolo[1,5-a]pyrimidinylmethyl, indolinylmethyl, dihydrobenzofuranylmethyl, chromanylmethyl, tetrahydroquinolylmethyl, tetrahydroisoquinolylmethyl, 1,4-benzodioxanylmethyl, 1,3-benzodioxolylmethyl, and the like.

The "aryloxy group" is a group in which the "aryl group" is substituted with an oxygen atom, and examples thereof include phenoxy, 1-naphthyloxy, 2-naphthyloxy, 2-anthryloxy, phenanthryloxy, 1-indanyloxy, 2-indanyloxy, 1,2,3,4-tetrahydronaphthalen-1-yloxy, 1,2,3,4-tetrahydronaphthalen-2-yloxy, 1,2,3,4-tetrahydronaphthalen-8-yloxy, and the like.

The "heteroaryloxy group" is a group in which the "heteroaryl group" is substituted with an oxygen atom, and examples thereof include, for example, pyrrolyloxy, furyloxy, thienyloxy, imidazolyloxy, pyrazolyloxy, oxazolyloxy, isoxazolyloxy, thiazolyloxy, isothiazolyloxy, pyridyloxy, pyridazinyloxy, pyrimidinyloxy, pyrazinyloxy, indolyloxy, quinolyloxy, isoquinolyloxy, indolinyloxy, dihydrobenzofuranyloxy, chromanyloxy, tetrahydroquinolyloxy, tetrahydroisoquinolyloxy, 1,4-benzodioxanyloxy, 1,3-benzodioxolyloxy, and the like.

The "aralkyloxy group" is a group in which the "aralkyl group" is substituted with an oxygen atom, and examples thereof include benzyloxy, phenethyloxy, 3-phenylpropoxy, 1-naphthylmethoxy, 2-naphthylmethoxy, 2-(1-naphthyl) ethoxy, 2-(2-naphthyl)ethoxy, 1-indanylmethoxy, 2-indanylmethoxy, 1,2,3,4-tetrahydronaphthalen-1-ylmethoxy, 1,2,3, 4-tetrahydronaphthalen-2-ylmethoxy, and the like.

The "heteroarylalkyloxy group" is a group in which the "heteroarylalkyl group" is substituted with an oxygen atom, and examples thereof include a "monocyclic heteroarylalkyl group" substituted with an oxygen atom, such as pyrrolylmethoxy, furylmethoxy, thienylmethoxy, imidazolylmethoxy, pyrazolylmethoxy, oxazolylmethoxy, isoxazolylmethoxy, thiazolylmethoxy, isothiazolylmethoxy, 1,2,3-triazolylmethoxy, 1,2,4-triazolylmethoxy, 1,2,3-oxadiazolylmethoxy, 1,2,4-oxadiazolylmethoxy, 1,3,4-oxadiazolylmethoxy, furazanylmethoxy, 1,2,3-thiadiazolylmethoxy, 1,2,4-thiadiazolylmethoxy, 1,3,4-thiadiazolylmethoxy, tetrazolylmethoxy, pyridylmethoxy, pyridazinylmethoxy, pyrimidinylmethoxy, pyrazinylmethoxy, 1,2,3-triazinylmethoxy, 1,2,4-triazinylmethoxy, 1,3,5-triazinylmethoxy, 2H-1,2,3-thiadiazinylmethoxy, 4H-1,2,4-thiadiazinylmethoxy, 6H-1,3,4-thiadiazinylmethoxy, 1,4-diazepinylmethoxy, 1,4-oxazepinylmethoxy, and the like, and a "ring-fused heteroarylalkyl group" which is optionally partly hydrogenated and is substituted with an oxygen atom, such as indolylmethoxy, isoindolylmethoxy, benzofuranylmethoxy, isobenzofuranylmethoxy, benzothienylmethoxy, isobenzothienylmethoxy, benzoxazolylmethoxy, 1,2-benzisoxazolylmethoxy, benzothiazolylmethoxy, 1,2-benzisothiazolylmethoxy, 1H-benzimidazolylmethoxy, 1H-indazolylmethoxy, 1H-benzotriazolylmethoxy, 2,1,3-benzothiadiazinylmethoxy, chromenylmethoxy, isochromenylmethoxy, 4H-1,4-benzoxazinylmethoxy, 4H-1, 4-benzothiazinylmethoxy, quinolylmethoxy, isoquinolylmethoxy, cinnolinylmethoxy, quinazolinylmethoxy, quinoxalinylmethoxy, phthalazinylmethoxy, benzoxazepinylmethoxy, benzoazepinylmethoxy, benzodiazepinylmethoxy, naphthyridinylmethoxy, purinylmethoxy, pteridinylmethoxy, carbazolylmethoxy, carbolinylmethoxy, acridinylmethoxy, phenoxazinylmethoxy, phenothiazinylmethoxy, phenazinylmethoxy, phenoxathiinylmethoxy, thianthrenylmethoxy, phenanthridinylmethoxy, phenanthrolinylmethoxy, indolizinylmethoxy, thieno[3,2-c]pyridylmethoxy, thiazolo[5,4-c]pyridylmethoxy, pyrrolo[1, 2-b]pyridazinylmethoxy, pyrazolo[1,5-a]pyridylmethoxy, imidazo[1,2-a]pyridylmethoxy, imidazo[1,5-a]pyridylmethoxy, imidazo[1,2-b]pyridazinylmethoxy, imidazo[1,5-a]pyrimidinylmethoxy, 1,2,4-triazolo[4,3-a]pyridylmethoxy, 1,2,4-triazolo[4,3-b]pyridazinylmethoxy, 1H-pyrazolo[3,4-b]pyridylmethoxy, 1,2,4-triazolo[1,5-a]pyrimidinylmethoxy, indolinylmethoxy, dihydrobenzofuranylmethoxy, chromanylmethoxy, tetrahydroquinolylmethoxy, tetrahydroisoquinolylmethoxy, 1,4-benzodioxanylmethoxy, 1,3-benzodioxolylmethoxy, and the like.

The "non-aromatic heterocyclic oxy group" is a group in which the "non-aromatic heterocyclic" is substituted with an oxygen atom, and examples thereof include, for example, a 3- to 8-membered saturated or unsaturated non-aromatic heterocyclic oxy group, such as aziridinyloxy, azetidinyloxy, oxiranyloxy, oxetanyloxy, thietanyloxy, pyrrolidinyloxy, tetrahydrofuryloxy, thiolanyloxy, pyrazolinyloxy, pyrazolidinyloxy, piperidinyloxy, tetrahydropyranyloxy, piperazinyloxy, oxazolinyloxy, isoxazolinyloxy, oxazolidinyloxy, isoxazolidinyloxy, thiazolinyloxy, isothiazolinyloxy, thiazolidinyloxy, isothiazolidinyloxy, oxadiazolinyloxy, oxadiazolidinyloxy, morpholinyloxy, thiomorpholinyloxy, quinuclidinyloxy, oxepanyloxy, tetrahydrothiopyranyloxy, (1,1-1-dioxidetetrahydro-2H-thiopyran-4-yl)oxy, and the like.

Examples of the "halogen atom" include a fluorine atom, a chlorine atom, a bromine atom, and an iodine atom.

The "halogenated $C_{1-6}$ alkyl" is a group in which the "$C_{1-6}$ alkyl" is optionally substituted with 1 to 5 halogen atom(s). For example, trifluoromethyl, trifluoroethyl, tetrafluoroethyl, pentafluoroethyl, and the like are mentioned.

The "halogenated $C_{1-6}$ alkoxy" is a group in which the "$C_{1-6}$ alkoxy" is optionally substituted with 1 to 5 halogen atom(s). For example, trifluoromethoxy, trifluoroethoxy, tetrafluoroethoxy, pentafluoroethoxy, and the like are mentioned.

The "$C_{2-7}$ alkanoyl" means a "linear, branched, or cyclic $C_{2-7}$ alkylcarbonyl group" and is R—CO— (R is the "$C_{1-6}$ alkyl"). Examples thereof include acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, 2-methylcyclopropylcarbonyl, and the like.

The "arylcarbonyl" is a group in which a carbonyl group is bonded to the "aryl group", and examples thereof include $C_{6-14}$ arylcarbonyl such as benzoyl and naphthylcarbonyl.

The "heterocyclic carbonyl" means "heterocyclic carbonyl", and examples thereof include the "heterocyclic group" (for example, a heteroaryl group, a saturated or unsaturated non-aromatic heterocyclic group, and the like) to which a carbonyl group is bonded, including a carbonyl group to which the "monocyclic heteroaryl group" is bonded, such as pyrrolylcarbonyl, furylcarbonyl, thienylcarbonyl, imidazolylcarbonyl, pyrazolylcarbonyl, oxazolylcarbonyl, isoxazolylcarbonyl, thiazolylcarbonyl, isothiazolylcarbonyl, 1,2, 3-triazolylcarbonyl, 1,2,4-triazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, tetrazolylcarbonyl, pyridylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 2H-1,2,3-thiadiazinylcarbonyl, 4H-1,2,4-thiadiazinylcarbonyl, 6H-1,3,4-thiadiazinylcarbonyl, 1,4-diazepinylcarbonyl, and 1,4-oxazepinylcarbonyl; a carbonyl group to which the "ring-fused heteroaryl group" which is optionally partly hydrogenated is bonded, such as indolylcarbonyl, isoindolylcarbonyl, benzofuranylcarbonyl, isobenzofuranylcarbonyl, benzothienylcarbonyl, isobenzothienylcarbonyl, benzoxazolylcarbonyl, 1,2-benzisoxazolylcarbonyl, benzothiazolylcarbonyl, 1,2-berizisothiazolylcarbonyl, 1H-benzimidazolylcarbonyl, 1H-indazolylcarbonyl, 1H-benzotriazolylcarbonyl, 2,1,3-benzothiadiazinylcarbonyl, chromenylcarbonyl, isochromenylcarbonyl, 4H-1,4-benzoxazinylcarbonyl, 4H-1,4-benzothiazinylcarbonyl, quinolylcarbonyl, isoquinolylcarbonyl, cinnolinylcarbonyl, quinazolinylcarbonyl, quinoxalinylcarbonyl, phthalazinylcarbonyl, benzoxazepinylcarbonyl, benzoazepinylcarbonyl, benzodiazepinylcarbonyl, naphthyridinylcarbonyl, purinylcarbonyl, pteridinylcarbonyl, carbazolylcarbonyl, carbolinylcarbonyl, acridinylcarbonyl, phenoxazinylcarbonyl, phenothiazinylcarbonyl, phenazinylcarbonyl, phenoxathiinylcarbonyl, thianthrenylcarbonyl, phenanthridinylcarbonyl, phenanthrolinylcarbonyl, indolizinylcarbonyl, thieno[3,2-c]pyridylcarbonyl, thiazolo[5,4-c]pyridylcarbonyl, pyrrolo[1,2-b]pyridazinylcarbonyl, pyrazolo[1,5-a]pyridylcarbonyl, imidazo[1,2-a]pyridylcarbonyl, imidazo[1,5-a]pyridylcarbonyl, imidazo[1,2-b]pyridazinylcarbonyl, imidazo[1,5-a]pyrimidinylcarbonyl, 1,2,4-triazolo[4,3-a]pyridylcarbonyl, 1,2,4-triazolo[4,3-b]pyridazinylcarbonyl, 1H-pyrazolo[3,4-b]pyridylcarbonyl, 1,2,4-triazolo[1,5-a]pyrimidinylcarbonyl, indolinylcarbonyl, dihydrobenzofuranylcarbonyl, chromanylcarbonyl, tetrahydroquinolylcarbonyl, tetrahydroisoquinolylcarbonyl, 1,4-benzodioxanylcarbonyl, and 1,3-benzodioxolylcarbonyl, and a carbonyl group to which the "saturated or unsaturated non-aromatic heterocyclic group" is bonded, such as aziridinylcarbonyl, azetidinylcarbonyl, pyrrolidinylcarbonyl, tetrahydrofurylcarbonyl, piperidinylcarbonyl, tetrahydropyranylcarbonyl, piperazinylcarbonyl, and morpholinylcarbonyl.

In the "group: —$CO_2R^f$", examples of $R^f$ include a group arbitrarily selected from a hydrogen atom or a $C_{1-6}$ alkyl. Specifically, examples of $R^f$ include carboxyl or "$C_{1-6}$ alkoxycarbonyl".

The "$C_{1-6}$ alkoxycarbonyl" is a carbonyl group to which the above-mentioned "alkoxy group" is bonded, and is represented as —$CO_2R^{f1}$ ($R^{f1}$ is the above-mentioned "$C_{1-6}$ alkyl"). Specifically, the alkoxycarbonyl group is a carbonyl group to which a linier, branched, or cyclic alkoxy group is boned. Specific examples of the alkoxycarbonyl group include, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neo-pentyloxycarbonyl, tert-pentyloxycarbonyl, hexyloxycarbonyl, cyclopropyloxycarbonyl, cyclobutyloxycarbonyl, cyclopentyloxycarbonyl, cyclohexyloxycarbonyl, cyclopropylmethyloxycarbonyl, 1-cyclopropylethyloxycarbonyl, 2-cyclopropylethyloxycarbonyl, cyclobutylmethyloxycarbonyl, 2-cyclobutylethyloxycarbonyl, cyclopentylmethyloxycarbonyl, and the like.

In the "group: —$S(O)_iR^a$", i is an integer of 0 to 2, and $R^a$ is a group arbitrarily selected from $C_{1-6}$ alkyl or halogenated $C_{1-6}$ alkyl. When i is 0, examples of the "—$S(O)_iR^a$ group" include "$C_{1-6}$ alkylthio" and "halogenated $C_{1-6}$ alkylthio", when i is 1, examples of the "—$S(O)_iR^a$ group" include "$C_{1-6}$ alkylsulfinyl" and "halogenated $C_{1-6}$ alkylsulfinyl", and when i is 2, examples of the "—$S(O)_iR^a$ group" include "$C_{1-6}$ alkylsulfonyl" and "halogenated $C_{1-6}$ alkylsulfonyl".

The "$C_{1-6}$ alkylthio" means a linear, branched, or cyclic $C_{1-6}$ alkylthio group, and examples thereof include methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 3,3-dimethylbutylthio, cyclopropylthio, cyclobutylthio, cyclopentylthio, cyclohexylthio, cyclopropylmethylthio, 1-cyclopropylethylthio, 2-cyclopropylethylthio, cyclobutylmethylthio, 2-cyclobutylethylthio, cyclopentylmethylthio, 2-methylcyclopropylthio, and the like. The "halogenated $C_{1-6}$ alkylthio" is a group in which the "$C_{1-6}$ alkylthio" is optionally substituted with 1 to 5 halogen atom(s), and examples thereof include trifluoromethylthio, and the like.

The "$C_{1-6}$ alkylsulfinyl" means a linear, branched, or cyclic $C_{1-6}$ alkylsulfinyl group, and examples thereof include methylsulfinyl, ethylsulfinyl, propylsulfinyl, isopropylsulfinyl, cyclopropylsulfinyl, cyclopropylmethylsulfinyl, 2-methylcyclopropylsulfinyl, and the like. The "halogenated $C_{1-6}$ alkylsulfinyl" is a group in which the "$C_{1-6}$ alkylsulfinyl" is optionally substituted with 1 to 5 halogen atom(s), and examples thereof include trifluoromethylsulfinyl, and the like.

The "$C_{1-6}$ alkylsulfonyl" means a linear, branched, or cyclic $C_{1-6}$ alkylsulfonyl group, and examples thereof include methylsulfonyl, ethylsulfonyl, propylsulfonyl, isopropylsulfonyl, cyclopropylsulfonyl, cyclopropylmethylsulfonyl, 2-methylcyclopropylsulfonyl, and the like. The "halogenated $C_{1-6}$ alkylsulfonyl" is a group in which the "$C_{1-6}$ alkylsulfonyl" is optionally substituted with 1 to 5 halogen atom(s), and examples thereof include trifluoromethylsulfonyl, and the like.

The "group: —$SO_2NR^dR^e$", in which $R^d$ and $R^e$ are independently a group arbitrarily selected from a hydrogen atom or $C_{1-6}$ alkyl, means a sulfamoyl group in which 1 or 2 hydrogen atom(s) on a nitrogen atom of the sulfamoyl group is (are) optionally substituted with the "$C_{1-6}$ alkyl". Specifically, for example, sulfamoyl, methylsulfamoyl, ethylsulfamoyl, propylsulfamoyl, isopropylsulfamoyl, cyclopropylsulfamoyl, butylsulfamoyl, isobutylsulfamoyl, pentylsulfamoyl, isopentylsulfamoyl, hexylsulfamoyl, isohexylsulfamoyl, dimethylsulfamoyl, diethylsulfamoyl, dipropylsulfamoyl, di-isopropylsulfamoyl, dibutylsulfamoyl, dipentylsulfamoyl, ethylmethylsulfamoyl, methylpropylsulfamoyl, ethylpropylsulfamoyl, butylmethylsulfamoyl, butylethylsulfamoyl, butylpropylsulfamoyl, and the like are mentioned.

The "group: —$CONR^dR^e$", in which $R^d$ and $R^e$ are independently a group arbitrarily selected from a hydrogen atom or $C_{1-6}$ alkyl. Specifically, carbamoyl or "mono/di $C_{1-6}$ alkylcarbamoyl" are mentioned.

The "mono/di $C_{1-6}$ alkylcarbamoyl" means a carbamoyl group in which 1 or 2 hydrogen atom(s) on a nitrogen atom of the carbamoyl group is (are) substituted with the "$C_{1-6}$ alkyl". Specifically, for example, methylcarbamoyl, ethylcarbamoyl, propylcarbamoyl, isopropylcarbamoyl, cyclopropylcarbamoyl, butylcarbamoyl, isobutylcarbamoyl, pentylcarbamoyl, isopentylcarbamoyl, hexylcarbamoyl, isohexylcarbamoyl, dimethylcarbamoyl, diethylcarbamoyl, dipropylcarbamoyl, diisopropylcarbamoyl, dibutylcarbamoyl, dipentylcarbamoyl, ethylmethylcarbamoyl, methylpropylcarbamoyl, ethylpropylcarbamoyl, butylmethylcarbamoyl, butylethylcarbamoyl, butylpropylcarbamoyl, and the like are mentioned.

In the "group: —$NR^bR^c$", $R^b$ and $R^c$ are independently a group arbitrarily selected from a hydrogen atom, $C_{1-6}$ alkyl, halogenated $C_{1-6}$ alkyl, $C_{2-6}$ alkenyl, $C_{2-6}$ alkynyl, $C_{2-7}$ alkanoyl, $C_{1-6}$ alkylsulfonyl, arylcarbonyl or heterocyclic carbonyl. $R^b$ and $R^c$ optionally form, together with a nitrogen atom to which they are bonded, a 3- to 8-membered cyclic group, where in the cyclic group, one carbon atom is optionally substituted with an atom arbitrarily selected from an oxygen atom, a sulfur atom, or a nitrogen atom or with a carbonyl group, and the cyclic group is optionally further substituted with 1 to 5 substituent(s) RII. For example, amino, "mono/di $C_{1-6}$ alkylamino", "halogenated mono/di $C_{1-6}$ alkylamino", "$C_{2-7}$ alkanoylamino", "$C_{1-6}$ alkylsulfonylamino", "arylcarbonylamino", "heterocyclic carbonylamino", and the like are mentioned.

In the "group: —$NR^{b1}R^{c1}$", $R^{b1}$ and $R^{c1}$ are independently a group arbitrarily selected from a hydrogen atom, $C_{1-6}$ alkyl, $C_{2-7}$ alkanoyl, or $C_{1-6}$ alkylsulfonyl. For example, amino, "mono/di $C_{1-6}$ alkylamino", "$C_{2-7}$ alkanoylamino", "$C_{1-6}$ alkylsulfonylamino", and the like are mentioned.

The "mono/di $C_{1-6}$ alkylamino" means an amino group, 1 or 2 hydrogen atom(s) of which is (are) substituted with a linear, branched, or cyclic "$C_{1-6}$ alkyl". Specifically, methylamino, ethylamino, propylamino, isopropylamino, butylamino, isobutylamino, pentylamino, isopentylamino, hexylamino, isohexylamino, cyclopropylamino, cyclobutylamino, cyclopentylamino, cyclohexylamino, 1-cyclopropylmethylamino, 1-cyclobutylmethylamino, 1-cyclopentylmethylamino, 1-cyclohexylmethylamino, dimethylamino, diethylamino, dipropylamino, diisopropylamino, dibutylamino, dipentylamino, ethylmethylamino, propylmethylamino, propylethylamino, butylmethylamino, butylethylamino, butylpropylamino, N-cyclopropyl-N-methylamino, N-cyclobutyl-N-methylamino, N-cyclopentyl-N-methylamino, N-cyclohexyl-N-methylamino, and the like are mentioned.

The "halogenated mono/di $C_{1-6}$ alkylamino" is a group in which the "mono/di $C_{1-6}$ alkylamino" is optionally substituted with 1 to 5 halogen atom(s). For example, trifluoromethylamino, and the like are mentioned.

The "$C_{2-7}$ alkanoylamino" means an amino group, a hydrogen atom of which is substituted with a linear, branched, or cyclic "$C_{2-7}$ alkanoyl". Specifically, acetamido, propionamide, butylamide, isobutylamide, valeramide, isovaleramide, pivalamide, hexanamide, heptanamide, cyclopropanecarboxamide, cyclobutanecarboxamide, cyclopentanecarboxamide, cyclohexanecarboxamide, 2-methylcyclopropanecarboxamide, and the like are mentioned.

The "$C_{1-6}$ alkylsulfonylamino" means an amino group, a hydrogen atom of which is substituted with a linear, branched, or cyclic $C_{1-6}$ alkylsulfonyl group. Specifically, methylsulfonylamino, ethylsulfonylamino, propylsulfonylamino, isopropylsulfonylamino, cyclopropylsulfonylamino, cyclopropylmethylsulfonylamino, 2-methylcyclopropylsulfonylamino, and the like are mentioned.

The "arylcarbonylamino" means an amino group, a hydrogen atom of which is substituted with the "arylcarbonyl". Specifically, $C_{6-14}$ arylcarbonylamino such as benzamide and naphthamide is mentioned.

The "heterocyclic carbonylamino" means an amino group, a hydrogen atom of which is substituted with the "heterocyclic carbonyl". Specifically, pyrrolecarboxamide, furancarboxamide, thiophenecarboxamide, imidazolecarboxamide, pyrazolecarboxamide, pyridinecarboxamide, indolecarboxamide, quinolinecarboxamide, piperidinecarboxamide, and the like are mentioned.

With regard to "$R^b$ and $R^c$ optionally form, together with a nitrogen atom to which they are bonded, a 3- to 8-membered cyclic group", the 3- to 8-membered cyclic group specifically means, for example, a monovalent cyclic group obtained by removing a hydrogen atom which is bonded to a nitrogen atom from a ring that has a nitrogen atom in addition to carbon atoms in a 3- to 8-membered saturated or unsaturated non-aromatic heterocyclic group that is one of the "non-aromatic heterocyclic groups". For example, aziridinyl, azetidinyl, pyrrolidinyl, pyrazolinyl, pyrazolidinyl, piperidinyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and the like are mentioned.

As for $R^b$ and $R^c$, with regard to "where the nitrogen atom is substituted with a $C_{1-6}$ alkyl which is optionally substituted with 1 to 5 substituent(s) RI", examples of the cyclic group include 4-methylpiperazin-1-yl, 4-ethylpiperazin-1-yl, 4-propylpiperazin-1-yl, 4-trifluoromethylpiperazin-1-yl, and the like.

As for $R^b$ and $R^c$, with regard to "where in the cyclic group, one carbon atom is substituted with an oxygen atom or a sulfur atom, or a carbonyl group", examples of the cyclic group include oxazolinyl, isoxazolinyl, oxazolidinyl, isoxazolidinyl, thiazolinyl, isothiazolinyl, thiazolidinyl, isothiazolidinyl, morpholinyl, thiomorpholinyl, 2-oxopyrrolidinyl, and the like.

The "substituent RI" is a group arbitrarily selected from a halogen atom, —OH, cyano, a $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocyclic(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$, and R$^a$, R$^d$, R$^e$, R$^{b1}$, and R$^{c1}$ are the same as defined as R$^a$, R$^d$, R$^e$, R$^{b1}$, and R$^{c1}$ above), or non-aromatic heterocyclic oxy.

The "substituent RII" is a group arbitrarily selected from the same groups as in the case of the "substituent RI", or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy, or 1 to 5 group(s): —NR$^{b1}$R$^{c1}$ (each of R$^{b1}$ and R$^{c1}$ is the same as defined as R$^{b1}$ and R$^{c1}$ above)).

The "$C_{1-6}$ alkyl group which is optionally substituted with 1 to 5 substituent(s) RI" is a "$C_{1-6}$ alkyl group which is optionally substituted with 1 to 5 group(s) arbitrarily selected from a halogen atom, —OH, cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or non-aromatic heterocyclic oxy, and specific examples thereof include the followings.

For example, a "$C_{1-6}$ alkyl group which is optionally substituted with 1 to 5 halogen atom(s)" includes, in addition to the "$C_{1-6}$ alkyl", a group in which the alkyl group is optionally substituted with 1 to 5 halogen atom(s). Specifically, in addition to methyl, ethyl, propyl, isopropyl, butyl, isobutyl, sec-butyl, and tert-butyl, for example, trifluoromethyl, trifluoroethyl, tetrafluoroethyl, pentafluoroethyl, and the like are mentioned.

For example, a "$C_{1-6}$ alkyl group which is optionally substituted with 1 to 5 —OH" includes, in addition to the "$C_{1-6}$ alkyl", a group in which the alkyl group is optionally substituted with 1 to 5 hydroxy, and there are many regioisomers depending on a substitution position. Specifically, in addition to methyl, ethyl, propyl, isopropyl, butyl, isobutyl, sec-butyl, and tert-butyl, for example, hydroxymethyl, 2-hydroxyethyl, 1-hydroxyethyl, 3-hydroxy-1-propyl, 2-hydroxy-1-propyl, 1-hydroxy-1-propyl, 2,3-dihydroxy-1-propyl, 1-hydroxy-1-methyl-1-ethyl, 2-hydroxy-1-methyl-1-ethyl, 4-hydroxy-1-butyl, 3-hydroxy-1-butyl, 2-hydroxy-1-butyl, 1-hydroxy-1-butyl, 3-hydroxy-2-methylpropyl, 2-hydroxy-2-methylpropyl, 3-hydroxy-2-hydroxymethylpropyl, 2-hydroxy-1,1-dimethyl-1-ethyl, 1-hydroxy-2-methylpropyl, 5-hydroxy-1-pentyl, 4-hydroxy-1-pentyl, 3-hydroxy-1-pentyl, 2-hydroxy-1-pentyl, 1-hydroxy-1-pentyl, 4-hydroxy-3-methylbutyl, 4-hydroxy-2-methylbutyl, 4-hydroxy-1-methylbutyl, 3-hydroxy-3-methylbutyl, 3-hydroxy-2-methylbutyl, 3-hydroxy-1-methylbutyl, 2-hydroxy-3-methylbutyl, 2-hydroxy-2-methylbutyl, 2-hydroxy-1-methylbutyl, 3-hydroxy-2,2-dimethylpropyl, 3-hydroxy-1,1-dimethylpropyl, 3-hydroxy-2-hydroxymethyl-2-methylpropyl, 6-hydroxy-1-hexyl, 4-hydroxy-1,1-dimethyl-1-butyl, 4-hydroxy-3,3-dimethyl-1-butyl, 2-hydroxycyclopropyl, 4-hydroxycyclohexyl, and the like are mentioned.

For example, a "$C_{1-6}$ alkyl group which is optionally substituted with 1 to 5 $C_{1-6}$ alkoxy" includes, in addition to the "$C_{1-6}$ alkyl", a group in which the alkyl group is optionally substituted with 1 to 5 of the "$C_{1-6}$ alkoxy". Specifically, in addition to methyl, ethyl, propyl, isopropyl, butyl, isobutyl, sec-butyl, and tert-butyl, for example, methoxymethyl, methoxyethyl, methoxypropyl, and the like are mentioned.

For example, a "$C_{1-6}$ alkyl group which is optionally substituted with 1 to 5 halogenated $C_{1-6}$ alkoxy" includes, in addition to the "$C_{1-6}$ alkyl" and the "$C_{1-6}$ alkyl group which is optionally substituted with 1 to 5 $C_{1-6}$ alkoxy", a group in which the alkyl group is optionally substituted with 1 to 5 of the "$C_{1-6}$ alkoxy" which is optionally substituted with 1 to 5 halogen atom(s). Specifically, in addition to methyl, ethyl, propyl, isopropyl, butyl, isobutyl, sec-butyl, tert-butyl, methoxymethyl, methoxyethyl, and methoxypropyl, for example, trifluoromethoxymethyl, trifluoromethoxyethyl, trifluoromethoxypropyl, and the like are mentioned.

The alkyl group is optionally substituted with 2 to 5 groups arbitrarily selected from two or more kinds of a halogen atom, —OH, cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the non-aromatic heterocyclic is optionally substituted with —OH or a $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$) or non-aromatic heterocyclic oxy. For example, a $C_{1-6}$ alkyl group which is substituted with single —OH and single $C_{1-6}$ alkoxy, such as 2-hydroxy-3-methoxypropyl and 3-hydroxy-2-methoxypropyl, and the like are mentioned.

Similarly, the "$C_{2-6}$ alkenyl group which is optionally substituted with 1 to 5 substituent(s) RI" includes, in addition to the "$C_{2-6}$ alkenyl", a group in which the alkenyl group is optionally substituted with 1 to 5 halogen atom(s), 1 to 5 —OH, 1 to 5 cyano, 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$ group(s), 1 to 5 group(s): —CONR$^d$R$^e$, or 1 to 5 group(s): —NR$^{b1}$R$^{c1}$) or 1 to 5 non-aromatic heterocyclic oxy. Specifically, in addition to vinyl, allyl, isopropenyl, 2-methylallyl, butenyl, pentenyl, and hexenyl, for example, trifluorovinyl, 2-hydroxyvinyl, 2-methoxyvinyl, 2-trifluoromethoxyvinyl, and the like are mentioned.

The "$C_{2-6}$ alkynyl group which is optionally substituted with 1 to 5 substituent(s) RI" includes, in addition to the "$C_{2-6}$ alkynyl", a group in which the alkynyl group is optionally substituted with 1 to 5 halogen atom(s), 1 to 5 —OH, 1 to 5 cyano, 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5-group(s): SO$_2$NR$^d$R$^e$, 1 to 5 group(s): —CONR$^d$R$^e$, or 1 to 5 group(s): —NR$^{b1}$R$^{c1}$), or 1 to 5 non-aromatic heterocyclic oxy. Specifically, in addition to ethynyl, 1-propynyl, 2-propynyl, butynyl, pentynyl, and hexynyl, for example, fluoroethynyl, 2-hydroxyethynyl, 2-methoxyethynyl, 2-trifluoromethoxyethynyl, and the like are mentioned.

The "$C_{1-6}$ alkoxy group which is optionally substituted with 1 to 5 substituent(s) RI" includes, in addition to the "$C_{1-6}$ alkoxy", a group in which the alkoxy group is optionally substituted with 1 to 5 halogen atom(s), 1 to 5 —OH, 1 to 5 cyano, 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 non-aromatic heterocyclic oxy. Specifically, in addition to methoxy, ethoxy, propoxy, isopropoxy, butoxy, isobutoxy, sec-butoxy, and tert-butoxy, for example, trifluoromethoxy, hydroxymethoxy, 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2 methylpropoxy, 2-methoxyethoxy, 2-trifluoromethoxyethoxy, 2-methoxy-3-hydroxypropoxy, 2-hydroxy-3-methoxypropoxy, and the like are mentioned.

The "aryl group which is optionally substituted with 1 to 5 substituent(s) RII" is a group in which any hydrogen atom in the "aryl group" is optionally substituted with 1 to 5 substituent(s) RII. That is to say, the "aryl group which is optionally substituted with 1 to 5 substituent(s) RII" includes, in addition to the "aryl group", an "aryl group which is substituted with 1 to 5 group(s) arbitrarily selected from a halogen atom, —OH, cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), non-aromatic heterocyclic oxy or $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)".

Specifically, in addition to the "aryl group", for example, an "aryl group which is substituted with 1 to 5 halogen atom(s)", an "aryl group which is substituted with 1 to 5 group(s) arbitrarily selected from the "$C_{1-6}$ alkoxy" (the $C_{1-6}$ alkoxy is optionally substituted with a halogen atom, —OH, a $C_{1-6}$ alkoxy, non-aromatic heterocycle (the heterocyclic is optionally substituted with —OH or $C_{1-6}$ alkyl), a group: —S(O)$_i$R$^a$ (i is an integer of 0 to 2), a group: —SO$_2$NR$^d$R$^e$, a group: —CONR$^d$R$^e$, or a group: —NR$^{b1}$R$^{c1}$)", or non-aromatic heterocyclic oxy", and an "aryl group which is substituted with 1 to 5 group(s) arbitrarily selected from the "$C_{1-6}$ alkyl" (the $C_{1-6}$ alkyl is optionally substituted with a halogen atom, —OH, $C_{1-6}$ alkoxy, or a group: —NR$^{b1}$R$^{c1}$)", and the like are mentioned.

The aryl group is optionally substituted with 2 to 5 groups arbitrarily selected from two or more kinds of a halogen atom, —OH, cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), non-aromatic heterocyclic oxy or $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$). Specifically, for example, an "aryl group which is optionally substituted with 1 or 2 of the "$C_{1-6}$ alkyl" and 1 or 2 of the "$C_{1-6}$ alkoxy" (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$)" and the like are mentioned.

Specific examples of the "aryl group which is optionally substituted with 1 to 5 substituent(s) RII" include, in addition to phenyl, naphthyl, indanyl, and tetrahydronaphthyl, for example, (2-, 3-, or 4-)fluorophenyl, (2-, 3-, or 4-)chlorophenyl, (2-, 3-, or 4-)hydroxyphenyl, (2-, 3-, or 4-)methoxyphenyl, (2-, 3-, or 4-)trifluoromethoxyphenyl, (2-, 3-, or 4-)methylphenyl, (2-, 3-, or 4-)trifluoromethylphenyl, 3,5-dimethoxyphenyl, 2,6-dimethylphenyl, 3,5-ditrifluoromethoxyphenyl, 4-(2-hydroxyethoxy)-2,6-dimethylphenyl, 4-(3-hydroxypropoxy)-2,6-dimethylphenyl, 4-(2,3-dihydroxypropoxy)-2,6-dimethylphenyl, 4-(3-hydroxybutoxy)-2,6-dimethylphenyl, 4-(3-hydroxy-2-hydroxymethylpropoxy)-2,6-dimethylphenyl, 4-(3-hydroxy-2-hydroxymethyl-2-methylpropoxy)-2,6-dimethylphenyl, 4-(3-hydroxybutoxy)-2,6-dimethylphenyl, 4-(3-hydroxy-3-methylbutoxy)-2,6-dimethylphenyl, 4-(3-hydroxy-n-propoxy)-2,5-dimethylphenyl, 4-(3-hydroxy-3-methylbutoxy)-2,5-dimethylphenyl, 4-(3-hydroxy-3-methylbutoxy)-2,3-dimethylphenyl, 4-(3-hydroxy-3-methylbutoxy)-2-methylphenyl, 3-(3-hydroxy-3-methylbutoxy)-2-methylphenyl, and the like.

The "heterocyclic group which is optionally substituted with 1 to 5 substituent(s) RII" is a group in which any hydrogen atom in the "heterocyclic group" is optionally substituted with 1 to 5 substituent(s) RII. Namely, the "heterocyclic group which is optionally substituted with 1 to 5 substituent(s) RII" is, in addition to the unsubstituted "heteroaryl group" and the "non-aromatic heterocyclic group" both exemplified above as a "heterocyclic group" (these rings are each a monovalent group obtained by removing any hydrogen atom from a ring having a monocycle or a fused ring that is a 3- to 14-membered ring, or preferably, a 3- to 12-membered ring, containing, in addition to carbon atoms, at least one hetero atom (preferably 1 to 4 atom(s)) arbitrarily selected from N, O, and S), a "heterocyclic group which is substituted with 1 to 5 group(s) arbitrarily selected from a halogen atom, —OH, a cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), non-aromatic heterocyclicoxy or $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)".

Specific examples of the "heterocyclic group which is optionally substituted with 1 to 5 substituent(s) RII" include, in addition to the "heterocyclic group", a "heterocyclic group substituted with 1 to 5 halogen atom(s)", a "heterocyclic group substituted with 1 to 5 group(s) arbitrarily selected from "$C_{1-6}$ alkoxy" (the $C_{1-6}$ alkoxy is optionally substituted with a halogen atom, —OH, $C_{1-6}$ alkoxy, non-aromatic heterocycle(s) (the heterocyclic is optionally substituted with —OH or $C_{1-6}$ alkyl), a group: —S(O)$_i$R$^a$ (i is an integer of 0 to 2), a group: —SO$_2$NR$^d$R$^e$, a group: —CONR$^d$R$^e$, or a group: —NR$^{b1}$R$^{c1}$)", and a "heterocyclic group substituted with 1 to 5 group(s) arbitrarily selected from "$C_{1-6}$ alkyl" (the $C_{1-6}$ alkyl is optionally substituted with a halogen atom, —OH, $C_{1-6}$ alkoxy, or a group: —NR$^{b1}$R$^{c1}$)". More specific examples thereof include a "heteroaryl group substituted with 1 to 5 group(s) arbitrarily selected from "$C_{1-6}$ alkoxy" (the $C_{1-6}$ alkoxy is optionally substituted with a halogen atom, —OH, a $C_{1-6}$ alkoxy, non-aromatic heterocycle (the heterocyclic is optionally substituted with $C_{1-6}$ alkyl), a —S(O)$_i$R$^a$ (i is an integer of 0 to 2) group, a —SO$_2$NR$^d$R$^e$ group, a —CONR$^d$R$^e$ group, or a group: —NR$^{b1}$R$^{c1}$)".

Furthermore, the heterocyclic group is optionally substituted with 2 to 5 groups arbitrarily selected from 2 or more kinds of a halogen atom, —OH, cyano, $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), non-aromatic heterocyclic oxy, or $C_{1-6}$ alkyl (the $C_{1-6}$ alkyl is optionally substituted with 1 to 5 halogen atom(s), 1 to 5 —OH, 1 to 5 $C_{1-6}$ alkoxy, or group(s): 1 to 5 —NR$^{b1}$R$^{c1}$). Specific examples thereof include a "heterocyclic group optionally substituted with 1 or 2 "$C_{1-6}$ alkyl" and 1 or 2 "$C_{1-6}$ alkoxy" (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$)".

The "heteroaryl group" in the "heterocyclic group which is optionally substituted with 1 to 5 substituent(s) RII" may be monocyclic or ring-fused. The monocyclic heteroaryl group preferably has a 5- to 7-membered ring, and examples thereof include those groups described in the definition of the "heteroaryl group", such as pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, and 1,4-oxazepinyl. The ring-fused heteroaryl group preferably has an 8- to 12-membered ring, and examples thereof include a monovalent group obtained by removing any hydrogen atom from a fused ring formed by fusing the 5- to 7-membered heterocyclic ring and a monocyclic aryl group (such as a benzene ring) or a monocyclic heteroaryl group. The hydrogen atom is optionally removed from any of the fused rings. Specific examples include those groups described in the definition of the "heteroaryl group", such as indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, and 1,2,4-triazolo[1,5-a]pyrimidinyl. Specific examples thereof also include a ring-fused heteroaryl group which is partly hydrogenated, such as indolinyl, dihydrobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl. The ring-fused heteroaryl group which is partly hydrogenated preferably has an 8- to 12-membered ring, namely a monovalent group obtained by removing any hydrogen atom from a fused ring which is partly hydrogenated and formed by fusing the 5- to 7-membered heterocyclic ring and a monocyclic aryl group (such as a benzene ring) or a monocyclic heteroaryl group. Any of the hydrogen atom in the aryl group or in the heterocyclic moiety and of the hydrogen atom in the hydrogenated moiety is optionally removed. In the case of tetrahydroquinolyl, examples of the partially hydrogenated ring-fused heteroaryl group include 5,6,7,8-tetrahydroquinolyl and 1,2,3,4-tetrahydroquinolyl. Depending on the position in these groups from which any hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" in the "heterocyclic group which is optionally substituted with 1 to 5 substituent(s) RII" include a 3- to 8-membered saturated or unsaturated non-aromatic heterocyclic group. Examples thereof include aziridinyl, azetidinyl, oxiranyl, oxetanyl, thietanyl, pyrrolidinyl, tetrahydrofuryl, thiolanyl, pyrazolinyl, pyrazolidinyl, piperidinyl, tetrahydropyranyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, oxepanyl, and the like. The "non-aromatic heterocyclic group" means a monovalent group obtained by removing any hydrogen atom from the ring.

In addition to pyrrolyl, furyl, pyrazolyl, isoxazolyl, pyridyl, indolyl, quinolyl, 1,4-benzodioxanyl, piperidinyl, and the like, specific examples of the "heterocyclic group which is optionally substituted with 1 to 5 substituent(s) RII" include, 2-pyrrolyl, 3-pyrrolyl, 2-furyl, 3-furyl, 1-pyrazolyl, 3-pyrazolyl, 4-pyrazolyl, 5-pyrazolyl, 3-isoxazolyl, 4-isoxazolyl, 5-isoxazolyl, 2-pyridyl, 3-pyridyl, 4-pyridyl, 1-indolyl, 2-indolyl, 3-indolyl, 4-indolyl, 5-indolyl, 6-indolyl, 7-indolyl, 2-quinolyl, 3-quinolyl, 4-quinolyl, 5-quinolyl, 6-quinolyl, 7-quinolyl, 8-quinolyl, 1,4-benzodioxazine-2-yl, 1,4-benzodioxazine-3-yl, 1,4-benzodioxazine-5-yl, 1,4-benzodioxazine-6-yl, piperidine-1-yl, piperidine-2-yl, piperidine-3-yl, piperidine-4-yl, and the like. Any hydrogen atom of the groups is optionally substituted with 1 to 5 substituent(s) RII. Specific examples thereof include 1-methylpyrazol-4-yl, 3,5-dimethylisoxazol-4-yl, (2-, 4-, 5-, or 6-)chloropyridine-3-yl, (2-, 4-, 5-, or 6-)hydroxypyridine-3-yl, (2-, 4-, 5-, or 6-)methoxypyridine-3-yl, (2-, 4-, 5-, or 6-)methylpyridine-3-yl, 6-(2-hydroxyethoxy)-2,4-dimethylpyridine-3-yl, 6-(3-hydroxypropoxy)-2,4-dimethylpyridine-3-yl, 6-(2,3-dihydroxypropoxy)-2,4-dimethylpyridine-3-yl, 6-(3-hydroxybutoxy)-2,4-dimethylpyridine-3-yl, 6-(3-hydroxy-2-hydroxymethylpropoxy)-2,4-dimethylpyridine-3-yl, 6-(3-hydroxy-2-hydroxymethyl-2-methylpropoxy)-2,4-dimethylpyridine-3-yl, 6-(3-hydroxybutoxy)-2,4-dimethylpyridine-3-yl, 6-(3-hydroxy-3-methylbutoxy)-2,4-dimethylpyridine-3-yl, 6-(1-piperidinyl)pyridine-3-yl, 2-(2-hydroxyethoxy)-4,6-dimethylpyrimidine-5-yl, 2-(3-hydroxy-3-methylbutoxy)-4,6-dimethylpyrimidine-5-yl, (2-, 4-, 5-, 6-, 7- or 8-)methylquinolone-3-yl, 6-(3-hydroxy-3-methylbutoxy)-2-methylpyridine-3-yl, 6-(3-hydroxy-3-methylbutoxy)-4-methylpyridine-3-yl, 6-(3-hydroxy-3-methylbutoxy)-2-methoxypyridine-3-yl, and the like.

The "aralkyl group which is optionally substituted with 1 to 5 substituent(s) RII" is the "aralkyl group" includes, in addition the unsubstituted groups exemplified as the "aralkyl group": the unsubstituted aralkyl group which is substituted with 1 to 5 halogen atom(s), 1 to 5 —OH, 1 to 5 cyano group(s), 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)". The substituent(s) of the aralkyl group may be substituted with either the aryl moiety or the alkyl moiety. Specific examples thereof include, in addition to unsubstituted benzyl, phenethyl, 1-naphthylmethyl, or 2-naphthylmethyl: (2-, 3-, or 4-)fluorobenzyl, (2-, 3-, or 4-)chlorobenzyl, (2-, 3-, or 4-)hydroxybenzyl, (2-, 3-, or 4-)methoxybenzyl, (2-, 3-, or 4-)trifluoromethoxybenzyl, (2-, 3-, or 4-)methylbenzyl, (2-, 3-, or 4-)trifluoromethylbenzyl, 2,6-dimethylbenzyl, and 3,5-ditrifluoromethylbenzyl.

The "heteroarylalkyl group which is optionally substituted with 1 to 5 substituent(s) RII" is the "heteroarylalkyl group" includes, in addition to the unsubstituted groups exemplified as the "heteroarylalkyl group": the unsubstituted heteroarylalkyl group which is substituted with 1 to 5 halogen atom(s), 1 to 5 —OH, 1 to 5 cyano groups, 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)". The substituent(s) of the heteroarylalkyl group may be substituted with either the heteroaryl moiety or the alkyl moiety. Specific examples thereof include, in addition to unsubstituted pyrrolylmethyl, furylmethyl, pyridylmethyl, or quinolylmethyl: (2-, 4-, 5-, or 6-)chloropyridine-3-ylmethyl, (2-, 4-, 5-, or 6-)hydroxypyridine-3-ylmethyl, (2-, 4-, 5-, or 6-)methoxypyridine-3-ylmethyl, (2-, 4-, 5-, or 6-)methylpyridine-3-ylmethyl, and 6-(3-hydroxy-3-methylbutoxy)-2,4-dimethylpyridine-3-ylmethyl.

The "aryloxy group which is optionally substituted with 1 to 5 substituent(s) RII" is the "aryloxy group" includes, in addition to the unsubstituted groups exemplified as the "aryloxy group": the aryloxy group which is substituted with 1 to 5 halogen atom(s), 1 to 5 —OH, 1 to 5 cyano group(s), 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)" Specific examples thereof include, in addition to unsubstituted phenoxy, 1-naphthyloxy, 2-naphthyloxy, 1-indanyloxy, or 2-indanyloxy: (2-, 3-, or 4-)fluorophenoxy, (2-, 3-, or 4-)chlorophenoxy, (2-, 3-, or 4-)hydroxyphenoxy, (2-, 3-, or 4-)methoxyphenoxy, (2-, 3-, or 4-)trifluoromethoxyphenoxy, (2-, 3-, or 4-)methylphenoxy, (2-, 3-, or 4-)trifluoromethylphenoxy, 2,6-dimethylphenoxy, and 4-(3-hydroxy-3-methylbutoxy)-phenoxy.

The "heteroaryloxy group which is optionally substituted with 1 to 5 substituent(s) RII" is the "heteroaryloxy group" includes, in addition to the unsubstituted groups exemplified as the "heteroaryloxy group": the heteroaryloxy group which is substituted with 1 to 5 halogen atom(s), 1 to 5 —OH, 1 to 5 cyano group(s), 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)". Specific examples thereof include, in addition to pyrrolyloxy, furyloxy, pyridyloxy, or quinolyloxy: (2-, 4-, 5-, or 6-)chloropyridine-3-yloxy, (2-, 4-, 5-, or 6-)hydroxypyridine-3-yloxy, (2-, 4-, 5-, or 6-)methoxypyridine-3-yloxy, (2-, 4-, 5-, or 6-)methylpyridine-3-yloxy, 6-(3-hydroxy-3-methylbutoxy)-2,4-dimethylpyridine-3-yloxy, and 6-(3-hydroxy-3-methylbutoxy)-pyridine-3-yloxy.

The "aralkyloxy group which is optionally substituted with 1 to 5 substituent(s) RII" is the "aralkyloxy group" includes, in addition to the unsubstituted groups exemplified as the "aralkyloxy group": the aralkyloxy group which is substituted with 1 to 5 halogen atom(s), 1 to 5 —OH, 1 to 5 cyano group(s), 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)". The substituent(s) of the aralkyloxy group may be substituted with the aryl moiety or the alkyl moiety. Specific examples thereof include, in addition to benzyloxy, phenethyloxy, 1-naphthylmethoxy, or 2-naphthylmethoxy: (2-, 3-, or 4-)fluorobenzyloxy, (2-, 3-, or 4-)chlorobenzyloxy, (2-, 3-, or 4-)hydroxybenzyloxy, (2-, 3-, or 4-)methoxybenzyloxy, (2-, 3-, or 4-)trifluoromethoxybenzyloxy, (2-, 3-, or 4-)methylbenzyloxy, (2-, 3-, or 4-)trifluoromethylbenzyloxy, (2-, 3-, or 4-)methoxyphenethyloxy, and 2,6-dimethylbenzyloxy.

The "heteroarylalkyloxy group which is optionally substituted with 1 to 5 substituent(s) RII" is the "heteroarylalkyloxy group" includes, in addition to the unsubstituted groups exemplified as the "heteroarylalkyloxy group": the heteroarylalkyloxy group which is substituted with 1 to 5 halogen atom(s), 1 to 5 —OH, 1 to 5 cyano group(s), 1 to 5 $C_{1-6}$ alkoxy (the $C_{1-6}$ alkoxy is optionally substituted with 1 to 5 halogen atom(s), 1 to 5 —OH, 1 to 5 $C_{1-6}$ alkoxy, 1 to 5 non-aromatic heterocycle(s) (the heterocyclic is optionally substituted with —OH or $C_{1-6}$ alkyl), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$), or 1 to 5 $C_{1-6}$ alkyl (the $C_{1-6}$ alkyl is optionally substituted with 1 to 5 halogen atom(s), 1 to 5 —OH, 1 to 5 $C_{1-6}$ alkoxy, or 1 to 5 group(s): —NR$^{b1}$R$^{c1}$)". The substituent(s) of the heteroarylalkyloxy group may be substituted with either the heteroaryl moiety or the alkyl moiety. Specific examples thereof include, in addition to pyrrolylmethoxy, furylmethoxy, pyridylmethoxy, or quinolylmethoxy: (2-, 4-, 5-, or 6-)chloropyridine-3-ylmethoxy, (2-, 4-, 5-, or 6-)hydroxypyridine-3-ylmethoxy, (2-, 4-, 5-, or 6-)methoxypyridine-3-ylmethoxy, (2-, 4-, 5-, or 6-)methylpyridine-3-ylmethoxy, and 6-(3-hydroxy-3-methylbutoxy)-2,4-dimethylpyridine-3-ylmethoxy.

The "substituents L" are a group arbitrarily selected from a halogen atom, —OH, a $C_{1-6}$ alkoxy group, a non-aromatic heterocyclic group (the heterocyclic group is optionally substituted with —OH or a $C_{1-6}$ alkyl group), a group: —S(O)$_i$R$^a$ (i is an integer of 0 to 2), a group: —CO$_2$R$^f$, a group: —SO$_2$NR$^d$R$^e$, a group: —CONR$^d$R$^e$, or a group: —NR$^b$R$^c$.

The "$C_{1-6}$ alkoxy group which is substituted with 1 to 5 substituent(s) L" is the "$C_{1-6}$ alkoxy group" in which any hydrogen atom is optionally substituted with 1 to 5 substituent(s) L. Specifically, the "$C_{1-6}$ alkoxy group which is substituted with 1 to 5 substituent(s) L" is the "$C_{1-6}$ alkoxy group" which is substituted with 1 to 5 group(s) arbitrarily selected from "a halogen atom, —OH, $C_{1-6}$ alkoxy, a non-aromatic heterocycle (the heterocyclic is optionally substituted with —OH or $C_{1-6}$ alkyl), a group: —S(O)$_i$R$^a$ (i is an integer of 0 to 2), a group: —CO$_2$R$^f$, a group: —SO$_2$NR$^d$R$^e$, a group: —CONR$^d$R$^e$, or a group: —NR$^b$R$^c$. The $C_{1-6}$ alkoxy group is optionally substituted with 2 to 5 groups arbitrarily selected from two or more kinds of a halogen atom, —OH, $C_{1-6}$ alkoxy, a non-aromatic heterocycle (the heterocyclic is optionally substituted with —OH or $C_{1-6}$ alkyl), a group: —S(O)$_i$R$^a$ (i is an integer of 0 to 2), a group: —CO$_2$R$^f$, a group: —SO$_2$NR$^d$R$^e$, a —CONR$^d$R$^e$, or a group: —NR$^b$R$^c$. Specific examples include, for example, "a $C_{1-6}$ alkoxy group which is arbitrarily substituted with 1 to 2 —OH and 1 to 2 of the "$C_{1-6}$ alkoxy", and the like.

More preferable examples of the "$C_{1-6}$ alkoxy group which is substituted with 1 to 5 substituent(s) L" include, for example, "a $C_{1-6}$ alkoxy group arbitrarily substituted with 1 to 5 —OH", "a $C_{1-6}$ alkoxy group substituted with 1 to 5 group(s) arbitrarily selected from the "$C_{1-6}$ alkoxy", "a $C_{1-6}$ alkoxy group substituted with 1 to 5 group(s) arbitrarily selected from the group: —S(O)$_i$R$^a$", "$C_{1-6}$ alkoxy group substituted with 1 to 5 group(s) arbitrarily selected from the group: —NR$^b$R$^c$", and the like. Specific Examples of the "$C_{1-6}$ alkoxy group which is substituted with 1 to 5 substituent(s) L" include, for example, hydroxymethoxy, 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2 methylpropoxy, 2-methoxyethoxy, 3-aminopropoxy, 3-(2-oxo-1-pyrrolidinyl)propoxy, 2-methoxy-3-hydroxypropoxy, 2-hydroxy-3-methoxypropoxy, 2-methylsulfonylethoxy, 3-methylsulfonyl-propoxy, 2-ethylsulfonyl-ethoxy, 3-ethylsulfonyl-propoxy, and the like.

The "$C_{2-6}$ alkenyloxy group which is substituted with 1 to 5 substituent(s) L" is a group in which any hydrogen atom in the "$C_{2-6}$ alkenyloxy group" is optionally substituted with 1 to 5 substituent(s) L. Specifically, the "$C_{2-6}$ alkenyloxy group which is substituted with 1 to 5 substituent(s) L" is a group the "$C_{2-6}$ alkenyloxy group" is substituted with 1 to 5 group(s) arbitrarily selected from "a halogen atom, —OH, $C_{1-6}$ alkoxy, a non-aromatic heterocycle (the heterocyclic is optionally substituted with —OH or $C_{1-6}$ alkyl), a group: —S(O)$_i$R$^a$ (i is an integer of 0 to 2), a group: —CO$_2$R$^f$, a group: —SO$_2$NR$^d$R$^e$, a group: —CONR$^d$R$^e$, or a group: —NR$^b$R$^c$". Specific examples of the "$C_{2-6}$ alkenyloxy group which is substituted with 1 to 5 substituent(s) L" include, for example, 2-hydroxyvinyloxy, 3-hydroxyallyloxy, 3-hydroxy-3-butenyloxy, 2,3-dihydroxyallyloxy, 3-hydroxy-2-hydroxymethylallyloxy, 2-methoxyvinyloxy, 3-aminoallyloxy, 3-(2-oxo-1-pyrrolidinyl)allyloxy, 2-methoxy-3-hydroxyallyloxy, 2-hydroxy-3-methoxyallyloxy, 2-methylsulfonyl-vinyloxy, 3-methylsulfonyl-allyloxy, 2-ethylsulfonyl-vinyloxy, 3-ethylsulfonyl-allyloxy, and the like.

The "$C_{2-6}$ alkynyloxy group which is substituted with 1 to 5 substituent(s) L" is a group in which any hydrogen atom in the "$C_{2-6}$ alkynyloxy group" is optionally substituted with 1 to 5 substituent(s) L. Specifically, the "$C_{2-6}$ alkynyloxy group which is substituted with 1 to 5 substituent(s) L" is a group in which the "$C_{2-6}$ alkynyloxy group" is substituted with 1 to 5 group(s) arbitrarily selected from "a halogen atom, —OH, $C_1$ alkoxy, a non-aromatic heterocycle (the heterocyclic group is optionally substituted with —OH or $C_{1-6}$ alkyl), a group: —S(O)$_i$R$^a$ (i is an integer of 0 to 2), a group: —CO$_2$R$^f$, a group: —SO$_2$NR$^d$R$^e$, a group: —CONR$^d$R$^e$, or a group: —NR$^b$R$^c$". Specific examples of the "$C_{2-6}$ alkynyloxy group which is substituted with 1 to 5 substituent(s) L" include, for example, 2-hydroxyethynyloxy, 3-hydroxy-1-propynyloxy, 3-hydroxy-2-propynyloxy, 3-(2-oxo-1-pyrrolidinyl)-1-propynyloxy, 2-methylsulfonyl-ethynyloxy, 3-methylsulfonyl-1-propynyloxy, 3-methylsulfonyl-2-propynyloxy, and the like.

In the compound of Formulas (I), (Ia), and (Ib), the 3-hydroxy-isoxazolyl group is a group that can be a 3(2H)-isoxazolonyl group by proton tautomerism, and the resultant tautomer is included in Formula (I), all tautomers thereof are included in the scope of the present invention. The abundance ratio of this structure can vary depending on whether the compound of Formulas (I), (Ia), and (Ib) is in the solid state or in the dissolved state in a liquid.

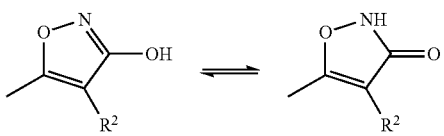

The description of any specific types of tautomers in any structural formulae of the present specification is not intended to limit the present invention, but is intended to represent the whole set of tautomers that are applicable.

Specifically, for example, a tautomer, namely, 5-(4-(1,2,3,4-tetrahydronaphthalene-1-yloxy)phenyl)-3(2H)-isoxazolone, of the compounds described as 5-(4-(1,2,3,4-tetrahydronaphthalene-1-yloxy)phenyl)isoxazol-3-ol among compounds of Example 1 is also categorized as a compound of Example 1.

The preferable substituents according to Aspect [1] are specifically described below.

[1-1] In the compound of Formula (I) according to Aspect [1], p is an integer of 0 to 4. Preferably, p is 0 or 1, and more preferably, 0.

[1-2] In the compound of Formula (I) according to Aspect [1], j is an integer of 0 to 3, while k is an integer of 0 to 2. Preferably, j is 0, 1, or 2, while k is 0. More preferably, j is 0 or 1, while k is 0.

[1-3] In the compound of Formula (I) according to Aspect [1], the ring B is a benzene ring, a pyridine ring, or a pyrimidine ring. The ring B is preferably a benzene ring or a pyridine ring. More preferably, the ring B is a benzene ring.

[1-4] In the compound of Formula (I) according to Aspect [1], X is —$CH_2$—, an oxygen atom, —$S(O)_i$— (i is an integer of 0 to 2) or —$NR^7$— ($R^7$ is the same as defined as $R^7$ above) (with a proviso that X is not —$CH_2$— when a ring A is Formula (A) mentioned above). X is preferably an oxygen atom, a sulfur atom, or —$NR^7$—.

[1-4-a] X is more preferably an oxygen atom or —NH—, and X is further preferably an oxygen atom.

[1-5] In the compound of Formula (I) according to Aspect [1], $R^1$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI (the above-mentioned substituent(s) RI are the same as or different from each other, and are the same as defined as RI above), —SH, a group: —$S(O)_iR^a$ (i is an integer of 0 to 2, and $R^a$ is the same as defined as $R^a$ above) or a group: —$NR^bR^c$ ($R^b$ and $R^c$ are the same as defined as $R^b$ and $R^c$ above).

[1-5-a] Preferable examples of $R^1$s include a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI (the above-mentioned substituent(s) RI are the same as or different from each other and are the same as defined as the substituent(s) RI above).

[1-5-b] More preferable examples of $R^1$s include a halogen atom, a cyano group, a $C_{1-6}$ alkyl group which is optionally substituted with 1 to 5 halogen atom(s). Specific examples of $R^1$s include a fluorine atom, a chlorine atom, a bromine atom, cyano, methyl, ethyl, propyl, isopropyl, butyl, isobutyl, sec-butyl, tert-butyl, trifluoromethyl, and the like.

[1-6] In the compound of Formula (I) according to Aspect [1], $R^2$ is preferably a hydrogen atom, a halogen atom, a cyano group, or a $C_{1-6}$ alkyl group which is optionally substituted with 1 to 5 substituent(s) RI (the RI(s) are the same as or different from each other and are the same as defined as the substituent(s) RI above).

[1-6-a] More preferable examples of $R^2$ include a hydrogen atom, a halogen atom, a cyano group, or a $C_{1-6}$ alkyl group which is optionally substituted with 1 to 5 halogen atom(s).

[1-6-b] Further preferable examples of $R^2$s include a hydrogen atom, a halogen atom, or a $C_{1-6}$ alkyl group. Specific examples of $R^2$ include a hydrogen atom, a fluorine atom, a chlorine atom, a bromine atom, methyl, isopropyl, and the like.

[1-7] In the compound of Formula (I) according to Aspect [1], preferably, $R^3$, $R^4$, $R^5$, $R^6$, and $R^7$ are independently a group arbitrarily selected from a hydrogen atom, a $C_{1-6}$ alkyl group, or a halogenated $C_{1-6}$ alkyl group.

[1-7-a] More preferably, $R^3$, $R^4$, $R^5$, $R^6$, and $R^7$ are a hydrogen atom.

[1-8] In the compound of Formula (I) according to Aspect [1], when the ring A is Formula (A), the ring A' is a benzene ring, a pyridine ring, or a pyrimidine ring. The ring A' is preferably a benzene ring or a pyridine ring. The ring A' is more preferably a pyridine ring.

[1-9] In the compound of Formula (I) according to Aspect [1], q is an integer of 0 to 4, q is preferably 0, 1, or 2, and more preferably 1 or 2.

[1-10] In the compound of Formula (I) according to Aspect [1], r is an integer of 0 to 4. r is preferably 0, 1, or 2, and more preferably 0 or 1.

[1-11] In the compound of Formula (I) according to Aspect [1], s is an integer of 1 to 2. s is preferably 1.

[1-12] In the compound of Formula (I) according to Aspect [1], v is a single bond or an oxygen atom.

[1-12-a] v is preferably a single bond.

[1-13] In the compound of Formula (I) according to Aspect [1], preferably, $R^8$s are independently a group arbitrarily selected from a $C_{1-6}$ alkoxy group which is substituted with 1 to 5 substituent(s) L, a $C_{2-6}$ alkenyloxy group which is substituted with 1 to 5 substituent(s) L, a $C_{2-6}$ alkynyloxy group which is substituted with 1 to 5 substituent(s) L, and a non-aromatic heterocyclic oxy group;

the substituents L are independently a group arbitrarily selected from a halogen atom, —OH, a $C_{1-6}$ alkoxy group, a non-aromatic heterocycle (the heterocyclic is optionally substituted with —OH or $C_{1-6}$ alkyl), a group: —$S(O)_iR^a$ (i is an integer of 0 to 2), a group: —$CO_2R^f$, a group: —$SO_2NR^dR^e$, a group: —$CONR^dR^e$, or a group: —$NR^bR^c$;

$R^a$ is a group arbitrarily selected from a $C_{1-6}$ alkyl group or a halogenated $C_{1-6}$ alkyl group;

$R^d$, $R^e$ and $R^f$ are independently a group arbitrarily selected from a hydrogen atom or a $C_{1-6}$ alkyl group; and $R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, or a $C_{2-6}$ alkynyl group, or $R^b$ and $R^c$ optionally form together with a nitrogen atom to which $R^b$ and $R^c$ are bonded, a 3- to 8-membered cyclic group, where in the cyclic group, one carbon atom is optionally substituted with an atom arbitrarily selected from an oxygen atom, or a sulfur atom, or with a carbonyl group.

[1-13-a] More preferable examples of $R^8$s include a $C_{1-6}$ alkoxy group which is substituted with 1 to 5 group(s) arbitrarily selected from —OH, a $C_{1-6}$ alkoxy group, a non-aromatic heterocycle (the heterocyclic is optionally substituted with $C_{1-6}$ alkyl), a —S(O)$_i$R$^a$ (i is an integer of 0 to 2) group and a —NR$^b$R$^c$ group, or a non-aromatic heterocyclic oxy group. R$^a$ is a group arbitrarily selected from a $C_{1-6}$ alkyl group or a halogenated $C_{1-6}$ alkyl group. R$^b$ and R$^c$ are independently a group arbitrarily selected from a hydrogen atom, a $C_{1-6}$ alkyl group, or a halogenated $C_{1-6}$ alkyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom or a sulfur atom, or with a carbonyl group.

[1-13-b] Further preferable examples of $R^8$s include a $C_{1-6}$ alkoxy group which is substituted with 1 to 5 group(s) arbitrarily selected from —OH, a $C_{1-6}$ alkoxy group, a —S(O)$_i$R$^a$ (i is an integer of 0 to 2) group, or a —NR$^b$R$^c$ group. R$^a$ is a $C_{1-6}$ alkyl group. R$^b$ and R$^c$ are independently a group arbitrarily selected from a hydrogen atom, or a $C_{1-6}$ alkyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with a carbonyl group.

[1-13-c] Particularly preferable examples of $R^8$s include a $C_{1-6}$ alkoxy group substituted with 1 to 5 —OH, 1 to 5 methylsulfonyl, 1 to 5 ethylsulfonyl, 1 to 5 —NH$_2$, or 1 to 5 2-oxo-1-pyrrolidinyl. The number of groups substituted with —OH, methylsulfonyl, ethylsulfonyl, —NH$_2$, or 2-oxo-1-pyrrolidinyl is preferably 1 or 2.

Specific examples of $R^8$s include 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2-methylpropoxy, 2-methylsulfonyl-ethoxy, 3-methylsulfonyl-propoxy, 2-ethylsulfonyl-ethoxy, 3-ethylsulfonyl-propoxy, 3-aminopropoxy, 3-(2-oxo-1-pyrrolidinyl)propoxy, and the like.

[1-14] In the compound of Formula (I) according to Aspect [1], preferably, $R^9$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI; and
the substituents RI are the same as or different from each other and are each a group arbitrarily selected from a halogen atom, —OH, a cyano group, a $C_{1-6}$ alkoxy group, or a halogenated $C_{1-6}$ alkoxy group.

[1-14-a] More preferable examples of $R^9$s include a halogen atom or a $C_{1-6}$ alkyl group (the $C_{1-6}$ alkyl groups are the same as or different from each other and optionally substituted with 1 to 5 group(s) arbitrarily selected from a halogen atom, —OH, a cyano group, a $C_{1-6}$ alkoxy group, or a halogenated $C_{1-6}$ alkoxy group).

[1-14-b] Further preferable examples of $R^9$s include a halogen atom and a $C_{1-6}$ alkyl group which optionally substituted with 1 to 5 halogen atom(s). Specific examples of $R^9$s include a fluorine atom, a chlorine atom, a bromine atom, methyl, ethyl, propyl, isopropyl, butyl, isobutyl, sec-butyl, tert-butyl, trifluoromethyl, and the like. Particularly preferable examples of $R^9$s include methyl.

[1-15] In the compound of Formula (I) according to Aspect [1], preferably, $R^{10}$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI; and
the substituents RI are the same as or different from each other and are each a group arbitrarily selected from a halogen atom, —OH, a cyano group, a $C_{1-6}$ alkoxy group, or a halogenated $C_{1-6}$ alkoxy group.

[1-15-a] More preferable examples of $R^{10}$s include a halogen atom and a $C_{1-6}$ alkyl group (the $C_{1-6}$ alkyl groups are the same as or different from each other and optionally substituted with 1 to 5 group(s) arbitrarily selected from a halogen atom, —OH, a cyano group, a $C_{1-6}$ alkoxy group, or a halogenated $C_{1-6}$ alkoxy group).

[1-15-b] Further preferable examples of $R^{10}$s include a halogen atom and a $C_{1-6}$ alkyl group which optionally substituted with 1 to 5 halogen atom(s). Specific examples of $R^{10}$s include a fluorine atom, a chlorine atom, a bromine atom, methyl, ethyl, propyl, isopropyl, butyl, isobutyl, sec-butyl, tert-butyl, trifluoromethyl, and the like. Particularly preferable examples of $R^{10}$s include methyl.

[1-16] In a combination of the ring A', V, and the substitution position, in Formula (1), the benzene ring in which the ring A'-V- is bonded is Partial Structural Formula (A):

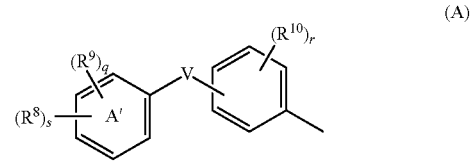

(where q, r, s, the ring A', V, R$^8$, R$^9$, and R$^{10}$ are the same as defined in the above Formula (I), and preferable aspects of q, r, s, the ring A', V, R$^8$, R$^9$, and R$^{10}$ are the same as the preferable aspects described in any of Aspects [1] to [1-15]). In the Formula (I), the binding positions of the ring A'-V- and R$^{10}$s are any positions at which they can be optionally bonded in the benzene ring, and the binding positions of R$^8$s and R$^9$s are any positions at which they can be optionally bonded in the ring A'.

Preferable examples of Formula (A) include Formula (A1) or Formula (A2):

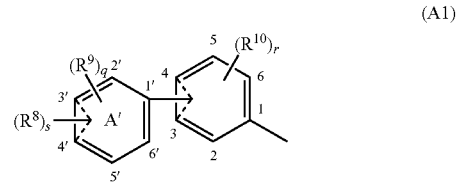

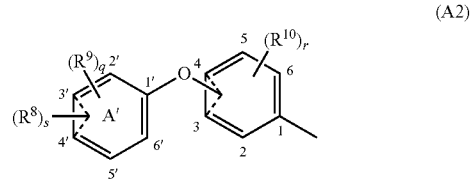

(where q, r, s, the ring A', R$^8$s, R$^9$s, and R$^{10}$s are the same as defined in the above Formula (I), preferable aspects of q, r, s, the ring A', R$^8$s, R$^9$s, and R$^{10}$s are the same as the preferable aspects described in any of Aspects [1] to [1-15], and the broken lines and the figures 3 and 4 or the figures 3' and 4' indicate where the ring A', the ring A'-O—, or $R^8$s are bonded).

In Formula (A1), when the position of the single bond of the phenyl group (the binding position of the linker moiety containing X) is determined as the first position, the binding position of the ring A' is preferably at the third or fourth position, and more preferably at the third position. In Formula (A1), when the binding position of the ring A' with the phenyl group is determined as the first' position, the binding position of $R^8$s is preferably at the third' or fourth' position.

In Formula (A2), when the position of the single bond of the phenyl group (the binding position of the linker moiety containing X) is determined as the first position, the binding position of the ring A'-O— is preferably at the third or fourth position, and more preferably at the third position. In Formula (A2), when the binding position of the ring A' with the phenyl group —O— is determined as the first' position, the binding position of $R^8$s is preferably at the third' or fourth' position.

[1-16-a] Specifically, Formula (A) is preferably the above Partial Structural Formula (A1).

[1-16-b] Specifically, Formula (A) is preferably the above Partial Structural Formula (A1), where s is 1.

[1-16-c] More preferably, Formula (A) is Formula (A1a) or Formula (A1b) when s is 1 in Formula (A1):

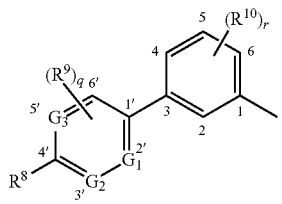

(A1a)

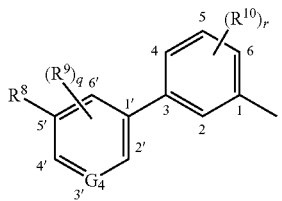

(A1b)

(where q, r, $R^8$, $R^9$ and $R^{10}$ are the same as defined in the above Formula (I); preferable aspects of q, r, $R^8$, $R^9$ and $R^{10}$ are the same as the preferable aspects described in any of Aspects [1] to [1-15]; $G_1$, $G_2$, $G_3$, and $G_4$ is a =CH— group, a =$CR^9$— group or a nitrogen atom (with the proviso that when $G_1$ is a nitrogen atom, $G_2$ and $G_3$ are each a =CH— group or a =$CR^9$— group)).

In Formula (A1a) or Formula (A1b), when the position of the single bond of the phenyl group (the binding position of the linker moiety containing X) is determined as the first position, $R^{10}$ can be bonded at the second, fourth, fifth, or sixth position. The binding position of $R^9$ is any positions in the ring including $G_1$ or $G_4$.

Specifically, Formula (A) is further preferably Formula (A1a).

[1-16-d] In Formula (A1a), preferably, $G_1$ is a =CH— group or a =$CR^9$— group, $G_2$ and $G_3$ are independently a =CH— group, a =$CR^9$— group, or a nitrogen atom. More preferably, $G_1$ and $G_3$ are independently a =CH— group or a =$CR^9$— group, $G_2$ is a =CH— group, a =$CR^9$— group, or a nitrogen atom.

[1-16-e] In Formula (A1a) or Formula (A1b), at least one of the binding positions of $R^{10}$(s) is preferably the second position, and when r is 1, the binding position of $R^{10}$(s) is preferably the second position.

[1-16-f] In Formula (A1a), when the binding position of the ring containing $G_1$ with the third position of the phenyl group is determined as the first' position, when q is 1, the binding position of $R^9$ is preferably the second' position (except for the case in which $G_1$ is a nitrogen atom) or the sixth' position. When q is 2, the binding positions of $R^9$s are preferably the second' and sixth' positions, the second' and fifth' positions, or the fifth' and sixth' positions (except for the case in which the binding position is a nitrogen atom), and more preferably, the second' and sixth' positions.

[1-16-g] In Formula (A1a), r is preferably 0 or 1. When r is 1, the binding position of $R^{10}$ is preferably the second position. When $G_1$ is a =CH— group or a =$CR^9$-group, $G_2$ is a =CH— group or a nitrogen atom, $G_3$ is a =CH— group or a =$CR^9$— group, and q is 1 or 2, the binding position(s) of $R^9$(s) is more preferably the second' or the sixth' positions, second' and the sixth' positions, second' and fifth' positions, or fifth' and sixth' positions.

[1-17] The isoxazolyl group and the substituent of $R^1$ in the ring B in Formula (I) can be bonded at the second, third, fourth, fifth, or sixth position when the binding position of the linker moiety containing X is determined as the first position in Partial Structural Formula (B):

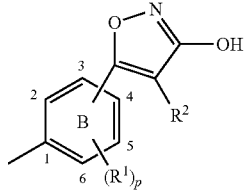

(B)

(where p, the ring B, $R^1$, and $R^2$ are the same as defined in the above Formula (I), and preferable aspects of p, the ring B, $R^1$, and $R^2$ are the same as the preferable aspects described in any of Aspects [1] to [1-15]).

Preferable examples of Formula (B) include Formula (B1) or Formula (B2):

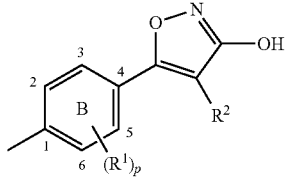

(B1)

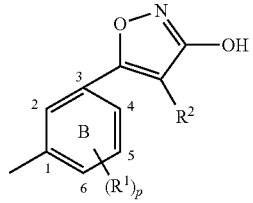

(B2)

(where p, the ring B, $R^1$, and $R^2$ are the same as defined in the above Formula (I), and preferable aspects of p, the ring B, $R^1$, and $R^2$ are the same as the preferable aspects described in any of Aspects [1] to [1-15]). When the binding position of the linker moiety containing X is determined as the first position, $R^1$ can be bonded at the second, third, fifth, or sixth position in Formula (B1), and $R^1$ can be bonded at the second, fourth, fifth, or sixth position in Formula (B2).

[1-17-a] Formula (B) is preferably Formula (B1).

[1-17-1] More preferable examples of Formula (B) include Formula (B1a) and Formula (B1b):

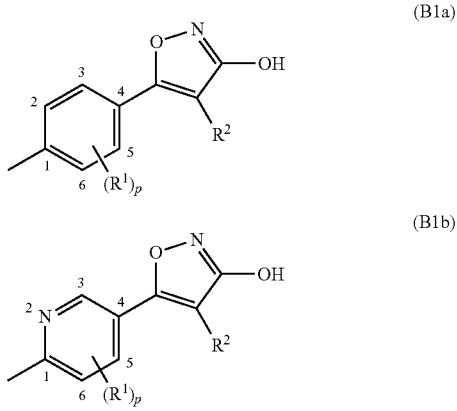

(where p, $R^1$, and $R^2$ are the same as defined in the above Formula (I), and preferable aspects of p, $R^1$, and $R^2$ are the same as the preferable aspects described in any of Aspects [1] to [1-15]).

In Formula (B1a) and Formula (B1b), preferable examples of $R^1$ include a halogen atom or a $C_{1-4}$ alkyl group optionally substituted with 1 to 5 halogen atom(s). Specifically, $R^1$ is preferably a fluorine atom, a chlorine atom, a bromine atom, methyl, ethyl, propyl, isopropyl, butyl, isobutyl, sec-butyl, tert-butyl, or trifluoromethyl. p is preferably 0 or 1. p is more preferably 0.

In Formula (B1a) and Formula (B1b), $R^2$ is preferably a hydrogen atom or a halogen atom, specifically, a hydrogen atom, a fluorine atom, a chlorine atom, or a bromine atom, and more preferably a hydrogen atom.

[1-17-c] Further preferable examples of Formula (B) include Formula (B1a).

[1-18] In a combination of j, k, X, $R^3$, $R^4$, $R^5$, and $R^6$, in Formula (I), the linker moiety containing X bonded to the ring A and the ring B is Partial Structural Formula (C):

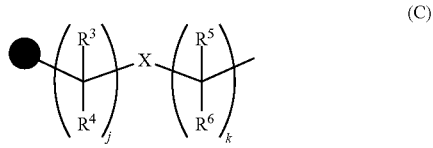

(where j, k, X, $R^3$, $R^4$, $R^5$, and $R^6$ are the same as defined in the above Formula (I), preferable aspects of j, k, X, $R^3$, $R^4$, $R^5$, and $R^6$ are the same as the preferable aspects described in any of Aspects [1] to [1-15], and ● is a single bond with the ring A).

Specific examples of Formula (C) include Formula (c1) to Formula (c6):

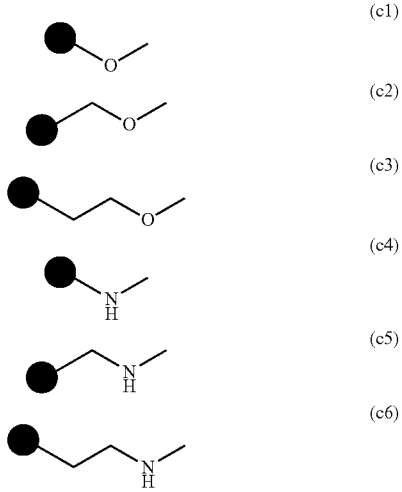

[1-18-a] When the ring A is Formula (A) in Formula (I), Formula (C) is more preferably Formula (c2), Formula (c3), Formula (c5), or Formula (c6). Formula (C) is further preferably Formula (c2) or Formula (c5), and particularly preferably Formula (c2).

[1-18-b] When the ring A is Formula (AA) in Formula (I), Formula (C) is more preferably Formula (c1), Formula (c2), Formula (c4), or Formula (c5). Formula (C) is further preferably Formula (c1) or Formula (c4), and particularly preferably Formula (c1).

[1-19] In the compound of Formula (I) according to Aspect [1], when the ring A is Formula (AA), the ring A" is a benzene ring or a pyridine ring, and the ring A" is preferably a benzene ring.

[1-20] In the compound of Formula (I) according to Aspect [1], f is an integer of 0 to 2 and g is an integer of 1 to 4. f is preferably 0 or 1 and g is 1, 2, or 3, more preferably f is 0 and g is 2 or 3, and further preferably f is 0 and g is 2.

[1-21] In the compound of Formula (I) according to Aspect [1], q1 is an integer of 0 to 4. q1 is preferably 0, 1, or 2, and more preferably 1.

[1-22] In the compound of Formula (I) according to Aspect [1], r1 is an integer of 0 to 2. r1 is preferably 0.

[1-23] In the compound of Formula (I) according to Aspect [1], T is —$CH_2$—, an oxygen atom, —$S(O)_i$— (i is an integer of 0 to 2), or —$NR^7$—.

[1-23-a] T is preferably —$CH_2$— or an oxygen atom.

[1-23-b] T is more preferably —$CH_2$—.

[1-24] In the compound of Formula (I) according to Aspect [1], $R^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —S(O)$_i$R$^a$ (i is an integer of 0 to 2), or a group: —NR$^b$R$^c$;

R$^a$ is a group arbitrarily selected from a C$_{1-6}$ alkyl group or a halogenated C$_{1-6}$ alkyl group;

R$^b$ and R$^c$ are independently a group arbitrarily selected from a hydrogen atom, a C$_{1-6}$ alkyl group, a halogenated C$_{1-6}$ alkyl group, a C$_{2-6}$ alkenyl group, a C$_{2-6}$ alkynyl group, a C$_{2-7}$ alkanoyl group, a C$_{1-6}$ alkylsulfonyl group, an arylcarbonyl group or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a C$_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or C$_{1-6}$ alkyl), 1 to 5 group(s): —S(O)$_i$R$^a$ (i is an integer of 0 to 2, and R$^a$ is the same as defined as R$^a$ above), 1 to 5 group(s): —SO$_2$NR$^d$R$^e$, 1 to 5 group(s): —CONR$^d$R$^e$ (R$^d$ and R$^e$ are the same as defined as R$^a$ and R$^e$ above), or 1 to 5 group(s): —NR$^{b1}$R$^{c1}$), or non-aromatic heterocyclic oxy;

the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), or 1 to 5 group(s): —NR$^{b1}$R$^{c1}$); and the above-mentioned substituents R$^{b1}$ and R$^{c1}$ are independently a group arbitrarily selected from a hydrogen atom, a C$_{1-6}$ alkyl group, a C$_{2-7}$ alkanoyl group, or a C$_{1-6}$ alkylsulfonyl group.

[1-24-a] Preferable examples of R$^{11}$s include a halogen atom, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, a C$_{2-6}$ alkynyl group which is optionally substituted with 1 to 5 substituent(s) RI, a C$_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, and a heteroarylalkyloxy group which is optionally substituted with 1 to 5 substituent(s) RII (the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2, and R$^a$ is the same as defined as R$^a$ above), or 1 to 5 group(s): —NR$^{b1}$R$^c$) or a non-aromatic heterocyclic oxy group; and the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$).

[1-24-b] More preferable examples of R$^{11}$s include a halogen atom, a cyano group, a C$_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, and a heteroarylalkyloxy group which is optionally substituted with 1 to 5 substituent(s) RII (the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2, and R$^a$ is the same as defined as R$^a$ above), or 1 to 5 group(s): —NR$^{b1}$R$^{c1}$), or a non-aromatic heterocyclic oxy group; and the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$)).

[1-24-c] Further preferable examples of R$^{11}$s include a halogen atom, a cyano group, a C$_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, an aryloxy group which is optionally substituted with 1 to 5 substituent(s) RII, and an aralkyloxy group which is optionally substituted with 1 to 5 substituent(s) RII (the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2, and R$^a$ is the same as defined as R$^a$ above), or 1 to 5 group(s): —NR$^{b1}$R$^{c1}$), or a non-aromatic heterocyclic oxy group; and the above-mentioned substituents RII are the same as or different from each other and are each a group arbitrarily selected from the above-mentioned substituent RI, or a C$_{1-6}$ alkyl group (the $C_{1-6}$ alkyl group is optionally substituted with 1 to 5 halogen atom(s), 1 to 5 —OH, 1 to 5 $C_{1-6}$ alkoxy group(s) or 1 to 5 group(s): —$NR^{b1}R^{c1}$)).

[1-22-d] Particularly preferable examples of $R^{11}$ include a halogen atom, a cyano group, a $C_{1-6}$ alkoxy group (the $C_{1-6}$ alkoxy group is optionally substituted with 1 to 5 halogen atom(s), 1 to 5 —OH, or 1 to 5 $C_{1-6}$ alkoxy), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, an aryloxy group which is optionally substituted with 1 to 5 substituent(s) RIIa, and an aralkyloxy group which is optionally substituted with 1 to 5 substituent(s) RIIa (the above-mentioned substituent(s) RIIa are the same as or different from each other and are each a group arbitrarily selected from a halogen atom, a $C_{1-6}$ alkoxy group (the $C_{1-6}$ alkoxy group is optionally substituted with 1 to 5 halogen atom(s), 1 to 5 —OH, or 1 to 5 $C_{1-6}$ alkoxy), or 1 to 5 group(s): —$S(O)_iR^a$ (i is an integer of 0 to 2, and $R^a$ is the same as defined as $R^a$ above)), or a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group). The number of the substituent(s) RIIa is preferably 1 to 3.

More specific examples of $R^{11}$s include a fluorine atom, a chlorine atom, a bromine atom, cyano, methoxy, phenyl, (2-, 3-, or 4-)methoxyphenyl, 3-isopropoxyphenyl, 3,5-dimethoxyphenyl, 4-(2,3-dihydroxypropoxy)-2-methylphenyl, 4-(((2S)- or (2R)-)2,3-dihydroxypropoxy)-2-methylphenyl, 4-(2,3-dihydroxypropoxy)-(2,6-, 2,5-, or 2,3-)dimethylphenyl, 4-(((2S)- or (2R)-)2,3-dihydroxypropoxy)-(2,6-, 2,5-, or 2,3-)dimethylphenyl, 4-(3-hydroxybutoxy)-2-methylphenyl, 4-(((3S)- or (3R)-)-3-hydroxybutoxy)-2-methylphenyl, 4-(3-hydroxybutoxy)-(2,6-, 2,5-, or 2,3-)dimethylphenyl, 4-(((3S)- or (3R)-)-3-hydroxybutoxy)-(2,6-, 2,5-, or 2,3-)dimethylphenyl, 4-(3-hydroxy-3-methylbutoxy)-2-methylphenyl, 4-(3-hydroxy-3-methylbutoxy)-(2,6-, 2,5-, or 2,3-)dimethylphenyl, 4-(3-methylsulfonyl-propoxy)-2-methylphenyl, 4-(3-methylsulfonyl-propoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, (2-, 3-, or 4-)trifluoromethylphenyl, 2,6-dimethylphenyl, 1-methylpyrazol-4-yl, 3,5-dimethylisoxazol-4-yl, (2-, or 6-)methoxypyridine-3-yl, (2-, or 6-)isopropoxypyridine-3-yl, 6-(2,3-dihydroxypropoxy)-(2-, or 4-)methylpyridine-3-yl, 6-(((2S) or (2R)-)2,3-dihydroxypropoxy)-(2-, or 4-)methylpyridine-3-yl, 6-(2,3-dihydroxypropoxy)-(2,4-, 2,5-, or 4,5-)dimethylpyridine-3-yl, 6-(((2S)- or (2R)-)2,3-dihydroxypropoxy)-(2,4-, 2,5-, or 4,5-)dimethylpyridine-3-yl, 6-(3-hydroxybutoxy)-(2-, or 4-)methylpyridine-3-yl, 6-(((3S)- or (3R)-)-3-hydroxybutoxy)-(2-, or 4-)methylpyridine-3-yl, 6-(3-hydroxybutoxy)-(2,4-, 2,5-, or 4,5-)dimethylpyridine-3-yl, 6-(((3S)- or (3R)-)-3-hydroxybutoxy)-(2,4-, 2,5-, or 4,5-)dimethylpyridine-3-yl, 6-(3-hydroxy-3-methylbutoxy)-(2-, or 4-)methylpyridine-3-yl, 6-(3-hydroxy-3-methylbutoxy)-(2,4-, 2,5-, or 4,5-)dimethylpyridine-3-yl, 6-(3-methylsulfonyl-propoxy)-(2-, or 4-)methylpyridine-3-yl, 6-(3-methylsulfonyl-propoxy)-(2,4-, 2,5-, or 4,5-)dimethylpyridine-3-yl, 6-(3-(2-oxo-1-pyrrolidinyl)propoxy)-(2-, or 4-)methylpyridine-3-yl, 6-(3-(2-oxo-1-pyrrolidinyl)propoxy)-(2,4-, 2,5-, or 4,5-)dimethylpyridine-3-yl, 6-(1-piperidinyl)pyridine-3-yl, 5-pyrimidinyl, 6-indolyl, 3-quinolyl, 1,4-benzodioxane-6-yl, benzyl, phenoxy, 4-methoxyphenoxy, benzyloxy, phenethyloxy, (2-, 3-, or 4-)methoxybenzyloxy, (2-, 3-, or 4-)trifluoromethylbenzyloxy, (2-, 3-, or 4-)methoxyphenethyloxy, and the like.

[1-25] In the compound of Formula (I) according to Aspect [1], $R^{12}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI (the above-mentioned substituents RI are the same as or different from each other and are the same as defined as the substituents RI above), —SH, a group: —$S(O)_iR^a$ (i is an integer of 0 to 2, and $R^a$ is the same as defined as $R^a$ above), or a group: —$NR^bR^c$ ($R^a$ and $R^c$ is the same as defined as $R^a$ and $R^c$ above)).

[1-25-a] Preferable examples of $R^{12}$s include a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, and a $C_{1-6}$ alkoxy group which is optionally substituted with 1 to 5 substituent(s) RI (the above-mentioned substituent(s) RI are the same as or different from each other and are the same as defined as the substituent(s) RI above).

[1-25-b] More preferable examples of $R^{12}$s include a halogen atom or a $C_{1-6}$ alkyl group which is optionally substituted with 1 to 5 halogen atom(s). More specific examples of $R^2$s include a fluorine atom, a chlorine atom, a bromine atom, methyl, ethyl, propyl, isopropyl, butyl, isobutyl, sec-butyl, tert-butyl, trifluoromethyl, and the like.

[1-26] In a combination of f, g, the ring A" and T, in Formula (I), the fused ring including the ring A" and T is Partial Structural Formula (AA):

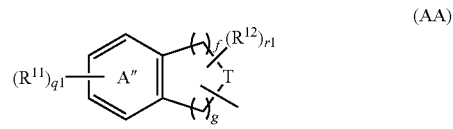

(AA)

(where f, g, q1, r1, the ring A", T, $R^{11}$, and $R^{12}$ are the same as defined in the above Formula (I), and preferable aspects of f, g, q1, r1, the ring A", T, $R^{11}$, and $R^{12}$ are the same as the preferable aspects described in any of Aspects [1] to [1-25]).

Specifically, examples of Formula (AA) include Formula (AA1) and Formula (AA2):

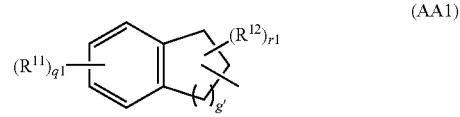

(AA1)

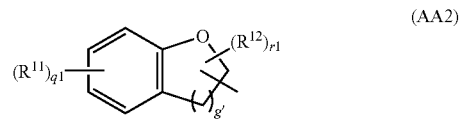

(AA2)

(where q1, r1, $R^{11}$, and $R^{12}$ are the same as defined in the above Formula (I), preferable aspects of q1, r1, $R^{11}$, and $R^{12}$ are the same as the preferable aspects described in any of Aspects [1] to [1-25], and g' is an integer of 1 or 2).

[1-26-a] Specifically, Formula (AA) is preferably Formula (AA1).

[1-26-b] Specifically, Formula (AA) is more preferably Formula (AA1) where g' is 1.

[1-26-c] The binding position of the linker moiety containing X in the fused ring including T in Formula (I) is any position at which it can be optionally bonded in the ring including T, and is Formula (AA1a) or Formula (AA1b) when g' is 1 in Formula (AA1):

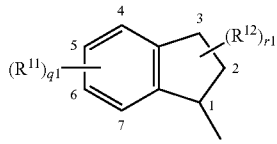

(AA1a)

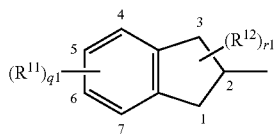

(AA1b)

(where q1, r1, $R^{11}$, and $R^{12}$ are the same as defined in the above Formula (I), and preferable aspects of q1, r1, $R^{11}$, and $R^{12}$ are the same as the preferable aspects described in any of Aspects [1] to [1-25]). In Formula (AA1a), when the binding position of the linker moiety containing X is determined as the first position, $R^{11}$s can be bonded at the fourth, fifth, sixth, or seventh position, and $R^{12}$s can be bonded at the first, second, or third position. In Formula (AA1b), when the binding position of the linker moiety containing X is determined as the second position, $R^{11}$s can be bonded at the fourth, fifth, sixth, or seventh position, and $R^{12}$s can be bonded at the first, second, or third position. Specifically, Formula (AA) is preferably Formula (AA1a).

[1-26-d] In Formula (AA1a), the substitution position of $R^{11}$ is preferably the fourth or fifth position, and more preferably the fourth position.

[1-27] In the compound of Formula (I) according to Aspect [1], compounds produced by optionally combining the groups of the ring A (on the left of the left wavy line), Partial Structural Formula (B) (on the right of the right wavy line), and Partial Structural Formula (C) (between the wavy lines) in Formula (I) can be produced optionally:

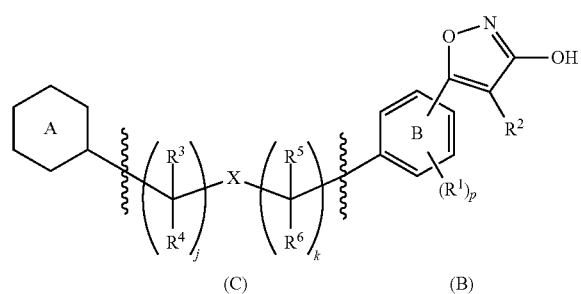

(I)

Specifically, the ring A is a group arbitrarily selected from Formula (A), Formula (A1), Formula (A2), Formula (A1a), Formula (A1b), Formula (AA), Formula (AA1), Formula (AA2), Formula (AA1a), and Formula (AA1b), described in Aspects [1-16], [1-16-c], [1-26], and [1-26-c], Partial Structural Formula (B) is a group arbitrarily selected from Formula (B1), Formula (B2), Formula (B1a), and Formula (B1b) described in Aspects [1-17] and [1-17-b], and Partial Structural Formula (C) is a group arbitrarily selected from Formula (c1) to Formula (c6) described in Aspect [1-18]. Any combination of these formulae forms part of the compound of Formula (I) according to the present invention.

[1-27-a] In the compound of Formula (I) according to Aspect [1], preferably, the ring A is Formula (A1a), Formula (A1b), Formula (AA 1a), or Formula (AA 1b), Partial Structural Formula (B) is Formula (B1a) or Formula (B1b), and Partial Structural Formula (C) is Formula (c1), Formula (c2), Formula (c4) or Formula (c5). More preferably, the ring A is Formula (A1a) or Formula (AA1a), Partial Structural Formula (B) is Formula (B1a), and Partial Structural Formula (C) is Formula (c1) or Formula (c2). Further preferably, the ring A is Formula (A1a), Partial Structural Formula (B) is Formula (B1a), and Partial Structural Formula (C) is Formula (c2).

[1-28] Aspects [1-1] to [1-27] of the present invention described above, their respective preferable aspects, and the definition of the substituents can be optionally combined, so that the preferable aspects of the compound of Formula (I) according to Aspect [1] can be optionally provided.

Next, preferable substituents in Aspect [1a] will be described below.

[1a-1] In the compound of Formula (Ia) according to Aspect [1a], preferably, $R^8$s are independently a group arbitrarily selected from a $C_{1-6}$ alkoxy group which is substituted with 1 to 5 substituent(s) L, a $C_{2-6}$ alkenyloxy group which is substituted with 1 to 5 substituent(s) L, a $C_{2-6}$ alkynyloxy group which is substituted with 1 to 5 substituent(s) L, and a non-aromatic heterocyclic oxy group;

the substituent(s) L are independently a group arbitrarily selected from a halogen atom, —OH, a $C_{1-6}$ alkoxy group, a non-aromatic heterocyclic group (the heterocyclic is optionally substituted with —OH or a $C_{1-6}$ alkyl group), a group: —S(O)$_i$R$^a$ (i is an integer of 0 to 2), a group: —CO$_2$R$^f$, a group: —SO$_2$NR$^d$R$^e$, a group: —CONR$^d$R$^e$, or a group: —NR$^b$R$^c$;

R$^a$ is a group arbitrarily selected from a $C_{1-6}$ alkyl group or a halogenated $C_{1-6}$ alkyl group;

R$^d$, R$^e$ and R$^f$ are independently a group arbitrarily selected from a hydrogen atom or a $C_{1-6}$ alkyl group; and R$^b$ and R$^c$ are independently a group arbitrarily selected from a hydrogen atom, a $C_{1-6}$ alkyl group, a halogenated $C_{1-6}$ alkyl group, a $C_{2-6}$ alkenyl group, or a $C_{2-6}$ alkynyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom or a sulfur atom, or with a carbonyl group.

[1a-1-a] More preferable examples of $R^8$s include —OH, a $C_{1-6}$ alkoxy group, a non-aromatic heterocyclic group (the heterocyclic is optionally substituted with —OH or a $C_{1-6}$ alkyl group), a $C_{1-6}$ alkoxy group substituted with 1 to 5 group(s) arbitrarily selected from a group: —S(O)$_i$R$^a$ (i is an integer of 0 to 2) or a group: —NR$^b$R$^c$, or a non-aromatic heterocyclic oxy group. R$^a$ is a group arbitrarily selected from a $C_{1-6}$ alkyl group or a halogenated $C_{1-6}$ alkyl group. R$^b$ and R$^c$ are independently a group arbitrarily selected from a hydrogen atom, a $C_{1-6}$ alkyl group, or a halogenated $C_{1-6}$ alkyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, or a sulfur atom, or with a carbonyl group.

[1a-1-b] Further preferable examples of $R^8$s include —OH, a $C_{1-6}$ alkoxy group, and a $C_{1-6}$ alkoxy group substituted with 1 to 5 group(s) arbitrarily selected from group(s): —S(O)$_i$R$^a$ (i is an integer of 0 to 2) or group(s): —NR$^b$R$^c$. R$^a$ is a $C_{1-6}$ alkyl group; R$^b$ and R$^c$ are independently a group arbitrarily selected from a hydrogen atom or a $C_{1-6}$ alkyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with a carbonyl group.

[1a-1-c] Particularly preferable examples of $R^8$s include a $C_{1-6}$ alkoxy group substituted with 1 to 5 —OH, 1 to 5 methylsulfonyl, 1 to 5 ethylsulfonyl, 1 to 5 —NH$_2$, or 1 to 5 2-oxo-1-pyrrolidinyl. The number of groups substituted with —OH, methylsulfonyl, ethylsulfonyl, —NH$_2$, or 2-oxo-1-pyrrolidinyl is preferably 1 or 2.

Specific examples of $R^8$s include 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-ethoxyethoxy, (4-hydroxy-1,1-dioxiedtetrahydro-2H-thiopyran-4-yl)methoxy, (3-methyloxetan-3-yl)methoxy, 2-methylsulfonyl-ethoxy, 3-methylsulfonyl-propoxy, 2-ethylsulfonyl-ethoxy, 3-ethylsulfonyl-propoxy, 2-aminoethoxy, 3-aminopropoxy, 2-acetylamino-ethoxy, 3-acetylamino-propoxy, 2-methylsulfonylamino-ethoxy, 3-methylsulfonylamino-propoxy, 2-(2-oxo-1-pyrrolidinyl)ethoxy, 3-(2-oxo-1-pyrrolidinyl)propoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, 3-dimethylsulfamoyl-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, (1,1-dioxiedtetrahydro-2H-thiopyran-4-yl)oxy, and the like.

[1a-2] In the compound of Formula (Ia) according to Aspect [1a], preferably, $R^9$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI; and
the substituent(s) RI are the same as or different from each other and are group(s) arbitrarily selected from a halogen atom, —OH, a cyano group, a $C_{1-6}$ alkoxy group, or a halogenated $C_{1-6}$ alkoxy group.

[1a-2-a] More preferable examples of $R^9$s include a halogen atom and a $C_{1-6}$ alkyl group (the $C_{1-6}$ alkyl groups are the same as or different from each other and optionally substituted with 1 to 5 group(s) arbitrarily selected from a halogen atom, —OH, a cyano group, a $C_{1-6}$ alkoxy group, or a halogenated $C_{1-6}$ alkoxy group).

[1a-2-b] Further preferable examples of $R^9$s include a halogen atom and a $C_{1-4}$ alkyl group which optionally substituted with 1 to 5 halogen atom(s). More specific examples of $R^9$s include a fluorine atom, a chlorine atom, a bromine atom, methyl, ethyl, propyl, isopropyl, butyl, isobutyl, sec-butyl, tert-butyl, trifluoromethyl, and the like. Particularly preferable examples of $R^9$s include methyl.

[1a-3] In the compound of Formula (Ia) according to Aspect [1a], preferably, $R^{10}$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI; and
the substituent(s) RI are the same as or different from each other and are group(s) arbitrarily selected from a halogen atom, —OH, a cyano group, a $C_{1-6}$ alkoxy group, or a halogenated $C_{1-6}$ alkoxy group.

[1a-3-a] More preferable examples of $R^{10}$s include a halogen atom and a $C_{1-6}$ alkyl group (the $C_{1-6}$ alkyl groups are the same as or different from each other and optionally substituted with 1 to 5 group(s) arbitrarily selected from a halogen atom, —OH, a cyano group, a $C_{1-6}$ alkoxy group, or a halogenated $C_{1-6}$ alkoxy group).

[1a-3-b] Further preferable examples of $R^{10}$s include a halogen atom and a $C_{1-4}$ alkyl group which optionally substituted with 1 to 5 halogen atom(s). More specific examples of $R^{10}$ include a fluorine atom, a chlorine atom, a bromine atom, methyl, ethyl, propyl, isopropyl, butyl, isobutyl, sec-butyl, tert-butyl, trifluoromethyl, and the like. Particularly preferable examples of $R^{10}$s include methyl.

[1a-4] In the compound of Formula (Ia) according to Aspect [1a], preferably, $R^1$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI; and
the substituent(s) RI are the same as or different from each other, and a group arbitrarily selected from a halogen atom, —OH, a cyano group, a $C_{1-6}$ alkoxy group, or a halogenated $C_{1-6}$ alkoxy group.

[1a-4-a] Preferable examples of $R^1$s include a halogen atom or a $C_{1-6}$ alkyl group (the $C_{1-6}$ alkyl groups are the same as or different from each other and optionally substituted with 1 to 5 group(s) arbitrarily selected from a halogen atom, —OH, a cyano group, a $C_{1-6}$ alkoxy group, or a halogenated $C_{1-6}$ alkoxy group)

[1a-4-b] More preferable examples of $R^1$s include a halogen atom or a $C_{1-4}$ alkyl group which is optionally substituted with 1 to 5 halogen atom(s). Specific examples of $R^1$s include a fluorine atom, a chlorine atom, a bromine atom, methyl, ethyl, propyl, isopropyl, butyl, isobutyl, sec-butyl, tert-butyl, trifluoromethyl, and the like.

[1a-5] In the compound of Formula (Ia) according to Aspect [1a], preferably, $R^2$s are a hydrogen atom, a halogen atom, or a cyano group.

[1a-5-a] More preferable examples of $R^2$s include a hydrogen atom and a halogen atom. Specific examples of $R^2$s include a hydrogen atom, a fluorine atom, a chlorine atom, a bromine atom, and the like.

[1a-6] In the compound of Formula (Ia) according to Aspect [1a], preferably, $R^3$, $R^4$, $R^5$, $R^6$, and $R^7$ are independently a group arbitrarily selected from a hydrogen atom, a $C_{1-6}$ alkyl group or a halogenated $C_{1-6}$ alkyl group.

[1a-6-a] More preferably, $R^3$, $R^4$, $R^5$, $R^6$, and $R^7$ are a hydrogen atom.

[1a-7] In the compound of Formula (Ia) according to Aspect [1a], X is an oxygen atom, —S(O)$_i$— (i is an integer of 0 to 2) or —NR$^7$— (R$^7$ is the same as defined as R$^7$ above). X is preferably an oxygen atom, a sulfur atom, or —NR$^7$—.

[1a-7-a] X is more preferably an oxygen atom or —NH—.

[1a-7-b] X is further preferably an oxygen atom.

[1a-8] In the compound of Formula (Ia) according to Aspect [1a], j is preferably an integer of 1 to 3 and k is an integer of 0 to 2. More preferably, j is 1 or 2 and k is 0. Further preferably, j is 1 and k is 0.

[1a-9] In the compound of Formula (Ia) according to Aspect [1a], V is a single bond or an oxygen atom.

[1a-9-a] V is preferably a single bond.

[1a-10] In the compound of Formula (Ia) according to Aspect [1a], the ring A' is a benzene ring, a pyridine ring, or a pyrimidine ring. The ring A' is preferably a benzene ring or a pyridine ring.

[1a-11] In the compound of Formula (Ia) according to Aspect [1a], the ring B is preferably a benzene ring or a pyridine ring. The ring B is more preferably a benzene ring.

[1a-12] In the compound of Formula (Ia) according to Aspect [1a], s is an integer of 1 to 2. s is preferably 1.

[1a-13] In the compound of Formula (Ia) according to Aspect [1a], q is an integer of 0 to 4. q is preferably an integer of 0 to 3, and more preferably 1 or 2.

[1a-14] In the compound of Formula (Ia) according to Aspect [1a], r is an integer of 0 to 4. r is preferably 0, 1, or 2, and more preferably 0 or 1.

[1a-15] In the compound of Formula (Ia) according to Aspect [1a], p is an integer of 0 to 4. p is preferably 0 or 1, and more preferably 0.

[1a-16] In a combination of the ring A', V, and the substitution position, in Formula (I), the benzene ring in which the ring A'-V- is bonded is Partial Structural Formula (Aa):

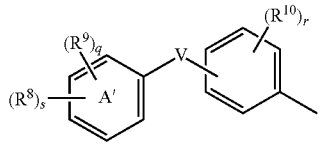

(Aa)

(where q, r, s, the ring A', V, $R^8$, $R^9$, and $R^{10}$ are the same as defined in the above Formula (Ia), and preferable aspects of q, r, s, the ring A', V, $R^8$, $R^9$, and $R^{10}$ are the same as the preferable aspects described in any of Aspects [1a] to [1a-15]). In Formula (Ia), the binding positions of the ring A'-V- and $R^{10}$s are any positions at which they can be optionally bonded in the benzene ring, and the binding positions of $R^8$s and $R^9$s are any positions at which they can be optionally bonded in the ring A'.

Preferable examples of Formula (Aa) include Formula (Aa1) or Formula (Aa2):

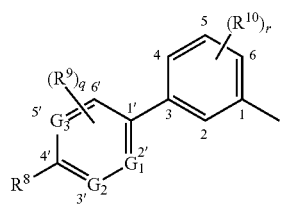

(Aa1)

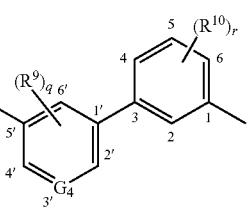

(Aa2)

(where q, r, s, the ring A', $R^8$s, $R^9$s, and $R^{10}$s are the same as defined in the above Formula (Ia), preferable aspects of q, r, s, the ring A', $R^8$s, $R^9$s, and $R^{10}$s are the same as the preferable aspects described in any of Aspects [1a] to [1a-15], and the broken lines and the figures 3 and 4 or the figures 3' and 4' indicate where the ring A', the ring A'-O—, or $R^8$s are bonded).

In Formula (Aa1), when the position of the single bond of the phenyl group (the binding position of the linker moiety containing X) is determined as the first position, the binding position of the ring A' is preferably at the third or fourth position, and more preferably at the third position. In Formula (Aa1), when the binding position of the ring A' with the phenyl group is determined as the first' position, the binding position of $R^8$s is preferably at the third' or fourth' position.

In Formula (Aa2), when the position of the single bond of the phenyl group (the binding position of the linker moiety containing X) is determined as the first position, the binding position of the ring A'-O— is preferably at the third or fourth position, and more preferably at the third position. In Formula (Aa2), when the binding position of the ring A' with the phenyl group —O— is determined as the first' position, the binding position of $R^8$s is preferably at the third' or fourth' position.

[1a-16-a] Specifically, Formula (Aa) is preferably the above Partial Structural Formula (Aa1).

[1a-16-b] Specifically, Formula (Aa) is preferably the above Partial Structural Formula (Aa1), where s is 1.

[1a-16-c] More preferably, Formula (Aa) is Formula (Aa1a) or Formula (Aa1b) when s is 1 in Formula (Aa1):

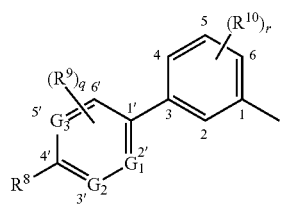

(Aa1a)

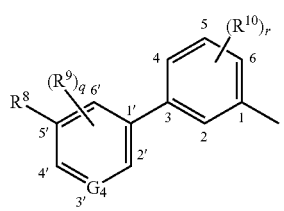

(Aa1b)

(where q, r, $R^8$, $R^9$ and $R^{10}$ are the same as defined in the above Formula (Ia), preferable aspects of q, r, $R^8$, $R^9$ and $R^{10}$ are the same as the preferable aspects described in any of Aspects [1a] to [1a-15], $G_1$, $G_2$, $G_3$, or $G_4$ is a =CH— group, a =CR$^9$— group or a nitrogen atom (with the proviso that when $G_1$ is a nitrogen atom, $G_2$ and $G_3$ are each a =CH— group or a =CR$^9$— group)).

In Formula (Aa1a) or Formula (Aa1b), when the position of the single bond of the phenyl group (the binding position of the linker moiety containing X) is determined as the first position, $R^{10}$s can be bonded at the second, fourth, fifth, or sixth positions. The binding position of $R^9$s is any positions in the ring including $G_1$ or $G_4$.

Formula (Aa) is further preferably Formula (Aa1a).

[1a-16-d] In Formula (Aa1a), preferably, $G_1$ is a =CH— group or a =CR$^9$— group, $G_2$ and $G_3$ are independently a =CH— group, a =CR$^9$— group, or a nitrogen atom. More preferably, $G_1$ and $G_3$ are independently a =CH— group or a =CR$^9$— group, and $G_2$ is a =CH— group, a =CR$^9$— group, or a nitrogen atom.

[1a-16-e] In Formula (Aa1a) or Formula (Aa1b), at least one of the binding positions of $R^{10}$s is preferably the second position, and when r is 1, the binding position of $R^{10}$ is preferably the second position.

[1a-16-f] In Formula (Aa1a), when the binding position of the ring containing $G_1$ with the third position of the phenyl group is determined as the first' position, when q is 1, the binding position of $R^9$s is preferably the second' position (except for the case in which $G_1$ is a nitrogen atom) or the sixth' position. When q is 2, the binding positions of $R^9$s are preferably the second' and sixth' positions, the second' and fifth' positions, or the fifth' and sixth' positions (except for the case in which the binding position is a nitrogen atom), and more preferably, the second' and sixth' positions.

[1a-16-g] In Formula (Aa1a), r is preferably 0 or 1. When r is 1, the binding position of $R^{10}$ is preferably the second position. When $G_1$ is a =CH— group or a =$CR^9$-group, $G_2$ is a =CH— group or a nitrogen atom, $G_3$ is a =CH— group, and q is 1 or 2, the binding position(s) of $R^9$(s) is more preferably the second' or the sixth' positions, the second' and the sixth' positions, the second' or the fifth' positions, or the fifth' or the sixth' positions.

[1a-16-h] In Formula (Ia), Formula (Aa), Formula (Aa1), Formula (Aa2), Formula (Aa1a) and Formula (Aa1b), specific examples of Partial Structural Formula (A'):

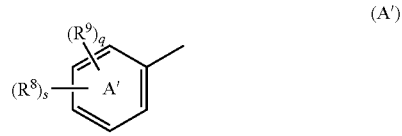

(A')

(where q, s, the ring A', $R^8$, and $R^9$ are the same as defined in the above Formula (I)) include (2-, 3- or 4-)trifluoromethoxyphenyl, 4-(2-hydroxyethoxy)-2-methylphenyl, 4-(2,3-dihydroxypropoxy)-2-methylphenyl, 4-(3-hydroxy-3-methylbutoxy)-2-methylphenyl, 3-(3-hydroxy-3-methylbutoxy)-2-methylphenyl, 4-(2-hydroxyethoxy)-(2,6-, 2,5-, or 2,3-)dimethylphenyl, 4-(3-hydroxypropoxy)-2-methylphenyl, 4-(3-hydroxypropoxy)-(2,6-, 2,5-, or 2,3-)dimethylphenyl, 4-(2,3-dihydroxypropoxy)-(2,6-, 2,5-, or 2,3-)dimethylphenyl, 4-((2R)-2,3-dihydroxypropoxy)-(2,6-, 2,5-, or 2,3-)dimethylphenyl, 4-((2S)-2,3-dihydroxypropoxy)-(2,6-, 2,5-, or 2,3-)dimethylphenyl, 4-(3-hydroxy-2-hydroxymethylpropoxy)-2-methylphenyl, 4-(3-hydroxy-2-hydroxymethyl-2-methylpropoxy)-2-methylphenyl, 4-(3-hydroxybutoxy)-2-methylphenyl, 4-((3S)-3-hydroxybutoxy)-2-methylphenyl, 4-((3R)-3-hydroxybutoxy)-2-methylphenyl, 4-(3-hydroxy-2-hydroxymethylpropoxy)-(2,6-, 2,5-, or 2,3-)dimethylphenyl, 4-(3-hydroxy-2-hydroxymethyl-2-methylpropoxy)-(2,6-, 2,5-, or 2,3-)dimethylphenyl, 4-(3-hydroxybutoxy)-(2,6-, 2,5-, or 2,3-)dimethylphenyl, 4-((3S)-3-hydroxybutoxy)-(2,6-, 2,5-, or 2,3-)dimethylphenyl, 4-((3R)-3-hydroxybutoxy)-(2,6-, 2,5-, or 2,3-)dimethylphenyl, 4-(3-hydroxy-3-methylbutoxy)-(2,6-, 2,5-, or 2,3-)dimethylphenyl, 4-(3-aminopropoxy)-2-methylphenyl, 4-(3-aminopropoxy)-(2,6-, 2,5-, or 2,3-)dimethylphenyl, 4-(2-(2-oxo-1-pyrrolidinyl)ethoxy)-2-methylphenyl, 4-(3-(2-oxo-1-pyrrolidinyl)ethoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, 4-(2-ethoxy-ethoxy)-2-methylphenyl, 4-(2-ethoxy-ethoxy)-(2,6-, 2,5-, or 2,3-)dimethylphenyl, 4-(3-methoxy-butoxy)-2-methylphenyl, 4((3S)-3-methoxy-butoxy)-2-methylphenyl, 4((3R)-3-methoxy-butoxy)-(2,6-, 2,5-, or 2,3-)dimethylphenyl, 4((3S)-3-methoxy-butoxy)-(2,6-, 2,5-, or 2,3-)dimethylphenyl, 4((3R)-3-methoxy-butoxy)-(2,6-, 2,5-, or 2,3-)dimethylphenyl, 4-(3-methoxy-3-methylbutoxy)-2-methylphenyl, 4-(3-methoxy-3-methylbutoxy)-(2,6-, 2,5-, or 2,3-)dimethylphenyl, 4-(2-methylsulfonyl-ethoxy)-2-methylphenyl, 4-(2-methylsulfonyl-ethoxy)-(2,6-, 2,5-, or 2,3-)dimethylphenyl, 4-(3-methylsulfonyl-propoxy)-2-methylphenyl, 4-(3-methylsulfonyl-propoxy)-(2,6-, 2,5-, or 2,3-)dimethylphenyl, 4-((1,1-dioxiedtetrahydro-2H-thiopyran-4-yl)oxy)-2-methylphenyl, 4-((1,1-dioxiedtetrahydro-2H-thiopyran-4-yl)oxy)-(2,6-, 2,5-, or 2,3-)dimethylphenyl, 4-((4-hydroxy-1,1-dioxiedtetrahydro-2H-thiopyran-4-yl)methoxy)-2-methylphenyl, 4-((4-hydroxy-1,1-dioxiedtetrahydro-2H-thiopyran-4-yl)methoxy)-(2,6-, 2,5-, or 2,3-)dimethylphenyl, 4-((3-methyloxetan-3-yl)methoxy)-2-methylphenyl, 4-((3-methyloxetan-3-yl)methoxy)-(2,6-, 2,5-, or 2,3-)dimethylphenyl, 4-(2-acetylamino-ethoxy)-2-methylphenyl, 4-(2-acetylamino-ethoxy)-(2,6-, 2,5-, or 2,3-)dimethylphenyl, 4-(3-acetylamino-propoxy)-2-methylphenyl, 4-(3-acetylamino-propoxy)-(2,6-, 2,5-, or 2,3-)dimethylphenyl, 4-(2-methylsulfonylamino-ethoxy)-2-methylphenyl, 4-(2-methylsulfonylamino-ethoxy)-(2,6-, 2,5-, or 2,3-)dimethylphenyl, 4-(3-methylsulfonylamino-propoxy)-2-methylphenyl, 4-(3-methylsulfonylamino-propoxy)-(2,6-, 2,5-, or 2,3-)dimethylphenyl, 4-(2-carbamoyl-ethoxy)-2-methylphenyl, 4-(2-carbamoyl-ethoxy)-(2,6-, 2,5-, or 2,3-)dimethylphenyl, 4-(3-carbamoyl-propoxy)-2-methylphenyl, 4-(3-carbamoyl-propoxy)-(2,6-, 2,5-, or 2,3-)dimethylphenyl, 4-(2-methylcarbamoyl-ethoxy)-2-methylphenyl, 4-(2-methylcarbamoyl-ethoxy)-(2,6-, 2,5-, or 2,3-)dimethylphenyl, 4-(3-methylcarbamoyl-propoxy)-2-methylphenyl, 4-(3-methylcarbamoyl-propoxy)-(2,6-, 2,5-, or 2,3-)dimethylphenyl, 4-(2-dimethylcarbamoyl-ethoxy)-2-methylphenyl, 4-(2-dimethylcarbamoyl-ethoxy)-(2,6-, 2,5-, or 2,3-)dimethylphenyl, 4-(3-dimethylcarbamoyl-propoxy)-2-methylphenyl, 4-(3-dimethylcarbamoyl-propoxy)-(2,6-, 2,5-, or 2,3-)dimethylphenyl, 4-(2-sulfamoyl-ethoxy)-2-methylphenyl, 4-(2-sulfamoyl-ethoxy)-(2,6-, 2,5-, or 2,3-)dimethylphenyl, 4-(3-sulfamoyl-propoxy)-2-methylphenyl, 4-(3-sulfamoyl-propoxy)-(2,6-, 2,5-, or 2,3-)dimethylphenyl, 4-(2-methylsulfamoyl-ethoxy)-2-methylphenyl, 4-(2-methylsulfamoyl-ethoxy)-(2,6-, 2,5-, or 2,3-)dimethylphenyl, 4-(3-methylsulfamoyl-propoxy)-2-methylphenyl, 4-(3-methylsulfamoyl-propoxy)-(2,6-, 2,5-, or 2,3-)dimethylphenyl, 4-(2-dimethylsulfamoyl-ethoxy)-2-methylphenyl, 4-(2-dimethylsulfamoyl-ethoxy)-(2,6-, 2,5-, or 2,3-)dimethylphenyl, 4-(3-dimethylsulfamoyl-propoxy)-2-methylphenyl, 4-(3-dimethylsulfamoyl-propoxy)-(2,6-, 2,5-, or 2,3-)dimethylphenyl, 3-fluoro-4-(2-hydroxyethoxy)-2-methylphenyl, 3-fluoro-4-(2,3-dihydroxypropoxy)-2-methylphenyl, 3-fluoro-4-(3-hydroxy-3-methylbutoxy)-2-methylphenyl, 3-fluoro-4-(2-hydroxyethoxy)-(2,6- or 2,5-)dimethylphenyl, 4-((2R)-2,3-dihydroxypropoxy)-3-fluoro-(2,6- or 2,5-)dimethylphenyl, 4-((2S)-2,3-dihydroxypropoxy)-3-fluoro-(2,6- or 2,5-)dimethylphenyl, 3-fluoro-4-(3-hydroxypropoxy)-2-methylphenyl, 3-fluoro-4-(3-hydroxypropoxy)-(2,6- or 2,5-)dimethylphenyl, 3-fluoro-4-(2,3-dihydroxypropoxy)-(2,6- or 2,5-)dimethylphenyl, 3-fluoro-4-(3-hydroxy-2-hydroxymethylpropoxy)-2-methylphenyl, 3-fluoro-4-(3-hydroxy-2-hydroxymethylpropoxy)-(2,6- or 2,5-)dimethylphenyl, 3-fluoro-4-(3-hydroxy-2-hydroxymethyl-2-methylpropoxy)-2-methylphenyl, 3-fluoro-4-(3-hydroxy-2-hydroxymethyl-2-methylpropoxy)-(2,6- or 2,5-)dimethylphenyl, 3-fluoro-4-(3-hydroxybutoxy)-2-methylphenyl, 3-fluoro-4-(3-hydroxybutoxy)-(2,6- or 2,5-)dimethylphenyl, 3-fluoro-4-(3-hydroxy-3-methylbutoxy)-(2,6- or 2,5-)dimethylphenyl, 3-fluoro-4-(3-aminopropoxy)-2-methylphenyl, 3-fluoro-4-

(3-aminopropoxy)-(2,6- or 2,5-)dimethylphenyl, 3-fluoro-4-(2-(2-oxo-1-pyrrolidinyl)ethoxy)-2-methylphenyl, 3-fluoro-4-(3-(2-oxo-1-pyrrolidinyl)ethoxy)-(2,6- or 2,5-)dimethylphenyl, 3-fluoro-4-(3-(2-oxo-1-pyrrolidinyl)propoxy)-2-methylphenyl, 3-fluoro-4-(3-(2-oxo-1-pyrrolidinyl)propoxy)-(2,6- or 2,5-)dimethylphenyl, 3-fluoro-4-(2-ethoxy-ethoxy)-2-methylphenyl, 3-fluoro-4-(2-ethoxy-ethoxy)-(2,6- or 2,5-)dimethylphenyl, 3-fluoro-4-(3-methoxy-butoxy)-2-methylphenyl, 3-fluoro-4-((3S)-3-methoxy-butoxy)-2-methylphenyl, 3-fluoro-4-((3R)-3-methoxy-butoxy)-2-methylphenyl, 3-fluoro-4-(3-methoxy-butoxy)-(2,6- or 2,5-)dimethylphenyl, 3-fluoro-4-((3S)-3-methoxy-butoxy)-(2,6- or 2,5-)dimethylphenyl, 3-fluoro-4-((3R)-3-methoxy-butoxy)-(2,6- or 2,5-)dimethylphenyl, 3-fluoro-4-(3-methoxy-3-methylbutoxy)-2-methylphenyl, 3-fluoro-4-(3-methoxy-3-methylbutoxy)-(2,6- or 2,5-)dimethylphenyl, 3-fluoro-4-(2-methylsulfonyl-ethoxy)-2-methylphenyl, 3-fluoro-4-(2-methylsulfonyl-ethoxy)-(2,6-, 2,5-, or 2,3-)dimethylphenyl, 3-fluoro-4-(3-methylsulfonyl-propoxy)-2-methylphenyl, 3-fluoro-4-(3-methylsulfonyl-propoxy)-(2,6- or 2,5-)dimethylphenyl, 3-fluoro-4-((1,1-dioxiedtetrahydro-2H-thiopyran-4-yl)oxy)-2-methylphenyl, 3-fluoro-4-((1,1-dioxiedtetrahydro-2H-thiopyran-4-yl)oxy)-(2,6- or 2,5-)dimethylphenyl, 3-fluoro-4-((4-hydroxy-1,1-dioxiedtetrahydro-2H-thiopyran-4-yl)methoxy)-2-methylphenyl, 3-fluoro-4-((4-hydroxy-1,1-dioxiedtetrahydro-2H-thiopyran-4-yl)methoxy)-(2,6- or 2,5-)dimethylphenyl, 3-fluoro-4-((3-methyloxetan-3-yl)methoxy)-2-methylphenyl, 3-fluoro-4-((3-methyloxetan-3-yl)methoxy)-(2,6- or 2,5-)dimethylphenyl, 3-fluoro-4-(2-acetylamino-ethoxy)-2-methylphenyl, 3-fluoro-4-(2-acetylamino-ethoxy)-(2,6- or 2,5-)dimethylphenyl, 3-fluoro-4-(3-acetylamino-propoxy)-2-methylphenyl, 3-fluoro-4-(3-acetylamino-propoxy)-(2,6- or 2,5-)dimethylphenyl, 3-fluoro-4-(2-methylsulfonylamino-ethoxy)-2-methylphenyl, 3-fluoro-4-(2-methylsulfonylamino-ethoxy)-(2,6- or 2,5-)dimethylphenyl, 3-fluoro-4-(3-methylsulfonylamino-propoxy)-2-methylphenyl, 3-fluoro-4-(3-methylsulfonylamino-propoxy)-(2,6- or 2,5-)dimethylphenyl, 3-fluoro-4-(2-carbamoyl-ethoxy)-2-methylphenyl, 3-fluoro-4-(2-carbamoyl-ethoxy)-(2,6- or 2,5-)dimethylphenyl, 3-fluoro-4-(3-carbamoyl-propoxy)-2-methylphenyl, 3-fluoro-4-(3-carbamoyl-propoxy)-(2,6- or 2,5-)dimethylphenyl, 3-fluoro-4-(2-methylcarbamoyl-ethoxy)-2-methylphenyl, 3-fluoro-4-(2-methylcarbamoyl-ethoxy)-(2,6- or 2,5-)dimethylphenyl, 3-fluoro-4-(3-methylcarbamoyl-propoxy)-2-methylphenyl, 3-fluoro-4-(3-methylcarbamoyl-propoxy)-(2,6- or 2,5-)dimethylphenyl, 3-fluoro-4-(2-dimethylcarbamoyl-ethoxy)-2-methylphenyl, 3-fluoro-4-(2-dimethylcarbamoyl-ethoxy)-(2,6- or 2,5-)dimethylphenyl, 3-fluoro-4-(3-dimethylcarbamoyl-propoxy)-2-methylphenyl, 3-fluoro-4-(3-dimethylcarbamoyl-propoxy)-(2,6- or 2,5-)dimethylphenyl, 3-fluoro-4-(2-sulfamoyl-ethoxy)-2-methylphenyl, 3-fluoro-4-(2-sulfamoyl-ethoxy)-(2,6- or 2,5-)dimethylphenyl, 3-fluoro-4-(3-sulfamoyl-propoxy)-2-methylphenyl, 3-fluoro-4-(3-sulfamoyl-propoxy)-(2,6- or 2,5-)dimethylphenyl, 3-fluoro-4-(2-methylsulfamoyl-ethoxy)-2-methylphenyl, 3-fluoro-4-(2-methylsulfamoyl-ethoxy)-(2,6- or 2,5-)dimethylphenyl, 3-fluoro-4-(3-methylsulfamoyl-propoxy)-2-methylphenyl, 3-fluoro-4-(3-methylsulfamoyl-propoxy)-(2,6- or 2,5-)dimethylphenyl, 3-fluoro-4-(2-dimethylsulfamoyl-ethoxy)-2-methylphenyl, 3-fluoro-4-(2-dimethylsulfamoyl-ethoxy)-(2,6- or 2,5-)dimethylphenyl, 3-fluoro-4-(3-dimethylsulfamoyl-propoxy)-2-methylphenyl, 3-fluoro-4-(3-dimethylsulfamoyl-propoxy)-(2,6- or 2,5-)dimethylphenyl, 4-(2-hydroxyethoxy)-2-hydroxymethylphenyl, 4-(2,3-dihydroxypropoxy)-2-hydroxymethylphenyl, 4-(3-hydroxy-3-methylbutoxy)-2-hydroxymethylphenyl, 4-(2-hydroxyethoxy)-6-methyl-2-hydroxymethylphenyl, 4-(3-hydroxypropoxy)-2-hydroxymethylphenyl, 4-(3-hydroxypropoxy)-6-methyl-2-hydroxymethylphenyl, 4-(2,3-dihydroxypropoxy)-6-methyl-2-hydroxymethylphenyl, 4-(3-hydroxy-2-hydroxymethylpropoxy)-2-hydroxymethylphenyl, 4-(3-hydroxy-2-hydroxymethylpropoxy)-6-methyl-2-hydroxymethylphenyl, 4-(3-hydroxy-2-hydroxymethyl-2-methylpropoxy)-2-hydroxymethylphenyl, 4-(3-hydroxy-2-hydroxymethyl-2-methylpropoxy)-6-methyl-2-hydroxymethylphenyl, 4-(3-hydroxybutoxy)-2-hydroxymethylphenyl, 4-(3-hydroxybutoxy)-6-methyl-2-hydroxymethylphenyl, 4-(3-hydroxy-3-methylbutoxy)-6-methyl-2-hydroxymethylphenyl, 4-(3-aminopropoxy)-2-hydroxymethylphenyl, 4-(3-aminopropoxy)-6-methyl-2-hydroxymethylphenyl, 4-(2-(2-oxo-1-pyrrolidinyl)ethoxy)-2-hydroxymethylphenyl, 4-(3-(2-oxo-1-pyrrolidinyl)ethoxy)-6-methyl-2-hydroxymethylphenyl, 4-(3-(2-oxo-1-pyrrolidinyl)propoxy)-2-hydroxymethylphenyl, 4-(3-(2-oxo-1-pyrrolidinyl)propoxy)-6-methyl-2-hydroxymethylphenyl, 4-(2-ethoxy-ethoxy)-2-hydroxymethylphenyl, 4-(2-ethoxy-ethoxy)-6-methyl-2-hydroxymethylphenyl, 4-(3-methoxy-butoxy)-2-hydroxymethylphenyl, 4-(3-methoxy-butoxy)-6-methyl-2-hydroxymethylphenyl, 4-(3-methoxy-3-methylbutoxy)-2-hydroxymethylphenyl, 4-(3-methoxy-3-methylbutoxy)-6-methyl-2-hydroxymethylphenyl, 4-(2-methylsulfonyl-ethoxy)-2-hydroxymethylphenyl, 4-(2-methylsulfonyl-ethoxy)-6-methyl-2-hydroxymethylphenyl, 4-(3-methylsulfonyl-propoxy)-2-hydroxymethylphenyl, 4-(3-methylsulfonyl-propoxy)-6-methyl-2-hydroxymethylphenyl, 4-((1,1-dioxiedtetrahydro-2H-thiopyran-4-yl)oxy)-2-hydroxymethylphenyl, 4-((1,1-dioxiedtetrahydro-2H-thiopyran-4-yl)oxy)-6-methyl-2-hydroxymethylphenyl, 4-((4-hydroxy-1,1-dioxyiedtetrahydro-2H-thiopyran-4-yl)methoxy)-2-hydroxymethylphenyl, 4-((4-hydroxy-1,1-dioxiedtetrahydro-2H-thiopyran-4-yl)methoxy)-6-methyl-2-hydroxymethylphenyl, 4-((3-methyloxetan-3-yl)methoxy)-2-hydroxymethylphenyl, 4-((3-methyloxetan-3-yl)methoxy)-6-methyl-2-hydroxymethylphenyl, 4-(2-acetylamino-ethoxy)-2-hydroxymethylphenyl, 4-(2-acetylamino-ethoxy)-6-methyl-2-hydroxymethylphenyl, 4-(3-acetylamino-propoxy)-2-hydroxymethylphenyl, 4-(3-acetylamino-propoxy)-6-methyl-2-hydroxymethylphenyl, 4-(2-methylsulfonylamino-ethoxy)-2-hydroxymethylphenyl, 4-(2-methylsulfonylamino-ethoxy)-6-methyl-2-hydroxymethylphenyl, 4-(3-methylsulfonylamino-propoxy)-2-hydroxymethylphenyl, 4-(3-methylsulfonylamino-propoxy)-6-methyl-2-hydroxymethylphenyl, 4-(2-carbamoyl-ethoxy)-2-hydroxymethylphenyl, 4-(2-carbamoyl-ethoxy)-6-methyl-2-hydroxymethylphenyl, 4-(3-carbamoyl-propoxy)-2-hydroxymethylphenyl, 4-(3-carbamoyl-propoxy)-6-methyl-2-hydroxymethylphenyl, 4-(2-methylcarbamoyl-ethoxy)-2-hydroxymethylphenyl, 4-(2-methylcarbamoyl-ethoxy)-6-methyl-2-hydroxymethylphenyl, 4-(3-methylcarbamoyl-propoxy)-2-hydroxymethylphenyl, 4-(3-methylcarbamoyl-propoxy)-6-methyl-2-hydroxymethylphenyl, 4-(2-dimethylcarbamoyl-ethoxy)-2-hydroxymethylphenyl, 4-(2-dimethylcarbamoyl-ethoxy)-6-methyl-2-hydroxymethylphenyl, 4-(3-dimethylcarbamoyl-propoxy)-2-hydroxymethylphenyl, 4-(3-dimethylcarbamoyl-propoxy)-6-methyl-2-hydroxymethylphenyl, 4-(2-sulfamoyl-ethoxy)-2-hydroxymethylphenyl, 4-(2-sulfamoyl-ethoxy)-6-methyl-2-hydroxymethylphenyl, 4-(3-sulfamoyl-propoxy)-2- hydroxymethylphenyl, 4-(3-sulfamoyl-propoxy)-6-methyl-2-hydroxymethylphenyl, 4-(2-methylsulfamoyl-ethoxy)-2-hydroxymethylphenyl, 4-(2-methylsulfamoyl-ethoxy)-6-methyl-2-hydroxymethylphenyl, 4-(3-methylsulfamoyl-propoxy)-2-hydroxymethylphenyl, 4-(3-methylsulfamoyl-propoxy)-6-methyl-2-hydroxymethylphenyl, 4-(2-dimethylsulfamoyl-ethoxy)-2-hydroxymethylphenyl, 4-(2-dimethylsulfamoyl-ethoxy)-6-methyl-2-hydroxymethylphenyl, 4-(3-dimethylsulfamoyl-propoxy)-2-hydroxymethylphenyl, 4-(3-dimethylsulfamoyl-propoxy)-6-methyl-2-hydroxymethylphenyl, 6-(2-hydroxyethoxy)-(2-, or 4-)methylpyridin-3-yl, 6-(3-hydroxypropoxy)-(2-, or 4-)methylpyridin-3-yl, 6-(2,3-dihydroxypropoxy)-(2-, or 4-)methylpyridin-3-yl, 6-((2R)-2,3-dihydroxypropoxy)-(2-, or 4-)methylpyridin-3-yl, 6-((2S)-2,3-dihydroxypropoxy)-(2-, or 4-)methylpyridyl-3-yl, 6-((3S)-3-hydroxybutoxy)-(2-, or 4-)methylpyridyl-3-yl, 6-((3R)-3-hydroxybutoxy)-(2-, or 4-)methylpyridyl-3-yl, 6-(3-hydroxy-3-methylbutoxy)-(2-, or 4-)methylpyridin-3-yl, 6-(3-hydroxy-2-hydroxymethylpropoxy)-(2-, or 4-)methylpyridin-3-yl, 6-(3-hydroxy-2-hydroxymethyl-2-methylpropoxy)-(2-, or 4-)methylpyridin-3-yl, 6-(3-hydroxybutoxy)-(2-, or 4-)methylpyridin-3-yl, 6-(2-ethoxyethoxy)-(2-, or 4-)methylpyridin-3-yl, 6-(3-methoxybutoxy)-(2-, or 4-)methylpyridin-3-yl, 6-(3-methoxy-3-methylbutoxy)-(2-, or 4-)methylpyridin-3-yl, 6-(2-methylsulfonyl-ethoxy)-(2-, or 4-)methylpyridin-3-yl, 6-(3-methylsulfonyl-propoxy)-(2-, or 4-)methylpyridin-3-yl, 6-((1,1-dioxiedtetrahydro-2H-thiopyran-4-yl)oxy)-(2-, or 4-)methylpyridin-3-yl, 6-((4-hydroxy-1,1-dioxiedtetrahydro-2H-thiopyran-4-yl)methoxy)-(2-, or 4-)methylpyridin-3-yl, 6-((3-methyloxetan-3-yl)methoxy)-(2-, or 4-)methylpyridin-3-yl, 6-(2-hydroxyethoxy)-(2,4-, 2,5-, or 4,5-)dimethylpyridin-3-yl, 6-(3-hydroxypropoxy)-(2,4-, 2,5-, or 4,5-)dimethylpyridin-3-yl, 6-(2,3-dihydroxypropoxy)-(2,4-, 2,5-, or 4,5-)dimethylpyridin-3-yl, 6-(3-hydroxy-2-hydroxymethylpropoxy)-(2,4-, 2,5-, or 4,5-)dimethylpyridin-3-yl, 6-(3-hydroxy-2-hydroxymethyl-2-methylpropoxy)-(2,4-, 2,5-, or 4,5-)dimethylpyridin-3-yl, 6-(3-hydroxybutoxy)-(2,4-, 2,5-, or 4,5-)dimethylpyridin-3-yl, 6-(3-hydroxy-3-methylbutoxy)-(2,4-, 2,5-, or 4,5-)dimethylpyridin-3-yl, 6-(2-ethoxyethoxy)-(2,4-, 2,5-, or 4,5-)dimethylpyridin-3-yl, 6-(3-methoxy-butoxy)-(2,4-, 2,5-, or 4,5-)dimethylpyridin-3-yl, 6((3S)-3-methoxy-butoxy)-(2,4-, 2,5-, or 4,5-)dimethylpyridin-3-yl, 6((3R)-3-methoxy-butoxy)-(2,4-, 2,5-, or 4,5-)dimethylpyridin-3-yl, 6-(3-methoxy-methylbutoxy)-(2,4-, 2,5-, or 4,5-)dimethylpyridin-3-yl, 6-(2-methylsulfonyl-ethoxy)-(2,4-, 2,5-, or 4,5-)dimethylpyridin-3-yl, 6-(3-methylsulfonyl-propoxy)-(2,4-, 2,5-, or 4,5-)dimethylpyridin-3-yl, 6-((1,1-dioxiedtetrahydro-2H-thiopyran-4-yl)oxy)-(2,4-, 2,5-, or 4,5-)dimethylpyridin-3-yl, 6-((4-hydroxy-1,1-dioxiedtetrahydro-2H-thiopyran-4-yl)methoxy)-(2,4-, 2,5-, or 4,5-)dimethylpyridin-3-yl, 6-((3-methyloxetan-3-yl)methoxy)-(2,4-, 2,5-, or 4,5-)dimethylpyridin-3-yl, 6-(2-aminoethoxy)-(2-, or 4-)methylpyridin-3-yl, 6-(2-aminoethoxy)-(2,4-, 2,5-, or 4,5-)dimethylpyridin-3-yl, 6-(3-aminopropoxy)-(2-, or 4-)methylpyridin-3-yl, 6-(3-aminopropoxy)-(2,4-, 2,5-, or 4,5-)dimethylpyridin-3-yl, 6-(2-acetylamino-ethoxy)-(2-, or 4-)methylpyridin-3-yl, 6-(2-acetylamino-ethoxy)-(2,4-, 2,5-, or 4,5-)dimethylpyridin-3-yl, 6-(3-acetylamino-propoxy)-(2-, or 4-)methylpyridin-3-yl, 6-(3-acetylamino-propoxy)-(2,4-, 2,5-, or 4,5-)dimethylpyridin-3-yl, 6-(2-methylsulfonylamino-ethoxy)-(2-, or 4-)methylpyridin-3-yl, 6-(2-methylsulfonylamino-ethoxy)-(2,4-, 2,5-, or 4,5-)dimethylpyridin-3-yl, 6-(3-methylsulfonylamino-propoxy)-(2-, or 4-)methylpyridin-3-yl, 6-(3-methylsulfonylamino-propoxy)-(2,4-, 2,5-, or 4,5-)dimethylpyridin-3-yl, 6-(2-carbamoyl-ethoxy)-(2-, or 4-)methylpyridin-3-yl, 6-(2-carbamoyl-ethoxy)-(2,4-, 2,5-, or 4,5-)dimethylpyridin-3-yl, 6-(3-carbamoyl-propoxy)-(2-, or 4-)methylpyridin-3-yl, 6-(3-carbamoyl-propoxy)-(2,4-, 2,5-, or 4,5-)dimethylpyridin-3-yl, 6-(2-methylcarbamoyl-ethoxy)-(2-, or 4-)methylpyridin-3-yl, 6-(2-methylcarbamoyl-ethoxy)-(2,4-, 2,5-, or 4,5-)dimethylpyridin-3-yl, 6-(3-methylcarbamoyl-propoxy)-(2-, or 4-)methylpyridin-3-yl, 6-(3-methylcarbamoyl-propoxy)-(2,4-, 2,5-, or 4,5-)dimethylpyridin-3-yl, 6-(2-dimethylcarbamoyl-ethoxy)-(2-, or 4-)methylpyridin-3-yl, 6-(2-dimethylcarbamoyl-ethoxy)-(2,4-, 2,5-, or 4,5-)dimethylpyridin-3-yl, 6-(3-dimethylcarbamoyl-propoxy)-(2-, or 4-)methylpyridin-3-yl, 6-(3-dimethylcarbamoyl-propoxy)-(2,4-, 2,5-, or 4,5-)dimethylpyridin-3-yl, 6-(2-sulfamoyl-ethoxy)-(2-, or 4-)methylpyridin-3-yl, 6-(2-sulfamoyl-ethoxy)-(2,4-, 2,5-, or 4,5-)dimethylpyridin-3-yl, 6-(3-sulfamoyl-propoxy)-(2-, or 4-)methylpyridin-3-yl, 6-(3-sulfamoyl-propoxy)-(2,4-, 2,5-, or 4,5-)dimethylpyridin-3-yl, 6-(2-methylsulfamoyl-ethoxy)-(2-, or 4-)methylpyridin-3-yl, 6-(2-methylsulfamoyl-ethoxy)-(2,4-, 2,5-, or 4,5-)dimethylpyridin-3-yl, 6-(3-methylsulfamoyl-propoxy)-(2-, or 4-)methylpyridin-3-yl, 6-(3-methylsulfamoyl-propoxy)-(2,4-, 2,5-, or 4,5-)dimethylpyridin-3-yl, 6-(2-dimethylsulfamoyl-ethoxy)-(2-, or 4-)methylpyridin-3-yl, 6-(2-dimethylsulfamoyl-ethoxy)-(2,4-, 2,5-, or 4,5-)dimethylpyridin-3-yl, 6-(3-dimethylsulfamoyl-propoxy)-(2-, or 4-)methylpyridin-3-yl, 6-(3-dimethylsulfamoyl-propoxy)-(2,4-, 2,5-, or 4,5-)dimethylpyridin-3-yl, 6-(2-(2-oxo-1-pyrrolidinyl)ethoxy)-(2-, or 4-)methylpyridin-3-yl, 6-(2-(2-oxo-1-pyrrolidinyl)ethoxy)-(2,4-, 2,5-, or 4,5-)dimethylpyridin-3-yl, 6-(3-(2-oxo-1-pyrrolidinyl)propoxy)-(2-, or 4-)methylpyridin-3-yl, 6-(3-(2-oxo-1-pyrrolidinyl)propoxy)-(2,4-, 2,5-, or 4,5-)dimethylpyridin-3-yl, 2-(2-hydroxyethoxy)-4-methylpyrimidin-5-yl, 2-(3-hydroxypropoxy)-4-methylpyrimidin-5-yl, 2-(2,3-dihydroxypropoxy)-4-methylpyrimidin-5-yl, 2-(3-hydroxy-3-methylbutoxy)-4-methylpyrimidin-5-yl, 2-(3-hydroxy-2-hydroxymethylpropoxy)-4-methylpyrimidin-5-yl, 2-(3-hydroxy-2-hydroxymethyl-2-methylpropoxy)-4-methylpyrimidin-5-yl, 2-(3-hydroxybutoxy)-4-methylpyrimidin-5-yl, 2-(2-ethoxyethoxy)-4-methylpyrimidin-5-yl, 2-(3-methoxy-butoxy)-4-methylpyrimidin-5-yl, 2-(3-methoxy-3-methylbutoxy)-4-methylpyrimidin-5-yl, 2-(2-methylsulfonyl-ethoxy)-4-methylpyrimidin-5-yl, 2-(3-methylsulfonyl-propoxy)-4-methylpyrimidin-5-yl, 2-((1,1-dioxiedtetrahydro-2H-thiopyran-4-yl)oxy)-4-methylpyrimidin-5-yl, 2-((4-hydroxy-1,1-dioxiedtetrahydro-2H-thiopyran-4-yl)methoxy)-4-methylpyrimidin-5-yl, 2-((3-methyloxetan-3-yl)methoxy)-4-methylpyrimidin-5-yl, 2-(2-hydroxyethoxy)-4,6-dimethylpyrimidin-5-yl, 2-(3-hydroxypropoxy)-4,6-dimethylpyrimidin-5-yl, 2-(2,3-dihydroxypropoxy)-4,6-dimethylpyrimidin-5-yl, 2-(3-hydroxy-2-hydroxymethylpropoxy)-4,6-dimethylpyrimidin-5-yl, 2-(3-hydroxy-2-hydroxymethyl-2-methylpropoxy)-4,6-dimethylpyrimidin-5-yl, 2-(3-hydroxybutoxy)-4,6-dimethylpyrimidin-5-yl, 2-((2R)-2,3-dihydroxypropoxy)-4,6-dimethylpyrimidin-5-yl, 2-((2S)-2,3-dihydroxypropoxy)-4,6-dimethylpyrimidin-5-yl, 2-((3S)-3-hydroxybutoxy)-4,6-dimethylpyrimidin-5-yl, 6-((3R)-3-hydroxybutoxy)-4,6-dimethylpyrimidin-5-yl, 2-(3-hydroxy-3-methylbutoxy)-4,6-dimethylpyrimidin-5-yl, 2-(2-ethoxyethoxy)-4,6-dimethylpyrimidin-5-yl, 2-(3-methoxy-butoxy)-4,6-dimethylpyrimidin-5-yl, 2-(3-methoxy-3-methylbutoxy)-4,6-dimethylpyrimidin-5-yl, 2-(2-methylsulfonyl-ethoxy)-4,6-dimethylpyrimidin-5-yl, 2-(3-methylsulfonyl-propoxy)-4,6-dimethylpyrimidin-5-yl, 2-((1,1-dioxiedtetrahydro-2H-thiopyran-4-yl)oxy)-4,6-dimethylpyrimidin-5-yl, 6-((4-hydroxy-1,1-dioxiedtetrahydro-2H-thiopyran-4-yl)

methoxy)-4,6-dimethylpyrimidin-5-yl, 2-((3-methyloxetan-3-yl)methoxy)-4,6-dimethylpyrimidin-5-yl, 2-(2-aminoethoxy)-4-methylpyrimidin-5-yl, 2-(2-aminoethoxy)-4,6-dimethylpyrimidin-5-yl, 2-(3-aminopropoxy)-4-methylpyrimidin-5-yl, 2-(3-aminopropoxy)-4,6-dimethylpyrimidin-5-yl, 2-(2-acetylamino-ethoxy)-4-methylpyrimidin-5-yl, 2-(2-acetylamino-ethoxy)-4,6-dimethylpyrimidin-5-yl, 2-(3-acetylamino-propoxy)-4-methylpyrimidin-5-yl, 2-(3-acetylamino-propoxy)-4,6-dimethylpyrimidin-5-yl, 2-(2-methylsulfonylamino-ethoxy)-4-methylpyrimidin-5-yl, 2-(2-methylsulfonylamino-ethoxy)-4,6-dimethylpyrimidin-5-yl, 2-(3-methylsulfonylamino-propoxy)-4-methylpyrimidin-5-yl, 2-(3-methylsulfonylamino-propoxy)-4,6-dimethylpyrimidin-5-yl, 2-(2-carbamoyl-ethoxy)-4-methylpyrimidin-5-yl, 2-(2-carbamoyl-ethoxy)-4,6-dimethylpyrimidin-5-yl, 2-(3-carbamoyl-propoxy)-4-methylpyrimidin-5-yl, 2-(3-carbamoyl-propoxy)-4,6-dimethylpyrimidin-5-yl, 2-(2-methylcarbamoyl-ethoxy)-4-methylpyrimidin-5-yl, 2-(2-methylcarbamoyl-ethoxy)-4,6-dimethylpyrimidin-5-yl, 2-(3-methylcarbamoyl-propoxy)-4-methylpyrimidin-5-yl, 2-(3-methylcarbamoyl-propoxy)-4,6-dimethylpyrimidin-5-yl, 2-(2-dimethylcarbamoyl-ethoxy)-4-methylpyrimidin-5-yl, 2-(2-dimethylcarbamoyl-ethoxy)-4,6-dimethylpyrimidin-5-yl, 2-(3-dimethylcarbamoyl-propoxy)-4-methylpyrimidin-5-yl, 2-(3-dimethylcarbamoyl-propoxy)-4,6-dimethylpyrimidin-5-yl, 2-(2-sulfamoyl-ethoxy)-4-methylpyrimidin-5-yl, 2-(2-sulfamoyl-ethoxy)-4,6-dimethylpyrimidin-5-yl, 2-(3-sulfamoyl-propoxy)-4-methylpyrimidin-5-yl, 2-(3-sulfamoyl-propoxy)-4,6-dimethylpyrimidin-5-yl, 2-(2-methylsulfamoyl-ethoxy)-4-methylpyrimidin-5-yl, 2-(2-methylsulfamoyl-ethoxy)-4,6-dimethylpyrimidin-5-yl, 2-(3-methylsulfamoyl-propoxy)-4-methylpyrimidin-5-yl, 2-(3-methylsulfamoyl-propoxy)-4,6-dimethylpyrimidin-5-yl, 2-(2-dimethylsulfamoyl-ethoxy)-4-methylpyrimidin-5-yl, 2-(2-dimethylsulfamoyl-ethoxy)-4,6-dimethylpyrimidin-5-yl, 2-(3-dimethylsulfamoyl-propoxy)-4-methylpyrimidin-5-yl, 2-(3-dimethylsulfamoyl-propoxy)-4,6-dimethylpyrimidin-5-yl, 2-(2-(2-oxo-1-pyrrolidinyl)ethoxy)-4-methylpyrimidin-5-yl, 2-(2-(2-oxo-1-pyrrolidinyl)ethoxy)-4,6-dimethylpyrimidin-5-yl, 2-(3-(2-oxo-1-pyrrolidinyl)propoxy)-4-methylpyrimidin-5-yl, 2-(3-(2-oxo-1-pyrrolidinyl)propoxy)-4,6-dimethylpyrimidin-5-yl, and the like.

[1a-17] The isoxazolyl group and the substituent of $R^1$ in the ring B in Formula (Ia) can be bonded at the second, third, fourth, fifth, or sixth position when the binding position of the linker moiety containing X is determined as the first position in Partial Structural Formula (Ba):

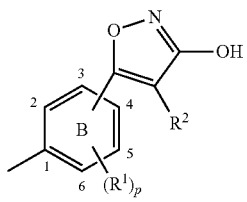

(Ba)

(where p, the ring B, $R^1$, and $R^2$ are the same as defined in the above Formula (Ia) and preferable aspects of p, the ring B, $R^1$, and $R^2$ are the same as the preferable aspects described in any of Aspects [1a] to [1a-15]).

Preferable examples of Formula (Ba) include Formula (Ba1) or Formula (Ba2):

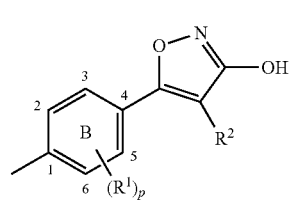

(Ba1)

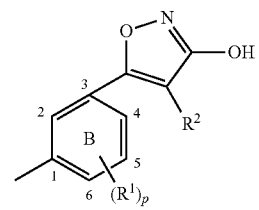

(Ba2)

(where p, the ring B, $R^1$, and $R^2$ are the same as defined in the above Formula (Ia) and preferable aspects of p, the ring B, $R^1$, and $R^2$ are the same as the preferable aspects described in any of Aspects [1a] to [1a-15]). When the binding position of the linker moiety containing X is determined as the first position, $R^1$ can be bonded at the second, third, fifth, or sixth position in Formula (Ba1), and $R^1$ can be bonded at the second, fourth, fifth, or sixth position in Formula (Ba2).

[1a-17-a] Formula (Ba) is preferably Formula (Ba1).

[1a-17-b] More preferable examples of Formula (Ba) include Formula (Ba1a) and Formula (Ba1b):

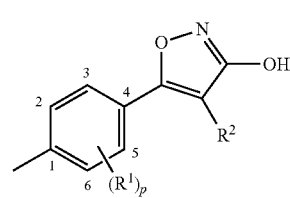

(Ba1a)

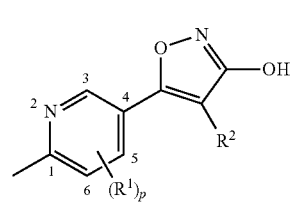

(Ba1b)

(where p, $R^1$, and $R^2$ are the same as defined in the above Formula (Ia), and preferable aspects of p, $R^1$, and $R^2$ are the same as the preferable aspects described in any of Aspects [1a] to [1a-15]).

In Formula (Ba1a) and Formula (Ba1b), $R^1$ is preferably a halogen atom, or a $C_{1-4}$ alkyl group optionally substituted with 1 to 5 halogen atom(s). Specifically, $R^1$ is preferably a fluorine atom, a chlorine atom, a bromine atom, methyl, ethyl, propyl, isopropyl, butyl, isobutyl, sec-butyl, tert-butyl, or trifluoromethyl. p is preferably 0 or 1, and more preferably, 0.

In Formula (Ba1a) and Formula (Ba1b), $R^2$ is preferably a hydrogen atom or a halogen atom, more specifically, a hydrogen atom, a fluorine atom, a chlorine atom, or a bromine atom, and more preferably, a hydrogen atom.

[1a-17-c] Further preferable examples of Formula (Ba) include Formula (Ba1a).

[1a-18] In a combination of j, k, X, $R^3$, $R^4$, $R^5$, and $R^6$, in Formula (Ia), the linker moiety containing X bonded to the ring A'-V-benzene ring and the ring B is Partial Structural Formula (Ca):

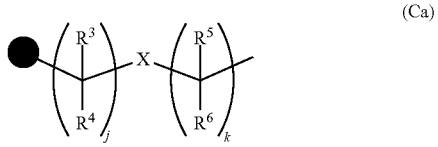

(Ca)

(where j, k, X, $R^3$, $R^4$, $R^5$, and $R^6$ are the same as defined in the above Formula (Ia), preferable aspects of j, k, X, $R^3$, $R^4$, $R^5$, and $R^6$ are the same as the preferable aspects described in any of Aspects [1a] to [1a-15], and ● is a single bond with the ring A'-V-benzene ring).

Specific examples of Formula (Ca) include Formula (c2), Formula (c3), Formula (c5), or Formula (c6):

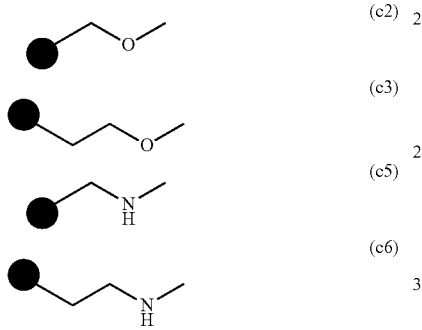

(c2)

(c3)

(c5)

(c6)

[1a-18-a] More preferably, Formula (Ca) is Formula (c2) or Formula (c5), and more preferably, Formula (c2).

[1a-19] In the compound of Formula (Ia) according to Aspect [1a], compounds produced by optionally combining the groups of Partial Structural Formula (Aa) (on the left of the left wavy line), Partial Structural Formula (Ba) (on the right of the right wavy line), Partial Structural Formula (Ca) (between the two wavy lines) in Formula (Ia) can be produced optionally:

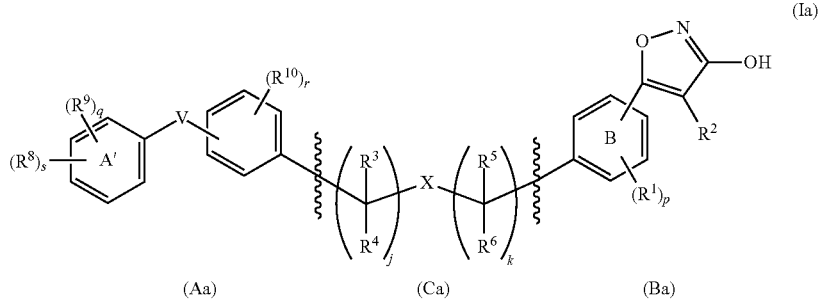

(Aa)  (Ca)  (Ba)

Specifically, Partial Structural Formula (Aa) is a group arbitrarily selected from Formula (Aa1), Formula (Aa2), Formula (Aa1a), and Formula (Aa1b), described in Aspects [1a-16] and [1a-16-c], Partial Structural Formula (Ba) is a group arbitrarily selected from Formula (Ba1), Formula (Ba2), Formula (Ba1a), and Formula (Ba1b) described in Aspects [1a-17] and [1a-17-b], and Partial Structural Formula (Ca) is a group arbitrarily selected from Formula (c2), Formula (c3), Formula (c5), or Formula (c6) described in Aspect [1a-18]. Any combination of these formulae forms part of the compound of Formula (Ia) according to the present invention.

[1a-19-a] In the compound of Formula (Ia) according to Aspect [1a], preferably, Partial Structural Formula (Aa) is Formula (Aa1a), or Formula (Aa1b), Partial Structural Formula (Ba) is Formula (Ba1a) or Formula (Ba1b), and Partial Structural Formula (Ca) is Formula (c2) or Formula (c5). More preferably, Partial Structural Formula (Aa) is Formula (Aa1a), Partial Structural Formula (Ba) is Formula (Ba1a), and Partial Structural Formula (Ca) is Formula (c2). Any combination of these formulae forms part of the preferable compound of Formula (Ia) according to the present invention.

[1a-20] An aspect [1a-20] of the present invention is the compound of Formula (Ia-A):

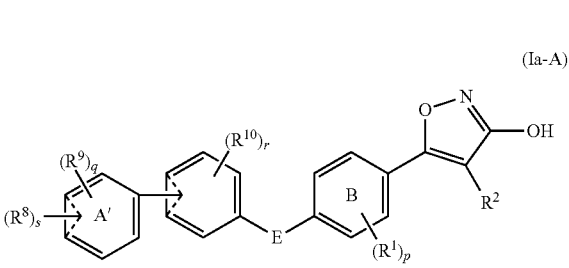

(Ia-A)

(where p, q, r, s, the ring A', the ring B, $R^8$, $R^9$, $R^{10}$ $R^1$, and $R^2$ are the same as defined in the above Formula (Ia), the broken lines are defined as the same as with Formula (Aa1) described in Aspect [1a-16], E is a group arbitrarily selected from Formula (c2), Formula (c3), Formula (c5), or Formula (c6) serving as specific examples of Formula (C) described in Aspect [1-12]), a salt of the compound, or a solvate of the compound or the salt.

Specifically, the definition and preferable aspects of p, q, r, s, the ring A', the ring B, $R^8$, $R^9$, $R^{10}$, $R^1$, $R^2$, and E are the same as defined in any one of Aspects [1a-1] to [1a-19].

[1a-21] An aspect [1a-21] of the present invention is the compound of Formula (Ia-B):

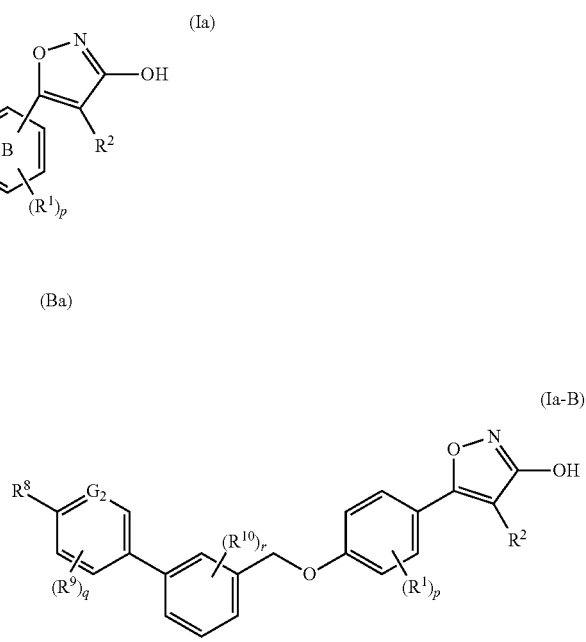

(Ia-B)

(where p, q, r, $R^8$, $R^9$, $R^0$, $R^1$, and $R^2$ are the same as defined in the above Formula (Ia), $G_2$ is the same as defined in the above Formula (Aa1a) described in Aspect [1a-16-c]), a salt of the compound, or a solvate of the compound or the salt.

Specifically, the definition and preferable aspects of p, q, r, $R^8$, $R^9$, $R^{10}$, $R^1$, $R^2$, and $G_2$ are the same as defined in any one of Aspects [1a-1] to [1a-19].

[1a-22] Aspects [1a-1] to [1a-21] of the present invention described above, their respective preferable aspects, and the definition of the substituents can be optionally combined, so that the preferable aspects of the compound of Formula (Ia) according to Aspect [1a] can be optionally provided.

[1a-23] Examples of preferable compounds as the compound of Formula (Ia) according to Aspects [1a] include the following:

5-(4-((3-(6-(3-hydroxy-3-methylbutoxy)-4-methylpyridin-3-yl)-2-methylphenyl)methoxy)phenyl)isoxazol-3-ol (Example 38);

5-(4-((3-(6-(3-hydroxy-3-methylbutoxy)-2-methylpyridin-3-yl)-2-methylphenyl)methoxy)phenyl)isoxazol-3-ol (Example 39);

5-(4-((3-(2,4-dimethyl-6-(3-hydroxy-3-methylbutoxy)pyridin-3-yl)-2-methylphenyl)methoxy)phenyl)isoxazol-3-ol (Example 40);

5-(4-((3-(2,4-dimethyl-6-(3-hydroxy-3-methylbutoxy)pyridin-3-yl)phenyl)methoxy)phenyl)isoxazol-3-ol (Example 41);

5-[4-[[3-[2,6-dimethyl-4-(3-methylsulfonylpropoxy)phenyl]phenyl]methoxy]phenyl]-1,2-isoxazol-3-ol (Example 42);

1-[3-[4-[3-[[4-(3-hydroxy-1,2-oxazol-5-yl)phenoxy]methyl]phenyl]-3,5-dimethylphenoxy]propyl]pyrrolidin-2-on (Example 43);

(2R)-3-[4-[3-[[4-(3-hydroxy-1,2-oxazol-5-yl)phenoxy]methyl]-2-methylphenyl]-3,5-dimethylphenoxy]propane-1,2-diol (Example 44);

5-[4-[[3-[4-(3-hydroxy-3-methylbutoxy)-2,6-dimethylphenyl]-2-methylphenyl]methoxy]phenyl]-1,2-oxazol-3-ol (Example 45);

5-[4-[[3-[6-(3-hydroxy-3-methylbutoxy)-4,5-dimethylpyridin-3-yl]-2-methylphenyl]methoxy]phenyl]-1,2-oxazol-3-ol (Example 46); and 5-[4-[[3-[6-(3-hydroxy-3-methylbutoxy)-2,5-dimethylpyridin-3-yl]-2-methylphenyl]methoxy]phenyl]-1,2-oxazol-3-ol (Example 47);

and salts of these compounds, solvates of the compounds or the salts, and isomers of the compounds, the salts, or the solvates.

Further, preferable substituents in Aspect [1b] will be described below.

[1b-1] In the compound of Formula (Ib) according to Aspect [1a], $R^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —S(O)$_i$R$^a$ (i is an integer of 0 to 2), or a group: —NR$^b$R$^c$;

$R^a$ is a group arbitrarily selected from a $C_{1-6}$ alkyl group or a halogenated $C_{1-6}$ alkyl group;

$R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or $R^b$ and $R^c$ optionally form together with a nitrogen atom to which $R^b$ and $R^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII);

the above-mentioned substituents RI are the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s): —S(O)$_i$R$^a$ (i is an integer of 0 to 2, and R$^a$ is the same as defined as R$^a$ above), 1 to 5 group(s): —SO$_2$NR$^d$R$^e$, 1 to 5 group(s): —CONR$^d$R$^e$ (R$^d$ and R$^e$ are the same as defined as R$^a$ and R$^e$ above), or 1 to 5 group(s): —NR$^{b1}$R$^{c1}$), or a non-aromatic heterocyclic oxy;

the above-mentioned substituents RII are the same as or different from each other and are each a group arbitrarily selected from the above-mentioned substituent RI, or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), or 1 to 5 group(s): —NR$^{b1}$R$^{c1}$); and the above-mentioned substituents $R^{b1}$ and $R^{c1}$ are independently a group arbitrarily selected from a hydrogen atom, a $C_{1-6}$ alkyl group, a $C_{2-7}$ alkanoyl group, or a $C_{1-6}$ alkylsulfonyl group.

[1b-1-a] Preferable examples of $R^{11}$s include a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, and a heteroarylalkyloxy group which is optionally substituted with 1 to 5 substituent(s) RII (the above-mentioned substituents RI are the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s):

—S(O)$_i$R$^a$ (i is an integer of 0 to 2, and R$^a$ is the same as defined as R$^a$ above), or 1 to 5 group(s): —NR$^{b1}$R$^{c1}$), or a non-aromatic heterocyclic oxy group; and the above-mentioned substituents RII are the same as or different from each other and are each a group arbitrarily selected from the above-mentioned substituent RI or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$).

[1b-1-b] More preferable examples of R$^{11}$s include a halogen atom, a cyano group, a C$_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, and a heteroarylalkyloxy group which is optionally substituted with 1 to 5 substituent(s) RII (the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2, and R$^a$ is the same as defined as R$^a$ above), or 1 to 5 group(s): —NR$^{b1}$R$^{c1}$), or a non-aromatic heterocyclic oxy group; and the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$)).

[1b-1-c] Further preferable examples of R$^{11}$s include a halogen atom, a cyano group, a C$_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, an aryloxy group which is optionally substituted with 1 to 5 substituent(s) RII, an aralkyloxy group which is optionally substituted with 1 to 5 substituent(s) RII (the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2, and R$^a$ is the same as defined as R$^a$ above), or 1 to 5 group(s): —NR$^{b1}$R$^{c1}$), or a non-aromatic heterocyclic oxy group; and the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$)).

[1b-1-d] Particularly preferable examples of R$^{11}$s include a halogen atom, a cyano group, a C$_{1-6}$ alkoxy group (the C$_{1-6}$ alkoxy group is optionally substituted with 1 to 5 halogen atom(s), 1 to 5 —OH, or 1 to 5 C$_{1-6}$ alkoxy), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, an aryloxy group which is optionally substituted with 1 to 5 substituent(s) RIIa, and an aralkyloxy group which is optionally substituted with 1 to 5 substituent(s) RIIa (the above-mentioned substituent(s) RIIa are the same as or different from each other and are each a group arbitrarily selected from a halogen atom, a C$_{1-6}$ alkoxy group (the C$_{1-6}$ alkoxy group is optionally substituted with 1 to 5 halogen atom(s), 1 to 5 —OH, or 1 to 5 C$_{1-6}$ alkoxy, or 1 to 5 group(s): —S(O)$_i$R$^a$ (i is an integer of 0 to 2, and R$^a$ is the same as defined as R$^a$ above)), or a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group). The number of the substituent(s) RIIa is preferably 1 to 3.

Specific example of R$^{11}$s include a fluorine atom, a chlorine atom, a bromine atom, cyano, methoxy, phenyl, (2-, 3-, or 4-)methoxyphenyl, 3-isopropoxyphenyl, 3,5-dimethoxyphenyl, 4-(2,3-dihydroxypropoxy)-2-methylphenyl, 4-(((2S)- or (2R)-)2,3-dihydroxypropoxy)-2-methylphenyl, 4-(2,3-dihydroxypropoxy)-(2,6-, 2,5-, or 2,3-)dimethylphenyl, 4(((2S)- or (2R)-)2,3-dihydroxypropoxy)-(2,6-, 2,5-, or 2,3-)dimethylphenyl, 4-(3-hydroxybutoxy)-2-methylphenyl, 4-(((3S)- or (3R)-)-3-hydroxybutoxy)-2-methylphenyl, 4-(3-hydroxybutoxy)-(2,6-, 2,5-, or 2,3-)dimethylphenyl, 4(((3S)- or (3R)-)-3-hydroxybutoxy)-(2,6-, 2,5-, or 2,3-)dimethylphenyl, 4-(3-hydroxy-3-methylbutoxy)-2-methylphenyl, 4-(3-hydroxy-3-methylbutoxy)-(2,6-, 2,5-, or 2,3-)dimethylphenyl, 4-(3-methylsulfonyl-propoxy)-2-methylphenyl, 4-(3-methylsulfonyl-propoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, (2-, 3-, or 4-)trifluoromethylphenyl, 2,6-dimethylphenyl, 1-methylpyrazol-4-yl, 3,5-dimethylisoxazol-4-yl, (2-, or 6-)methoxypyridin-3-yl, (2-, or 6-)isopropoxypyridin-3-yl, 6-(2,3-dihydroxypropoxy)-(2-, or 4-)methylpyridin-3-yl, 6-(((2S) or (2R)-)2,3-dihydroxypropoxy)-(2-, or 4-)methylpyridin-3-yl, 6-(2,3-dihydroxypropoxy)-(2,4-, 2,5-, or 4,5-)dimethylpyridin-3-yl, 6-(((2S)- or (2R)-)2,3-dihydroxypropoxy)-(2,4-, 2,5-, or 4,5-)dimethylpyridin-3-yl, 6-(3-hydroxybutoxy)-(2-, or 4-)methylpyridin-3-yl, 6-(((3S)- or (3R)-)-3-hydroxybutoxy)-(2-, or 4-)methylpyridin-3-yl, 6-(3-hydroxybutoxy)-(2,4-, 2,5-, or 4,5-)dimethylpyridin-3-yl, 6-(((3S)- or (3R)-)-3-hydroxybutoxy)-(2,4-, 2,5-, or 4,5-)dimethylpyridin-3-yl, 6-(3-hydroxy-3-methylbutoxy)-(2-, or 4-)methylpyridin-3-yl, 6-(3-hydroxy-3-methylbutoxy)-(2,4-, 2,5-, or 4,5-)dimethylpyridin-3-yl, 6-(3-methylsulfonyl-propoxy)-(2-, or 4-)methylpyridin-3-yl, 6-(3-methylsulfonyl-propoxy)-(2,4-, 2,5-, or 4,5-)dimethylpyridin-3-yl, 6-(3-(2-oxo-1-pyrrolidinyl)propoxy)-(2-, or 4-)methylpyridin-3-yl, 6-(3-(2-oxo-1-pyrrolidinyl)propoxy)-(2,4-, 2,5-, or 4,5-)dimethylpyridin-3-yl, 6-(1-piperidinyl)pyridin-3-yl, 5-pyrimidinyl, 6-indolyl, 3-quinolyl, 1,4-benzodioxan-6-yl, benzyl, phenoxy, 4-methoxyphenoxy, benzyloxy, phenethyloxy, (2-, 3-, or 4-)methoxybenzyloxy, (2-, 3-, or 4-)trifluoromethylbenzyloxy, (2-, 3-, or 4-)methoxyphenethyloxy, and the like. Also, preferable examples of R$^{11}$s include the groups enumerated in the specific examples of Formula (A') in Aspects [1a-16-h].

[1b-2] In the compound of Formula (Ib) according to Aspect [1b], R$^1$s are independently a group arbitrarily selected from a halogen atom, —OH, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, a $C_{2-6}$ alkynyl group which is optionally substituted with 1 to 5 substituent(s) RI, or a $C_{1-6}$ alkoxy group which is optionally substituted with 1 to 5 substituent(s) RI (the above-mentioned substituent(s) RI are the same as or different from each other, and are the same as defined as the substituents RI above), —SH, a group: —S(O)$_i$R$^a$ (i is an integer of 0 to 2, and R$^a$ is the same as defined as R$^a$ above), or a group: —NR$^b$R$^c$ (R$^a$ and R$^c$ is the same as defined as R$^a$ and R$^c$ above)).

[1b-2-a] Preferable examples of R$^1$s include a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, or a $C_{1-6}$ alkoxy group which is optionally substituted with 1 to 5 substituent(s) RI (the above-mentioned substituent(s) RI are the same as or different from each other, and are the same as defined as the substituents RI above).

[1b-2-b] More preferable examples of R$^1$s include a halogen atom, a cyano group, or a $C_{1-6}$ alkyl group which is optionally substituted with 1 to 5 halogen atom(s). Specific examples of R$^1$s include a fluorine atom, a chlorine atom, a bromine atom, cyano, methyl, ethyl, propyl, isopropyl, butyl, isobutyl, sec-butyl, tert-butyl, trifluoromethyl, and the like.

[1b-3] In the compound of Formula (Ib) according to Aspect [1b], preferably, R$^2$s are a hydrogen atom, a halogen atom, a cyano group, or a $C_{1-6}$ alkyl group which is optionally substituted with 1 to 5 substituent(s) RI (the RIs are the same as or different from each other, and are the same as defined as the substituents RI above).

[1b-3-a] More preferable examples of R$^2$s include a hydrogen atom, a halogen atom, a cyano group, and a $C_{1-6}$ alkyl group which is optionally substituted with 1 to 5 halogen atom(s).

[1b-3-b] Further preferable examples of R$^2$s include a hydrogen atom, a halogen atom, and a $C_{1-6}$ alkyl group, and specifically a hydrogen atom, a fluorine atom, a chlorine atom, a bromine atom, methyl, isopropyl, and the like.

[1b-4] In the compound of Formula (Ib) according to Aspect [1b], R$^{12}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI (the above-mentioned substituents RI(s) are the same as or different from each other, and are the same as defined as the substituents RI above), —SH, a group: —S(O)$_i$R$^a$ (i is an integer of 0 to 2, and R$^a$ is the same as defined as R$^a$ above), or a group: —NR$^b$R$^c$ (R$^a$ and R$^c$ is the same as defined as R$^a$ and R$^c$ above)).

[1b-4-a] Preferable examples of R$^{12}$s include a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, and a $C_{1-6}$ alkoxy group which is optionally substituted with 1 to 5 substituent(s) RI (the above-mentioned substituent(s) RI are the same as or different from each other and are the same as defined as the substituent(s) RI above).

[1b-4-b] More preferable examples of R$^{12}$ include a halogen atom or a $C_{1-6}$ alkyl group which is optionally substituted with 1 to 5 halogen atom(s). Specific examples of R$^{12}$s include a fluorine atom, a chlorine atom, a bromine atom, methyl, ethyl, propyl, isopropyl, butyl, isobutyl, sec-butyl, tert-butyl, trifluoromethyl, and the like.

[1b-5] In the compound of Formula (Ib) according to Aspect [1b], preferably, R$^3$, R$^4$, R$^5$, R$^6$, and R$^7$ are independently a group arbitrarily selected from a hydrogen atom, a $C_{1-6}$ alkyl group, or a halogenated $C_{1-6}$ alkyl group.

[1b-5-a] More preferably, R$^3$, R$^4$, R$^5$, R$^6$, and R$^7$ are a hydrogen atom.

[1b-6] In the compound of Formula (Ib) according to Aspect [1b], X is —CH$_2$—, an oxygen atom, —S(O)$_i$— (i is an integer of 0 to 2) or —NR$^7$—. X is preferably an oxygen atom, a sulfur atom, or —NR$^7$—.

[1b-6-a] X is more preferably an oxygen atom or —NR$^7$—.

[1b-6-b] X is further preferably an oxygen atom or —NH—.

[1b-7] In the compound of Formula (Ib) according to Aspect [1b], preferably, j and k are independently an integer of 0 to 2. More preferably, j is 0 or 1 and k is 0. Further preferably, j is 0 and k is 0.

[1b-8] In the compound of Formula (I) according to Aspect [1], T is —CH$_2$—, an oxygen atom, —S(O)$_i$— (i is an integer of 0 to 2), or —NR$^7$—.

[1b-8-a] T is preferably —CH$_2$— or an oxygen atom.

[1b-8-b] T is more preferably —CH$_2$—.

[1b-9] In the compound of Formula (Ib) according to Aspect [1b], f is an integer of 0 to 2 and g is an integer of 1 to 4. f is preferably 0 or 1 and g is 1, 2, or 3, more preferably f is 0 and g is 2 or 3, and further preferably f is 0 and g is 2.

[1b-10] In the compound of Formula (Ib) according to Aspect [1b], the ring A" is a benzene ring or a pyridine ring, and the ring A" is preferably a benzene ring.

[1b-11] In the compound of Formula (Ib) according to Aspect [1b], the ring B is a benzene ring or a pyridine ring, and the ring B is preferably a benzene ring.

[1b-12] In the compound of Formula (Ib) according to Aspect [1b], q1 is an integer of 0 to 4. q1 is preferably 0, 1, or 2, and more preferably 1.

[1b-13] In the compound of Formula (Ib) according to Aspect [1b], p is an integer of 0 to 4. p is preferably 0, or 1, and more preferably 0.

[1b-14] In the compound of Formula (Ib) according to Aspect [1b], r1 is an integer of 0 to 2. r1 is preferably 0.

[1b-15] In a combination of f, g, the ring A" and T, in Formula (Ib), the fused ring including the ring A" and T is Partial Structural Formula (Ab):

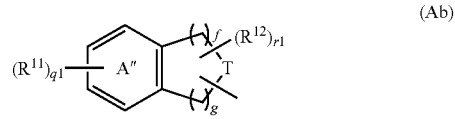

(Ab)

(where f, g, q1, r1, the ring A", T, R$^{11}$, and R$^{12}$ are the same as defined in the above Formula (Ib)).

Specifically, examples of Formula (Ab) include Formula (Ab1) and Formula (Ab2):

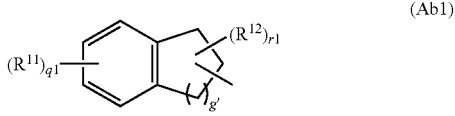

(Ab1)

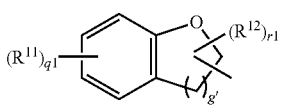
(Ab2)

(where q1, r1, $R^{11}$, and $R^{12}$ are the same as defined in the above Formula (Ib), and g' is an integer of 1 or 2).

[1b-15-a] Specifically, Formula (Ab) is preferably Formula (Ab1).

[1b-15-b] Specifically, Formula (Ab) is more preferably Formula (Ab1) where g' is 1.

[1b-15-c] The binding position of the linker moiety containing X in the fused ring including T in Formula (Ib) is any position at which it can be optionally bonded in the ring including T, and is Formula (Ab1a) or Formula (Ab1b) when g' is 1 in Formula (Ab1):

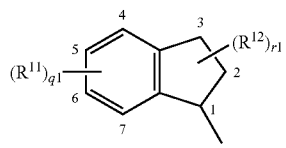
(Ab1a)

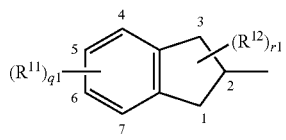
(Ab1b)

(where q1, r1, $R^{11}$, and $R^{12}$ are the same as defined in the above Formula (Ib)). In Formula (Ab1a), when the binding position of the linker moiety containing X is determined as the first position, $R^{11}$s can be bonded at the fourth, fifth, sixth, or seventh position, and $R^{12}$s can be bonded at the first, second, or third position. In Formula (Ab1b), when the binding position of the linker moiety containing X is determined as the second position, $R^{11}$s can be bonded at the fourth, fifth, sixth, or seventh position, and $R^{12}$s can be bonded at the first, second, or third position. Specifically, Formula (AA) is preferably Formula (Ab1a).

[1b-15-d] In Formula (Ab1a), the substitution position of $R^{11}$ is preferably the fourth or fifth position, and more preferably the fourth position.

[1b-16] The isoxazolyl group and the substituent of $R^1$ in the ring B in Formula (Ib) can be bonded at the second, third, fourth, fifth, or sixth position when the binding position of the linker moiety containing X is determined as the first position in Partial Structural Formula (Bb):

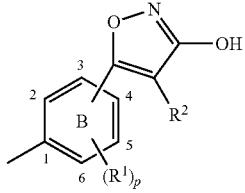
(Bb)

(where p, B, $R^1$, and $R^2$ are the same as defined in the above Formula (Ib)).

Specific examples of Formula (Bb) include Formula (Bb1) or Formula (Bb2):

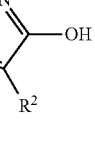
(Bb1)

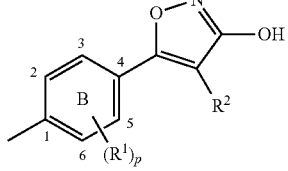
(Bb2)

(where p, B, $R^1$, and $R^2$ are the same as defined in the above Formula (Ib)). When the binding position of the linker moiety containing X is determined as the first position, $R^1$s can be bonded at the second, third, fifth, or sixth position in Formula (Bb1), and $R^1$s can be bonded at the second, fourth, fifth, or sixth position in Formula (Bb2).

[1b-16-a] Specifically, Formula (Bb) is preferably Formula (Bb1).

[1-16-b] Specific examples of Formula (Bb) include Formula (Bb1a) and Formula (Bb1b), and preferably Formula (Bb1a):

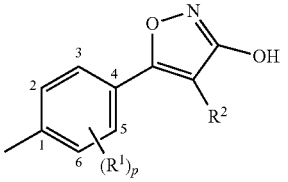
(Bb1a)

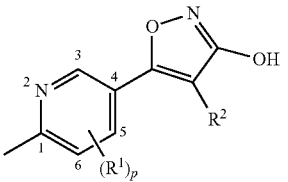
(Bb1b)

(where p, $R^1$, and $R^2$ are the same as defined in the above Formula (Ib)).

[1b-17] In a combination of j, k, X, $R^3$, $R^4$, $R^5$, and $R^6$, in Formula (I), the linker moiety containing X bonded to the fused ring including T and the ring B is Partial Structural Formula (Cb):

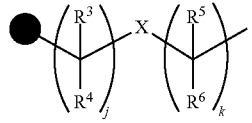
(Cb)

(where j, k, X, $R^3$, $R^4$, $R^5$, and $R^6$ are the same as defined in the above Formula (Ib), and ● is a single bond with the fused ring including T).

Specific examples of Formula (Cb) include Formula (c1), Formula (c2), Formula (c4), or Formula (c5):

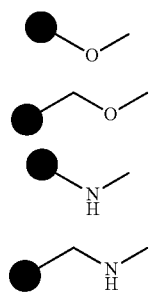

[1b-17-a] Specifically, Formula (Cb) is preferably Formula (c1) or Formula (c4), and more preferably Formula (c1).

[1b-18] In the compound of Formula (Ib) according to Aspect [1b], compounds produced by optionally combining the groups of Partial Structural Formula (Ab) (on the left of the left wavy line), Partial Structural Formula (Bb) (on the right of the right wavy line), Partial Structural Formula (Cb) (between the wavy lines) in Formula (Ib) can be produced optionally:

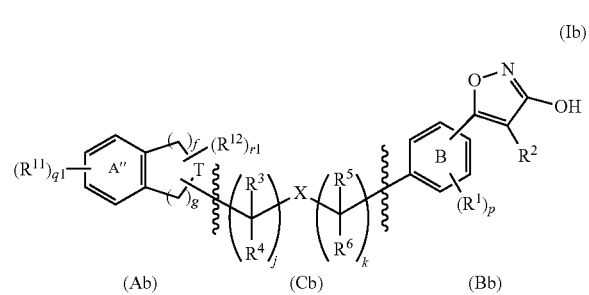

Specifically, Partial Structural Formula (Ab) is a group arbitrarily selected from Formula (Ab1), Formula (Ab2), Formula (Ab1a), and Formula (Ab1b) described in Aspects [1b-15] and [1b-15-c], Partial Structural Formula (Bb) is a group arbitrarily selected from Formula (Bb1), Formula (Bb2), Formula (Bb1a), and Formula (Bb1b) described in Aspects [1b-16] and [1b-16-b], and Partial Structural Formula (Cb) is a group arbitrarily selected from Formula (c1), Formula (c2), Formula (c4) or Formula (c5) described in Aspect [1b-17], and each formula forms part of the compound of Formula (Ib) according to the present invention.

[1b-18-a] In the compound of Formula (Ib) according to Aspect [1b], preferably, Partial Structural Formula (Ab) is Formula (Ab1a) or Formula (Ab1b), Partial Structural Formula (Bb) is Formula (Bb1a) or Formula (Bb1b), and Partial Structural Formula (Cb) is Formula (c1) or Formula (c4). More preferably, Partial Structural Formula (Ab) is Formula (Ab1a), Partial Structural Formula (Bb) is Formula (Bb1a), and Partial Structural Formula (Cb) is Formula (c1).

[1b-19] The compound of Formula (Ib) according to Aspect [1b] is more preferably Formula (Ib-A):

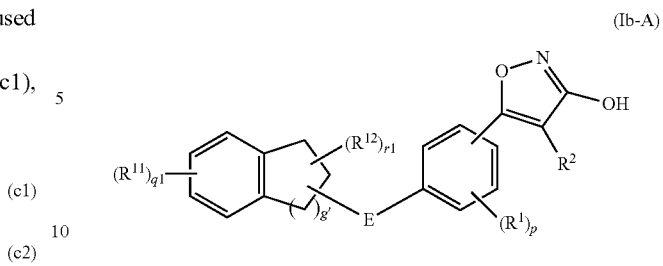

(where p, q1, r1, $R^{11}$, $R^1$, $R^2$ and $R^{12}$ are the same as defined in the above Formula (Ib), g' is the same as defined in the above Formula (Ab1) described in Aspect [1b-15], and E is a group arbitrarily selected from Formula (c1), Formula (c2), Formula (c4), or Formula (c5) serving as specific examples of Formula (Cb) described in Aspect [1b-17]).

Specifically, the definition and preferable aspects of p, q1, r1, $R^{11}$, $R^1$, $R^2$, $R^{12}$, g', and E are the same as defined in any one of Aspects [1b-1] to [1b-18].

[1b-20] The compound of Formula (Ib) according to Aspect [1b] is further preferably a compound of Formula (Ib-B):

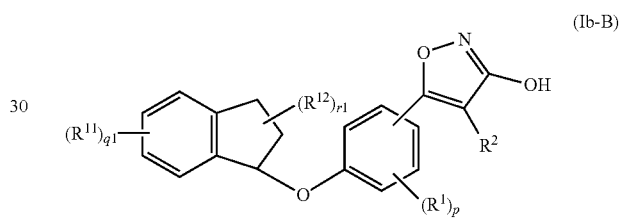

(where p, q1, r1, $R^{11}$, $R^1$, $R^2$ and a $R^{12}$ are the same as defined in the above Formula (Ib)).

Specifically, the definition and preferable aspects of p, q1, r1, $R^{11}$, $R^1$, $R^2$, and $R^{12}$ are the same as defined in any one of Aspects [1b-1] to [1b-18].

[1b-21] Aspects [1b-1] to [1b-20] of the present invention described above, their respective preferable aspects, and the definition of the substituents can be optionally combined, so that the preferable aspects of the compound of Formula (Ib) according to Aspect [1b] can be optionally provided.

[1b-22] Examples of preferable compounds as the compound of the above Formula (Ib) according to Aspects [1b] include the following:

5-(4-(1,2,3,4-tetrahydronaphthalen-1-yloxy)phenyl)isoxazol-3-ol (Example 1);
5-(4-(2,3-dihydro-1H-inden-2-yloxy)phenyl)isoxazol-3-ol (Example 2);
5-(4-(2,3-dihydro-1H-inden-1-yloxy)phenyl)isoxazol-3-ol (Example 3);
5-(4-(2,3-dihydrobenzofuran-3-yloxy)phenyl)isoxazol-3-ol (Example 4);
5-(4-(2,3-dihydro-3,3-dimethyl-1H-inden-1-yloxy)phenyl)isoxazol-3-ol (Example 5);
5-(4-(2,3-dihydro-1H-inden-1-yl)methoxy)phenyl)isoxazol-3-ol (Example 6);
5-(4-(R)-2,3-dihydro-1H-inden-1-yloxy)phenyl)isoxazol-3-ol (Example 7);
5-(4-(S)-2,3-dihydro-1H-inden-1-yloxy)phenyl)isoxazol-3-ol (Example 8);
5-(4-(2,3-dihydro-1H-inden-1-yloxy)phenyl)-4-fluoroisoxazol-3-ol (Example 9);

5-(4-(2,3-dihydro-1H-inden-1-yloxy)phenyl)-4-methylisoxazol-3-ol (Example 10);

5-(4-(4-chloro-2,3-dihydro-1H-inden-1-yloxy)phenyl)isoxazol-3-ol (Example 11);

5-(4-(4-cyano-2,3-dihydro-1H-inden-1-yloxy)phenyl)isoxazol-3-ol (Example 12);

5-(4-(5-chloro-2,3-dihydro-1H-inden-1-yloxy)phenyl)isoxazol-3-ol (Example 13);

5-(4-(5-bromo-2,3-dihydro-1H-inden-1-yloxy)phenyl)isoxazol-3-ol (Example 14);

5-(4-(6-chloro-2,3-dihydro-1H-inden-1-yloxy)phenyl)isoxazol-3-ol (Example 15);

5-(4-(7-chloro-2,3-dihydro-1H-inden-1-yloxy)phenyl)isoxazol-3-ol (Example 16);

optically-active 5-(4-(5-chloro-2,3-dihydro-1H-inden-1-yloxy)phenyl)isoxazol-3-ol (A) (Example 17);

optically-active 5-(4-(5-chloro-2,3-dihydro-1H-inden-1-yloxy)phenyl)isoxazol-3-ol (B) (Example 18);

5-(4-(4,5-dichloro-2,3-dihydro-1H-inden-1-yloxy)phenyl)isoxazol-3-ol (Example 19);

5-(4-(2,3-dihydro-4-(2-methoxyphenyl)-1H-inden-1-yloxy)phenyl)isoxazol-3-ol (Example 20);

5-(4-(2,3-dihydro-4-(3-methoxyphenyl)-1H-inden-1-yloxy)phenyl)isoxazol-3-ol (Example 21);

5-(4-(2,3-dihydro-4-(4-methoxyphenyl)-1H-inden-1-yloxy)phenyl)isoxazol-3-ol (Example 22);

5-(4-(2,3-dihydro-4-(2-methoxypyridin-3-yl)-1H-inden-1-yloxy)phenyl)isoxazol-3-ol (Example 23);

5-(4-(4-(6-(3-hydroxy-3-methylbutoxy)-2,4-dimethylpyridin-3-yl)-2,3-dihydro-1H-inden-1-yloxy)phenyl)isoxazol-3-ol (D) (Example 24);

5-(4-(4-(6-(3-hydroxy-3-methylbutoxy)-2,4-dimethylpyridin-3-yl)-2,3-dihydro-1H-inden-1-yloxy)phenyl)isoxazol-3-ol (C) (Example 25);

5-(4-(2,3-dihydro-4-phenoxy-1H-inden-1-yloxy)phenyl)isoxazol-3-ol (Example 26);

5-(4-(2,3-dihydro-4-(4-methoxyphenoxy-1H-inden-1-yloxy)phenyl)isoxazol-3-ol (Example 27);

5-(4-(4-benzyloxy-2,3-dihydro-1H-inden-1-yloxy)phenyl)isoxazol-3-ol (Example 28);

5-(4-(2,3-dihydro-4-(2-trifluoromethyl)benzyloxy)-1H-inden-1-yloxy)phenyl)isoxazol-3-ol (Example 29);

5-(4-(4-benzyl-2,3-dihydro-1H-inden-1-yloxy)phenyl)isoxazol-3-ol (Example 30);

5-(4-(5-chloro-2,3-dihydro-1H-inden-1-ylamino)phenyl)isoxazol-3-ol (Example 31);

5-(3-(2,3-dihydro-1H-inden-1-yloxy)phenyl)isoxazol-3-ol (Example 32);

5-(4-(2,3-dihydro-4-(pyrimidin-5-yl)-1H-inden-1-yloxy)phenyl)isoxazol-3-ol (Example 33);

5-(4-(2,3-dihydro-4-(1,4-benzodioxan-6-yl)-1H-inden-1-yloxy)phenyl)isoxazol-3-ol (Example 34);

5-(4-(2,3-dihydro-4-(1H-indol-6-yl)-1H-inden-1-yloxy)phenyl)isoxazol-3-ol (Example 35);

5-[4-[[4-[4-[(3R)-3-hydroxybutoxy]-2,6-dimethylphenyl]-2,3-dihydro-1H-inden-1-yl]oxy]phenyl]-1,2-oxazol-3-ol (Example 36); and 5-[4-[[4-[4-(3-hydroxy-3-methylbutoxy)-2,6-dimethylphenyl]-2,3-dihydro-1H-inden-1-yl]oxy]phenyl]-1,2-oxazol-3-ol (Example 37);

and salts of these compounds, solvates of the compounds or the salts, and isomers of the compounds, the salts, or the solvates.

[2] A second aspect of the present invention is a pharmaceutical composition, characterized by containing as an active ingredient, at least one of the compounds of Formulae (I), (Ia), (Ia-A), (Ia-B), (Ib), (Ib-A), or (Ib-B), a pharmaceutically acceptable salt of the compound, and a pharmaceutically acceptable solvate of the compound or the salt.

[3] A third aspect of the present invention is a prophylactic agent and/or a therapeutic agent for a GPR40-involving disease, characterized by containing as an active ingredient, at least one of the compounds of Formulae (I), (Ia), (Ia-A), (Ia-B), (Ib), (Ib-A), or (Ib-B), a pharmaceutically acceptable salt of the compound, and a pharmaceutically acceptable solvate of the compound or the salt.

[3-1] Specifically, a prophylactic agent and/or a therapeutic agent for each disease of diabetes [more specifically, any one of or all of Type 1 diabetes (insulin-dependent diabetes), Type 2 diabetes (non-insulin-dependent diabetes), and borderline type diabetes (impaired glucose tolerance (IGT) and/or impaired fasting glycemia (IFG))], obesity, and adiposity, characterized by containing as an active ingredient, at least one of the compounds of Formulae (I), (Ia), (Ia-A), (Ia-B), (Ib), (Ib-A), or (Ib-B), a pharmaceutically acceptable salt of the compound, and a pharmaceutically acceptable solvate of the compound or the salt. An inhibitor of Type 2 diabetes in the impaired glucose tolerance is also included in examples of the above prophylactic agent and therapeutic agent.

Here, in relationship between the blood glucose level and the disease, the diabetes is characterized by exhibiting a fasting blood glucose level of 126 mg/dL or more, or a casual blood glucose level or a 2 hours value of the 75 g oral glucose tolerance test (OGTT) of 200 mg/dL or more. The borderline type diabetes (called also as glucose tolerance disorders) refers to an impaired fasting glycemia (IFG) in which the fasting blood glucose level is 110 mg/dL or more and less than 126 mg/dL and/or an impaired glucose tolerance (IGT) in which a 2 hours value of the 75 g OGTT is 140 mg/dL or more and less than 200 mg/dL.

The insulin resistance refers to a pathological condition in which insulin becomes unable to lower the blood glucose level in the organism and is evaluated by a quantitative glucose clamp technique or HOMA-IR in clinical practice. It is known that the insulin resistance causes a hyperinsulinemia and becomes a risk of a hypertension and a coronary artery disease.

The "adiposity" is defined by the Japan Society for the Study of Obesity as "a pathological condition requiring medically a weight reduction in the case where an obesity-derived or -related health impairment is combined or such a combination is expected". The "obesity" defined here is evaluated by measuring BMI (body mass index, $kg/m^2$). Generally, a body having a BMI of 25 or more is diagnosed as obesity. Examples of the result of the therapy include the reduction of BMI.

[4] A fourth aspect of the present invention is an insulin secretagogues, characterized by containing as an active ingredient, at least one of the compounds of Formulae (I), (Ia), (Ia-A), (Ia-B), (Ib), (Ib-A), or (Ib-B), a pharmaceutically acceptable salt of the compound, and a pharmaceutically acceptable solvate of the compound or the salt.

[5] A fifth aspect of the present invention is a GPR40 activating agent containing one or more of the compounds of Formulae (I), (Ia), (Ia-A), (Ia-B), (Ib), (Ib-A), or (Ib-B), a pharmaceutically acceptable salt of the compound, and a pharmaceutically acceptable solvate of the compound or the salt.

In the second to fifth aspects and preferred aspects thereof, more preferred substituents and a combination thereof in Formulae (I), (Ia), (Ia-A), (Ia-B), (Ib), (Ib-A), or (Ib-B) are according to descriptions described in the first aspect.

In each aspect as described in [1] to [5] of the present invention, it is preferred to use a compound having a $EC_{50}$ value of preferably, 3 µM or less, more preferably, 1 µM or less, further preferably, 300 nM or less, and most preferably, 100 nM or less, when the GPR40 agonist action is measured by a method accordingly selected (for example, the below described pharmacological test example 1 (an agonist action on relative to GPR40 of human origin)).

In the above aspects of the present invention, the "therapeutic agent" is not only for treating diseases or symptoms, but also for improving diseases or symptoms.

In all of the above aspects, when the term "compound" is used, the compound refers also to a "pharmaceutically acceptable salt of the compound". In addition, there is the case where the compound of the present invention has an asymmetric carbon, and thus, the compound of the present invention includes a mixture of various stereoisomers such as a geometric isomer, a tautomer, and an optical isomer, and an isolated stereoisomer. The compound of Formula (I) may have an axial asymmetry due to a steric hindrance and an isomer caused by the axial asymmetry (axial chirality) is also included in the compound of Formula (I). The isolation and the purification of such stereoisomers can be performed by a person skilled in the art by an ordinary technique through an optical resolution or an asymmetric synthesis using a preferential crystallization or a column chromatography.

The compound of Formulae (I), (Ia), (Ia-A), (Ia-B), (Ib), (Ib-A), or (Ib-B) of the present invention may form an acid addition salt or a salt with a base depending on the type of the substituent. Such salt is not particularly limited so long as the salt is a pharmaceutically acceptable salt. Specific examples thereof include acid addition salts with: mineral acids such as hydrochloric acid, hydrobromic acid, hydriodic acid, sulfuric acid, nitric acid, and phosphoric acid; organic carboxylic acids, for example, an aliphatic monocarboxylic acid such as formic acid, acetic acid, propionic acid, butyric acid, valeric acid, enanthic acid, capric acid, myristic acid, palmitic acid, stearic acid, lactic acid, sorbic acid, and mandelic acid, an aromatic monocarboxylic acid such as benzoic acid and salicylic acid, an aliphatic dicarboxylic acid such as oxalic acid, malonic acid, succinic acid, fumaric acid, maleic acid, malic acid, and tartaric acid, an aliphatic tricarboxylic acid such as citric acid, cinnamic acid, glycolic acid, pyruvic acid, oxylic acid, salicylic acid, and N-acetylcysteine; organic sulfonic acids, for example, an aliphatic sulfonic acid such as methanesulfonic acid, ethanesulfonic acid, and 2-hydroxyethanesulfonic acid, and an aromatic sulfonic acid such as benzenesulfonic acid and p-toluenesulfonic acid; and acidic amino acids such as aspartic acid and glutamic acid, salts (including besides mono salts, disodium salts and dipotassium salts) with a metal, for example, alkali metals such as lithium, sodium, potassium, and cesium, and alkaline earth metals such as magnesium, calcium, and barium, salts with a metal such as aluminum, iron, copper, nickel, cobalt, and zinc, salts with an organic base such as methylamine, ethylamine, tert-butylamine, tert-octylamine, diethylamine, triethylamine, cyclohexylamine, dibenzylamine, ethanolamine, diethanolamine, triethanolamine, piperidine, morpholine, pyridine, lysine, arginine, ornithine, ethylenediamine, N-methylglucamine, glucosamine, a phenylglycine alkyl ester, and guanidine, and salts with glycine, histidine, choline, and ammonium.

These salts can be obtained by an ordinary method including, for example, mixing an equivalent of the compound of the present invention with a solution containing a desired acid, base, or the like, and collecting a desired salt by filtration or distillation-off of a solvent. The compound of the present invention or a salt of the compound can form a solvate with a solvent such as water, ethanol, and glycerol.

The salt of the compound of the present invention includes a mono-salt and a di-salt. The compound of the present invention can form both of an acid addition salt and a salt with a base simultaneously depending on the type of the substituent in the side chains. Further, the present invention encompasses also hydrates, various pharmaceutically acceptable solvates, and crystal polymorphs of the compound of Formulae (I), (Ia), (Ia-A), (Ia-B), (Ib), (Ib-A), or (Ib-B) of the present invention. Here, needless to say, the present invention is not limited to the compounds described in Examples below and encompasses all of the compounds of Formulae (I), (Ia), (Ia-A), (Ia-B), (Ib), (Ib-A), or (Ib-B) of the present invention and pharmaceutically acceptable salts of the compounds.

The salt of the compound of the present invention includes the case in which a 3-hydroxy-isoxazolyl group is the following Formula (where M is alkali metals such as the lithium, sodium, potassium, and cesium.

[Method for Producing the Compound of the Present Invention]

Methods for producing the compound of Formula (I) of the present invention will be described below.

The compound of Formula (I) of the present invention, a salt of the compound, and a solvate of the compound or the salt can be produced by a combination of commonly known chemical production methods. Typical production methods will be described below.

In each Formula in the production methods below, each definition of $R^1$, $R^2$, $R^3$, $R^4$, $R^5$, $R^6$, $R^7$, $R^8$, $R^9$, $R^{10}$, $R^{11}$, $R^{12}$, $R^a$, $R^b$, $R^c$, $R^d$, $R^e$, $R^f$, X, V, T, f, g, p, q, q1, r, r1, s, j, k, ring A, ring A', ring A", and ring B is the same as each definition in Formula (I), Formula (Ia), Formula (Ib) described in the first aspect and Aspects 1a and 1b above unless otherwise specified.

In the production methods, the definition of R' is a lower alkyl group such as a methyl group and an ethyl group unless otherwise specified.

In the production methods, the definition of Y and Z is a hydroxy group, halogen, or a sulfonyloxy group such as a methanesulfonyloxy group, a p-toluenesulfonyloxy group, and a trifluoromethanesulfonyloxy group unless otherwise specified.

In the production methods, for the definitions of $W^1$ and $W^2$, $W^2$ is boronic acid, a boronic ester, or a trifluoroborate salt when $W^1$ is a hydroxy group, a halogen atom, or a trifluoromethanesulfonyloxy group, and $W^2$ is a hydroxy group, a halogen atom, or a trifluoromethanesulfonyloxy group when $W^1$ is boronic acid, a boronic ester, or a trifluoroborate salt unless otherwise specified.

In the production methods, the definition of P' is a protective group for a hydroxy group (—OH), a thiol group (—SH), or an imino group (—NH—) unless otherwise specified. Examples of the protective group for a hydroxy group include an alkoxyalkyl group such as a methoxymethyl group, a methoxyethoxymethyl group, and a tetrahydropyranyl group; an arylmethyl group such as a benzyl group and a triphenylmethyl group; a silyl group such as a triethylsilyl group and a t-butyldimethylsilyl group; an alkanoyl group such as an acetyl group; an aroyl group such as a benzoyl group; an alkylcarbonyl group such as a methoxycarbonyl group; and an arylmethylcarbonyl group such as a benzyloxycarbonyl group. Examples of the protective group for a thiol group include an arylmethyl group such as a benzyl group and a triphenylmethyl group; an alkanoyl group such as an acetyl group and a pivaloyl group; and an aroyl group such as a benzoyl group. Examples of the protective group for an imino group include an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; an arylmethyl group such as a benzyl group and a triphenylmethyl group; and an aroyl group such as a benzoyl group.

In the production methods, the definition of $P^2$ is a protective group for a phenolic hydroxy group unless otherwise specified. Examples of the protective group include an alkoxyalkyl group such as a methoxymethyl group, a methoxyethoxymethyl group, and a tetrahydropyranyl group; an arylmethyl group such as a benzyl group; a silyl group such as a trimethylsilyl group and a t-butyldimethylsilyl group; an alkanoyl group such as an acetyl group and a pivaloyl group; an aroyl group such as a benzoyl group; an alkylcarbonyl group such as a methoxycarbonyl group; and an arylmethylcarbonyl group such as a benzyloxycarbonyl group.

Deprotection methods of such protective groups are different depending on the chemical properties of a protected reactive group (a hydroxy group, a thiol group, or an imino group) and an employed protective group. For example, an acyl-type protective group such as an alkanoyl group, an alkoxycarbonyl group, and an aroyl group can be hydrolyzed using a suitable base such as an alkali metal hydroxide including lithium hydroxide, sodium hydroxide, and potassium hydroxide for the deprotection. An alkoxyalkyl-type protective group such as a methoxymethyl group, a methoxyethoxymethyl group, and a tetrahydropyranyl group, a substituted methoxycarbonyl-type protective group such as a t-butoxycarbonyl group and a para-methoxybenzyloxycarbonyl group, and a silyl-type protective group such as a triethylsilyl group and a t-butyldimethylsilyl group can be removed using a suitable acid such as acetic acid, hydrochloric acid, hydrobromic acid, sulfuric acid, phosphoric acid, trifluoroacetic acid, and trifluoromethanesulfonic acid or a combination of them. The silyl-type protective group can also be removed using a suitable fluorine ion ($F^-$) generating reagent such as tetrabutylammonium fluoride and hydrogen fluoride. An arylmethoxycarbonyl group such as a benzyloxycarbonyl group, a para-methoxybenzyloxycarbonyl group, and a para-nitrobenzyloxycarbonyl group and an arylmethyl group such as a benzyl group can be removed by hydrogenolysis using a palladium carbon catalyst. A benzyl group can be removed by Birch reduction using metallic sodium in liquid ammonia. A triphenylmethyl group can be removed using a suitable acid such as acetic acid, hydrochloric acid, hydrobromic acid, sulfuric acid, phosphoric acid, trifluoroacetic acid, and trifluoromethanesulfonic acid or a combination of them. It can also be removed by Birch reduction using metallic sodium in liquid ammonia and removed by hydrogenolysis using a palladium carbon catalyst.

During the production of the compound of Formula (I) of the present invention, when it has a reactive group such as a hydroxy group, an amino group, and a carboxy group, such group may be properly protected in any reaction step, and the protective group may be removed in a suitable step. Methods for introducing and removing such protective groups are properly employed depending on the type of a group to be protected or a protective group. For example, such introduction and removal can be performed by methods described in [Protective Groups in Organic Synthesis, edited by Greene et al, the third edition (1999), John Wiley & Sons].

In each production step below, when X is a sulfur atom, the sulfur atom can be oxidized after an intermediate is properly selected or other functional groups are properly protected depending on the intermediate or the functional groups in each step. In accordance with methods known in literatures, for example, the method described in [*Jikken Kagaku Koza* (Experimental Chemistry Course), the fourth edition, vol. 20, Organic Synthesis V, Oxidation Reaction, pp. 276-280 (1992), Maruzen Co., Ltd.], the oxide can be produced by reacting the intermediate, in the presence of the compound to be reacted, in the presence of a peracid or a peroxide such as hydrogen peroxide water, m-chloroperbenzoic acid (MCPBA), peracetic acid, trifluoroperacetic acid, Oxone® (DuPont), and tert-butylhydroperoxide (TBHP), in a reaction inert solvent including a halogenated solvent such as dichloromethane and chloroform, an aromatic hydrocarbon solvent such as toluene and benzene, and a polar solvent such as acetonitrile, methanol, acetone, and water, at a temperature from 0° C. to a reflux temperature of the solvent. In the oxidation reaction, selection of an oxidizing agent and suitable selection of equivalent weight of a reagent, a reaction temperature, a reaction time, a solvent, and the like can produce a sulfoxide and a sulfone separately. Such sulfoxide and sulfone can be separated by common techniques such as column chromatography.

Required starting materials are commercially available or can be easily obtained from commercial products by usual production methods in organic chemistry.

Reaction conditions in the production methods are as follows unless otherwise specified. The reaction temperature is in a range from −78° C. to the reflux temperature of a solvent, and the reaction time is a time sufficient for a reaction. Examples of the reaction inert solvent include, but are not limited to, an aromatic hydrocarbon solvent such as toluene and benzene; a polar solvent such as water, methanol, N,N-dimethylformamide, dimethyl sulfoxide, and 1,3-dimethyl-2-imidazolidinone; a basic solvent such as triethylamine and pyridine; a halogenated solvent such as chloroform, methylene chloride, and 1,2-dichloroethane; an ether solvent such as diethyl ether, tetrahydrofuran, and dioxane; and a mixed solvent of them. Such solvents are properly selected depending on reaction conditions. Examples of the base include, but are not limited to, an inorganic base such as potassium carbonate, cesium carbonate, sodium hydroxide, potassium hydroxide, and sodium hydride; and an organic base such as triethylamine, pyridine, N,N-dialkylaniline, and lithium diisopropylamide. Examples of the acid include, but are not limited to, a mineral acid such as hydrochloric acid and sulfuric acid, and an organic acid such as methanesulfonic acid and p-toluenesulfonic acid.

Hereinafter, production methods will be described, but the present invention is not limited to these methods.

(1) Typical methods for producing the compound of Formula (I) of the present invention will be described below.

<Production Method A>
<When $R^2$=H in Formula (I)>

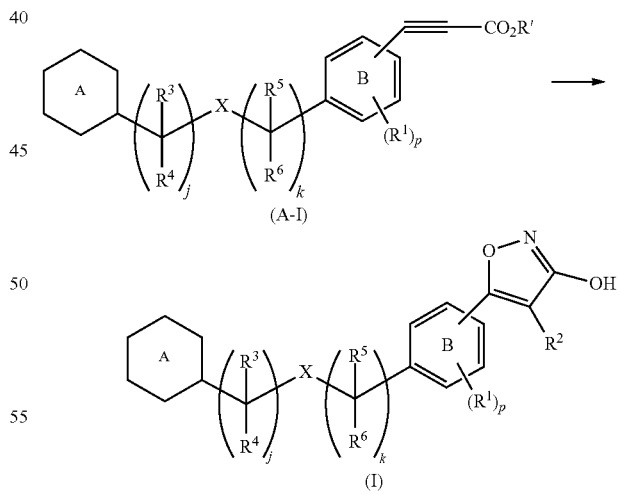

A compound of Formula (A-I) is subjected to isoxazole ring formation reaction. In accordance with methods known in literatures, for example, the methods described in [Journal of Medicinal Chemistry, vol. 45 (9), pp. 1785-1798, (2002)] and [WO 2008/066131 pamphlet, Examples 1], the compound of Formula (I) can be produced by reacting the compound of Formula (A-I) with an aqueous solution or a hydrochloride of hydroxyamine, or the like in the presence of a base such as sodium hydroxide, potassium hydroxide, and lithium hydroxide in a reaction inert solvent including an alcoholic solvent such as methanol, ethanol, and 2-propanol, and tetrahydrofuran, ethyl acetate, dichloromethane or a mixed solvent of them at a temperature from 0° C. to a reflux temperature of the solvent.

<Production Method B>
<When R²=H in Formula (I)>

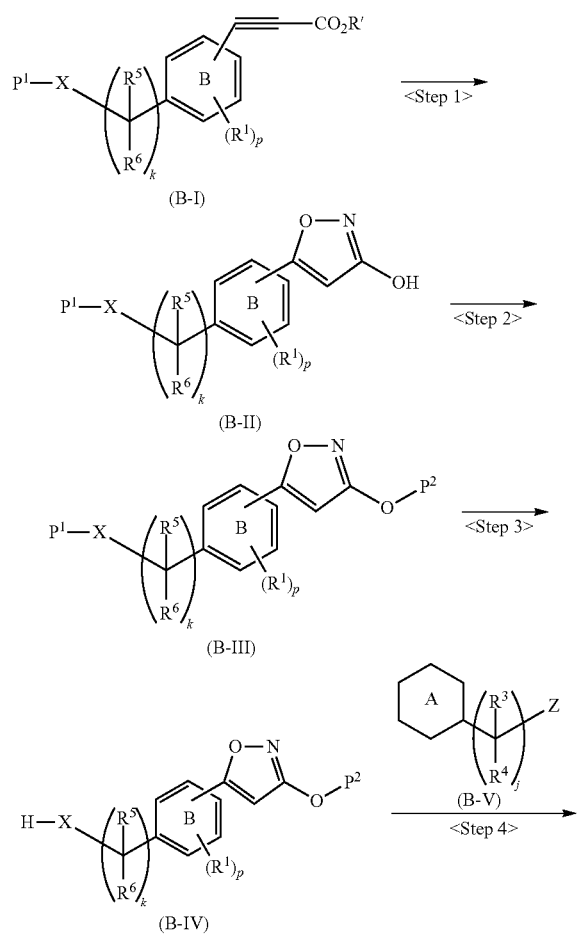

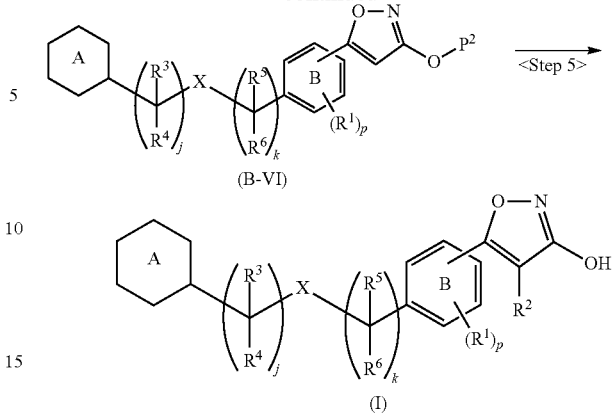

<Step 1>
A compound of Formula (B-I) is subjected to isoxazole ring formation reaction. A compound of Formula (B-II) can be produced by reacting the compound of Formula (B-I) in a similar manner to that in (Production Method A).

<Step 2>
The compound of Formula (B-II) is protected with a protective group P². A compound of Formula (B-III) can be produced by reacting the compound of Formula (B-II) with the protective group P² by a method suitable for the protective group.

<Step 3>
The protective group P¹ in the compound of Formula (B-III) is deprotected. A compound of Formula (B-IV) can be produced by deprotecting the protective group P¹ in the compound of Formula (B-III) by a method suitable for the protective group.

<Step 4>
The compound of Formula (B-IV) is subjected to alkylation with a compound of Formula (B-V).

<Step 5>
The protective group P² in a compound of Formula (B-VI) is deprotected. The compound of Formula (I) can be produced by deprotecting the protective group P² in the compound of Formula (B-VI) by a method suitable for the protective group.

(1a) Methods for producing the compound of Formula (Ia) of the present invention will be described below in detail.

<Production Method Aa>
<When R²=H in Formula (Ia)>

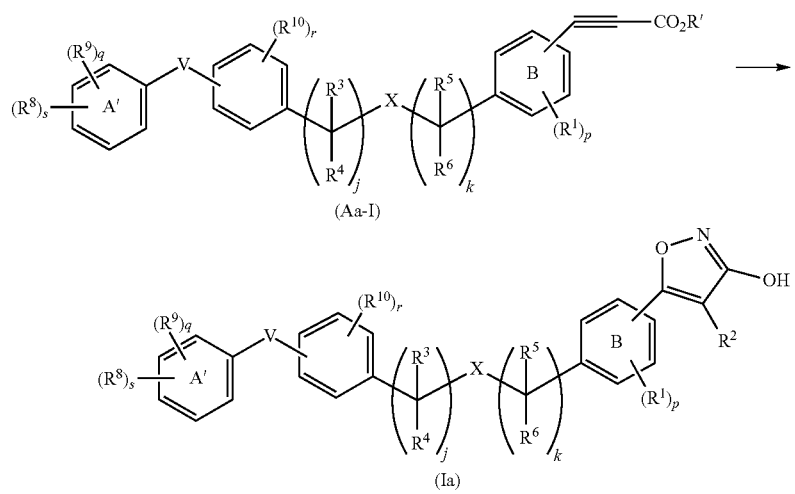

A compound of Formula (Aa-I) is subjected to isoxazole ring formation reaction. In accordance with methods known in literatures, for example, the methods described in [Journal of Medicinal Chemistry, vol. 45 (9), pp. 1785-1798, (2002)] and [WO 2008/066131 pamphlet, Examples 1], the compound of Formula (Ia) can be produced by reacting the compound of Formula (Aa-I) with an aqueous solution or a hydrochloride of hydroxyamine, or the like in the presence of a base such as sodium hydroxide, potassium hydroxide, and lithium hydroxide in a reaction inert solvent including an alcoholic solvent such as methanol, ethanol, and 2-propanol, and tetrahydrofuran, ethyl acetate, and dichloromethane or a mixed solvent of them at a temperature from 0° C. to a reflux temperature of the solvent.

<Production Method Ba>
<When $R^2$=H in Formula (Ia)>

<Step 1>
A compound of Formula (Ba-I) is subjected to isoxazole ring formation reaction. A compound of Formula (Ba-II) can be produced by reacting the compound of Formula (Ba-I) (it is known in the art or can be easily produced from a known compound as described later in (Production Method Ea), and, for example, is a compound that is obtained by properly protecting a compound in Reference Example 3 or a compound in Step 1 in Example 32 described later) in a similar manner to that in (Production Method Aa).

<Step 2>
The compound of Formula (Ba-II) is protected with a protective group $P^2$. A compound of Formula (Ba-III) can be produced by reacting the compound of Formula (Ba-II) with the protective group $P^2$ by a method suitable for the protective group.

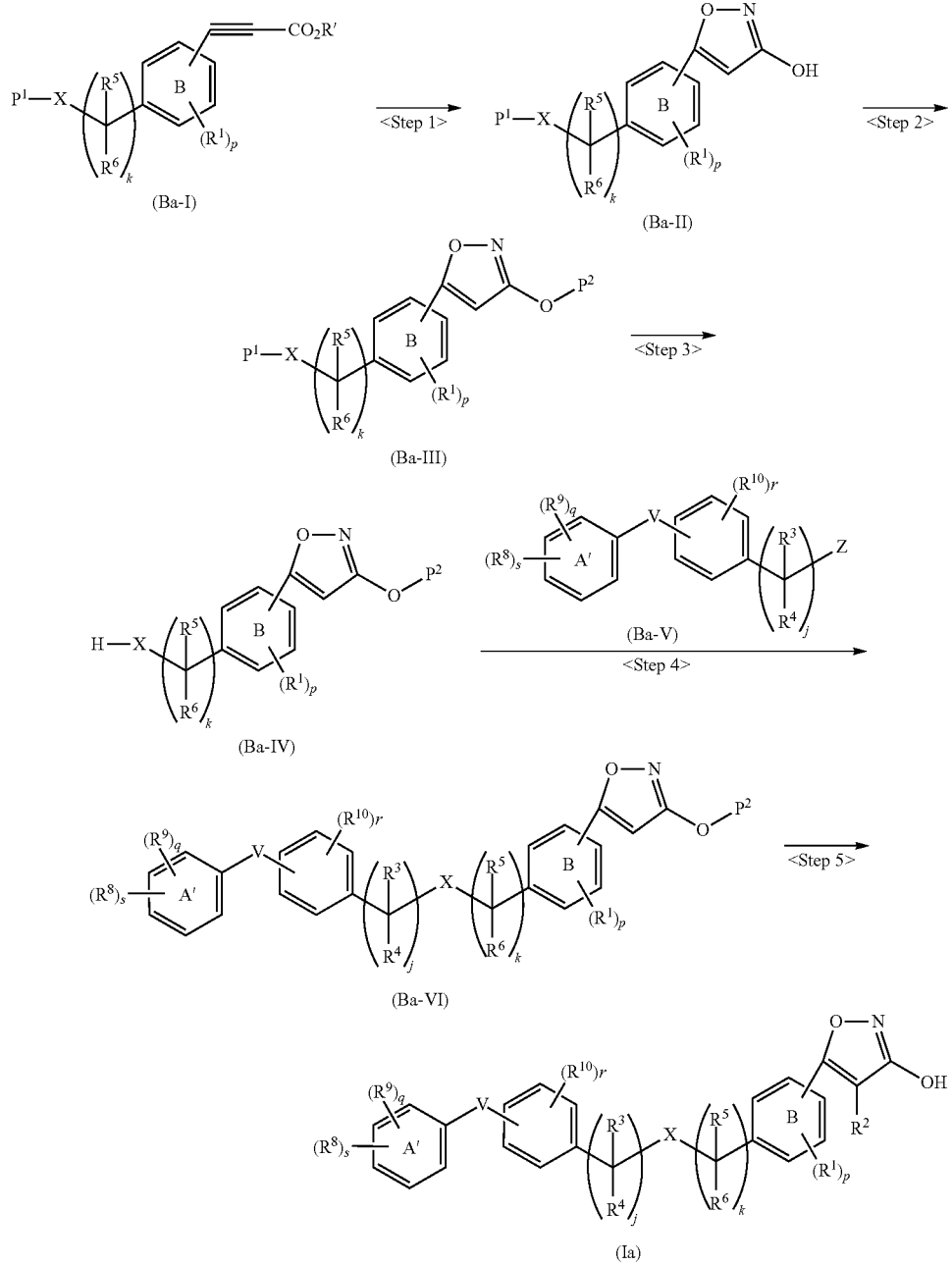

<Step 3>

The protective group P¹ in the compound of Formula (Ba-III) is deprotected. A compound of Formula (Ba-IV) can be produced by deprotecting the protective group P¹ in the compound of Formula (Ba-III) by a method suitable for the protective group.

<Step 4>

The compound of Formula (Ba-IV) is subjected to alkylation with a compound of Formula (Ba-V).

<When Z≠Hydroxy Group>

In accordance with methods known in literatures, for example, the methods described in [*Jikken Kagaku Koza* (Experimental Chemistry Course), the fourth edition, vol. 20, Organic Synthesis II, Alcohol and Amine, pp. 187-200 and 284-292 (1992), Maruzen Co., Ltd.] and [*Jikken Kagaku Koza* (Experimental Chemistry Course), the fourth edition, vol. 20, Organic Synthesis VI, Hetero Element- or Main Group Metal Element-Containing Compound, pp. 319-350 (1992), Maruzen Co., Ltd.], a compound of Formula (Ba-VI) can be produced by alkylation of the compound of Formula (Ba-IV) in the presence of the compound of Formula (Ba-V) in the presence or absence of a base such as triethylamine, pyridine, sodium hydride, sodium hydroxide, and potassium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from 0° C. to a reflux temperature of the solvent.

<When Z=Hydroxy Group, X≠—NR⁷—, and k=0>

In accordance with methods known in literatures, for example, the method described in [Journal of Medicinal Chemistry, vol. 51 (23), pp. 7640-7644 (2008)], a compound of Formula (Ba-VI) can be produced by Mitsunobu reaction of the compound of Formula (Ba-IV) in the presence of the compound of Formula (Ba-V) in the presence of an organophosphorus compound such as triphenylphosphine and an azo compound such as azodicarboxylic acid ester and azodicarboxylic amide in a reaction inert solvent such as a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from 0° C. to a reflux temperature of the solvent.

The compound of Formula (Ba-V) used in this step can be produced from a corresponding compound in accordance with methods known in literatures, for example, the methods described in [WO 2005/063729 pamphlet, Reference Examples 2 and 3 and the like], [WO 2008/001931 pamphlet, Reference Examples 15-19, and the like], and [WO 2009/054423 pamphlet, Production Examples 12, 24, and 37 and the like].

<Step 5>

The protective group P² in the compound of Formula (Ba-VI) is deprotected. The compound of Formula (Ia) can be produced by deprotecting the protective group P² in the compound of Formula (Ba-VI) by a method suitable for the protective group.

<Production Method Ca>

<When R²≠Halogen Atom in Formula (Ia)>

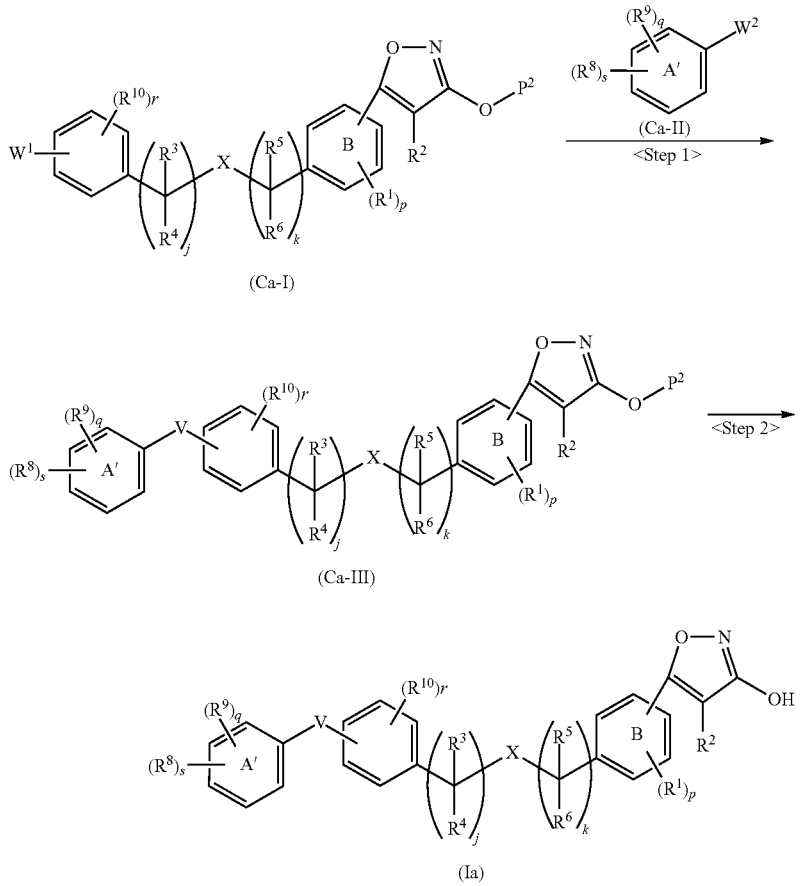

<Step 1>

A compound of Formula (Ca-I) is subjected to substitution reaction on the benzene ring.

<When V=Single Bond>

In accordance with methods known in literatures, for example, the method described in [Journal of Medicinal Chemistry, vol. 48 (20), pp. 6326-6339 (2005)], a compound of Formula (Ca-III) can be produced by reacting the compound of Formula (Ca-I) in the presence of a compound of Formula (Ca-II) in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, tris(o-tolyl)phosphine, and 2-dicyclohexylphosphino-2',6'-dimethoxybiphenyl, and an organic or inorganic base such as triethylamine, N,N-diisopropylethylamine, and potassium phosphate or in the presence of tetramethylammonium chloride, tetrabutylammonium chloride, or the like in place of the phosphine reagent, using a reaction inert solvent such as toluene, xylene, N,N-dimethylformamide, and N,N-dimethylacetamide or a mixed solvent of them at a temperature from 0° C. to a reflux temperature of the solvent.

<When V=Oxygen Atom>

In accordance with methods known in literatures, for example, the method described in [Tetrahedron Letters, vol. 44, pp. 3863-3865 (2003)], a compound of Formula (Ca-III) can be produced by reacting the compound of Formula (Ca-I) in the presence of the compound of Formula (Ca-II) in the presence of a copper catalyst such as copper (II) acetate and copper (II) trifluoroacetate and a base such as triethylamine, N,N-diisopropylethylamine, and pyridine, using a reaction inert solvent such as dichloromethane, 1,4-dioxane, tetrahydrofuran, and N,N-dimethylformamide or a mixed solvent of them at a temperature from 0° C. to a reflux temperature of the solvent.

In accordance with methods known in literatures, for example, the methods described in [WO 2005/063729 pamphlet, Reference Example 1 and the like], [WO 2008/001931 pamphlet, Reference Examples 1 and 54, and the like], and [WO 2009/054423 pamphlet, Production Example 37 and the like], the compound of Formula (Ca-II) used in this step can be produced from a corresponding compound.

<Step 2>

The protective group $P^2$ in the compound of Formula (Ca-III) is deprotected. The compound of Formula (Ia) can be produced by reacting the compound of Formula (Ca-III) in a similar manner to that in <Step 5> in (Production Method Ba).

<Production Method Da>

<When $R^2 \neq$ Hydrogen Atom in Formula (Ia)>

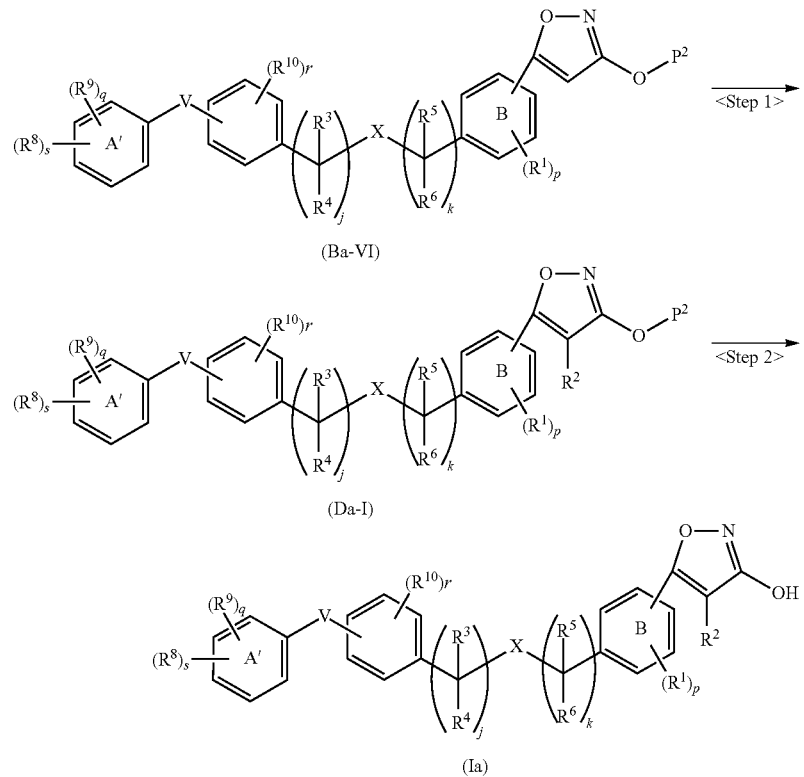

<Step 1>

The compound of Formula (Ba-VI) is subjected to substitution reaction on the isoxazole ring.

<When $R^2$=Halogen Atom, Alkyl Group>

In accordance with methods known in literatures, for example, the method described in [WO 1997/031906 pamphlet, Example 68], a compound of Formula (Da-I) can be produced by reacting the compound of Formula (Ba-VI) in the presence of a corresponding halogenating agent such as N-fluorodibenzenesulfonimide, N-chlorosuccinimide, N-bromosuccinimide, N-iodosuccinimide, and an alkyl halide including iodomethane and iodoethane in the presence of a base such as n-butyllithium, lithium diisopropylamide, lithium bis(trimethylsilyl)amide, sodium bis(trimethylsilyl)amide, and potassium bis(trimethylsilyl)amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from −78° C. to a reflux temperature of the solvent.

<When $R^2$=Cyano Group>

In accordance with methods known in literatures, for example, the method described in [Tetrahedron Letters, vol. 40 (47), pp. 8193-8195 (1999)], a compound of Formula (Da-I) can be produced by reacting the compound of Formula (Da-I) ($R^2$=I, Br) obtained in <When $R^2$=halogen atom> in <Step 1> in the presence of a corresponding cyanating agent such as zinc cyanide and potassium ferrocyanide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, and potassium phosphate or in the presence of tetramethylammonium chloride, tetrabutylammonium chloride, or the like in place of the phosphine reagent, using a reaction inert solvent such as toluene, xylene, N,N-dimethylformamide, and N,N-dimethylacetamide or a mixed solvent of them at a temperature from 0° C. to a reflux temperature of the solvent.

<When $R^2$=Alkenyl Group>

A compound of Formula (Da-I) can be produced by reacting the compound of Formula (Da-I) ($R^2$=I, Br) obtained in <When $R^2$=halogen atom> in <Step 1> in a similar manner to that in <Step 1> in (Production Method Ca).

<When $R^2$=Alkynyl Group>

In accordance with methods known in literatures, for example, the method described in [*Jikken Kagaku Koza* (Experimental Chemistry Course), the fourth edition, vol. 19, Organic Synthesis I, Hydrocarbon and Halogenated Compounds, pp. 318-335 (1992), Maruzen Co., Ltd.], a compound of Formula (Da-I) can be produced by reacting the compound of Formula (Da-I) ($R^2$=I, Br) obtained in <When $R^2$=halogen atom> in <Step 1> in the presence of a corresponding propargyl compound such as 1-propyne and 1-butyne in the presence of copper iodide (I)) or zinc bromide in the presence of a palladium catalyst such as palladium (II) acetate, tetrakis triphenylphosphine palladium, tris(dibenzylideneacetone)dipalladium, and [1,1'-bis(diphenylphosphino)ferrocene] dichloropalladium (II), a phosphine reagent such as triphenylphosphine, tris(tert-butyl)phosphine, and tris(o-tolyl) phosphine, and an organic or inorganic base such as triethylamine, N,N-diisopropylethylamine, potassium phosphate, and potassium carbonate, using a reaction inert solvent such as toluene, xylene, N,N-dimethylformamide, N,N-dimethylacetamide, and N-methylpyrrolidone or a mixed solvent of them at a temperature from 0° C. to a reflux temperature of the solvent.

<Step 2>

The protective group $P^2$ in the compound of Formula (Da-I) is deprotected. The compound of Formula (Ia) can be produced by reacting the compound of Formula (Da-I) in a similar manner to that in <Step 5> in (Production Method Ba).

(2a) Next, methods for producing the compounds of Formula (Aa-I) and Formula (Ba-I) will be described.

<Production Method Ea>

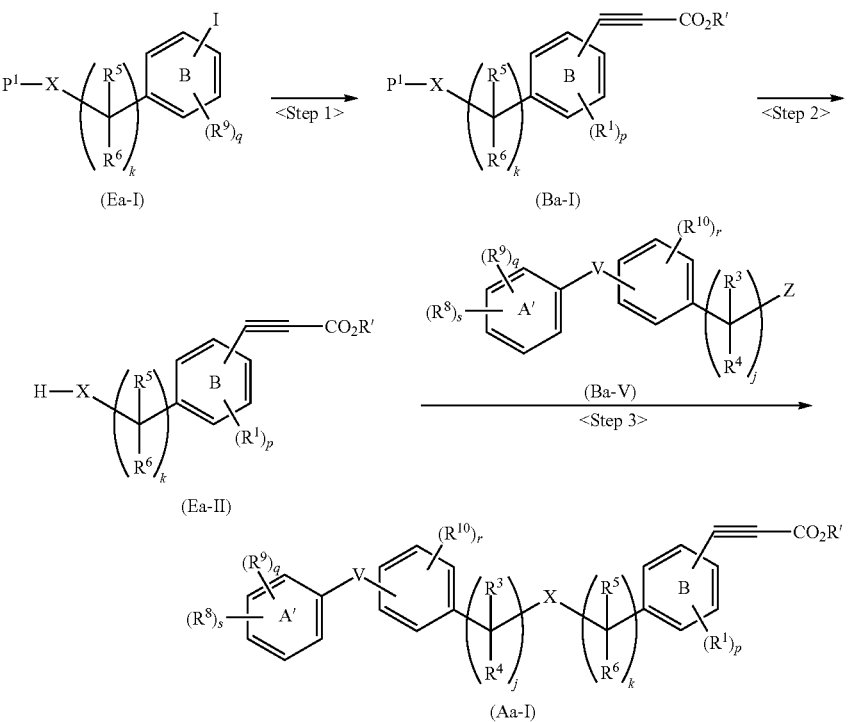

<Step 1>

A compound of Formula (Ea-I) is subjected to alkynylation. In accordance with methods known in literatures, for example, the methods described in [*Jikken Kagaku Kozo* (Experimental Chemistry Course), the fourth edition, vol. 19, Organic Synthesis I, Hydrocarbon and Halogenated Compounds, pp. 318-335 (1992), Maruzen Co., Ltd.] and [WO 2008/066131 pamphlet, Reference Example 1], the compound of Formula (Ba-I) can be produced by reacting the compound of Formula (Ea-I), which is known in the art or can be easily produced from a known compound, in the presence of a corresponding propiolic acid ester such as methyl propiolate and ethyl propiolate and copper oxide (II), using a reaction inert solvent such as toluene, xylene, N,N-dimethylformamide, and N,N-dimethylacetamide or a mixed solvent of them at a temperature from 0° C. to a reflux temperature of the solvent.

Alternatively, the compound of Formula (Ba-I) can be produced by reaction in the presence of an ortho ester of a corresponding propiolic acid such as 3,3,3-triethoxypropyne or a propiolic acid ester such as methyl propiolate and ethyl propiolate in the presence of copper iodide (I) or zinc bromide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, potassium phosphate, and potassium carbonate, using a reaction inert solvent such as toluene, xylene, N,N-dimethylformamide, and N,N-dimethylacetamide or a mixed solvent of them at a temperature from 0° C. to a reflux temperature of the solvent.

<Step 2>

The protective group $P^1$ in the compound of Formula (Ba-I) is deprotected. A compound of Formula (Ea-II) can be produced by reacting the compound of Formula (Ba-I) in a similar manner to that in <Step 3> in (Production Method Ba).

<Step 3>

The compound of Formula (Ea-II) is subjected to alkylation with the compound of Formula (Ba-V). The compound of Formula (Aa-I) can be produced by reacting the compound of Formula (Ea-II) with the compound of Formula (Ba-V) in a similar manner to that in <Step 4> in (Production Method Ba).

The compound of Formula (Aa-I) can also be produced by the following method.

<Production Method Fa>

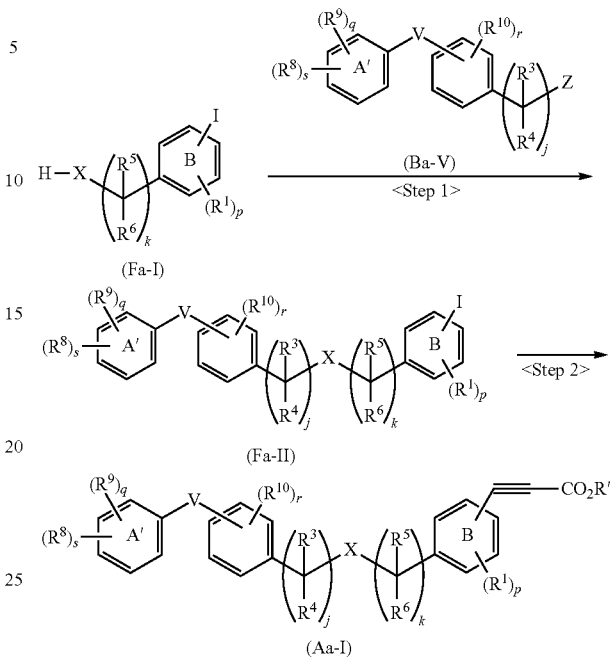

<Step 1>

A compound of Formula (Fa-I) is subjected to alkylation with the compound of Formula (Ba-V). A compound of Formula (Fa-II) can be produced by reacting the compound of Formula (Fa-I), which is known in the art or can be easily produced from a known compound, with the compound of Formula (Ba-V) in a similar manner to that in <Step 4> in (Production Method Ba).

<Step 2>

The compound of Formula (Fa-II) is subjected to alkynylation. The compound of Formula (Aa-I) can be produced by reacting the compound of Formula (Fa-II) in a similar manner to that in <Step 1> in (Production Method Ea).

(3a) Next, a method for producing the compound of Formula (Ca-I) will be described.

<Production Method Ga>

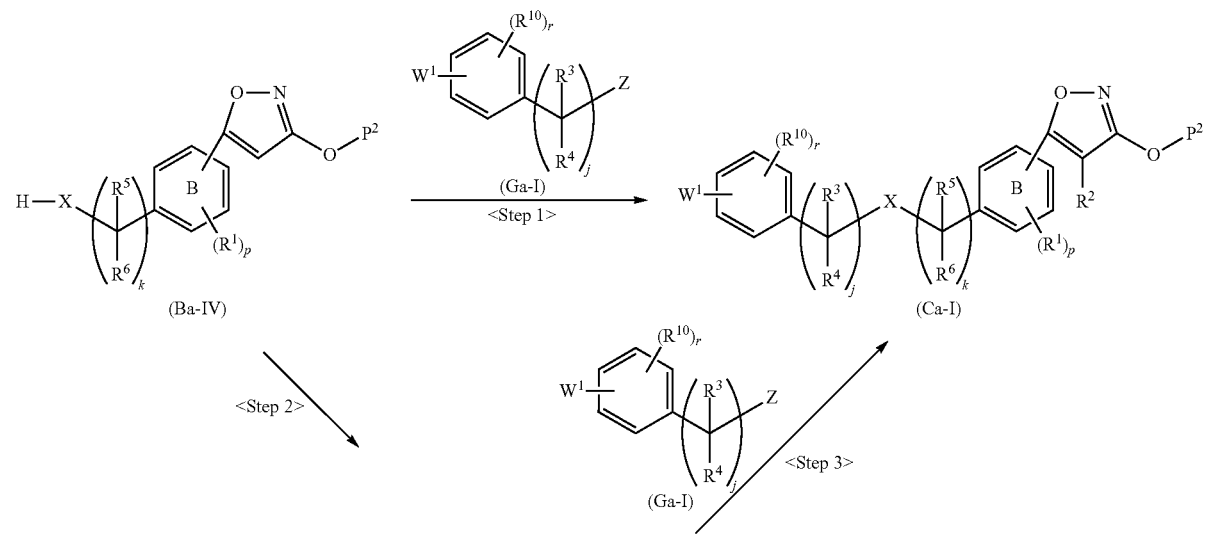

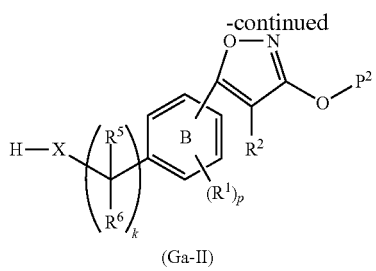
(Ga-II)

<When R²=Hydrogen Atom in Formula (Ia)>
<Step 1>

The compound of Formula (Ba-IV) is subjected to alkylation with a compound of Formula (Ga-I). The compound of Formula (Ca-I) can be produced by reacting the compound of Formula (Ga-I), which is known in the art or can be easily produced from a known compound, with the compound of Formula (Ba-IV) in a similar manner to that in <Step 4> in (Production Method Ba).

<When R²≠Hydrogen Atom in Formula (Ia)>
<Step 2>

The compound of Formula (Ba-IV) is subjected to substitution reaction on the isoxazole ring. A compound of Formula (Ga-II) can be produced by reacting the compound of Formula (Ba-IV) in a similar manner to that in <Step 1> in (Production Method Da).

<Step 3>

The compound of Formula (Ga-II) is subjected to alkylation with the compound of Formula (Ga-I). The compound of Formula (Ca-I) can be produced by reacting the compound of Formula (Ga-II) with the compound of Formula (Ga-I) in a similar manner to that in <Step 4> in (Production Method Ba).

(1b) Methods for producing the compound of Formula (Ib) of the present invention will be described below in detail.

<Production Method Ab>
<When R2=H in Formula (Ib)>

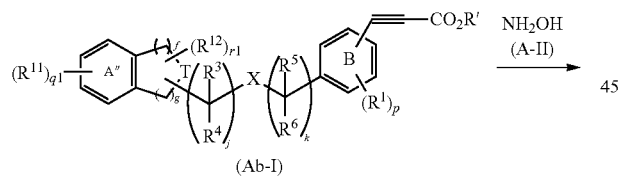
(Ab-I)

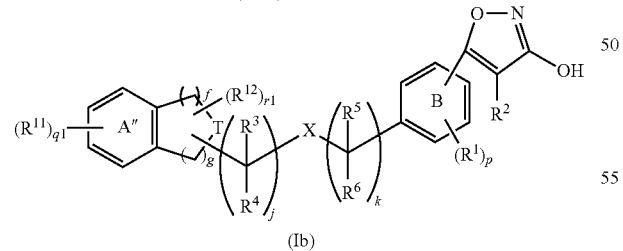
(Ib)

A compound of Formula (Ab-I) is subjected to isoxazole ring formation reaction. In accordance with methods known in literatures, for example, the methods described in [Journal of Medicinal Chemistry, vol. 45 (9), pp. 1785-1798, (2002)] and [WO 2008/066131 pamphlet, Examples 1], the compound of Formula (Ib) can be produced by reacting the compound of Formula (Ab-I) with hydroxylamine (A-II) in the presence of a base such as sodium hydroxide, potassium hydroxide, and lithium hydroxide in a reaction inert solvent including an alcoholic solvent such as methanol, ethanol, and 2-propanol at a temperature from 0 (C to a reflux temperature of the solvent.

<Production Method Bb>
<When R²=H and X=O, S, NR⁷ in Formula (Ib)>

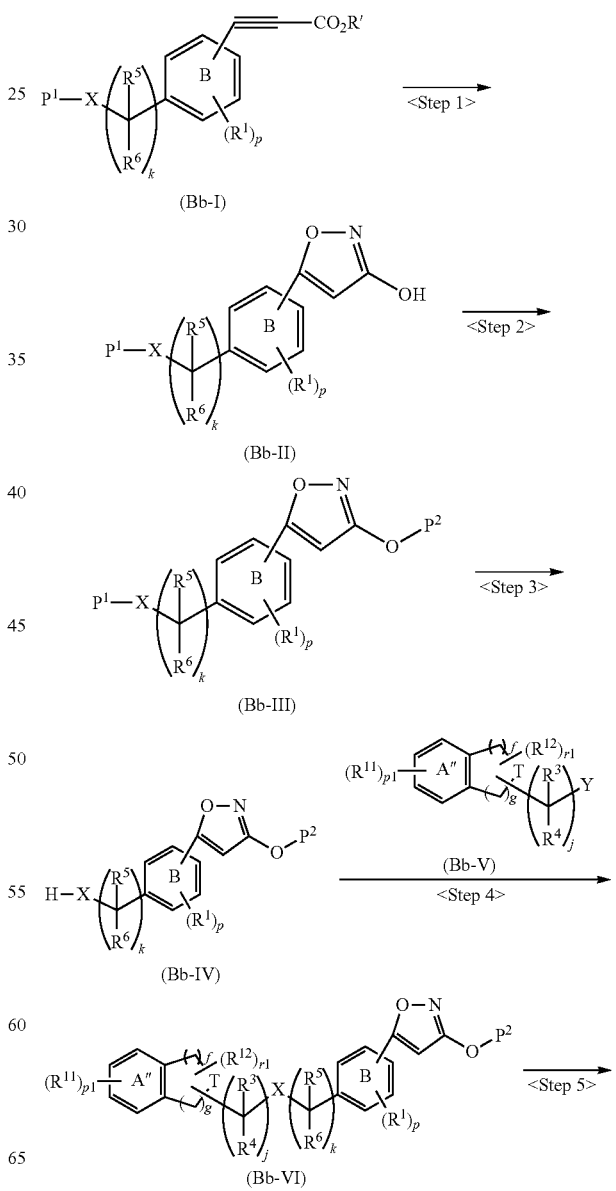

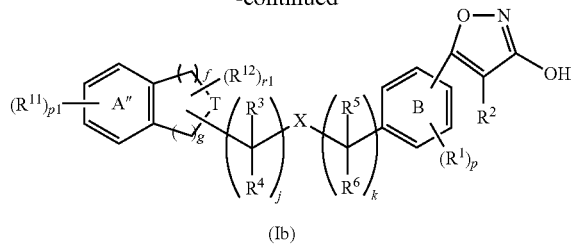

(Ib)

<Step 1>

A compound of Formula (Bb-I) is subjected to isoxazole ring formation reaction. A compound of Formula (Bb-II) can be produced by reacting the compound of Formula (Bb-I) (it is known in the art or can be easily produced from a known compound as described later in (Production Method Eb), and, for example, is a compound that is obtained by properly protecting a compound in Reference Example 3 or a compound in Step 1 in Example 32 described later) in a similar manner to that in (Production Method Ab).

<Step 2>

The compound of Formula (Bb-II) is protected with a protective group $P^2$. A compound of Formula (Bb-III) (for example, a compound in Reference Example 4 described later) can be produced by reacting the compound of Formula (Bb-II) with the protective group $P^2$ by a method suitable for the protective group.

<Step 3>

The protective group $P^1$ in the compound of Formula (Bb-III) is deprotected. A compound of Formula (Bb-IV) can be produced by deprotecting the protective group $P^1$ in the compound of Formula (Bb-III) by a method suitable for the protective group.

<Step 4>

The compound of Formula (Bb-IV) is subjected to alkylation with a compound of Formula (Bb-V).

In accordance with methods known in literatures, for example, the methods described in [*Jikken Kagaku Koza* (Experimental Chemistry Course), the fourth edition, vol. 20, Organic Synthesis II, Alcohol and Amine, pp. 187-200 and 284-292 (1992), Maruzen Co., Ltd.] and [*Jikken Kagaku Koza* (Experimental Chemistry Course), the fourth edition, vol. 20, Organic Synthesis VI, Hetero Element- or Main Group Metal Element-Containing Compound, pp. 319-350 (1992), Maruzen Co., Ltd.], a compound of Formula (Bb-VI) can be produced by alkylation of the compound of Formula (Bb-IV) in the presence of the compound of Formula (Bb-V) in the presence or absence of a base such as triethylamine, pyridine, sodium hydride, sodium hydroxide, and potassium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from 0° C. to a reflux temperature of the solvent.

<When Y=—OH, X=O, S, and k=0>

In accordance with methods known in literatures, for example, the method described in [Journal of Medicinal Chemistry, vol. 51 (23), pp. 7640-7644 (2008)], a compound of Formula (Bb-VI) can be produced by Mitsunobu reaction of the compound of Formula (Bb-IV) in the presence of the compound of Formula (Bb-V) in the presence of an organophosphorus compound such as triphenylphosphine and an azo compound such as azodicarboxylic acid ester and azodicarboxylic amide in a reaction inert solvent such as a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from 0° C. to a reflux temperature of the solvent.

The compound of Formula (Bb-V) used in this step can be produced from a corresponding compound in accordance with methods known in literatures, for example, the methods described in [WO 2005/063729 pamphlet, Reference Examples 2 and 3 and the like], [WO 2008/001931 pamphlet, Reference Examples 15-19, and the like], and [WO 2009/054423 pamphlet, Production Examples 12, 24, and 37 and the like].

<Step 5>

The protective group $P^2$ in the compound of Formula (Bb-VI) is deprotected. The compound of Formula (Ib) can be produced by deprotecting the protective group $P^2$ in the compound of Formula (Bb-VI) by a method suitable for the protective group.

<Production Method Cb>

<When $R^2 \neq$ Halogen Atom, $R^{11}$=Aryl Group, Heterocyclic Group, Arylalkyl Group in Formula (Ib)>

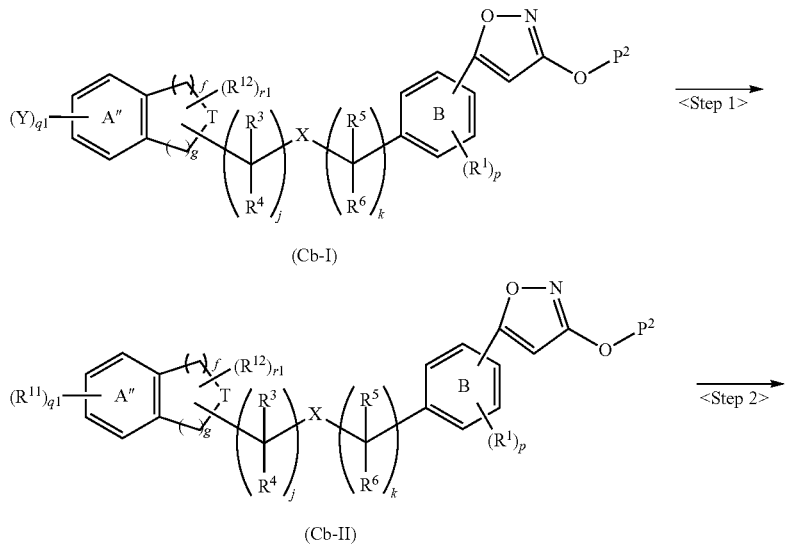

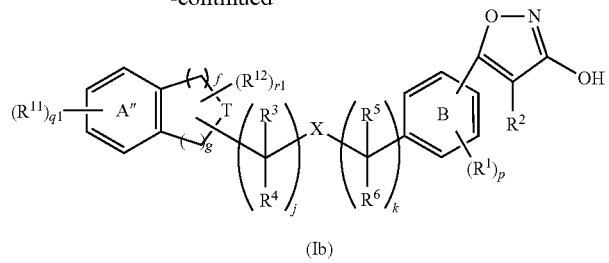

(Ib)

<Step 1>

A compound of Formula (Cb-I) is subjected to substitution reaction on the ring A.

In accordance with methods known in literatures, for example, the method described in [Journal of Medicinal Chemistry, vol. 48 (20), pp. 6326-6339 (2005)], a compound of Formula (Cb-II) can be produced by reacting the compound of Formula (Cb-I) (for example, compounds in Examples 11-2, 14-2, 15-2, 17-1, 17-2(A), 17-2(B), 20-2, 26-3, 26-4, and 31-5 of the application) in the presence of a corresponding boronic acid or boronic ester in the presence of a palladium catalyst such as palladium (II) acetate, tetrakis triphenylphosphine palladium, tris(dibenzylideneacetone)dipalladium, and [1,1'-bis(diphenylphosphino)ferrocene] dichloropalladium (II), a phosphine reagent such as triphenylphosphine, tris(tert-butyl)phosphine, tris(o-tolyl) phosphine, and 2-dicyclohexylphosphino-2',6'-dimethoxybiphenyl, and an organic or inorganic base such as triethylamine, N,N-diisopropylethylamine, and potassium phosphate or in the presence of tetramethylammonium chloride, tetrabutylammonium chloride, or the like in place of the phosphine reagent, using a reaction inert solvent such as toluene, xylene, N,N-dimethylformamide, and N,N-dimethylacetamide or a mixed solvent of them at a temperature from 0° C. to a reflux temperature of the solvent.

<Step 2>

The protective group $P^2$ in the compound of Formula (Cb-II) is deprotected. The compound of Formula (Ib) can be produced by reacting the compound of Formula (Cb-II) in a similar manner to that in <Step 5> in (Production Method Bb).

<Production Method Db>

<When $R^2$=Halogen Atom, Alkyl Group, Alkenyl Group, Alkynyl Group, Cyano Group in Formula (Ib)>

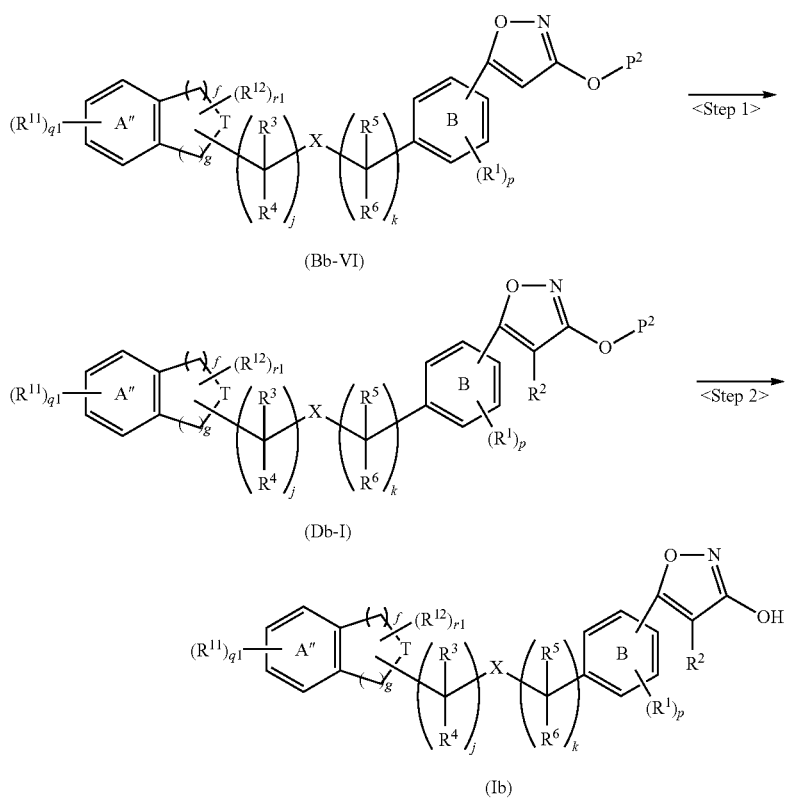

<Step 1>

The compound of Formula (Bb-VI) is subjected to substitution reaction on the isoxazole ring.

<When $R^2$=Halogen Atom, Alkyl Group>

In accordance with methods known in literatures, for example, the method described in [WO 1997/031906 pamphlet, Example 68], a compound of Formula (Db-I) can be produced by reacting the compound of Formula (Bb-VI) in the presence of a corresponding halogenating agent such as N-fluorodibenzenesulfonimide, N-chlorosuccinimide, N-bromosuccinimide, N-iodosuccinimide, and an alkyl halide including iodomethane and iodoethane in the presence of a base such as n-butyllithium, lithium diisopropylamide, lithium bis(trimethylsilyl)amide, sodium bis(trimethylsilyl) amide, and potassium bis(trimethylsilyl)amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide at a temperature from −78° C. to a reflux temperature of the solvent.

<When $R^2$=Cyano Group>

In accordance with methods known in literatures, for example, the method described in [Tetrahedron Letters, vol. 40 (47), pp. 8193-8195 (1999)], a compound of Formula (Db-I) can be produced by reacting the compound of Formula (Db-I) ($R^2$=I, Br) obtained in <When $R^2$=halogen atom> in <Step 1> in the presence of a corresponding cyanating agent such as zinc cyanide and potassium ferrocyanide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, and potassium phosphate or in the presence of tetramethylammonium chloride, tetrabutylammonium chloride, or the like in place of the phosphine reagent, using a reaction inert solvent such as toluene, xylene, N,N-dimethylformamide, and N,N-dimethylacetamide or a mixed solvent of them at a temperature from 0° C. to a reflux temperature of the solvent.

<When $R^2$=Alkenyl Group>

A compound of Formula (Db-I) can be produced by reacting the compound of Formula (Db-I) ($R^2$=I, Br) obtained in <When $R^2$=halogen atom> in <Step 1> in a similar manner to that in <Step 1> in (Production Method Cb).

<When $R^2$=Alkynyl Group>

In accordance with methods known in literatures, for example, the method described in [*Jikken Kagaku Koza* (Experimental Chemistry Course), the fourth edition, vol. 19, Organic Synthesis I, Hydrocarbon and Halogenated Compounds, pp. 318-335 (1992), Maruzen Co., Ltd.], a compound of Formula (Db-I) can be produced by reacting the compound of Formula (Db-I) ($R^2$=I, Br) obtained in <When $R^2$=halogen atom> in <Step 1> in the presence of a corresponding propargyl compound such as 1-propyne and 1-butyne in the presence of copper iodide (I)) or zinc bromide in the presence of a palladium catalyst such as palladium (II) acetate, tetrakis triphenylphosphine palladium, tris(dibenzylideneacetone)dipalladium, and [1,1'-bis(diphenylphosphino)ferrocene] dichloropalladium (II), a phosphine reagent such as triphenylphosphine, tris(tert-butyl)phosphine, and tris(o-tolyl) phosphine, and an organic or inorganic base such as triethylamine, N,N-diisopropylethylamine, potassium phosphate, and potassium carbonate, using a reaction inert solvent such as toluene, xylene, N,N-dimethylformamide, N,N-dimethylacetamide, and N-methylpyrrolidone or a mixed solvent of them at a temperature from 0° C. to a reflux temperature of the solvent.

<Step 2>

The protective group $P^2$ in the compound of Formula (Db-I) is deprotected. The compound of Formula (Ib) can be produced by reacting the compound of Formula (Db-I) in a similar manner to that in <Step 5> in (Production Method Bb).

(2b) Next, methods for producing the compounds of Formula (Ab-I) and Formula (Bb-I) will be described.

<Production Method Eb>

<When X=O, S, $NR^7$ in Formula (Ib)>

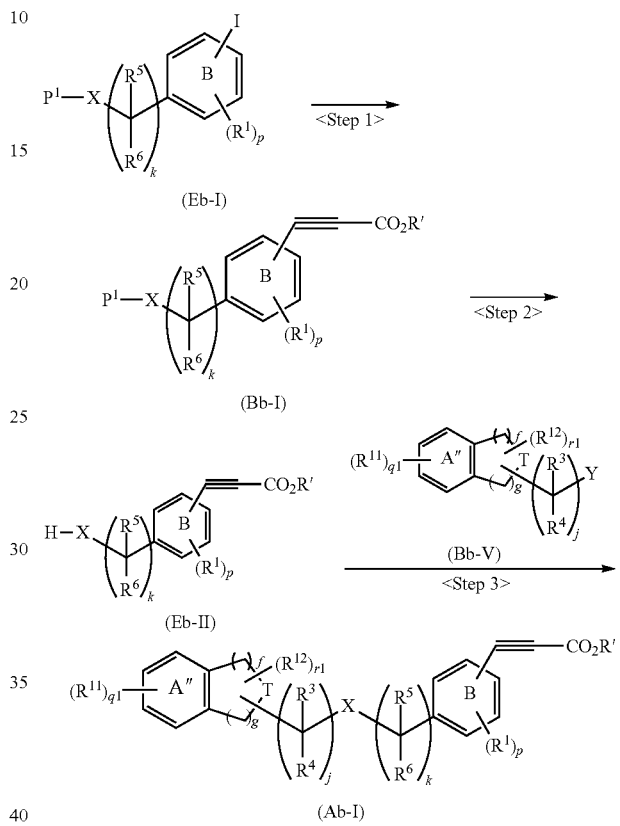

<Step 1>

A compound of Formula (Eb-I) is subjected to alkynylation. In accordance with methods known in literatures, for example, the methods described in [*Jikken Kagaku Kozo* (Experimental Chemistry Course), the fourth edition, vol. 19, Organic Synthesis I, Hydrocarbon and Halogenated Compounds, pp. 318-335 (1992), Maruzen Co., Ltd.] and [WO 2008/066131 pamphlet, Reference Example 1], the compound of Formula (Bb-I) can be produced by reacting the compound of Formula (Eb-I), which is known in the art or can be easily produced from a known compound, in the presence of a corresponding propiolic acid ester such as methyl propiolate and ethyl propiolate and copper oxide (II), using a reaction inert solvent such as toluene, xylene, N,N-dimethylformamide, and N,N-dimethylacetamide or a mixed solvent of them at a temperature from 0° C. to a reflux temperature of the solvent.

Alternatively, the compound of Formula (Bb-I) can be produced by reaction in the presence of a corresponding propiolic acid ester such as methyl propiolate and ethyl propiolate in the presence of copper iodide (I) or zinc bromide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, potassium phosphate, and potassium carbonate, using a reaction inert solvent such as toluene, xylene, N,N-dimethylformamide, and N,N-dimethylacetamide or a mixed solvent of them at a temperature from 0° C. to a reflux temperature of the solvent.

<Step 2>

The protective group $P^2$ in the compound of Formula (Bb-I) is deprotected. A compound of Formula (Eb-II) can be produced by reacting the compound of Formula (Bb-I) in a similar manner to that in <Step 3> in (Production Method Bb).

<Step 3>

The compound of Formula (Eb-II) is subjected to alkylation with the compound of Formula (Bb-V). The compound of Formula (Ab-I) can be produced by reacting the compound of Formula (Eb-II) with the compound of Formula (Bb-V) in a similar manner to that in <Step 4> in (Production Method Bb).

The compound of Formula (Ab-I) can also be produced by the following method.

<Production Method Fb>

<When X=O, S, $NR^7$ in Formula (Ib)>

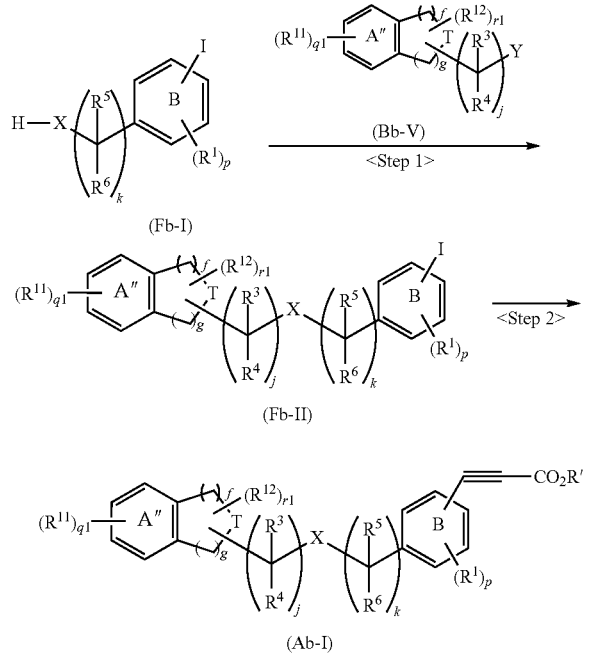

<Step 1>

A compound of Formula (Fb-I) is subjected to alkylation with the compound of Formula (Bb-V). A compound of Formula (Fb-II) can be produced by reacting the compound of Formula (Fb-I), which is known in the art or can be easily produced from a known compound, with the compound of Formula (Bb-V) in a similar manner to that in <Step 4> in (Production Method Bb).

<Step 2>

The compound of Formula (Fb-II) is subjected to alkynylation. The compound of Formula (Ab-I) can be produced by reacting the compound of Formula (Fb-II) in a similar manner to that in <Step 1> in (Production Method Eb).

(3b) The compound of Formula (Ib) can also be produced by the following method.

<Production Method Gb>

<When $R^2$, $R^3$, $R^4$=H, j=1, and X=—$CH_2$— in Formula (Ib)>

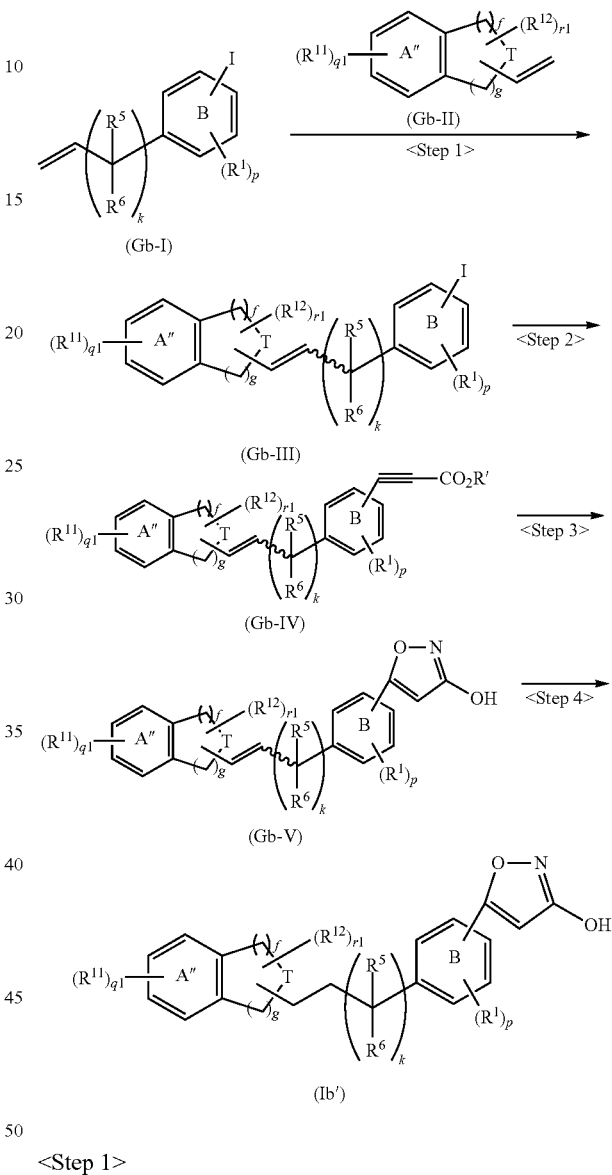

<Step 1>

A compound of Formula (Gb-I) is subjected to olefin metathesis with a compound of Formula (Gb-II). In accordance with methods known in literatures, for example, the method described in [Organic Letters, 1(6), 953-956 (1999)], a compound of Formula (Gb-III) can be produced by reacting the compound of Formula (Gb-I) and the compound of Formula (Gb-II) that are known in the art or can be easily produced from a known compound, in the presence of a ruthenium catalyst such as benzylidene bis(tricyclohexylphosphine) dichlororuthenium and benzylidene(1,3-bis(2,4,6-trimethylphenyl)-2-imidazolidinylidene)dichloro(tricyclohexyl phosphine)ruthenium, using a reaction inert solvent such as benzene, toluene, dichloromethane, dichloroethane, and tetrahydrofuran or a mixed solvent of them at a temperature from 0° C. to a reflux temperature of the solvent.

The compound of Formula (Gb-II) used in this step can be produced from a corresponding aldehyde compound in accordance with methods known in literatures, for example, the method described in [*Jikken Kagaku Koza* (Experimental Chemistry Course), the fourth edition, vol. 20, Organic Synthesis I, Hydrocarbon and Halogenated Compounds, pp. 59-78 (1992), Maruzen Co., Ltd.].

<Step 2>

The compound of Formula (Gb-III) is subjected to alkynylation. A compound of Formula (Gb-IV) can be produced by reacting the compound of Formula (Gb-III) in a similar manner to that in <Step 1> in (Production Method Eb).

<Step 3>

The compound of Formula (Gb-IV) is subjected to isoxazole ring formation reaction. A compound of Formula (Gb-V) can be produced by reacting the compound of Formula (Gb-IV) in a similar manner to that in (Production Method Ab).

<Step 4>

The compound of Formula (Gb-V) is subjected to double-bond reduction. In accordance with methods known in literatures, for example, the methods described in [*Jikken Kagaku Koza* (Experimental Chemistry Course), the fourth edition, vol. 26, Organic Synthesis VIII, Asymmetric Synthesis, Reduction, Sugar, and Labelled Compound, pp. 159-266 (1992), Maruzen Co., Ltd.] and the like, the compound of Formula (Ib) can be produced by reacting the compound of Formula (Gb-V) in the presence of a catalyst such as palladium/carbon (Pd—C) and Raney nickel (Raney-Ni) in a hydrogen atmosphere, using a reaction inert solvent including an alcoholic solvent such as methanol, ethanol, and 2-propanol, an ether solvent such as diethyl ether, tetrahydrofuran, 1,2-dimethoxyethane, and 1,4-dioxane, and a polar solvent such as ethyl acetate and methyl acetate or a mixed solvent of them at a temperature from 0° C. to a reflux temperature of the solvent.

[Concomitant Drug Containing Compound of the Present Invention]

The compound and pharmaceutical composition of the present invention can be used in combination with other drugs or medicines by a general method performed in medical practice. Particularly, such combination is used for the prevention, progress delay, and therapies of the mediating state of the GPR40 agonist, and is further particularly used against at least one disease selected from a group consisting of diabetes (Type 1 diabetes, Type 2 diabetes, and borderline type diabetes (impaired glucose tolerance (IGT) and/or impaired fasting glycemia (IFG))), insulin resistance, hyperinsulinemia, obesity, adiposity, and various diseases derived from or related to there diseases.

Examples of an insulin sensitizer and an anti-diabetic drug include 1) PPAR gamma agonists (specifically, pioglitazone, rosiglitazone, troglitazone, ciglitazone, darglitazone, englitazone, netoglitazone, etc.), 2) biguanide agents (specifically, metformin, buformin, phenformin, etc.), 3) sulfonylureas (specifically, tolbutamide, acetohexamide, chlorpropamide, glibenclamide, gliclazide, glipizide, glimepiride, glipentide, gliquidone, glisolamide, tolazamide, etc.), 4) rapid-acting insulin secretagogues (specifically, nateglinide, mitiglinide, repaglinide, etc.), 5) alpha-glucosidase inhibitors (specifically, acarbose, voglibose, miglitol, camiglibose, adiposin, emiglitate, pradimicin Q, salbostatin, etc.), 6) insulin or insulin derivatives (specifically, insulin zinc suspensions, insulin lispro, insulin aspart, regular insulin, NPH insulin, insulin glargine, insulin detemir, mixed insulin, etc.), 7) GLP-1 and GLP-1 agonists (specifically, exenatide, liraglutide, etc.), 8) DPP-IV inhibitors (specifically, sitagliptin, vildagliptin, alogliptin, saxagliptin, NVP-DPP-728, etc.), and 9) alpha-2 antagonists (specifically, midaglizole, isaglidole, deriglidole, idazoxan, efaroxan, etc.).

Examples of the hypolipidemic agent and the dyslipidemia therapeutic agent include 1) omega-3 fatty acids (specifically, ethyl icosapentate (EPA-E preparation), docosahexaenoic acid (DHA), etc.), 2) HMG-CoA reductase inhibitors (specifically, atorvastatin, simvastatin, pitavastatin, itavastatin, fluvastatin, lovastatin, pravastatin, rivastatin, rosuvastatin, etc.), 3) HMG-CoA synthase inhibitors, 4) cholesterol absorption inhibitors (specifically, ezetimibe), 5) acyl-CoA-cholesterol acyltransferase (ACAT) inhibitors, 6) CETP inhibitors, 7) squalene synthase inhibitors, 8) antioxidants (specifically, probucol, etc.), 9) PPAR alpha agonists (specifically, clofibrate, etofibrate, fenofibrate, bezafibrate, ciprofibrate, gemfibrozil, KRP-101, etc.), 10) PPAR delta agonists, 11) LXR agonists, 12) FXR agonists (specifically, INT-747, etc.), 13) MTTP inhibitors, 14) squalene epoxidase inhibitors, and 15) bile acid absorption inhibitors (specifically, cholestyramine, colestipol, etc).

In addition, examples of an anti-obesity agent. Specific examples of the anti-obesity agent include 1) CB-1 receptor antagonists (specifically, rimonabant, SR-147778, BAY-65-2520, etc.), 2) monoamine reuptake inhibitors (specifically, sibutramine, mazindol, etc.), 3) serotonin reuptake inhibitors (specifically, fluoxetine, paroxetine, etc.), 4) lipase inhibitors (specifically, orlistat, cetilistat, etc.), 5) neuropeptide Y (NPY) receptor antagonists (specifically, S-2367, etc.), 6) peptide YY (PYY) receptor antagonists, and 7) adrenergic beta-3 receptor agonists (specifically, KRP-204, TRK-380/TAC-301, etc).

The therapies can be performed in combination with not only other drugs, but also other therapies. Examples of the therapies include the improvement of lifestyle through weight control, exercise therapy, and diet therapy, and radiotherapy.

Against GPR40-involving diseases except for diabetes and obesity, the therapies can be performed in combination with drugs used in respective fields.

The combined use of the concomitant drug and conventional drugs against the diseases described above enables the dosage of the conventional drugs to be reduced, which can reduce the side effects of the conventional drugs. It is needless to say the combining method using the drugs is not limited to the diseases, and the drugs to be used in combination are not limited to the compounds exemplified above.

To use the compound of the present invention in combination with the drug to be used in combination, they may be individual preparations or be a drug combination. In the form of individual preparations, the compound and the drug can be taken at the same time or can be administered at different time.

[Producing Preparations of Prophylactic or Therapeutic Agents of the Present Invention]

The medicines of the present invention are administered in the form of pharmaceutical compositions.

The pharmaceutical compositions of the present invention may include at least the compound of Formula (I) or Formula (II) of the present invention and are produced in combination with pharmaceutically acceptable additives. More in detail, various dosage forms can be prepared by appropriately combining the compound of the present invention and, for example, excipients (for example, lactose, white soft sugar, mannitol, microcrystalline cellulose, silicic acid, corn starch, and potato starch), bonding agents (for example, celluloses (hydroxypropylcellulose (HPC), hydroxypropylmethylcellulose (HPMC), microcrystalline cellulose, saccharide (lactose, mannitol, white soft sugar, sorbitol, erythritol, and xylitol), starches (corn starch and potato starch), gelatinized starch, dextrin, polyvinylpyrrolidone (PVP), macrogol, polyvinyl alcohol (PVA)), lubricants (for example, magnesium stearate, calcium stearate, talc, and carboxymethylcellulose), disintegrants (for example, starches (corn starch and potato starch), sodium carboxymethyl starch, carmellose, carmellose calcium, croscarmellose sodium, and, crospovidone), coating agents (for example, celluloses (hydroxypropylcellulose (HPC), hydroxypropylmethylcellulose (HPMC), aminoalkylmethacrylate copolymers E, and methacrylic copolymers LD), plasticizers (for example, triethyl citrate and macrogol), masking agents (for example, titanium oxide), colorants, flavoring agents, antiseptics (for example, benzalkonium chloride and p-hydroxybenzoate esters), tonicity agents (for example, glycerin, sodium chloride, calcium chloride, mannitol, and dextrose), pH regulators (for example, sodium hydroxide, potassium hydroxide, sodium carbonate, hydrochloric acid, sulfuric acid, and buffer solutions such as phosphate buffer solutions), stabilizing agents (for example, sugar, sugar alcohol, and xanthan gum), dispersants, antioxidants (for example, ascorbic acid, butylated hydroxyanisole (BHA), propyl gallate, and dl-alpha-tocopherol), buffer agents, preservatives (for example, paraben, benzyl alcohol, and benzalkonium chloride), perfumes (for example, vanillin, l-menthol, and rose oil), solubilizing agents (for example, polyoxyethylene hydrogenated castor oil, polysorbate 80, polyethylene glycol, phospholipid cholesterol, and triethanolamine), absorbefacients (for example, sodium glycolate, sodium edetate, sodium caprate, acylcarnitines, and limonene), gelators, suspending agents, emulsifiers, and, generally used suitable additives and solvents.

Examples of the various dosage forms include tablets, capsules, granules, powders, pills, aerosols, inhalants, ointments, adhesive patches, suppositories, injections, troches, liquids, spirits, suspensions, extracts, and elixirs. The dosage forms can be administered to patients through oral administration, subcutaneous injection, intramuscular injection, intranasal administration, transdermal administration, intravenous injection, intraarterial injection, perineural administration, epidural administration, administration in subdural cavity, intraventricular administration, rectal administration, inhalation, or the like.

The dosage of the compound of the present invention is generally, 0.005 mg to 3.0 g, preferably, 0.05 mg to 2.5 g, and more preferably, 0.1 mg to 1.5 g per day for adults, but can be reduced or increased as needed depending on symptoms or administration routes.

The compound can be administered as a whole at once or be separately administered by being divided into two to six doses through oral administration or parenteral administration, or can be administered through repeated administration such as intravenous infusion.

The present specification incorporates, as references, the whole publications cited in the present specification, for example, related-art documents, publications of unexamined applications, patent publications, and other patent documents.

PHARMACOLOGICAL TEST EXAMPLES

The present invention is specifically described below with reference to test examples but is not limited to them.

The following pharmacological test examples 1 to 7 provide methods for investigating the efficacy of the compound of the present invention.

Pharmacological Test Example 1

Agonist Action on GPR40 of Human Origin

A CHO cell strain stably expressing GPR40 of human origin was used to determine the agonist action of a subject compound. This cell strain was seeded in a clear bottom 96 well plate at $4 \times 10^4$ cells/100 µL/well. The cell strain was cultured in a $CO_2$ incubator overnight using a Ham's F-12 medium containing a 10% fetal bovine serum, 100 U/mL penicillin, 0.1 mg/mL streptomycin, and 400 µg/mL Geneticin. Calcium 4 Assay Kit (Molecular Devices) was used as a fluorescent calcium indicator. One mL of 77 mg/mL probenecid (Invitrogen) was added to 100 mL of a calcium indicator solution to prepare a solution (loading solution) mixed with a 20 mM HEPES-containing Hanks' balanced salt solution (HBSS) in equal proportions. 200 µL of the loading solution was added to the cells from which the culture solution was removed, and the cells were cultured in a $CO_2$ incubator for 1 hour. The subject compound was diluted with a 20 mM HEPES-containing HBSS and was added to the cells by 50 µL, and the fluctuation of the $Ca^{2+}$ concentration was measured by an intracellular ion analyzer. The $EC_{50}$ value of the subject compound was calculated using the dose-response curve of fluorescence intensity variation. Table 1 indicates the compound of the present invention having an $EC_{50}$ value of less than 0.3 µM as A and the compound of the present invention having an $EC_{50}$ value of 0.3 µM or more and less than 3 µM as B.

TABLE 1

| Compound of Examples | $EC_{50}$ values |
|---|---|
| 2 | A |
| 11 | A |
| 12 | B |
| 13 | B |
| 14 | B |
| 19 | B |
| 21 | A |
| 23 | A |
| 24 | A |
| 26 | A |
| 29 | B |
| 30 | A |
| 31 | B |
| 34 | B |
| 35 | B |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |

Pharmacological Test Example 2

Oral Glucose Tolerance Test for Mouse

A reduction of blood glucose excursion of a subject compound after glucose load is examined using male C57BL/6J mice fasted overnight. The subject compound is suspended with a solvent (for example, 0.5% carboxymethylcellulose) and is orally administered before glucose load. The solvent is singly administered to the control group. Blood specimen collection is performed before compound administration (pre-administration blood collection), after compound administration and immediately before glucose load, during glucose load, after 15, 30, 60, and 120 minutes, and the blood glucose level of the collected blood is measured. The reduction of blood glucose excursion is obtained by orally administering a dosage of 3 to 10 mg/kg of the preferable compound of the compound of the present invention.

Pharmacological Test Example 3

Solubility Test (1) DMSO Precipitation Solubility (Kinetic Solubility)

A 10 mM DMSO solution of the compound of the present invention is added to a 50 mM phosphate buffer solution (pH 7.4) to the final concentration of 100 μM. The resultant solution is incubated while stirring at 600 rpm for 1.5 hours at room temperature, and then is filtered through a filter plate (4 μm, MultiScreen Solubility Filter Plate, Millipore). The absorbance of the obtained filtrate is measured at the maximum absorption wavelength using a plate reader (Powerscan HT, (Dainippon Pharmaceutical)). In this process, DMSO solutions of known concentration of the test compound (1, 3, 10, 30, and 100 μM) are prepared as standard solutions for a calibration curve. The absorbance of each of the standard solutions is measured to generate a calibration curve. The solubility (μM) of the compound is calculated using the absorbance values of the filtrate and the standard solutions.

(2) Crystal Solubility (Thermodynamic Solubility)

The compound of the present invention is added to water so as to be 1 mg/mL. The resultant solution is incubated at 37° C. for 24 hours, and then is centrifuged. The obtained supernatant is analyzed by HPLC to detect the peak at the maximum absorption wavelength, and thus, the peak area is calculated. Similarly, DMSO solutions of known concentration of the test compound (0.03, 0.1, 0.3, 1, 3, and 10 μg/mL) are prepared as standard solutions for a calibration curve. The peak area of each of the standard solutions is measured. The solubility (μg/mL) of the compound is calculated using the peak areas of the obtained calibration curve.

Pharmacological Test Example 4

Metabolic Stability Test

The 10 mM DMSO solution of the compound of the present invention is added to a solution containing liver microsome (human or mouse; XenoTech) and a NADPH generating system (water containing beta-NADP, Glucose-6-Phosphate, G-6-PDH(Y), and $MgCl_2$) to the final concentration of 1 μM. The resultant solution is incubated at 37° C. for 20 minutes, and then the reaction is terminated by adding acetonitrile. The reaction solution is filtrated by centrifugation using a filter plate (MultiScreen HTS-HV plate, Millipore). The test compound in the filtrate is measured by high performance liquid chromatogram/mass spectrometry. Similarly, a sample with a reaction time of 0 is measured as a control, and the decomposition rate (%) is calculated from the ratio between the microsome reaction sample and the control.

Pharmacological Test Example 5 hERG Inhibition Test by Patch-Clamp Technique

An effect against a human ether-a-go-go related gene (hERG) channel is measured using a fully automatic patch-clamp system (Patchliner (Manion)). To confirm the hERG $I_{kr}$ current of a cell (hERG-HEK (Upstate)), the membrane potential is kept at −80 mV, and a depolarizing pulse is applied to the cell on a regular basis. After the generated current became stable, a test compound is added. The effect of the test compound against the hERG channel was confirmed from change in tail current induced by a repolarizing pulse at −40 mV for 0.5 second subsequent to a depolarizing pulse at 40 mV for 0.5 second. The stimulation is performed at a frequency of once every 10 seconds. The measurement is performed at room temperature. The hERG channel inhibition rate is calculated as the reduction rate (suppression rate) of a tail current two minutes after the application of the test compound relative to the maximum tail current before the application.

The calculated suppression rate showed the possibility that drug-induced QT prolongation followed by fatal side effects (such as ventricular tachycardia and sudden death).

Pharmacological Test Example 6

Pharmacokinetics Study (Mouse Cassette Dosing PK)

The compound of the present invention is orally administrated in a single dose to 7- or 8-week-old male C57BL/6J Jcl at 1 mg/kg (the vehicle is DMSO:Tween 80:ultrapure water=1:1:8 and 10 mL/kg), and then the blood is collected from the abdominal aorta 0.25, 0.5, 1, and 2 hours after dosing. The blood is centrifuged (3000 rpm, 15 minutes, and 4° C.) to obtain plasma, and the test compound in the plasma is measured by high performance liquid chromatogram/mass spectrometry. Similarly, standard solutions of known concentration of the test compound (0.01, 0.02, 0.05, 0.1, 0.2, 0.5, and 1 μg/mL) are measured to generate a calibration curve. The concentration (μg/mL) of the compound in the plasma is calculated using the calibration curve, and the maximum concentration in the plasma is indicated by Cmax (μg/mL).

Pharmacological Test Example 7

Safety Assessment Study

The compound of the present invention is orally administrated in a single dose to mice or rats. When no death and no noticeable behavior disorder is observed, the safety of the compound of the present invention is shown.

As a result, the compound of the present invention showed an excellent GPR40 agonist action and reduced blood glucose excursion in the single oral dose glucose tolerance test using normal mice. In the safety assessment study, no abnormality indicates low toxicity of the compound of the present invention.

By performing the tests described above, the compound of the present invention is confirmed to have favorable properties in one regard, such as solubility, metabolic stability, pharmacokinetics, and the avoidance of an hERG channel inhibition.

Accordingly, the compound of the present invention is expected to be used as a GPR40 agonist for insulin secretagogues and prophylactic and/or therapeutic agents against diabetes (particularly, Type 2 diabetes or borderline type diabetes), obesity, and adiposity.

PREPARATION EXAMPLES

Examples of the pharmaceutical composition of the present invention are given below.

Preparation Example 1

Tablets

| | |
|---|---|
| Compound of Example 38 | 100 g |
| Lactose | 137 g |
| Microcrystalline cellulose | 30 g |
| Hydroxypropylcellulose | 15 g |
| Sodium carboxymethyl starch | 15 g |
| Magnesium stearate | 3 g |

The above components are weighed and then are uniformly mixed. The mixture is formed into tablets having a weight of 150 mg.

Preparation Example 2

Film Coating

| | |
|---|---|
| Hydroxypropylmethylcellulose | 9 g |
| Macrogol 6000 | 1 g |
| Titanium oxide | 2 g |

The above components are weighed. Subsequently, hydroxypropylmethylcellulose and macrogol 6000 are dissolved in water to disperse the titanium oxide. The resultant liquid is film coated on 300 g of the tablets of Preparation Example 1 to obtain film-coated tablets.

Preparation Example 3

Capsules

| | |
|---|---|
| Compound of Example 40 | 50 g |
| Lactose | 435 g |
| Magnesium stearate | 15 g |

The above components are weighed and then are uniformly mixed. Adequate hard capsules are each filled with 300 mg of the mixture by weight with a capsule inserter to produce capsules.

Preparation Example 4

Capsules

| | |
|---|---|
| Compound of Example 42 | 100 g |
| Lactose | 63 g |
| Corn starch | 25 g |
| Hydroxypropylcellulose | 10 g |
| Talc | 2 g |

The above components are weighed, and then the compound of Example 42, lactose, and corn starch are uniformly mixed. A hydroxypropylcellulose aqueous solution is added to the resultant mixture to produce granules by wet granulation. Talc is uniformly mixed with the granules, and adequate hard capsules are each filled with 200 mg of the mixture by weight to produce capsules.

Preparation Example 5

Powders

| | |
|---|---|
| Compound of Example 44 | 200 g |
| Lactose | 790 g |
| Magnesium stearate | 10 g |

The above components are weighed and then are uniformly mixed to produce 20% powdered drugs.

Preparation Example 6

Granules and Fine Granules

| | |
|---|---|
| Compound of Example 46 | 100 g |
| Lactose | 200 g |
| Microcrystalline cellulose | 100 g |
| Partially pregelatinized starch | 50 g |
| Hydroxypropylcellulose | 50 g |

The above components are weighed, and the compound of Example 46, lactose, microcrystalline cellulose, and partially pregelatinized starch are uniformly mixed. A hydroxypropylcellulose (HPC) aqueous solution is added to the resultant mixture to produce granules or fine granules by wet granulation. The granules or fine granules are dried to formulations of granules or fine granules.

EXAMPLES

Next, in order to describe the present invention in further detail, Examples will be described below which should not be construed as limiting the scope of the present invention.

For the measurement of the nuclear magnetic resonance spectrum (NMR), JEOL JNM-ECX300 FT-NMR (manufactured by JEOL Ltd.) and JEOL JNM-ECX400 FT-NMR (manufactured by JEOL Ltd.) were used. As the LC-Mass, a Waters Fraction Lynx MS system (manufactured by Waters Corporation) was used. As the column, Sun Fire column (4.6 mm×5 cm, 5 µm) (manufactured by Waters Corporation) was used for analytical isolation and a Sun Fire column (19 mm×5 cm, 5 µm) was used for preparative isolation. As a mobile phase, methanol: 0.05% acetic acid aqueous solution (or 0.05% trifluoro acetic acid aqueous solution)=1:9 (0 min)→10:0 (5 min)→10:0 (7 min) (gradient condition) was used for the analytical isolation system, and for the preparative isolation system, gradient conditions appropriately changed depending on the type of the compound were used.

Reference Example 1

Synthesis of 2-((3-bromo-2-methylphenyl)methoxy) tetrahydro-2H-pyran

To a suspension of 3-bromo-2-methylbenzyl alcohol (7.80 g) in dichloromethane (78.0 mL), 3,4-dihydro-2H-pyran (7.08 mL) and pyridinium p-toluenesulfonate (0.97 g) were sequentially added and the resultant reaction mixture was stirred at room temperature for 1.5 hours. From the reaction mixture, the solvent was distilled off under reduced pressure and the resultant residue was purified by silica gel column chromatography (eluate: n-hexane:ethyl acetate=100:0 to 95:5) to obtain the subject compound (11.6 g) as a colorless oil.

Reference Example 2

Synthesis of 4-(5-bromo-4,6-dimethylpyridin-2-yloxy)-2-methylbutan-2-ol

According to a method described in [WO 2009/054423 pamphlet, (Production Example 37)], from 5-bromo-4,6-dimethyl-2-hydroxypyridine (1.50 g) and 3-hydroxy-3-methylbutyl 4-methylbenzenesulfonate (2.11 g), the subject compound (1.50 g) was obtained as a colorless oil.

Reference Example 3

Synthesis of ethyl 3-(4-hydroxyphenyl)-2-propiolate

According to a method described in [WO 2008/066131 pamphlet, (Reference Example 1)], the subject compound (10.5 g) was obtained from 4-iodophenol (33.0 g) as a pale yellow solid.

Reference Example 4

Synthesis of 4-(3-(methoxymethoxy)isoxazol-5-yl)phenol

According to a method described in [WO 2008/066131 pamphlet, (Reference Example 5)], from 1-benzyloxy-4-iodobenzene (15.0 g), the subject compound (3.82 g) was obtained as a white solid.

Example 1

Synthesis of 5-(4-(1,2,3,4-tetrahydronaphthalen-1-yloxy)phenyl)isoxazol-3-ol

<Step 1> Synthesis of ethyl 3-(4-(1,2,3,4-tetrahydronaphthalen-1-yloxy)phenyl)propiolate To a solution of the compound (0.10 g) obtained in (Reference Example 3) and 1,2,3,4-tetrahydronaphthalen-1-ol (85.7 mg) in tetrahydrofuran (1.0 mL), diethyl azodicarboxylate (40% toluene solution) (0.36 mL) and triphenylphosphine (0.21 g) were sequentially added under ice-cooling and the resultant reaction mixture was stirred at room temperature for 14.5 hours. To the reaction mixture, 1,2,3,4-tetrahydronaphthalen-1-ol (40 mg), triphenylphosphine (0.1 g), and diethyl azodicarboxylate (40% toluene solution) (0.18 mL) were added and the resultant reaction mixture was stirred at room temperature further for 1 hour. To the reaction mixture, a small amount of methanol was added. From the organic phase, the solvent was distilled off under reduced pressure and the resultant residue was purified by silica gel column chromatography (eluate: n-hexane:ethyl acetate=90:10 to 85:15) to obtain the subject compound (177 mg) as a colorless oil.

<Step 2> Synthesis of 5-(4-(1,2,3,4-tetrahydronaphthalen-1-yloxy)phenyl)isoxazol-3-ol To a mixed solution of the compound (0.17 g) obtained in (Example 1) <Step 1> in tetrahydrofuran (1.0 mL)-ethanol (0.5 mL), a 50% hydroxylamine aqueous solution (0.1 mL) and a 2.5N sodium hydroxide aqueous solution (0.64 mL) were sequentially added and the resultant reaction mixture was stirred at room temperature for 23 hours. To the reaction mixture, a 10% citric acid aqueous solution was added and the resultant reaction mixture was extracted with ethyl acetate. The organic phase was washed sequentially with water and saturated saline and was dried over anhydrous sodium sulfate. From the organic phase, the solvent was distilled off under reduced pressure and the resultant residue was purified by silica gel column chromatography (eluate: n-hexane:ethyl acetate=70:30 to 50:50) to obtain the subject compound (83 mg) as a pale yellow solid.

Example 2

Synthesis of 5-(4-(2,3-dihydro-1H-inden-2-yloxy)phenyl)isoxazol-3-ol

<Step 1> Synthesis of ethyl 3-(4-(2,3-dihydro-1H-inden-2-yloxy)phenyl)propiolate According to the method of (Example 1) <Step 1>, from the compound (0.20 g) obtained in (Reference Example 3) and 2,3-dihydro-1H-inden-2-ol (0.21 g), the subject compound (286 mg) was obtained as a white solid.

<Step 2> Synthesis of 5-(4-(2,3-dihydro-1H-inden-2-yloxy)phenyl)isoxazol-3-ol

According to the method of (Example 1) <Step 2>, from the compound (0.27 g) obtained in (Example 2) <Step 1>, the subject compound (148 mg) was obtained as a pale yellow solid.

Example 3

Synthesis of 5-(4-(2,3-dihydro-1H-inden-1-yloxy)phenyl)isoxazol-3-ol

<Step 1> Synthesis of ethyl 3-(4-(2,3-dihydro-1H-inden-1-yloxy)phenyl)propiolate According to the method of (Example 1) <Step 1>, from the compound (0.20 g) obtained in (Reference Example 3) and 2,3-dihydro-1H-inden-1-ol (0.21 g), the subject compound (210 mg) was obtained as a white solid.

<Step 2> Synthesis of 5-(4-(2,3-dihydro-1H-inden-2-yloxy)phenyl)isoxazol-3-ol

According to the method of (Example 1) <Step 2>, from the compound (0.20 g) obtained in (Example 3) <Step 1>, the subject compound (125 mg) was obtained as a pale yellow solid.

Example 4

Synthesis of 5-(4-(2,3-dihydrobenzofuran-3-yloxy)phenyl)isoxazol-3-ol

<Step 1> Synthesis of 2,3-dihydrobenzofuran-3-ol

To a mixed solution of 2,3-dihydrobenzofuran-3-one (1.0 g) in methanol (10 mL)-tetrahydrofuran (10 mL), sodium borohydride (0.28 g) was added under ice-cooling and the resultant reaction mixture was stirred at room temperature for 1 hour. To the reaction mixture, water was added and the resultant reaction mixture was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=100:00 to 85:15) to obtain the subject compound (0.87 g) as a yellow oil.

<Step 2> Synthesis of 5-(4-(2,3-dihydrobenzofuran-3-yloxy)phenyl)-3-(methoxymethoxy)isoxazole According to the method of (Example 1) <Step 1>, from the compound (50 mg) obtained in (Reference Example 4) and the compound (37 mg) obtained in (Example 4) <Step 1>, the subject compound (51 mg) was obtained as a white solid.

<Step 3> Synthesis of 5-(4-(2,3-dihydrobenzofuran-3-yloxy)phenyl)isoxazol-3-ol

To a mixed solution of the compound (48 mg) obtained in (Example 4) <Step 2> in tetrahydrofuran (1.0 mL)-methanol (2.0 mL), 2N hydrochloric acid-ethanol (0.1 mL) was added and the resultant reaction mixture was stirred at room temperature for 1 hour. Ethyl acetate was added to the reaction mixture. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=80:20 to 50:50 to 30:70) to obtain the subject compound (15 mg) as a white solid.

Example 5

Synthesis of 5-(4-(2,3-dihydro-3,3-dimethyl-1H-inden-1-yloxy)phenyl)isoxazol-3-ol <Step 1> Synthesis of 2,3-dihydro-3,3-dimethyl-1H-inden-1-ol According to the method of (Example 4) <Step 1>, from 2,3-dihydro-3,3-dimethyl-1H-inden-1-one (1.24 g), the subject compound (1.21 g) was obtained as a colorless oil.

<Step 2> Synthesis of 5-(4-(2,3-dihydro-3,3-dimethyl-1H-inden-1-yloxy)phenyl)-3-(methoxymethoxy)isoxazole According to the method of (Example 1) <Step 1>, from the compound (50 mg) obtained in (Reference Example 4) and the compound (55 mg) obtained in (Example 5) <Step 1>, the subject compound (71.6 mg) was obtained as a pale yellow oil.

<Step 3> Synthesis of 5-(4-(2,3-dihydro-3,3-dimethyl-1H-inden-1-yloxy)phenyl)isoxazol-3-ol According to the method of (Example 4) <Step 3>, from the compound (68 mg) obtained in (Example 5) <Step 2>, the subject compound (33.4 mg) was obtained as a white solid.

Example 6

Synthesis of 5-(4-((2,3-dihydro-1H-inden-1-yl)methoxy)phenyl)isoxazol-3-ol

<Step 1> Synthesis of 2,3-dihydro-1H-inden-1-methanol

To a solution of 2,3-dihydro-1H-inden-1-carboxylic acid (0.50 g) in tetrahydrofuran (5.0 mL), lithium aluminum hydride (0.18 g) was added under ice-cooling and the resultant reaction mixture was stirred at room temperature for 30 minutes. To the reaction mixture, water was added under ice-cooling and the resultant reaction mixture was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=85:15 to 75:25) to obtain the subject compound (445 mg) as a colorless oil.

<Step 2> Synthesis of 5-(4-(2,3-dihydro-1H-inden-1-yl)methoxy)phenyl)-3-(methoxymethoxy)isoxazole According to the method of (Example 1) <Step 1>, from the compound (50 mg) obtained in (Reference Example 4) and the compound (50.3 mg) obtained in (Example 6) <Step 1>, the subject compound (84.5 mg) was obtained as a white solid.

<Step 3> Synthesis of 5-(4-((2,3-dihydro-1H-inden-1-yl)methoxy)phenyl)isoxazol-3-ol According to the method of (Example 4) <Step 3>, from the compound (80 mg) obtained in (Example 6) <Step 2>, the subject compound (50.3 mg) was obtained as a white solid.

Example 7

Synthesis of 5-(4-(R)-2,3-dihydro-1H-inden-1-yloxy)phenyl)isoxazol-3-ol

<Step 1> Synthesis of 5-(4-(R)-2,3-dihydro-1H-inden-1-yloxy)phenyl)-3-(methoxymethoxy)isoxazole According to the method of (Example 1) <Step 1>, from the compound (50 mg) obtained in (Reference Example 4) and 4-(S)-2,3-dihydro-1H-inden-1-ol (45.5 mg), the subject compound (67 mg) was obtained as a colorless oil.

<Step 2> Synthesis of 5-(4-(R)-2,3-dihydro-1H-inden-1-yloxy)phenyl)isoxazol-3-ol According to the method of (Example 4) <Step 3>, from the compound (65 mg) obtained in (Example 7) <Step 1>, the subject compound (21.5 mg) was obtained as a white solid.

Example 8

Synthesis of 5-(4-(S)-2,3-dihydro-1H-inden-1-yloxy)phenyl)isoxazol-3-ol

<Step 1> Synthesis of 5-(4-(S)-2,3-dihydro-1H-inden-1-yloxy)phenyl)-3-(methoxymethoxy)isoxazole According to the method of (Example 1) <Step 1>, from the compound (50 mg) obtained in (Reference Example 4) and 4-(R)-2,3-dihydro-1H-inden-1-ol (45.5 mg), the subject compound (68 mg) was obtained as a colorless oil.

<Step 2> Synthesis of 5-(4-(S)-2,3-dihydro-1H-inden-1-yloxy)phenyl)isoxazol-3-ol According to the method of (Example 4) <Step 3>, from the compound (65 mg) obtained in (Example 8) <Step 1>, the subject compound (18.2 mg) was obtained as a white solid.

Example 9

Synthesis of 5-(4-(2,3-dihydro-1H-inden-1-yloxy)phenyl)-4-fluoroisoxazol-3-ol

<Step 1> Synthesis of 5-(4-(2,3-dihydro-1H-inden-1-yloxy)phenyl)-3-(methoxymethoxy)isoxazole To a solution of the compound (1.11 g) obtained in (Example 3) <Step 2> in tetrahydrofuran (20 mL), 1,8-diazabicyclo[5.4.0]undeca-7-ene (0.85 mL) and chloromethyl methyl ether (0.43 mL) were sequentially added under ice-cooling and the resultant reaction mixture was stirred at room temperature for 1 hour. To the reaction mixture, water was added and the resultant reaction mixture was extracted with ethyl acetate. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=90:10 to 70:30) to obtain the subject compound (0.57 g) as a white amorphous.

<Step 2> Synthesis of 5-(4-(2,3-dihydro-1H-inden-1-yloxy)phenyl)-4-fluoro-3-(methoxymethoxy)isoxazole To a solution of the compound (0.10 g) obtained in (Example 9) <Step 1> in tetrahydrofuran (1.0 mL) in a dry ice-acetone bath, n-BuLi (1.68 M hexane solution; 0.21 mL) was added dropwise and the resultant reaction mixture was stirred at the same temperature for 20 minutes. To the reaction mixture, N-fluorobenzenesulfonimide (0.11 g) was added and the resultant reaction mixture was stirred at the same temperature for 30 minutes. To the reaction mixture, water was added and the resultant reaction mixture was extracted with ethyl acetate. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 85:15 to 70:30) to obtain the subject compound (69 mg) as a white solid.

<Step 3> Synthesis of 5-(4-(2,3-dihydro-1H-inden-1-yloxy)phenyl)-4-fluoroisoxazol-3-ol According to the method of (Example 4) <Step 3>, from the compound (67 mg) obtained in (Example 9) <Step 2>, the subject compound (26 mg) was obtained as a white solid.

Example 10

Synthesis of 5-(4-(2,3-dihydro-1H-inden-1-yloxy)phenyl)-4-methylisoxazol-3-ol

<Step 1> Synthesis of 5-(4-(2,3-dihydro-1H-inden-1-yloxy)phenyl)-3-(methoxymethoxy)-4-methylisoxazole According to the method of (Example 9) <Step 2>, from the compound (0.1 g) obtained in (Example 9) <Step 1> and methyl iodide (22 μL), the subject compound (80 mg) was obtained as a white solid.

<Step 2> Synthesis of 5-(4-(2,3-dihydro-1H-inden-1-yloxy)phenyl)-4-methylisoxazol-3-ol According to the method of (Example 4) <Step 3>, from the compound (76 mg) obtained in (Example 10) <Step 1>, the subject compound (29 mg) was obtained as a white solid.

Example 11

Synthesis of 5-(4-(4-chloro-2,3-dihydro-1H-inden-1-yloxy)phenyl)isoxazol-3-ol

<Step 1> Synthesis of 4-chloro-2,3-dihydro-1H-inden-1-ol

According to the method of (Example 4) <Step 1>, from 4-chloro-2,3-dihydro-1H-inden-1-one (0.13 g), the subject compound (132 mg) was obtained as a white solid.

<Step 2> Synthesis of 5-(4-(4-chloro-2,3-dihydro-1H-inden-1-yloxy)phenyl)-3-(methoxymethoxy)isoxazole According to the method of (Example 1) <Step 1>, from the compound (50 mg) obtained in (Reference Example 4) and the compound (57.2 mg) obtained in (Example 11) <Step 1>, the subject compound (66.4 mg) was obtained as a white solid.

<Step 3> Synthesis of 5-(4-(4-chloro-2,3-dihydro-1H-inden-1-yloxy)phenyl)isoxazol-3-ol According to the method of (Example 4) <Step 3>, from the compound (64 mg) obtained in (Example 11) <Step 2>, the subject compound (33.5 mg) was obtained as a white solid.

Example 12

Synthesis of 5-(4-(4-cyano-2,3-dihydro-1H-inden-1-yloxy)phenyl)isoxazol-3-ol

<Step 1> Synthesis of 4-cyano-2,3-dihydro-1H-inden-1-ol

According to the method of (Example 4) <Step 1>, from 4-cyano-2,3-dihydro-1H-inden-1-one (0.13 g), the subject compound (0.13 g) was obtained as a pale yellow solid.

<Step 2> Synthesis of 5-(4-(4-cyano-2,3-dihydro-1H-inden-1-yloxy)phenyl)-3-(methoxymethoxy)isoxazole According to the method of (Example 1) <Step 1>, from the compound (50 mg) obtained in (Reference Example 4)

and the compound (54 mg) obtained in (Example 12) <Step 1>, the subject compound (69 mg) was obtained as a pale yellow solid.

<Step 3> Synthesis of 5-(4-(4-cyano-2,3-dihydro-1H-inden-1-yloxy)phenyl)isoxazol-3-ol According to the method of (Example 4) <Step 3>, from the compound (66 mg) obtained in (Example 12) <Step 2>, the subject compound (42.7 mg) was obtained as a white solid.

Example 13

Synthesis of 5-(4-(5-chloro-2,3-dihydro-1H-inden-1-yloxy)phenyl)isoxazol-3-ol

<Step 1> Synthesis of 5-chloro-2,3-dihydro-1H-inden-1-ol

According to the method of (Example 4) <Step 1>, from 5-chloro-2,3-dihydro-1H-inden-1-one (0.80 g), the subject compound (0.85 g) was obtained as a pale yellow oil.

<Step 2> Synthesis of ethyl 3-(4-(5-chloro-2,3-dihydro-1H-inden-1-yloxy)phenyl)propiolate According to the method of (Example 1) <Step 1>, from the compound (0.20 g) obtained in (Reference Example 3) and the compound (0.27 g) obtained in (Example 13) <Step 1>, the subject compound (354 mg) was obtained as a pale yellow solid.

<Step 3> Synthesis of 5-(4-(5-chloro-2,3-dihydro-1H-inden-1-yloxy)phenyl)isoxazol-3-ol According to the method of (Example 1) <Step 2>, from the compound (0.35 g) obtained in (Example 13) <Step 2>, the subject compound (187 mg) was obtained as a pale yellow solid.

Example 14

Synthesis of 5-(4-(5-bromo-2,3-dihydro-1H-inden-1-yloxy)phenyl)isoxazol-3-ol

<Step 1> Synthesis of 5-bromo-2,3-dihydro-1H-inden-1-ol

According to the method of (Example 4) <Step 1>, from 5-bromo-2,3-dihydro-1H-inden-1-one (3.0 g), the subject compound (2.66 g) was obtained as a gray white solid <Step 2> Synthesis of 5-(5-bromo-2,3-dihydro-1H-inden-1-yloxy)phenyl)-3-(methoxymethoxy)isoxazole According to the method of (Example 1) <Step 1>, from the compound (50 mg) obtained in (Reference Example 4) and the compound (62.6 mg) obtained in (Example 14) <Step 1>, the subject compound (69 mg) was obtained as a white amorphous.

<Step 3> Synthesis of 5-(4-(5-bromo-2,3-dihydro-1H-inden-1-yloxy)phenyl)isoxazol-3-ol According to the method of (Example 4) <Step 3>, from the compound (63 mg) obtained in (Example 14) <Step 2>, the subject compound (29 mg) was obtained as a white solid.

Example 15

Synthesis of 5-(4-(6-chloro-2,3-dihydro-1H-inden-1-yloxy)phenyl)isoxazol-3-ol

<Step 1> Synthesis of 6-chloro-2,3-dihydro-1H-inden-1-ol

According to the method of (Example 4) <Step 1>, from 6-chloro-2,3-dihydro-1H-inden-1-one (2.0 g), the subject compound (2.0 g) was obtained as a white solid.

<Step 2> Synthesis of 5-(6-chloro-2,3-dihydro-1H-inden-1-yloxy)phenyl)-3-(methoxymethoxy)isoxazole According to the method of (Example 1) <Step 1>, from the compound (50 mg) obtained in (Reference Example 4) and the compound (49.6 mg) obtained in (Example 15) <Step 1>, the subject compound (64.3 mg) was obtained as a white amorphous.

<Step 3> Synthesis of 5-(4-(6-chloro-2,3-dihydro-1H-inden-1-yloxy)phenyl)isoxazol-3-ol According to the method of (Example 4) <Step 3>, from the compound (60 mg) obtained in (Example 15) <Step 2>, the subject compound (14 mg) was obtained as a white solid.

Example 16

Synthesis of 5-(4-(7-chloro-2,3-dihydro-1H-inden-1-yloxy)phenyl)isoxazol-3-ol

<Step 1> Synthesis of 7-chloro-2,3-dihydro-1H-inden-1-ol

According to the method of (Example 4) <Step 1>, from 7-chloro-2,3-dihydro-1H-inden-1-one (72 mg), the subject compound (62 mg) was obtained as a colorless oil.

<Step 2> Synthesis of 5-(7-chloro-2,3-dihydro-1H-inden-1-yloxy)phenyl)-3-(methoxymethoxy)isoxazole According to the method of (Example 1) <Step 1>, from the compound (50 mg) obtained in (Reference Example 4) and the compound (49.6 mg) obtained in (Example 16) <Step 1>, the subject compound (46.9 mg) was obtained as a white solid.

<Step 3> Synthesis of 5-(4-(7-chloro-2,3-dihydro-1H-inden-1-yloxy)phenyl)isoxazol-3-ol According to the method of (Example 4) <Step 3>, from the compound (43 mg) obtained in (Example 16) <Step 2>, the subject compound (30 mg) was obtained as a white solid.

Example 17

Synthesis of Optically Active 5-(4-(5-chloro-2,3-dihydro-1H-inden-1-yloxy)phenyl)isoxazol-3-ol (A)

<Step 1> Synthesis of 5-(4-(5-chloro-2,3-dihydro-1H-inden-1-yloxy)phenyl)-3-(methoxymethoxy)isoxazole According to the method of (Example 1) <Step 1>, from the compound (0.10 g) obtained in (Reference Example 4) and the compound (91.5 mg) obtained in (Example 13) <Step 1>, the subject compound (0.10 g) was obtained as a white solid.

<Step 2> Optical Resolution of 5-(4-(5-chloro-2,3-dihydro-1H-inden-1-yloxy)phenyl)-3-(methoxymethoxy)isoxazole The compound (0.10 g) obtained in (Example 17) <Step 1> was subjected to an optical resolution using a preparative chromatography (column: CHIRALPAK AD-H (2 cm×25 cm) (manufactured by Daicel Chemical Industries, Ltd.), eluate: ethanol, flow rate: 15 mL/min, detection: UV 254 nm) to obtain each enantiomer of the subject compound. The optical purity was determined using a chiral column.
Column: CHIRALPAK AD-H (0.46 cm×25.0 cm) (manufactured by Daicel Chemical Industries, Ltd.),
Eluate: ethanol,
Flow rate: 0.7 mL/min,
Detection: UV 280 nm,
40° C.
Primary fraction (34 mg, white solid, >99% ee, retention time 14.7 min (enantiomer A: Example 17-2(A)))
Secondary fraction (31 mg, white solid, >99% ee, retention time 17.2 min (enantiomer B: Example 17-2(B)))

<Step 3> Synthesis of Optically Active 5-(4-(5-chloro-2,3-dihydro-1H-inden-1-yloxy)phenyl)isoxazol-3-ol (A)

According to the method of (Example 4) <Step 3>, from the compound (Example 17-2(A)) (32 mg) obtained in (Example 17) <Step 2>, the subject compound (14.5 mg) was obtained as a white amorphous (>99% ee, retention time 7.1 min).
The optical purity was determined using a chiral column.
Column: CHIRALPAK AD-H (0.46 cm×25.0 cm) (manufactured by Daicel Chemical Industries, Ltd.),
Eluate: ethanol:trifluoroacetic acid=100:0.1,
Flow rate: 1.0 mL/min,
Detection: UV 280 nm,
40° C.

Example 18

Synthesis of Optically Active 5-(4-(5-chloro-2,3-dihydro-1H-inden-1-yloxy)phenyl)isoxazol-3-ol (B)

According to the method of (Example 4) <Step 3>, from the compound (Example 17-2(B)) (30 mg) obtained in (Example 17) <Step 2>, the subject compound (13.9 mg) was obtained as a white amorphous (>99% ee, retention time 10.1 min).
The optical purity was determined using a chiral column.
Column: CHIRALPAK AD-H (0.46 cm×25.0 cm) (manufactured by Daicel Chemical Industries, Ltd.),
Eluate: ethanol:trifluoroacetic acid=100:0.1,
Flow rate: 1.0 mL/min,
Detection: UV 280 nm,
40° C.

Example 19

Synthesis of 5-(4-(4,5-dichloro-2,3-dihydro-1H-inden-1-yloxy)phenyl)isoxazol-3-ol <Step 1> Synthesis of 3-(2,3-dichlorophenyl)propionic acid To a solution of 2,3-dichlorocinnamic acid (1.0 g) in methanol (50 mL), magnesium (1.34 g) was added under ice-cooling and the resultant reaction mixture was stirred at room temperature for 3 days. To the reaction mixture, a saturated ammonium chloride aqueous solution was added and the resultant reaction mixture was extracted with dichloromethane. The organic phase was washed with a saturated saline and was dried over anhydrous sodium sulfate. From the organic phase, the solvent was distilled off under reduced pressure to obtain the subject compound (912 mg) as a white solid.

<Step 2> Synthesis of 4,5-dichloro-2,3-dihydro-1H-inden-1-one

To a solution of the compound (0.90 g) obtained in (Example 19) <Step 1> in dichloromethane (15 mL), oxalyl chloride (0.42 mL) and N,N-dimethylformamide (one drop) were added and the resultant reaction mixture was stirred at room temperature for 4 hours. The reaction mixture was concentrated under reduced pressure and the residue was dissolved in dichloroethane (10 mL). To the reaction mixture, aluminum chloride (0.55 g) was added and the resultant reaction mixture was heated to reflux for 1 hour. The reaction mixture was poured into ice water, followed by extracting the reaction mixture with ethyl acetate. The organic phase was washed with a saturated aqueous sodium bicarbonate and saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 95:5 to 90:10) to obtain the subject compound (310 mg) as a yellow solid.

<Step 3> Synthesis of 4,5-dichloro-2,3-dihydro-1H-inden-1-ol

According to the method of (Example 4) <Step 1>, from the compound (0.30 g) obtained in (Example 19) <Step 2>, the subject compound (0.30 g) was obtained as a brown solid.

<Step 4> Synthesis of 5-(4-(4,5-dichloro-2,3-dihydro-1H-inden-1-yloxy)phenyl)-3-(methoxymethoxy)isoxazole According to the method of (Example 1) <Step 1>, from the compound (50 mg) obtained in (Reference Example 4) and the compound (59.7 mg) obtained in (Example 19) <Step 3>, the subject compound (55.5 mg) was obtained as a white solid.

<Step 5> Synthesis of 5-(4-(4,5-dichloro-2,3-dihydro-1H-inden-1-yloxy)phenyl)isoxazol-3-ol According to the method of (Example 4) <Step 3>, from the compound (40 mg) obtained in (Example 19) <Step 4>, the subject compound (11.8 mg) was obtained as a white solid.

Example 20

Synthesis of 5-(4-(2,3-dihydro-4-(2-methoxyphenyl)-1H-inden-1-yloxy)phenyl)isoxazol-3-ol <Step 1> Synthesis of 4-bromo-2,3-dihydro-1H-inden-1-ol According to the method of (Example 4) <Step 1>, from 4-bromo-2,3-dihydro-1H-inden-1-one (10.0 g), the subject compound (10.0 g) was obtained as a pale yellow solid.

<Step 2> Synthesis of 5-(4-bromo-2,3-dihydro-1H-inden-1-yloxy)phenyl)-3-(methoxymethoxy)isoxazole According to the method of (Example 1) <Step 1>, from the compound (3.0 g) obtained in (Reference Example 4) and the compound (4.33 g) obtained in (Example 20) <Step 1>, the subject compound (4.12 g) was obtained as a pale yellow solid.

<Step 3> Synthesis of 5-(4-(2,3-dihydro-4-(2-methoxyphenyl)-1H-inden-1-yloxy)phenyl)-3-(methoxymethoxy)isoxazole A suspension of the compound (50 mg) obtained in (Example 20) <Step 2>, 2-methoxyphenyl boronic acid (27.4 mg), tris(dibenzylideneacetone)dipalladium(0)-chloroform (12.4 mg), 2-dicyclohexylphosphino-2',6'-dimethoxybiphenyl (S-Phos; 9.9 mg), and a 3 M potassium phosphate aqueous solution (0.12 mL) in toluene (1.0 mL) was heated to reflux for 3 hours. The reaction mixture was filtered through a pad of Celite and the filtrate was concentrated under reduced pressure. The resultant residue was purified by silica gel column chromatography (eluate: n-hexane:ethyl acetate=100:0 to 95:5 to 85:15) to obtain the subject compound (34.8 mg) as a yellow solid.

<Step 4> Synthesis of 5-(4-(2,3-dihydro-4-(2-methoxyphenyl)-1H-inden-1-yloxy)phenyl)isoxazol-3-ol According to the method of (Example 4) <Step 3>, from the compound (34 mg) obtained in (Example 20) <Step 3>, the subject compound (13.5 mg) was obtained as a white solid.

Example 21

Synthesis of 5-(4-(2,3-dihydro-4-(3-methoxyphenyl)-1H-inden-1-yloxy)phenyl)isoxazol-3-ol <Step 1> Synthesis of 5-(4-(2,3-dihydro-4-(3-methoxyphenyl)-1H-inden-1-yloxy)phenyl)-3-(methoxymethoxy)isoxazole According to the method of (Example 20) <Step 3>, from the compound (50 mg) obtained in (Example 20) <Step 2> and 3-methoxyphenyl boronic acid (27.4 mg), the subject compound (31.2 mg) was obtained as a pale yellow solid.

<Step 2> Synthesis of 5-(4-(2,3-dihydro-4-(3-methoxyphenyl)-1H-inden-1-yloxy)phenyl)isoxazol-3-ol According to the method of (Example 4) <Step 3>, from the compound (31 mg) obtained in (Example 21) <Step 1>, the subject compound (17.9 mg) was obtained as a white solid.

Example 22

Synthesis of 5-(4-(2,3-dihydro-4-(4-methoxyphenyl)-1H-inden-1-yloxy)phenyl)isoxazol-3-ol <Step 1> Synthesis of 5-(4-(2,3-dihydro-4-(4-methoxyphenyl)-1H-inden-1-yloxy)phenyl)-3-(methoxymethoxy)isoxazole According to the method of (Example 20) <Step 3>, from the compound (50 mg) obtained in (Example 20) <Step 2> and 4-methoxyphenyl boronic acid (27.4 mg), the subject compound (31.2 mg) was obtained as a pale yellow solid.

<Step 2> Synthesis of 5-(4-(2,3-dihydro-4-(4-methoxyphenyl)-1H-inden-1-yloxy)phenyl)isoxazol-3-ol According to the method of (Example 4) <Step 3>, from the compound (20 mg) obtained in (Example 22) <Step 1>, the subject compound (11.2 mg) was obtained as a white solid.

Example 23

Synthesis of 5-(4-(2,3-dihydro-4-(2-methoxypyridin-3-yl)-1H-inden-1-yloxy)phenyl)isoxazol-3-ol <Step 1> Synthesis of 5-(4-(2,3-dihydro-4-(2-methoxypyridin-3-yl)-1H-inden-1-yloxy)phenyl)-3-(methoxymethoxy)isoxazole According to the method of (Example 20) <Step 3>, from the compound (50 mg) obtained in (Example 20) <Step 2> and 2-methoxypyridine-3-boronic acid (27.6 mg), the subject compound (30 mg) was obtained.

<Step 2> Synthesis of 5-(4-(2,3-dihydro-4-(2-methoxypyridin-3-yl)-1H-inden-1-yloxy)phenyl)isoxazol-3-ol According to the method of (Example 4) <Step 3>, from the compound (30 mg) obtained in (Example 23) <Step 1>, the subject compound (16 mg) was obtained as a white solid.

Example 24

Synthesis of 5-(4-(4-(6-(3-hydroxy-3-methylbutoxy)-2,4-dimethylpyridin-3-yl)-2,3-dihydro-1H-inden-1-yloxy)phenyl)isoxazol-3-ol (D)

<Step 1> Synthesis of 2,3-dihydro-4-(5,5-dimethyl-1,3,2-dioxaborinan-2-yl)-1H-inden-1-ol To a reaction mixture of the compound (0.20 g) obtained in (Example 20) <Step 1>, bis(pinacolato)diboron (0.28 g), and [1,1'-bis(diphenylphosphino)ferrocene]dichloropalladium (II) in dimethyl sulfide (4.7 mL), potassium acetate (0.28 g) was added and the resultant reaction mixture was heated while stirring at 100° C. for 2 hours. To the reaction mixture, water was added and the resultant reaction mixture was extracted with ethyl acetate. The organic phase was washed with water and a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 50:50) to obtain the subject compound (70 mg) as a light pink amorphous.

<Step 2> Synthesis of 4-(6-(3-hydroxy-3-methylbutoxy)-2,4-dimethylpyridin-3-yl)-2,3-dihydro-4-1H-inden-1-ol According to the method of (Example 20) <Step 3>, from 4-(5-bromo-4,6-dimethylpyridin-2-yloxy)-2-methylbutan-2-ol (60 mg) synthesized according to a method described in [WO 2009/054423 pamphlet, (Production Example 45)] and the compound (69.1 mg) obtained in (Example 24) <Step 1>, each diastereoisomer of the subject compound was obtained.

Primary fraction (n-hexane-ethyl acetate system of low polarity; 14 mg, viscous oil, (diastereoisomer C: Example 24-2(C)))

Secondary fraction (n-hexane-ethyl acetate system of high polarity; 14 mg, viscous oil, (diastereoisomer D: Example 24-2(D)))

<Step 3> Synthesis of 5-(4-(4-(6-(3-hydroxy-3-methylbutoxy)-2,4-dimethylpyridin-3-yl)-2,3-dihydro-1H-inden-1-yloxy)phenyl)-3-(methoxymethoxy)isoxazole (D)

According to the method of (Example 1) <Step 1>, from the compound (9.0 mg) obtained in (Reference Example 4) and Example 24-2(D) (13.9 mg) obtained in (Example 24) <Step 2>, the subject compound (8.0 mg) was obtained.

<Step 4> Synthesis of 5-(4-(4-(6-(3-hydroxy-3-methylbutoxy)-2,4-dimethylpyridin-3-yl)-2,3-dihydro-1H-inden-1-yloxy)phenyl)isoxazol-3-ol (D)

According to the method of (Example 4) <Step 3>, from the compound (8.0 mg) obtained in (Example 24) <Step 3>, the subject compound (5.5 mg) was obtained as a white solid.

Example 25

Synthesis of 5-(4-(4-(6-(3-hydroxy-3-methylbutoxy)-2,4-dimethylpyridin-3-yl)-2,3-dihydro-1H-inden-1-yloxy)phenyl)isoxazol-3-ol (C)

<Step 1> Synthesis of 5-(4-(4-(6-(3-hydroxy-3-methylbutoxy)-2,4-dimethylpyridin-3-yl)-2,3-dihydro-1H-inden-1-yloxy)phenyl)-3-(methoxymethoxy)isoxazole (C)

According to the method of (Example 1) <Step 1>, from the compound (9.0 mg) obtained in (Reference Example 4) and Example 24-2(C) (13.9 mg) obtained in (Example 24) <Step 2>, the subject compound (8.0 mg) was obtained.

<Step 2> Synthesis of 5-(4-(4-(6-(3-hydroxy-3-methylbutoxy)-2,4-dimethylpyridin-3-yl)-2,3-dihydro-1H-inden-1-yloxy)phenyl)isoxazol-3-ol (C)

According to the method of (Example 4) <Step 3>, from the compound (8.0 mg) obtained in (Example 25) <Step 1>, the subject compound (5.1 mg) was obtained as a white solid.

Example 26

Synthesis of 5-(4-(2,3-dihydro-4-phenoxy-1H-inden-1-yloxy)phenyl)isoxazol-3-ol

<Step 1> Synthesis of 4-(tert-butyldimethylsiloxy)-2,3-dihydro-1H-inden-1-one

To a solution of 2,3-dihydro-4-hydroxy-1H-inden-1-one (1.0 g) in N,N-dimethylformamide (10 mL), imidazole (1.01 g) and tert-butyldimethylsilyl chloride (1.32 g) were sequentially added and the resultant reaction mixture was stirred at room temperature for 5 hours. The reaction mixture was poured into ethyl acetate-saturated aqueous sodium bicarbonate and the resultant reaction mixture was subjected to a phase separation. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=95:5 to 90:10) to obtain the subject compound (1.63 g) as a pale yellow oil.

<Step 2> Synthesis of 4-(tert-butyldimethylsiloxy)-2,3-dihydro-1H-inden-1-ol

According to the method of (Example 4) <Step 1>, from the compound (1.60 g) obtained in (Example 26) <Step 1>, the subject compound (1.69 g) was obtained as a yellow oil.

<Step 3> Synthesis of 5-(4-(tert butyldimethylsiloxy)-2,3-dihydro-1H-inden-1-yloxy)phenyl)-3-(methoxymethoxy)isoxazole According to the method of (Example 1) <Step 1>, from the compound (0.76 g) obtained in (Reference Example 4) and the compound (1.09 g) obtained in (Example 26) <Step 2>, the subject compound (769 mg) was obtained as a light purple solid.

<Step 4> Synthesis of 5-(4-(2,3-dihydro-4-hydroxy-1H-inden-1-yloxy)phenyl)-3-(methoxymethoxy)isoxazole To a solution of the compound (0.75 g) obtained in (Example 26) <Step 3> in tetrahydrofuran (4.5 mL), a 1N tetrabutylammonium fluoride-tetrahydrofuran solution (1.68 mL) was added under ice-cooling and the resultant reaction mixture was stirred at room temperature for 15 minutes. To the reaction mixture, ethyl acetate, water, and a citric acid aqueous solution were sequentially added and the resultant reaction mixture was subjected to a phase separation. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=67:33 to 50:50) to obtain the subject compound (518 mg) as a white solid.

<Step 5> Synthesis of 5-(4-(2,3-dihydro-4-phenoxy-1H-inden-1-yloxy)phenyl)-3-(methoxymethoxy)isoxazole To a solution of the compound (30 mg) obtained in (Example 26) <Step 4> in dichloromethane (2.0 mL), molecular sieves 4 A (60 mg), phenyl boronic acid (20.7 mg), copper (II) acetate (15.4 mg), and triethylamine (59 μL) were sequentially added and the resultant reaction mixture was stirred at room temperature for 3 days. The reaction mixture was filtered through a pad of Celite. From the organic phase, the solvent was distilled off under reduced pressure and the resultant residue was purified by silica gel column chromatography (eluate: n-hexane:ethyl acetate=100:0 to 80:20) to obtain the subject compound (17.3 mg).

<Step 6> Synthesis of 5-(4-(2,3-dihydro-4-phenoxy-1H-inden-1-yloxy)phenyl)isoxazol-3-ol According to the method of (Example 4) <Step 3>, from the compound (17.3 mg) obtained in (Example 26) <Step 5>, the subject compound (8.2 mg) was obtained as a white solid.

Example 27

Synthesis of 5-(4-(2,3-dihydro-4-(4-methoxyphenoxy)-1H-inden-1-yloxy)phenyl)isoxazol-3-ol <Step 1> Synthesis of 5-(4-(2,3-dihydro-4-(4-methoxyphenoxy)-1H-inden-1-yloxy)phenyl)-3-(methoxymethoxy)isoxazole According to the method of (Example 26) <Step 5>, from the compound (30 mg) obtained in (Example 26) <Step 4> and 4-methoxyphenyl boronic acid (25.8 mg), the subject compound (24.8 mg) was obtained.

<Step 2> Synthesis of 5-(4-(2,3-dihydro-4-(4-methoxyphenoxy)-1H-inden-1-yloxy)phenyl)isoxazol-3-ol According to the method of (Example 4) <Step 3>, from the compound (24.8 mg) obtained in (Example 27) <Step 1>, the subject compound (11.3 mg) was obtained as a white solid.

Example 28

Synthesis of 5-(4-(4-benzyloxy-2,3-dihydro-1H-inden-1-yloxy)phenyl)isoxazol-3-ol <Step 1> Synthesis of 5-(4-(4-benzyloxy-2,3-dihydro-1H-inden-1-yloxy)phenyl)-3-(methoxymethoxy)isoxazole To a solution of the compound (30 mg) obtained in (Example 26) <Step 4> in N,N-dimethylformamide (2.0 mL), benzyl bromide (15 μL), potassium carbonate (17.6 mg), and potassium iodide (21.1 mg) were sequentially added and the resultant reaction mixture was heated while stirring at 80° C. for 6 hours and at 100° C. for 2 hours. The reaction mixture was subjected to a preparative purification by LC/MS to obtain the subject compound (26.7 mg).

<Step 2> Synthesis of 5-(4-(4-benzyloxy-2,3-dihydro-1H-inden-1-yloxy)phenyl)isoxazol-3-ol According to the method of (Example 4) <Step 3>, from the compound (26.7 mg) obtained in (Example 28) <Step 1>, the subject compound (3.0 mg) was obtained as a white solid.

Example 29

Synthesis of 5-(4-(2,3-dihydro-4-(2-(trifluoromethyl)benzyloxy)-1H-inden-1-yloxy)phenyl)isoxazol-3-ol <Step 1> Synthesis of 5-(4-(2,3-dihydro-4-(2-(trifluoromethyl)benzyloxy)-1H-inden-1-yloxy)phenyl)-3-(methoxymethoxy)isoxazole According to the method of (Example 28) <Step 1>, from the compound (30 mg) obtained in (Example 26) <Step 4> and 2-(trifluoromethyl)benzyl bromide (30.4 mg), the subject compound (31.3 mg) was obtained as a yellow oil.

<Step 2> Synthesis of 5-(4-(2,3-dihydro-4-(2-(trifluoromethyl)benzyloxy)-1H-inden-1-yloxy)phenyl)isoxazol-3-ol According to the method of (Example 4) <Step 3>, from the compound (31.3 mg) obtained in (Example 29) <Step 1>, the subject compound (17.3 mg) was obtained as a white solid.

Example 30

Synthesis of 5-(4-(4-benzyl-2,3-dihydro-1H-inden-1-yloxy)phenyl)isoxazol-3-ol

<Step 1> Synthesis of 5-(4-(4-benzyl-2,3-dihydro-1H-inden-1-yloxy)phenyl)-3-(methoxymethoxy)isoxazole According to the method of (Example 20) <Step 3>, from the compound (50 mg) obtained in (Example 20) <Step 2> and benzylboronic acid pinacol ester (39.3 mg), the subject compound (30.1 mg) was obtained as a pale yellow solid.

<Step 2> Synthesis of 5-(4-(4-benzyl-2,3-dihydro-1H-inden-1-yloxy)phenyl)isoxazol-3-ol According to the method of (Example 4) <Step 3>, from the compound (30.1 mg) obtained in (Example 30) <Step 1>, the subject compound (1.4 mg) was obtained as a white solid.

Example 31

Synthesis of 5-(4-(5-chloro-2,3-dihydro-1H-inden-1-ylamino)phenyl)isoxazol-3-ol

<Step 1> Synthesis of ethyl 3-(4-nitrophenyl)propiolate

According to the method of (Reference Example 3), from 1-iodo-4-nitrobenzene (5.0 g) and ethyl propiolate (6.1 mL), the subject compound (2.94 g) was obtained as a pale yellow solid.

<Step 2> Synthesis of 5-(4-nitrophenyl)isoxazol-3-ol

According to the method of (Example 1) <Step 2>, from the compound (1.0 g) obtained in (Example 31) <Step 1>, the subject compound (0.32 g) was obtained as a pale yellow solid.

<Step 3> Synthesis of 3-(methoxymethoxy)-5-(4-nitrophenyl)isoxazole

According to the method of (Example 9) <Step 1>, from the compound (0.32 g) obtained in (Example 31) <Step 2>, the subject compound (336 mg) was obtained as a white solid.

<Step 4> Synthesis of 5-(4-aminophenyl)-3-(methoxymethoxy)isoxazole

To a mixed solution of the compound (0.50 g) obtained in (Example 31) <Step 3> in methanol (10 mL)-ethyl acetate (10 mL), 10% palladium/carbon (Pd/C) (75 mg) was added and the resultant reaction mixture was stirred in a hydrogen atmosphere for 75 minutes. The reaction mixture was filtered through a pad of Celite. From the organic phase, the solvent was distilled off under reduced pressure and the resultant residue was purified by silica gel column chromatography (eluate: n-hexane:ethyl acetate=80:20 to 65:35) to obtain the subject compound (331 mg) as a yellow oil.

<Step 5> Synthesis of 5-(4-(5-chloro-2,3-dihydro-1H-inden-1-ylamino)phenyl)-3-(methoxymethoxy)isoxazole To a solution of the compound (50 mg) obtained in (Example 31) <Step 4> in methanol (4.5 mL), 5-chloro-2,3-dihydro-1H-inden-1-one (37.8 mg) and decaborane (8.3 mg) were added and the resultant reaction mixture was stirred at room temperature for 16 hours 30 minutes. The reaction mixture was poured into water, followed by extracting the reaction mixture with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=90:10 to 82:18) to obtain the subject compound (72 mg) as a white solid.

<Step 6> Synthesis of 5-(4-(5-chloro-2,3-dihydro-1H-inden-1-ylamino)phenyl)isoxazol-3-ol According to the method of (Example 4) <Step 3>, from the compound (70 mg) obtained in (Example 31) <Step 5>, the subject compound (41.8 mg) was obtained as a white solid.

Example 32

Synthesis of 5-(3-(2,3-dihydro-1H-inden-1-yloxy)phenyl)isoxazol-3-ol

<Step 1> Synthesis of ethyl 3-(3-hydroxyphenyl)propiolate

According to the method of (Reference Example 3), from 3-iodophenol (1.18 g) and ethyl propiolate (1.0 g), the subject compound (746 mg) was obtained as a yellow solid.

<Step 2> Synthesis of ethyl 3-(3-(2,3-dihydro-1H-inden-2-yloxy)phenyl)propiolate According to the method of (Example 1) <Step 1>, from the compound (150 mg) obtained in (Example 32) <Step 1> and 2,3-dihydro-1H-inden-1-ol (168 mg), the subject compound (180 mg) was obtained as a colorless oil.

<Step 3> Synthesis of 5-(3-(2,3-dihydro-1H-inden-1-yloxy)phenyl)isoxazol-3-ol

According to the method of (Example 1) <Step 2>, from the compound (170 mg) obtained in (Example 32) <Step 2>, the subject compound (100 mg) was obtained as a white amorphous.

Example 33

Synthesis of 5-(4-(2,3-dihydro-4-(pyrimidin-5-yl)-1H-inden-1-yloxy)phenyl)isoxazol-3-ol <Step 1> Synthesis of 5-(4-(2,3-dihydro-4-(pyrimidin-5-yl)-1H-inden-1-yloxy)phenyl)-3-(methoxymethoxy)isoxazole According to the method of (Example 20) <Step 3>, from the compound (50 mg) obtained in (Example 20) <Step 2> and 5-pyrimidinylboronic acid (22.3 mg), the subject compound (25.2 mg) was obtained.

<Step 2> Synthesis of 5-(4-(2,3-dihydro-4-(pyrimidin-5-yl)-1H-inden-1-yloxy)phenyl)isoxazol-3-ol According to the method of (Example 4) <Step 3>, from the compound (25.1 mg) obtained in (Example 33) <Step 1>, the subject compound (12.3 mg) was obtained as a pale yellow solid.

Example 34

Synthesis of 5-(4-(2,3-dihydro-4-(1,4-benzodioxan-6-yl)-1H-inden-1-yloxy)phenyl)isoxazol-3-ol <Step 1> Synthesis of 5-(4-(2,3-dihydro-4-(1,4-benzodioxan-6-yl)-1H-inden-1-yloxy)phenyl)-3-(methoxymethoxy)isoxazole According to the method of (Example 20) <Step 3>, from the compound (50 mg) obtained in (Example 20) <Step 2> and 1,4-benzodioxan-6-ylboronic acid (32.4 mg), the subject compound (50.8 mg) was obtained.

<Step 2> Synthesis of 5-(4-(2,3-dihydro-4-(1,4-benzodioxan-6-yl)-1H-inden-1-yloxy)phenyl)isoxazol-3-ol According to the method of (Example 4) <Step 3>, from the compound (50.8 mg) obtained in (Example 34) <Step 1>, the subject compound (23.5 mg) was obtained as a pale yellow solid.

Example 35

Synthesis of 5-(4-(2,3-dihydro-4-(1H-indol-6-yl)-1H-inden-1-yloxy)phenyl)isoxazol-3-ol <Step 1> Synthesis of 5-(4-(2,3-dihydro-4-(1H-indol-6-yl)-1H-inden-1-yloxy)phenyl)-3-(methoxymethoxy)isoxazole According to the method of (Example 20) <Step 3>, from the compound (50 mg) obtained in (Example 20) <Step 2> and 1H-indol-6-ylboronic acid (30 mg), the subject compound (33 mg) was obtained.

<Step 2> Synthesis of 5-(4-(2,3-dihydro-4-(1H-indol-6-yl)-1H-inden-1-yloxy)phenyl)isoxazol-3-ol According to the method of (Example 4) <Step 3>, from the compound (33 mg) obtained in (Example 35) <Step 1>, the subject compound (8.0 mg) was obtained as a pale yellow solid.

Example 36

Synthesis of 5-[4-[[4-[4-[(3R)-3-hydroxybutoxy]-2,6-dimethylphenyl]-2,3-dihydro-1H-inden-1-yl]oxy]phenyl]-1,2-oxazol-3-ol <Step 1> Synthesis of (2R)-4-(4-bromo-3,5-dimethylphenoxy)butan-2-ol To 4-bromo-3,5-dimethylphenol (5.4 g) in dehydrated N,N-dimethylformamide (60 mL), sodium hydride (1.1 g) was added under ice-cooling and the resultant reaction mixture was stirred for 30 minutes. To the reaction mixture, (R)-3-hydroxybutyl 4-methylbenzenesulfonate (5.0 g) was added and the resultant reaction mixture was stirred at room temperature for 45 minutes. To the reaction mixture, a saturated ammonium chloride aqueous solution was added, followed by extracting the reaction mixture with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate-95:5 to 80:20) to obtain the subject compound (4.2 g) as a colorless solid.

<Step 2> Synthesis of acetic acid [(2R)-4-(4-bromo-3,5-dimethylphenoxy)butan-2-yl]ester To a solution of the compound (4.0 g) obtained in (Example 36) <Step 1> and triethylamine (3.0 mL) in methylene chloride (70 mL), acetyl chloride (1.3 mL) was added under ice-cooling and the resultant reaction mixture was stirred at room temperature for 2 hours. To the reaction mixture, under ice-cooling, methanol (5 mL) was added, water was added, and the resultant reaction mixture was extracted with methylene chloride. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 80:20) to obtain the subject compound (3.1 g) as a colorless oil.

<Step 3> Synthesis of 2-((4-bromo-2,3-dihydro-1H-inden-1-yl)oxy)tetrahydro-2H-pyran According to the method of (Reference Example 1), from the compound (6.0 g) obtained in (Example 20) <Step 1>, the subject compound (8.3 g) was obtained as a pale yellow oil.

<Step 4> Synthesis of 5,5-dimethyl-2-(1-((tetrahydro-2H-pyran-2-yl)oxy)-2,3-dihydro-1H-inden-4-yl)-1,3,2-dioxaborinane According to the method of (Example 24) <Step 1>, from the compound (8.0 g) obtained in (Example 36) <Step 3>, the subject compound (8.5 g) was obtained as an orange oil.

<Step 5> Synthesis of acetic acid [(2R)-4-[3,5-dimethyl-4-[1-(oxan-2-yloxy)-2,3-dihydro-1H-inden-4-yl]phenoxy]butan-2-yl]ester According to the method of (Example 20) <Step 3>, from the compound (1.0 g) obtained in (Example 36) <Step 2> and the compound (1.2 g) obtained in (Example 36) <Step 4>, the subject compound (0.74 g) was obtained as a red oil.

<Step 6> Synthesis of acetic acid [(2R)-4-[4-(1-hydroxy-2,3-dihydro-1H-inden-4-yl)-3,5-dimethylphenoxy]butan-2-yl]ester To a mixed solution of the compound (0.7 g) obtained in (Example 36) <Step 5> in tetrahydrofuran (2 mL) and water (1 mL), acetic acid (4 mL) was added and the resultant reaction mixture was heated while stirring under a nitrogen stream at 60° C. for 2 hours. To the reaction mixture, ethyl acetate and water were added, followed by extracting the reaction mixture with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 80:20) to obtain the subject compound (0.38 g) as a colorless oil.

<Step 7> Synthesis of 3-[4-[[4-[4-[(3R)-3-acetyloxybutoxy]-2,6-dimethylphenyl]-2,3-dihydro-1H-inden-1-yl]oxy]phenyl]prop-2-ynoic acid ethyl ester To a solution of the compound (0.10 g) obtained in (Example 36) <Step 6>, the compound (61 mg) obtained in (Reference Example 3), and 1,1'-azobis(N,N-dimethylformamide) (0.14 g) in tetrahydrofuran (5.0 mL), tri-n-butylphosphine (0.20 mL) was added under ice-cooling and the resultant reaction mixture was stirred at room temperature for 1 hour. To the reaction mixture, water was added and the resultant reaction mixture was extracted with ethyl acetate. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 50:50) to obtain the subject compound (87 mg) as a colorless oil.

<Step 8> Synthesis of 5-[4-[[4-[4-[(3R)-3-hydroxybutoxy]-2,6-dimethylphenyl]-2,3-dihydro-1H-inden-1-yl]oxy]phenyl]-1,2-oxazol-3-ol According to the method of (Example 1) <Step 2>, from the compound (60 mg) obtained in (Example 36) <Step 7>, the subject compound (52 mg) was obtained as a colorless solid.

Example 37

Synthesis of 5-[4-[[4-[4-(3-hydroxy-3-methylbutoxy)-2,6-dimethylphenyl]-2,3-dihydro-1H-inden-1-yl]oxy]phenyl]-1,2-oxazol-3-ol <Step 1> Synthesis of 4-(4-bromo-3,5-dimethylphenoxy)-2-methylbutan-2-ol According to the method of (Example 36) <Step 1>, from 3-hydroxy-3-methylbutyl 4-methylbenzenesulfonate (5.1 g) and 4-bromo-3,5-dimethylphenol (3.6 g), the subject compound (5.2 mg) was obtained as a colorless oil.

<Step 2> Synthesis of 4-(3,5-dimethyl-4-(1-((tetrahydro-2H-pyran-2-yl)oxy)-2,3-dihydro-1H-inden-4-yl)phenoxy)-2-methylbutan-2-ol According to the method of (Example 20) <Step 3>, from the compound (0.35 g) obtained in (Example 37) <Step 1> and the compound (0.40 g) obtained in (Example 36) <Step 4>, the subject compound (0.37 g) was obtained as a yellow oil.

<Step 3> Synthesis of 4-(4-(3-hydroxy-3-methylbutoxy)-2,6-dimethylphenyl)-2,3-dihydro-1H-inden-1-ol According to the method of (Example 36) <Step 6>, from the compound (0.36 g) obtained in (Example 37) <Step 2>, the subject compound (0.26 g) was obtained as a colorless oil.

<Step 4> Synthesis of 4-[4-[1-[4-[3-(methoxymethoxy)-1,2-oxazol-5-yl]phenoxy]-2,3-dihydro-1H-inden-4-yl]-3,5-dimethylphenoxy]-2-methylbutan-2-ol According to the method of (Example 1) <Step 1>, from the compound (0.15 g) obtained in (Example 37) <Step 3> and the compound (0.40 g) obtained in (Reference Example 4), the subject compound (0.21 g) was obtained as a white solid.

<Step 5> Synthesis of 5-[4-[[4-[4-(3-hydroxy-3-methylbutoxy)-2,6-dimethylphenyl]-2,3-dihydro-1H-inden-1-yl ]oxy]phenyl]-1,2-oxazol-3-ol According to the method of (Example 4) <Step 3>, from the compound (0.20 g) obtained in (Example 37) <Step 4>, the subject compound (99 mg) was obtained as a white solid.

Example 38

Synthesis of 5-(4-((3-(6-(3-hydroxy-3-methylbutoxy)-4-methylpyridin-3-yl)-2-methylphenyl)methoxy)phenyl)isoxazol-3-ol <Step 1> Synthesis of 5,5-dimethyl-2-(2-methyl-3-((tetrahydro-2H-pyran-2-yloxy)methyl)phenyl)-1,3,2-dioxaborinane To a solution of the compound (2.57 g) obtained in (Reference Example 1) and bis(neopentyl glycolate)diboron (2.65 g) in 1,4-dioxane (45 mL), potassium acetate (2.65 g) and [1,1'-bis(diphenylphosphino)ferrocene]dichloro palladium (II)-dichloromethane adduct (0.74 g) were added and the inside of the reaction system was deaerated, followed by heating to reflux the resultant reaction mixture for 1 hour. To the reaction mixture, water was added and the resultant reaction mixture was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate; n-hexane:ethyl acetate=100:0 to 90:10) to obtain the subject compound (2.21 g) as a colorless oil.

<Step 2> Synthesis of 4-(5-bromo-4-methylpyridin-2-yloxy)-2-methylbutan-2-ol To a suspension of sodium hydride (to which about 40% of a mineral oil was added, 0.23 g) in N,N-dimethylformamide (10 mL), 5-bromo-2-hydroxy-4-methylpyridine (1.00 g) was added under ice-cooling and the resultant reaction mixture was stirred for 30 minutes. To the reaction mixture, 3-hydroxy-3-methylbutyl 4-methylbenzene sulfonate (1.51 g) was added and the resultant reaction mixture was stirred at 60° C. for 4 hours. To the reaction mixture, a saturated ammonium chloride aqueous solution was added and the resultant reaction mixture was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate; n-hexane:ethyl acetate=50:50 to 33:67) to obtain the subject compound (0.92 g) as a pale yellow oil.

<Step 3> Synthesis of (3-(6-(3-hydroxy-3-methylbutoxy)-4-methylpyridin-3-yl)-2-methylphenyl)methanol To a solution of the compound (2.32 g) obtained in (Example 38) <Step 1> and the compound (2.00 g) obtained in (Example 38) <Step 2> in toluene (20 mL), palladium acetate (82 mg), 2-dicyclohexylphosphino-2',6'-dimethoxybiphenyl (SPhos, 0.30 g), and a 7.3M potassium phosphate aqueous solution (3.0 mL) were sequentially added and the resultant reaction mixture was heated to reflux for 30 minutes. To the reaction mixture, acetic acid (40 mL) and water (10 mL) were added and the reaction mixture was heated to reflux further for 2 hours. The reaction mixture was subjected to a phase separation and the organic phase was filtered through a pad of Celite. To the resultant filtrate, a saturated aqueous sodium bicarbonate was added and the filtrate was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate; n-hexane:ethyl acetate=70:30 to 50:50 to 40:60) to obtain the subject compound (0.48 g) as a colorless oil.

The aqueous phase was alkalized with a 1N sodium hydroxide aqueous solution and was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate; n-hexane:ethyl acetate=70:30 to 50:50 to 40:60) to obtain the subject compound (0.89 g) as a colorless oil.

The obtained compounds were combined to obtain the subject compound (1.37 g) as a colorless oil.

<Step 4> Synthesis of ethyl 3-(4-((3-(6-(3-hydroxy-3-methylbutoxy)-4-methylpyridin-3-yl)-2-methylphenyl)methoxy)phenyl)propiolate To a solution of the compound (0.40 g) obtained in (Example 38) <Step 3>, the compound (0.24 g) obtained in (Reference Example 3), and 1,1'-azobis(N,N-dimethylformamide) (0.66 g) in tetrahydrofuran (13.0 mL), tri-n-butylphosphine (1.22 mL) was added under ice-cooling and the resultant reaction mixture was stirred at room temperature for 1 hour. To the reaction mixture, water was added and the resultant reaction mixture was extracted with ethyl acetate. The organic phase was washed sequentially with water and a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 50:50) to obtain a crude product (0.30 g) of the subject compound as a colorless oil.

<Step 5> Synthesis of 5-(4-((3-(6-(3-hydroxy-3-methylbutoxy)-4-methylpyridin-3-yl)-2-methylphenyl)methoxy)phenyl)isoxazol-3-ol To a solution of the crude product (0.30 g) obtained in (Example 38) <Step 4> in ethanol (6.0 mL), a 50% hydroxylamine aqueous solution (0.12 mL) and a 10% sodium hydroxide aqueous solution (0.74 mL) were sequentially added and the resultant reaction mixture was heated to reflux for 1 hour. To the reaction mixture, a saturated ammonium chloride aqueous solution was added and the resultant reaction mixture was extracted with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 60:40 to 40:60) to obtain a crude product (0.15 g) of the subject compound as an amorphous. The resultant crude product was purified again by thin-layer silica gel column chromatography to obtain the subject compound (11 mg) as a yellow amorphous.

Example 39

Synthesis of 5-(4-((3-(6-(3-hydroxy-3-methylbutoxy)-2-methylpyridin-3-yl)-2-methylphenyl)methoxy)phenyl)isoxazol-3-ol <Step 1> Synthesis of 4-(5-bromo-6-methylpyridin-2-yloxy)-2-methylbutan-2-ol According to the method of (Example 38) <Step 2>, from 5-bromo-2-hydroxy-6-methylpyridine (1.0 g), the subject compound (1.3 g) was obtained as a pale yellow oil.

<Step 2> Synthesis of (3-(6-(3-hydroxy-3-methylbutoxy)-2-methylpyridin-3-yl)-2-methylphenyl)methanol According to the method of (Example 38) <Step 3>, from the compound (2.00 g) obtained in (Example 39) <Step 1> and the compound (2.32 g) obtained in (Example 38) <Step 1>, the subject compound (1.46 g) was obtained as a colorless oil.

<Step 3> Synthesis of ethyl 3-(4-((3-(6-(3-hydroxy-3-methylbutoxy)-2-methylpyridin-3-yl)-2-methylphenyl)methoxy)phenyl)propiolate To a solution of the compound (0.80 g) obtained in (Example 39) <Step 2>, the compound (0.48 g) obtained in (Reference Example 3), and tri-n-butylphosphine (1.88 mL) in tetrahydrofuran (20.0 mL), 1,1'-azobis(N,N-dimethylformamide) (2.20 g) was added under ice-cooling and the resultant reaction mixture was stirred at room temperature for 1 hour. From the organic phase, the solvent was distilled off under reduced pressure and the resultant residue was purified by silica gel column chromatography (eluate: n-hexane:ethyl acetate=70:30 to 50:50) to obtain a crude product (0.89 g) of the subject compound as a colorless oil.

<Step 4> Synthesis of 5-(4-((3-(6-(3-hydroxy-3-methylbutoxy)-2-methylpyridin-3-yl)-2-methylphenyl)methoxy) phenyl)isoxazol-3-ol To a solution of the compound (0.85 g) obtained in (Example 39) <Step 3> in ethanol (17 mL), a 50% hydroxylamine aqueous solution (0.34 mL) and a 2.5N sodium hydroxide aqueous solution (2.13 mL) were sequentially added and the resultant reaction mixture was heated to reflux for 1 hour. To the reaction mixture, a saturated ammonium chloride aqueous solution was added and the resultant reaction mixture was extracted with ethyl acetate. The organic phase was washed with a saturated saline and was dried over anhydrous sodium sulfate. From the organic phase, the solvent was distilled off under reduced pressure and the resultant residue was triturated with diethyl ether to obtain the subject compound (0.39 g) as a white solid.

Example 40

Synthesis of 5-(4-((3-(2,4-dimethyl-6-(3-hydroxy-3-methylbutoxy)pyridin-3-yl)-2-methylphenyl)methoxy)phenyl)isoxazol-3-ol Method A <Step 1> Synthesis of (3-(2,4-dimethyl-6-(3-hydroxy-3-methylbutoxy)pyridin-3-yl)-2-methylphenyl)methanol According to the method of (Example 38) <Step 3>, from the compound (2.00 g) obtained in (Reference Example 2) and the compound (2.21 g) obtained in (Example 38) <Step 1>, the subject compound (1.63 g) was obtained as a colorless oil.

<Step 2> Synthesis of ethyl 3-(4-((3-(2,4-dimethyl-6-(3-hydroxy-3-methylbutoxy)pyridin-3-yl)-2-methylphenyl)methoxy)phenyl)propiolate According to the method of (Example 39) <Step 3>, from the compound (1.40 g) obtained in (Example 40) <Step 1>, the subject compound (1.30 g) was obtained as a colorless oil.

<Step 3> Synthesis of 5-(4-((3-(2,4-dimethyl-6-(3-hydroxy-3-methylbutoxy)pyridin-3-yl)-2-methylphenyl)methoxy)phenyl)isoxazol-3-ol According to the method of (Example 39) <Step 4>, from the compound (1.20 g) obtained in (Example 40) <Step 2>, the subject compound (0.77 g) was obtained as a white solid.

Method B

<Step 4> Synthesis of 5-(4-((3-(2,4-dimethyl-6-(3-hydroxy-3-methylbutoxy)pyridin-3-yl)-2-methylphenyl)methoxy)phenyl)-3-(methoxymethoxy)isoxazole To a solution of the compound (21 mg) obtained in (Example 40) <Step 1>, the compound (31 mg) obtained in (Reference Example 4), and triphenylphosphine (37 mg) in tetrahydrofuran (1.0 mL), diethyl azodicarboxylate (40% toluene solution) (63 μl) was added under ice-cooling and the resultant reaction mixture was stirred at room temperature for 1 hour. The reaction mixture was concentrated under reduced pressure and the resultant residue was purified by thin-layer silica gel chromatography (NH-silica gel, eluate: n-hexane: ethyl acetate=60:40) to obtain the subject compound (41 mg) as a colorless oil.

<Step 5> Synthesis of 5-(4-((3-(2,4-dimethyl-6-(3-hydroxy-3-methylbutoxy)pyridin-3-yl)-2-methylphenyl)methoxy)phenyl)isoxazol-3-ol To a mixed solution of the compound (38 mg) obtained in (Example 40) <Step 4> in tetrahydrofuran (1.0 mL)-methanol (2.0 mL), 2N hydrochloric acid-ethanol (0.1 mL) was added and the resultant reaction mixture was stirred at room temperature for 6.5 hours. To the reaction mixture, water was added, and the resultant reaction mixture was adjusted to pH 5 to 6 with a 10% citric acid aqueous solution, followed by extracting the reaction mixture with ethyl acetate. The organic phase was washed with a saturated saline and was dried over anhydrous sodium sulfate. From the organic phase, the solvent was distilled off under reduced pressure and the resultant residue was triturated with n-hexane-ethyl acetate (50:50) to obtain the subject compound (15 mg) as a white solid.

Example 41

Synthesis of 5-(4-((3-(2,4-dimethyl-6-(3-hydroxy-3-methylbutoxy)pyridin-3-yl)phenyl)methoxy)phen yl)isoxazol-3-ol <Step 1> Synthesis of (3-(2,4-dimethyl-6-(3-hydroxy-3-methylbutoxy)pyridin-3-yl)phenyl)methanol To a mixed solution of the compound (0.90 g) obtained in (Reference Example 2) and 3-(hydroxymethyl)phenyl boronic acid (0.62 g) in toluene (15 mL)-water (1.5 mL), palladium acetate (35 mg), 2-dicyclohexylphosphino-2',6'-dimethoxybiphenyl (SPhos; 0.13 g), and potassium phosphate (0.92 g) were added and the resultant reaction mixture was heated to reflux for 2 hours. The reaction mixture was filtered through a pad of Celite, and the filtrate was washed with ethyl acetate and was concentrated under reduced pressure. The residue was purified by silica gel column chromatography (eluate: n-hexane:ethyl acetate=90:10 to 50:50) to obtain the subject compound (0.45 g) as a yellow oil.

<Step 2> Synthesis of ethyl 3-(4-((3-(2,4-dimethyl-6-(3-hydroxy-3-methylbutoxy)pyridin-3-yl)phenyl)methoxy)phen yl)propiolate According to the method of (Example 39) <Step 3>, from the compound (0.14 g) obtained in (Example 41) <Step 1>, the subject compound (0.18 g) was obtained as a colorless oil.

<Step 3> Synthesis of 5-(4-((3-(2,4-dimethyl-6-(3-hydroxy-3-methylbutoxy)pyridin-3-yl)phenyl)methoxy)phenyl)isoxazol-3-ol According to the method of (Example 39) <Step 4>, from the compound (0.16 g) obtained in (Example 4) <Step 2>, the subject compound (105 mg) was obtained as a white solid.

Example 42

Synthesis of 5-[4-[[3-[2,6-dimethyl-4-(3-methylsulfonylpropoxy)phenyl]phenyl]methoxy]phenyl]-1,2-oxazol-3-ol <Step 1> Synthesis of 5-[4-[[3-[2,6-dimethyl-4-(3-methylsulfonylpropoxy)phenyl]phenyl]methoxy] phenyl]-3-(methoxymethoxy)-1,2-oxazole According to the method of (Example 36) <Step 7>, from a compound (0.20 g) in [WO 2008/001931 pamphlet, (Reference Example 19)] and the compound (0.15 g) in (Reference Example 4), the subject compound (0.26 g) was obtained as a white solid.

<Step 2> Synthesis of 5-[4-[[3-[2,6-dimethyl-4-(3-methylsulfonylpropoxy)phenyl]phenyl]methoxy] phenyl]-1,2-oxazol-3-ol According to the method of (Example 4) <Step 3>, from the compound (0.26 g) obtained in (Example 42) <Step 1>, the subject compound (0.20 g) was obtained as a white solid.

Example 43

Synthesis of 1-[3-[4-[3-[[4-(3-hydroxy-1,2-oxazol-5-yl)phenoxy]methyl]phenyl]-3,5-dimethylphenoxy] propyl]pyrrolidin-2-one <Step 1> Synthesis of 1-[3-(4-bromo-3,5-dimethylphenoxy)propyl]pyrrolidin-2-one According to the method of (Example 36) <Step 7>, from 1-(3-hydroxypropyl)pyrrolidin-2-one (3.8 mL) and 4-bromo-3,5-dimethylphenol (5.0 g), a crude product (14.6 g) containing the subject compound was obtained.

<Step 2> Synthesis of 1-[3-[4-[3-(hydroxymethyl) phenyl]-3,5-dimethylphenoxy]propyl]pyrrolidin-2-one According to the method of (Example 20) <Step 3>, from the compound (1.0 g) obtained in (Example 43) <Step 1> and ((3-(hydroxymethyl)phenyl)boronic acid (0.70 g), the subject compound (0.66 g) was obtained as a colorless solid.

<Step 3> Synthesis of 1-[3-[4-[3-[[4-[3-(methoxymethoxy)-1,2-oxazol-5-yl]phenoxy]methyl]phenyl]-3,5-dimethylphenoxy]propyl]pyrrolidin-2-one According to the method of (Example 36) <Step 7>, from the compound (0.15 g) in (Example 43) <Step 2> and the compound (0.26 g) in (Reference Example 4), the subject compound (0.43 g) was obtained as a colorless solid.

<Step 4> Synthesis of 1-[3-[4-[3-[[4-(3-hydroxy-1,2-oxazol-5-yl)phenoxy]methyl]phenyl]-3,5-dimethylphenoxy]propyl]pyrrolidin-2-one According to the method of (Example 4) <Step 3>, from the compound (0.25 g) obtained in (Example 43) <Step 3>, the subject compound (0.15 g) was obtained as a colorless solid.

Example 44

Synthesis of (2R)-3-[4-[3-[[4-(3-hydroxy-1,2-oxazol-5-yl)phenoxy]methyl]-2-methylphenyl]-3,5-dimethylphenoxy]propane-1,2-diol <Step 1> Synthesis of (4S)-4-[(4-bromo-3,5-dimethylphenoxy)methyl]-2,2-dimethyl-1,3-dioxolane According to the method of (Example 36) <Step 1>, from 4-bromo-3,5-dimethylphenol (3.2 g) and (R)-(2,2-dimethyl-1,3-dioxolan-4-yl)methyl 4-methylbenzenesulfonic acid ester (5.0 g), the subject compound (2.7 g) was obtained as a colorless oil.

<Step 2> Synthesis of (3-(5,5-dimethyl-1,3,2-dioxaborinan-2-yl)-2-methylphenyl)methanol According to the method of (Example 24) <Step 1>, from 3-bromo-2-methylbenzyl alcohol (5.0 g), the subject compound (5.6 g) was obtained as an orange oil.

<Step 3> Synthesis of [3-[4-[[(4S)-2,2-dimethyl-1,3-dioxolan-4-yl]methoxy]-2,6-dimethylphenyl]-2-methylphenyl]methanol According to the method of (Example 20) <Step 3>, from the compound (2.0 g) obtained in (Example 44) <Step 1> and the compound (1.6 g) obtained in (Example 44) <Step 2>, the subject compound (1.4 g) was obtained as an orange oil.

<Step 4> Synthesis of 5-[4-[[3-[4-[[(4S)-2,2-dimethyl-1,3-dioxolan-4-yl]methoxy]-2,6-dimethylphenyl]-2-methyl phenyl]methoxy]phenyl]-3-(methoxymethoxy)-1,2-oxazole According to the method of (Example 36) <Step 7>, from the compound (0.30 g) in (Example 44) <Step 3> and the compound (0.19 g) in (Reference Example 4), the subject compound (0.14 g) was obtained as a yellow oil.

<Step 5> Synthesis of (2R)-3-[4-[3-[[4-(3-hydroxy-1,2-oxazol-5-yl)phenoxy]methyl]-2-methylphenyl]-3,5-dimethylphenoxy]propane-1,2-diol According to the method of (Example 4) <Step 3>, from the compound (0.11 g) obtained in (Example 44) <Step 4>, the subject compound (58 mg) was obtained as a pale yellow solid.

Example 45

Synthesis of 5-[4-[[3-[4-(3-hydroxy-3-methylbutoxy)-2,6-dimethylphenyl]-2-methylphenyl]methoxy]phenyl]-1,2-oxazol-3-ol <Step 1> Synthesis of 4-[4-[3-(hydroxymethyl)-2-methylphenyl]-3,5-dimethylphenoxy]-2-methylbutan-2-ol According to the method of (Example 20) <Step 3>, the crude product resulting from the compound (5.0 g) obtained in (Example 37) <Step 1> and the compound (1.6 g) obtained in (Example 38) <Step 1> was dissolved in methanol (60 mL). To the reaction mixture, 2N hydrochloric acid (20 mL) was added and the resultant reaction mixture was stirred at room temperature for 16 hours. From the organic phase, the solvent was distilled off under reduced pressure. To the reaction mixture, ethyl acetate and water were added, followed by extracting the reaction mixture with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=75:25 to 60:40) to obtain the subject compound (3.2 g) as a pale yellow solid.

<Step 2> Synthesis of [3-[4-(3-hydroxy-3-methylbutoxy)-2,6-dimethylphenyl]-2-methylphenyl]methyl 4-methylbenzenesulfonic acid ester To a solution of the compound (0.50 g) obtained in (Example 45) <Step 1> and pyridine (0.19 mL) in methylene chloride (20 mL), p-toluenesulfonic anhydride (0.59 g) was added under ice-cooling and the resultant reaction mixture was stirred at the same temperature for 30 minutes. To the reaction mixture, 1N hydrochloric acid was added and the resultant reaction mixture was extracted with methylene chloride. The organic phase was washed sequentially with water and a saturated saline and was dried over anhydrous sodium sulfate to obtain the subject compound (0.78 g) as a light brown oil.

<Step 3> 3-[4-[[3-[4-(3-hydroxy-3-methylbutoxy)-2,6-dimethylphenyl]-2-methylphenyl]methoxy]phenyl] prop-2-ynoic acid ethyl ester A solution (suspension) of the compound (0.78 g) obtained in (Example 45) <Step 2>, the compound (0.29 g) in (Reference Example 3), and calcium carbonate (0.41 g) in dimethylformamide (20 mL) was stirred under a nitrogen stream at room temperature for 1 hour. The reaction mixture was filtered through a pad of Celite. To the reaction mixture, ethyl acetate and water were added, followed by extracting the reaction mixture with ethyl acetate. The organic phase was washed with a saturated saline and was dried over anhydrous sodium sulfate. From the organic phase, the solvent was distilled off under reduced pressure and the resultant residue was purified by silica gel column chromatography (eluate: n-hexane:ethyl acetate=100:0 to 50:50) to obtain the subject compound (0.42 g) as a colorless oil.

<Step 4> Synthesis of 5-[4-[[3-[4-(3-hydroxy-3-methylbutoxy)-2,6-dimethylphenyl]-2-methylphenyl]methoxy]phenyl]-1,2-oxazol-3-ol According to the method of (Example 1) <Step 2>, from the compound (0.40 g) obtained in (Example 45) <Step 3>, the subject compound (0.29 g) was obtained as a colorless solid.

Example 46

Synthesis of 5-[4-[[3-[6-(3-hydroxy-3-methylbutoxy)-4,5-dimethylpyridin-3-yl]-2-methylphenyl]methoxy]phenyl]-1,2-oxazol-3-ol <Step 1> Synthesis of 4-(5-bromo-3,4-dimethylpyridin-2-yl)oxy-2-methylbutan-2-ol According to the method of (Example 36) <Step 1>, from 5-bromo-3,4-dimethylpyridin-2-ol (3.0 g) and 3-hydroxy-3-methylbutyl 4-methylbenzenesulfonate (4.2 g), the subject compound (2.1 g) was obtained as a white solid.

<Step 2> Synthesis of 4-[5-[3-(hydroxymethyl)-2-methylphenyl]-3,4-dimethylpyridin-2-yl]oxy-2-methylbutan-2-ol According to the method of (Example 45) <Step 1>, from the compound (3.0 g) obtained in (Example 46) <Step 1> and the compound (1.0 g) obtained in (Example 38) <Step 1>, the subject compound (0.39 g) was obtained as a white solid.

<Step 3> 3-[4-[[3-[6-(3-hydroxy-3-methylbutoxy)-4,5-dimethylpyridin-3-yl]-2-methylphenyl]methoxy]phenyl]prop-2-ynoic acid ethyl ester According to the method of (Example 1) <Step 1>, from the compound (0.10 g) obtained in (Example 46) <Step 2> and the compound (64 mg) obtained in (Reference Example 3), the subject compound (0.11 g) was obtained as a colorless oil.

<Step 4> Synthesis of 5-[4-[[3-[6-(3-hydroxy-3-methylbutoxy)-4,5-dimethylpyridin-3-yl]-2-methylphenyl]methoxy]phenyl]-1,2-oxazol-3-ol According to the method of (Example 1) <Step 2>, from the compound (0.10 g) obtained in (Example 46) <Step 3>, the subject compound (72 mg) was obtained as a colorless solid.

Example 47

Synthesis of 5-[4-[[3-[6-(3-hydroxy-3-methylbutoxy)-2,5-dimethylpyridin-3-yl]-2-methylphenyl]methoxy]phenyl]-1,2-oxazol-3-ol <Step 1> 4-(5-bromo-3,6-dimethylpyridin-2-yl)oxy-2-methylbutan-2-ol According to the method of (Example 36) <Step 1>, from 5-bromo-3,6-dimethylpyridin-2-ol (0.74 g) and 3-hydroxy-3-methylbutyl 4-methylbenzenesulfonate (1.0 g), the subject compound (0.80 g) was obtained as a white solid.

<Step 2> Synthesis of 4-[5-[3-(hydroxymethyl)-2-methylphenyl]-3,6-dimethylpyridin-2-yl]oxy-2-methylbutan-2-ol According to the method of (Example 45) <Step 1>, from the compound (0.92 g) obtained in (Example 47) <Step 1> and the compound (1.0 g) obtained in (Example 38) <Step 1>, the subject compound (0.39 g) was obtained as a white solid.

<Step 3> 3-[4-[[3-[6-(3-hydroxy-3-methylbutoxy)-2,5-dimethylpyridin-3-yl]-2-methylphenyl]methoxy]phenyl]prop-2-ynoic acid ethyl ester According to the method of (Example 1) <Step 1>, from the compound (0.10 g) obtained in (Example 46) <Step 2> and the compound (64 mg) obtained in (Reference Example 3), the subject compound (0.11 g) was obtained as a colorless oil.

<Step 4> Synthesis of 5-[4-[[3-[6-(3-hydroxy-3-methylbutoxy)-4,5-dimethylpyridin-3-yl]-2-methylphenyl]methoxy]phenyl]-1,2-oxazol-3-ol According to the method of (Example 1) <Step 2>, from the compound (99 mg) obtained in (Example 46) <Step 3>, the subject compound (34 mg) was obtained as a colorless solid.

The structures of the final compounds synthesized in the above (Example 1) to (Example 47) are shown below. LC/MS data and NMR data (no mark: 300 MHz NMR, *: 400 MHz NMR) of these final compounds of Examples are also shown in Tables below. The structures of the intermediate compounds synthesized in Examples respectively and the compounds of Reference Examples, LC/MS data (in Table 2, #: TFA, *: data for [M-H]⁻, **: data for [M+Na]⁺) of these intermediate compounds and the compounds of Reference Examples, and NMR data (in Table 3, no mark: 300 MHz NMR, *: 400 MHz NMR) of these intermediate compounds and the compounds of Reference Examples are also shown in Tables below. Here, with respect to the intermediate compound, for example, the compound obtained in (Example 1) <Step 1> is expressed as "1-1".

Example 1

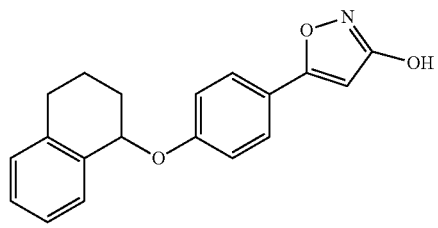

Example 2

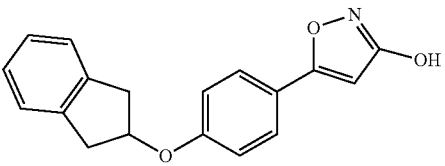

Example 3
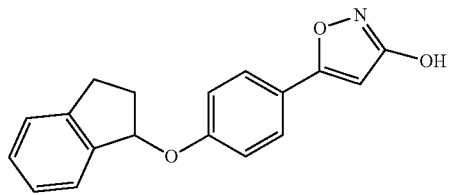
Example 5
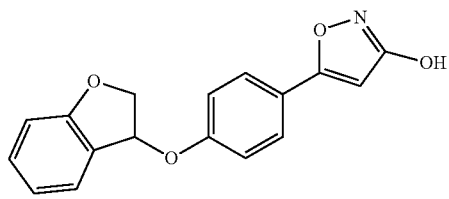
Example 6
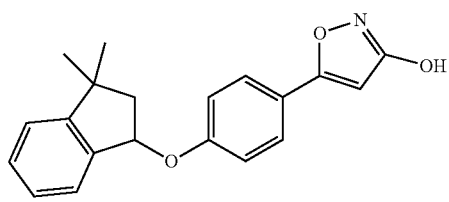
Example 6
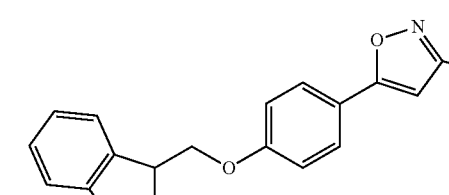
Example 7
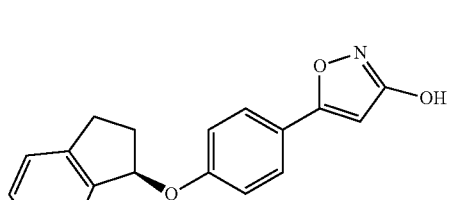
Example 8
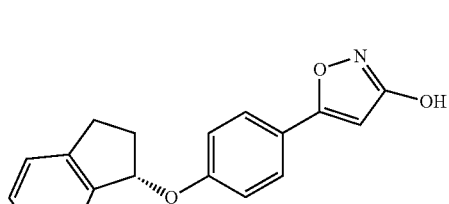
Example 9
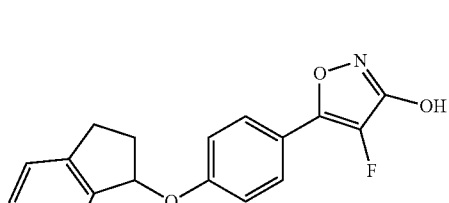
Example 10
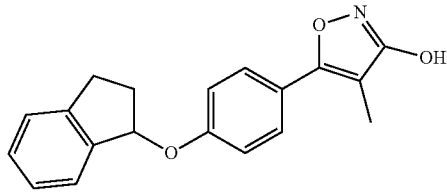
Example 11
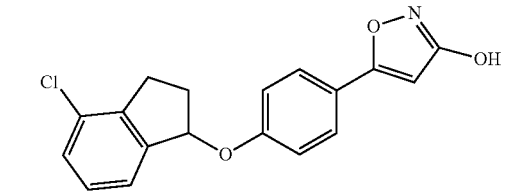
Example 12
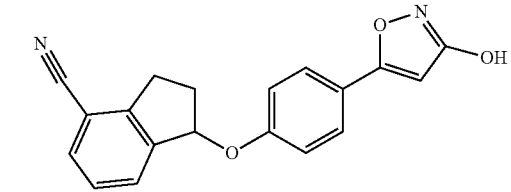
Example 13
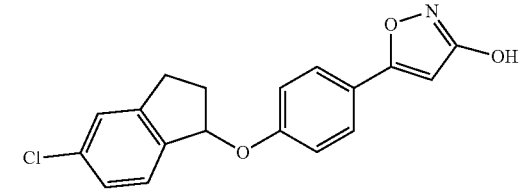
Example 14
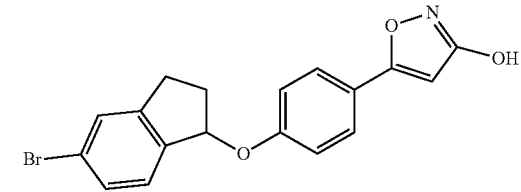
Example 15
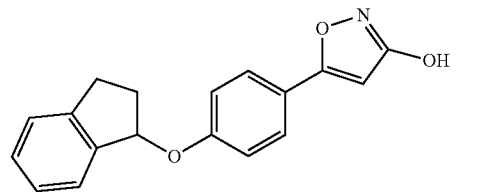
Example 16
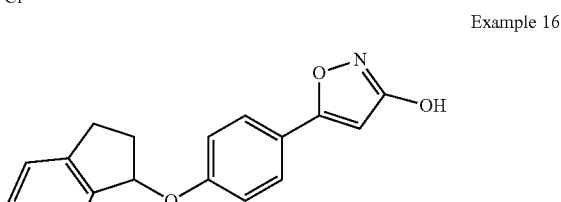

Example 17(A)
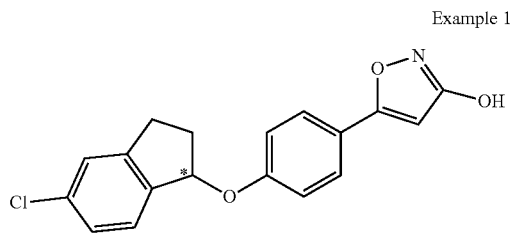
Example 18(B)
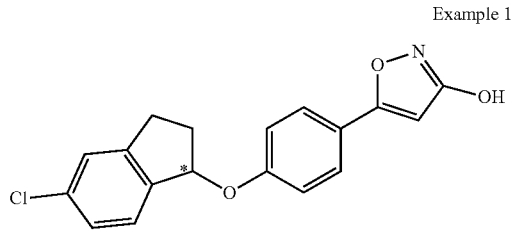
Example 19
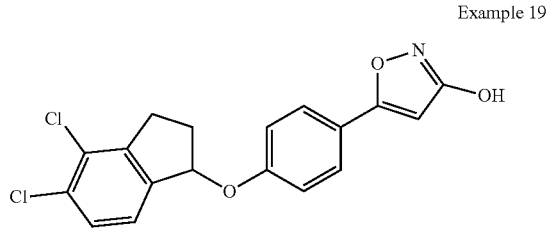
Example 20
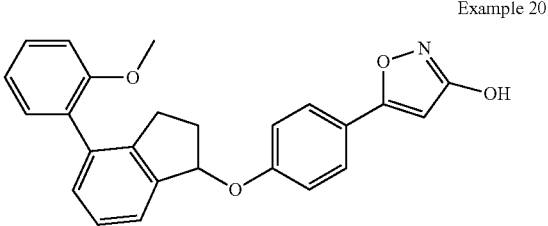
Example 21
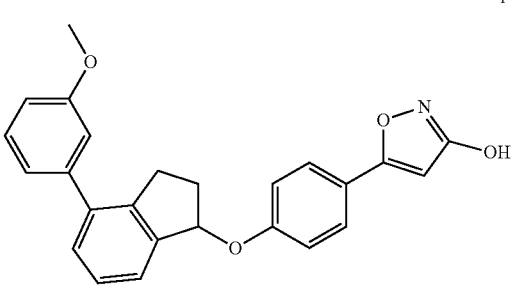
Example 22
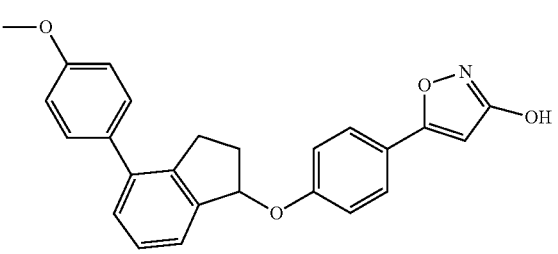
Example 23
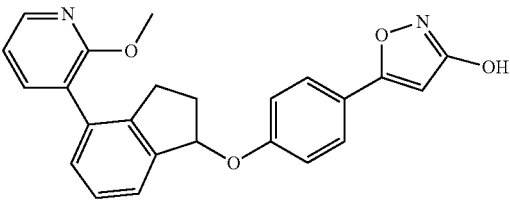
Example 17(A)
Optically Active Intermediate, a Compound Obtained Using Example 17-2(A)
Example 18(B)
Optically Active Intermediate, a Compound Obtained Using Example 17-2(B)
Example 24(D)
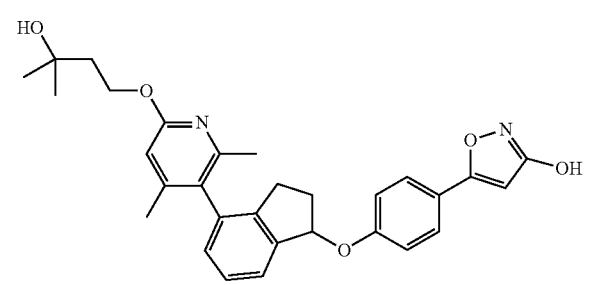
Example 25(C)
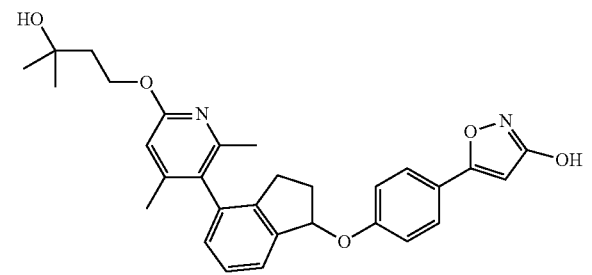
Example 26
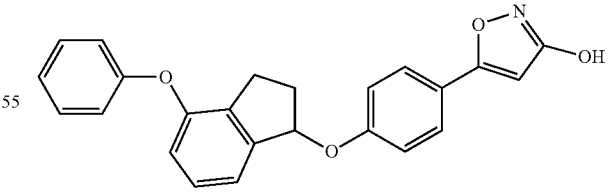
Example 27
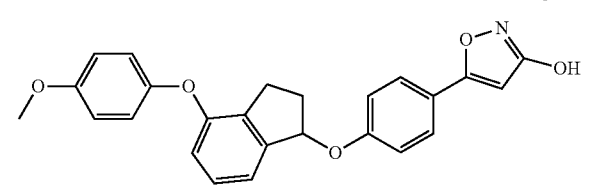

Example 28
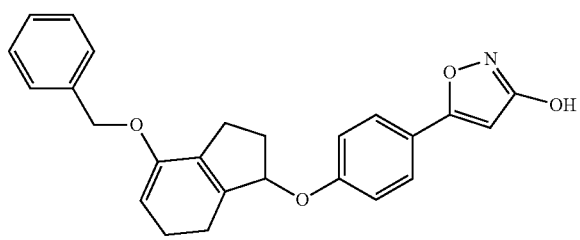
Example 29
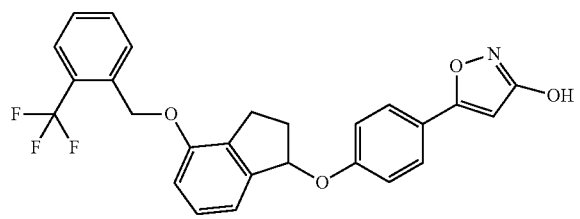
Example 30
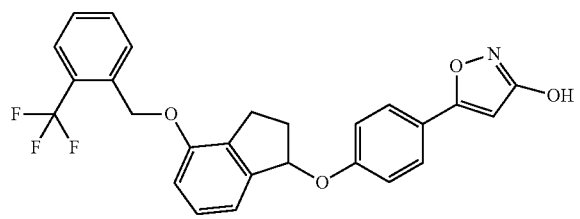
Example 31
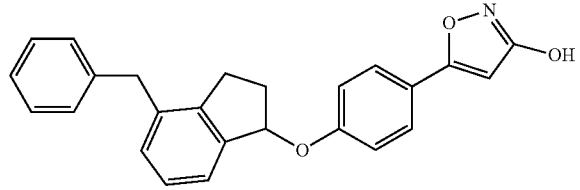
Example 32
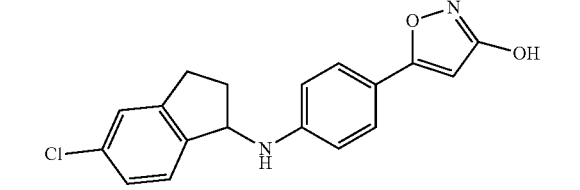
Example 33
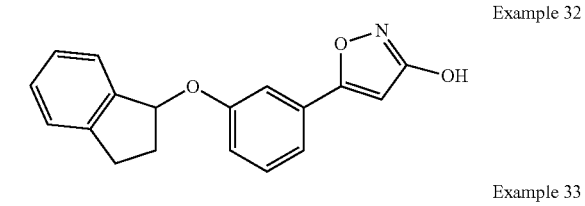
Example 38
Example 34
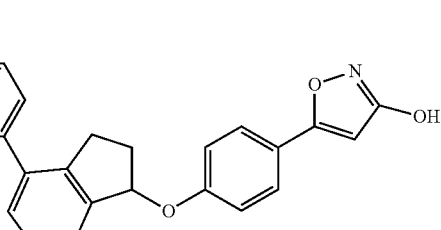
Example 35
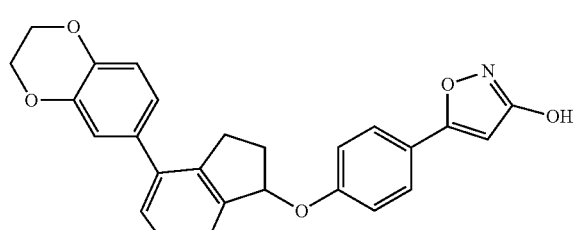
Example 36
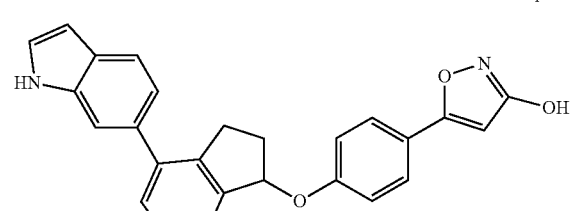
Example 37
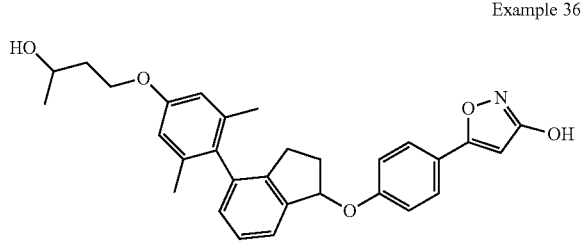
Example 24(D)
Intermediate, a Compound Obtained Using Example 24-2(D)
Example 25(C)
Intermediate, a Compound Obtained Using Example 24-2(C)
Example 39
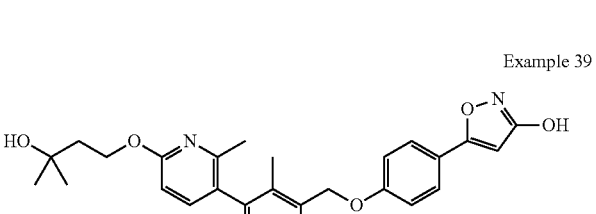

-continued
Example 40
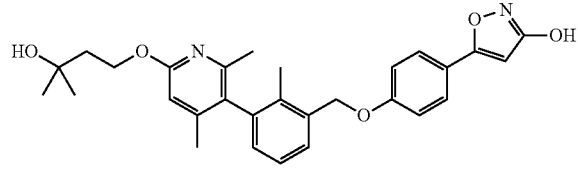
Example 41
Example 42
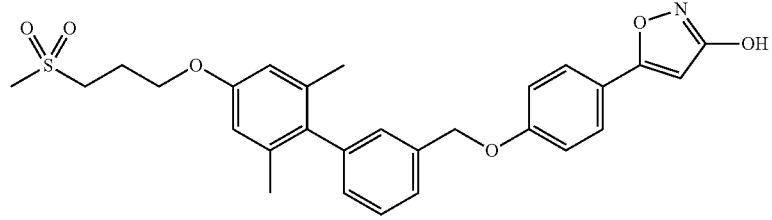
Example 43
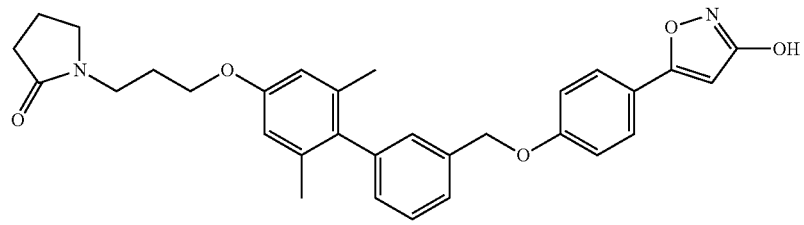
Example 44
Chiral
Example 45
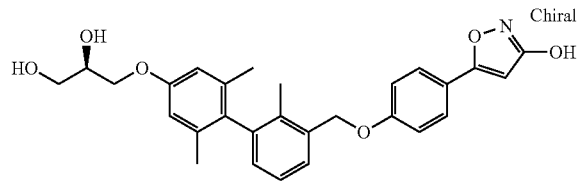
Example 46
Example 47
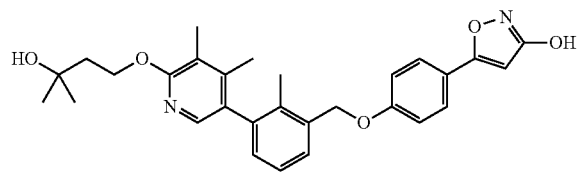
Example 1-1
Example 2-1
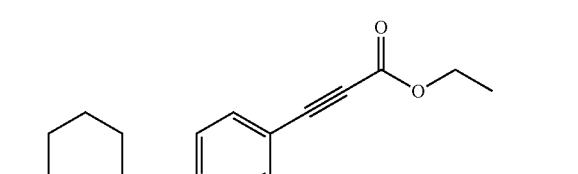
Example 3-1
Example 4-1
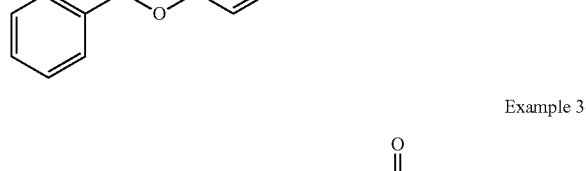

-continued
Example 4-2
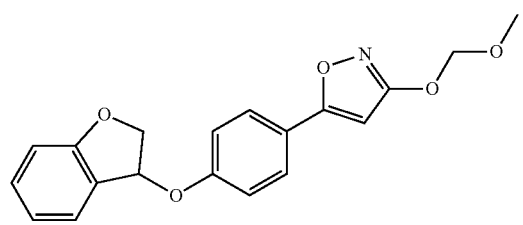
Example 5-1
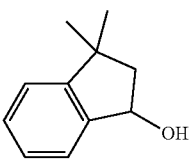
Example 5-2
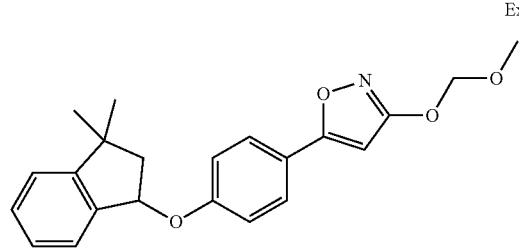
Example 6-1
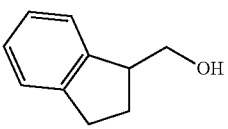
Example 6-2
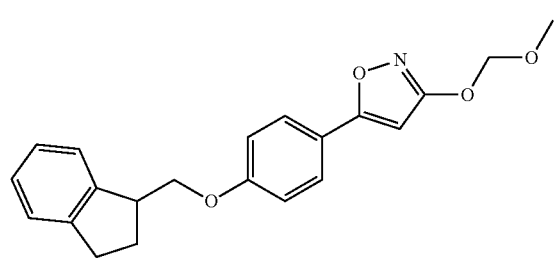
Example 7-1
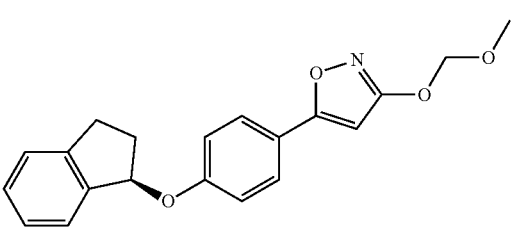
Example 8-1
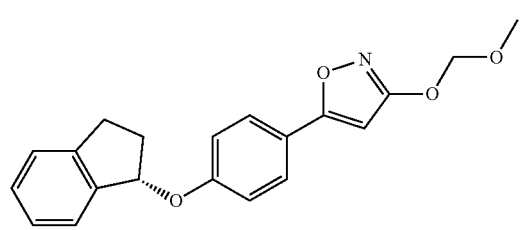
Example 9-1
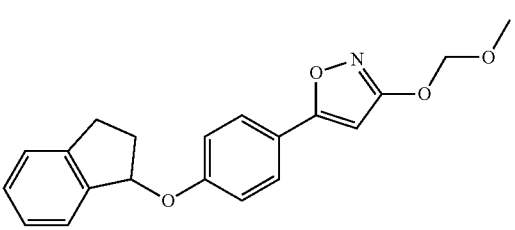
Example 9-2
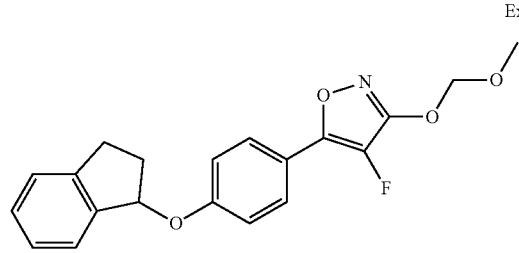
Example 10-1
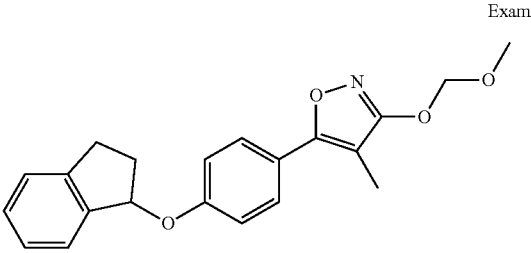
Example 11-1
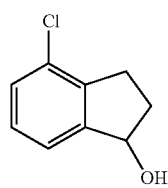
Example 11-2
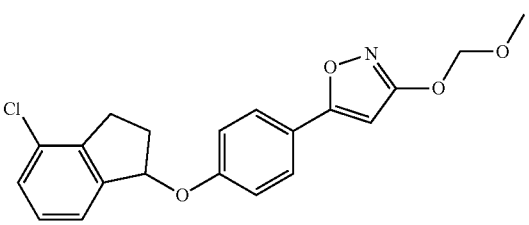

Example 12-1
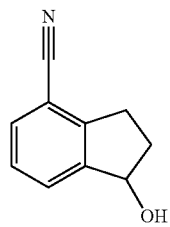
Example 12-2
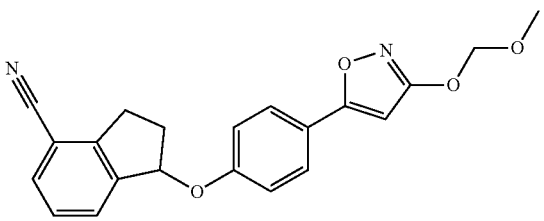
Example 13-1
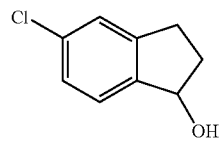
Example 13-2
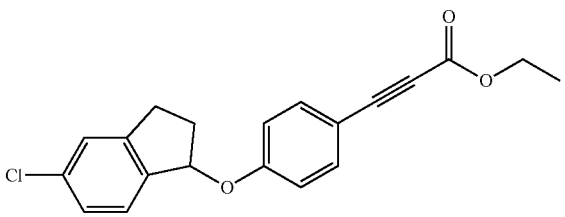
Example 14-1
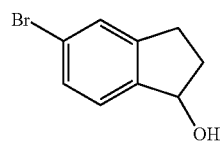
Example 14-2
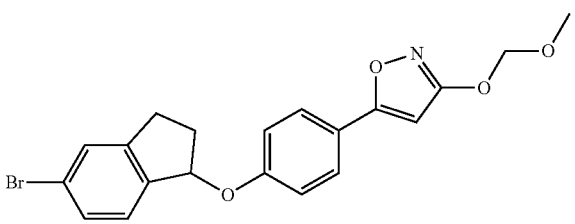
Example 15-1
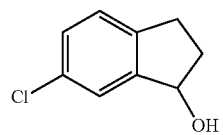
Example 15-2
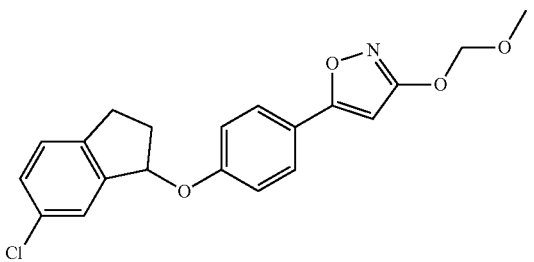
Example 16-1
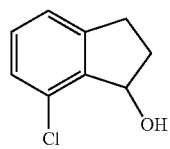
Example 16-2
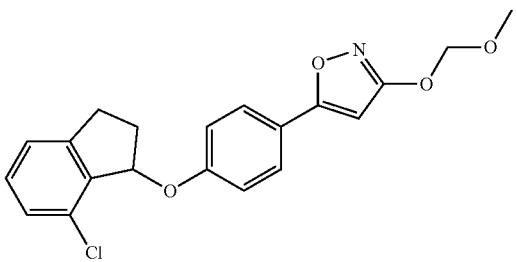
Example 17-1
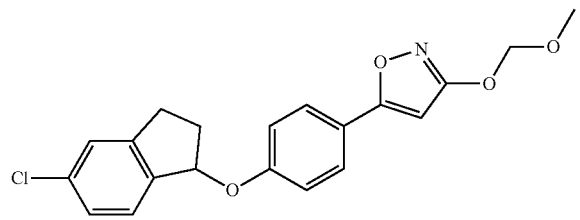
Example 17-2(A)
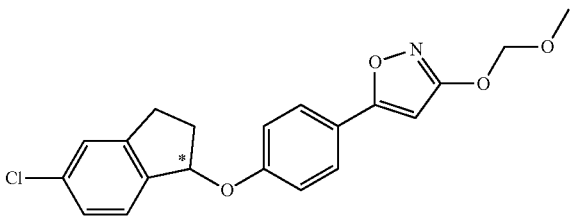

-continued
Example 17-2(B)
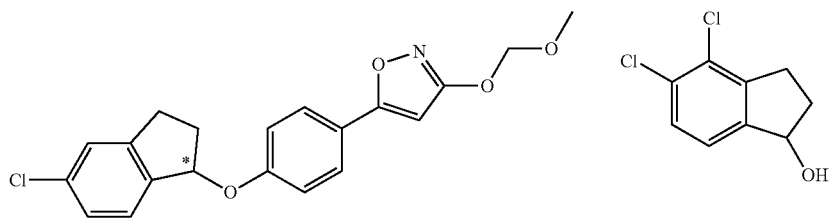
Example 19-3
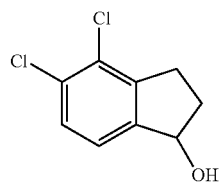
Example 19-4
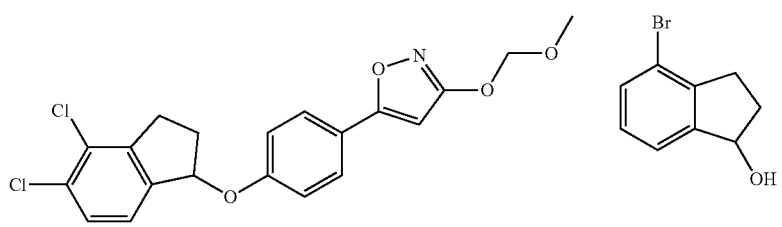
Example 20-1
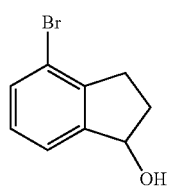
Example 20-2
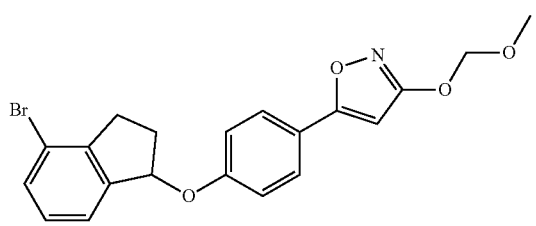
Example 20-3
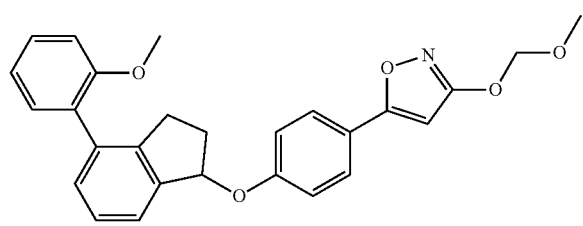
Example 21-1
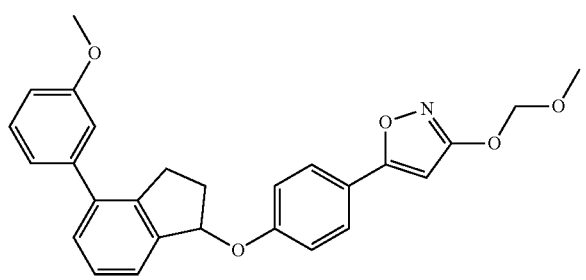
Example 22-1
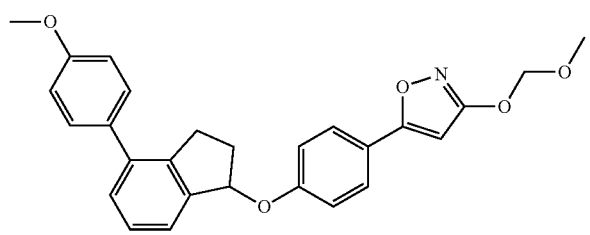
Example 23-1
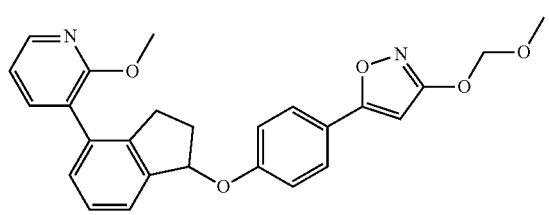
Example 24-1
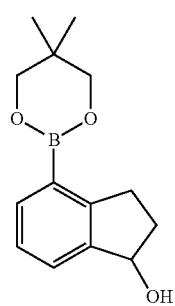

-continued
Example 24-2(C)
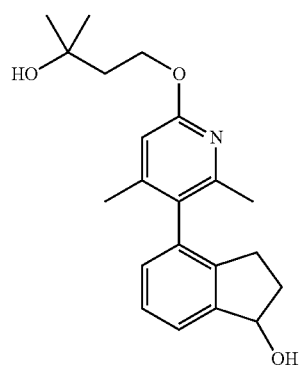
Example 24-2(D)
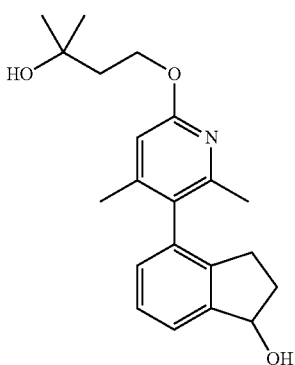
Example 24-3
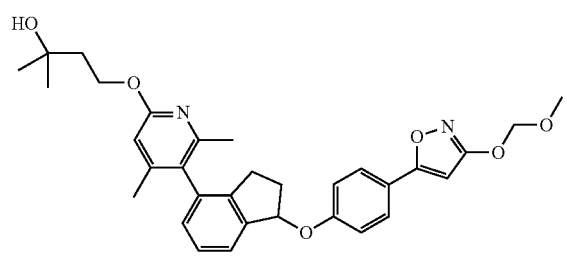
Example 25-1
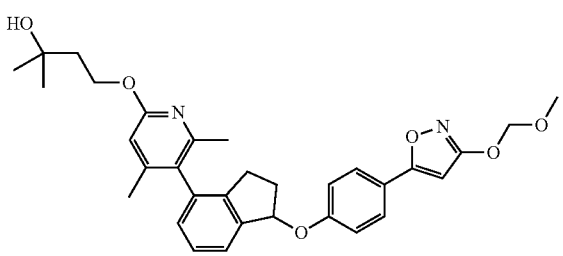
Example 26-2
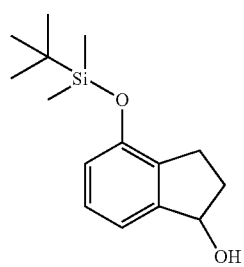
Example 26-3
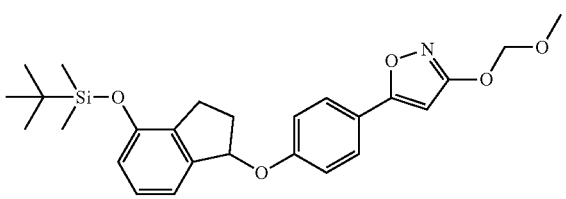
Example 26-4
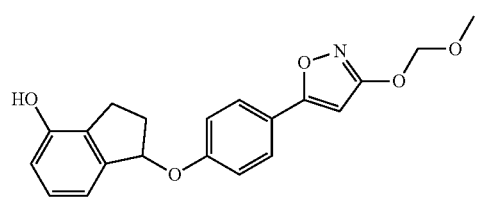
Example 26-5
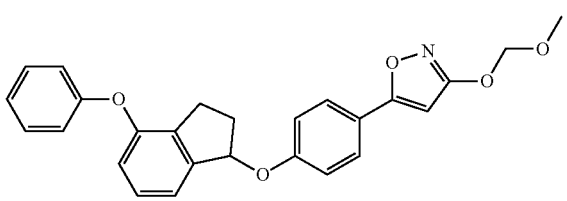
Example 27-1
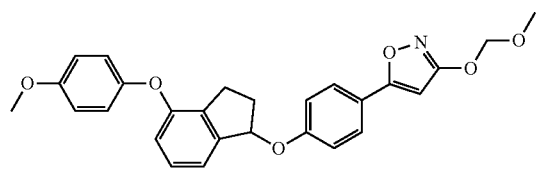
Example 28-1
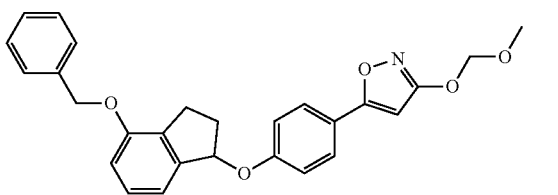
Example 29-1
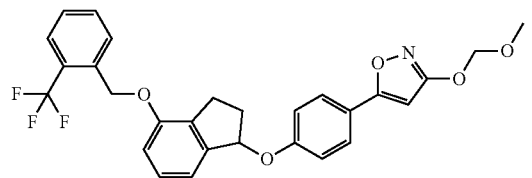
Example 30-1
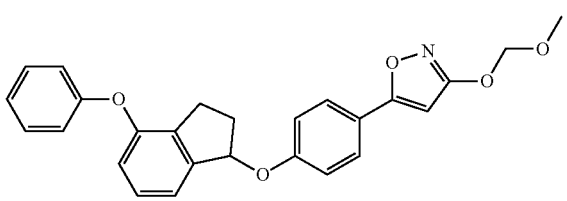

-continued
Example 31-2
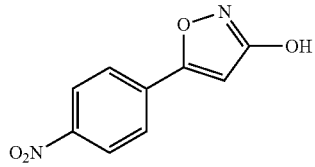
Example 31-3
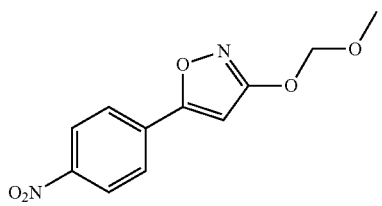
Example 31-4
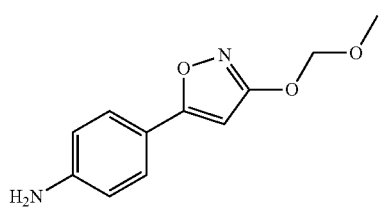
Example 31-5
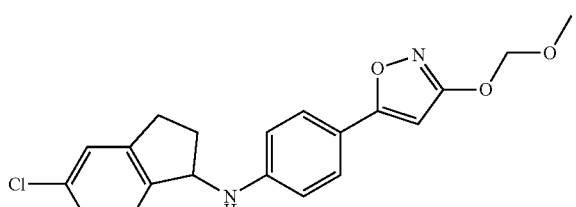
Example 32-1
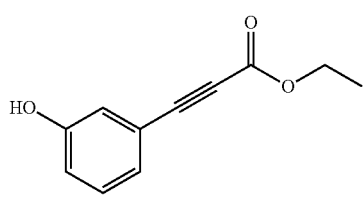
Example 32-2
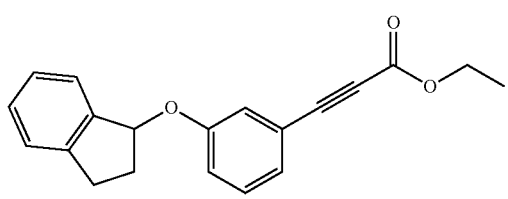
Example 33-1
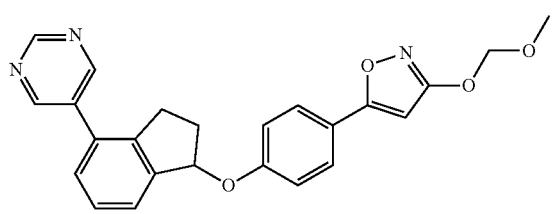
Example 34-1
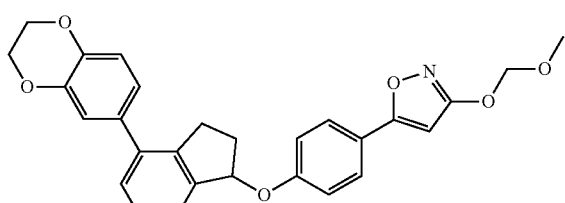
Example 35-1
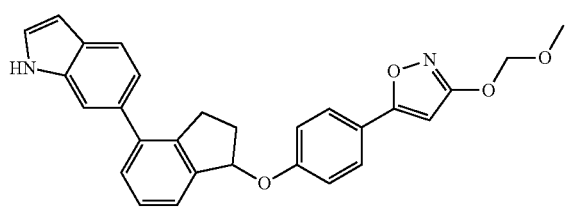
Example 36-1
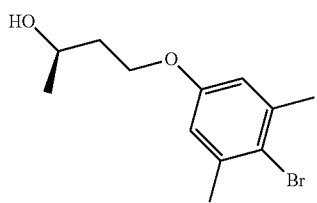
Example 36-2
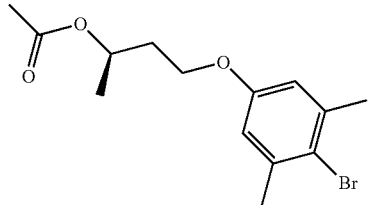
Example 36-3
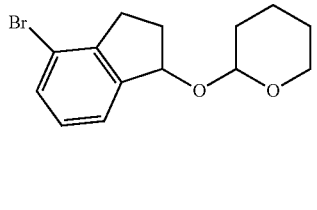
Example 36-4
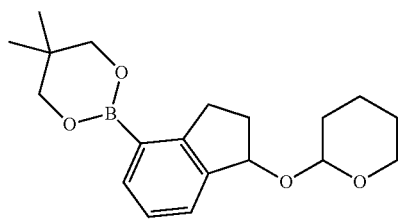
Example 36-5
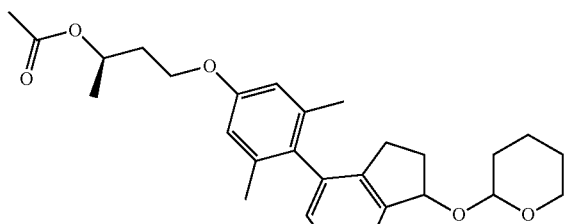

Example 36-6
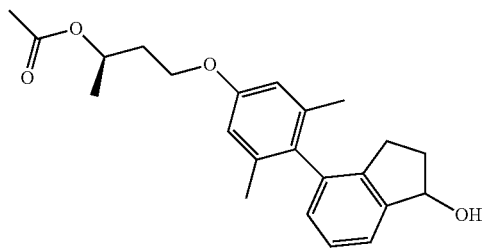
Example 36-7
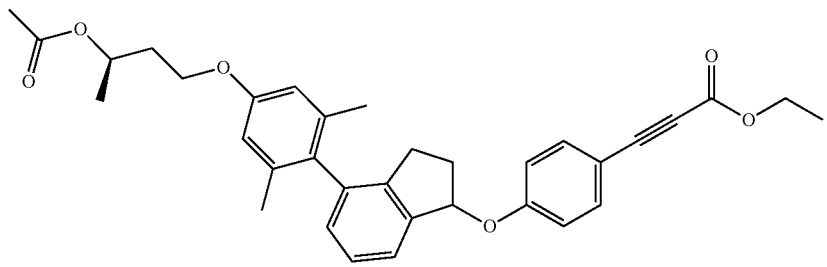
Example 37-1
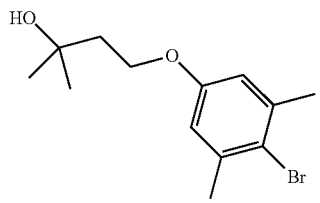
Example 37-2
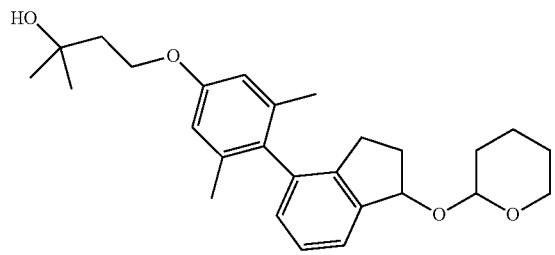
Example 37-3
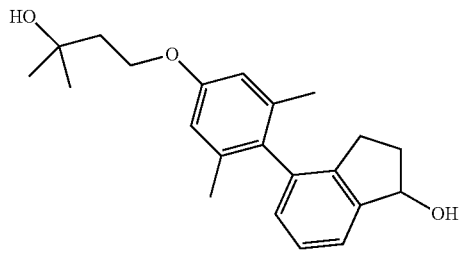
Example 37-4
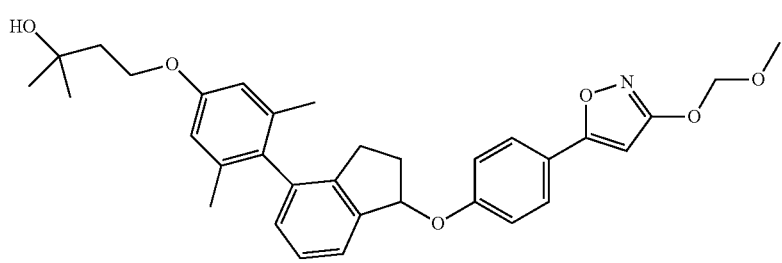
Example 38-1
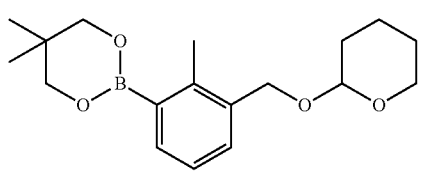
Example 38-2
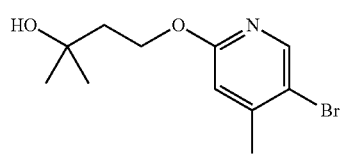

-continued
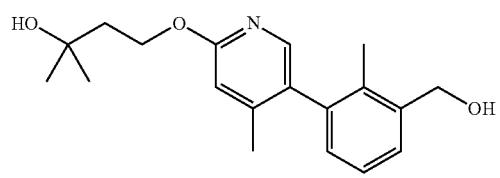
Example 38-3
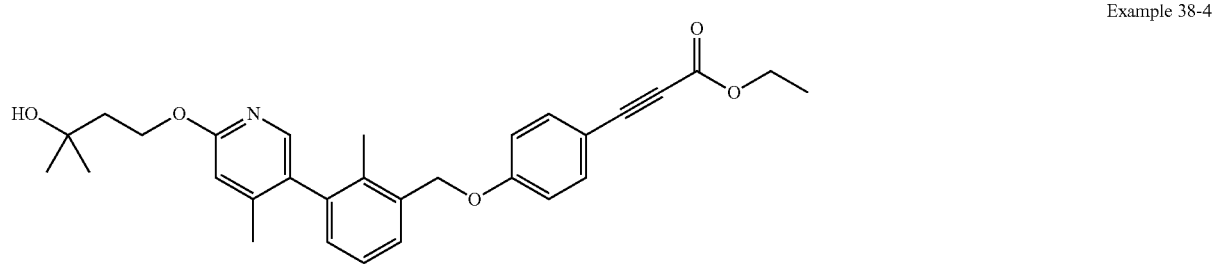
Example 38-4
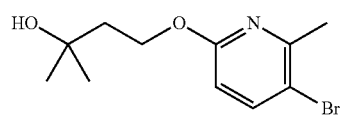
Example 39-1
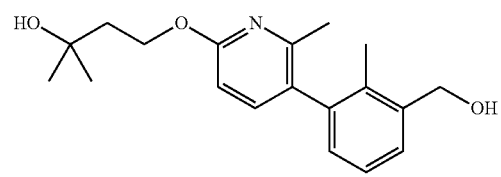
Example 39-2
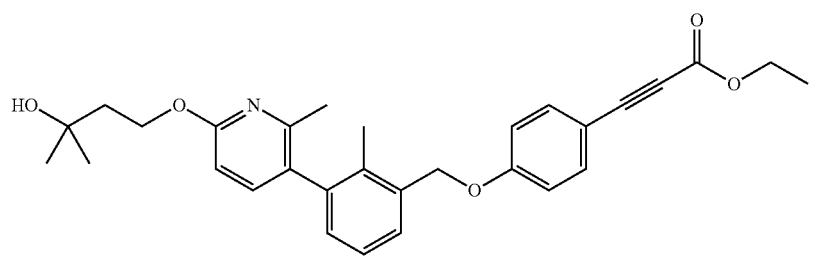
Example 39-3
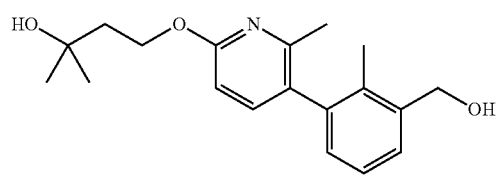
Example 40-1
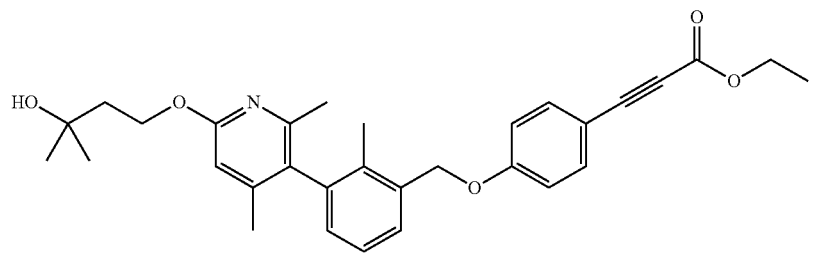
Example 40-2
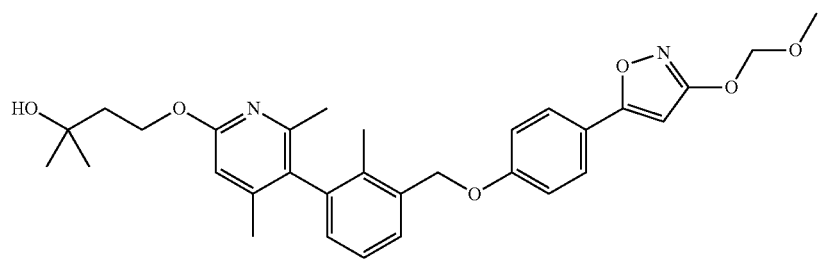
Example 40-4

Example 41-1
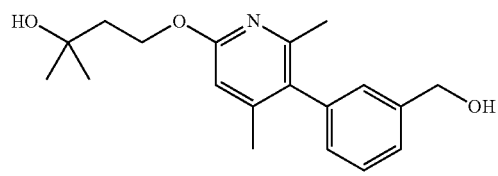
Example 41-2
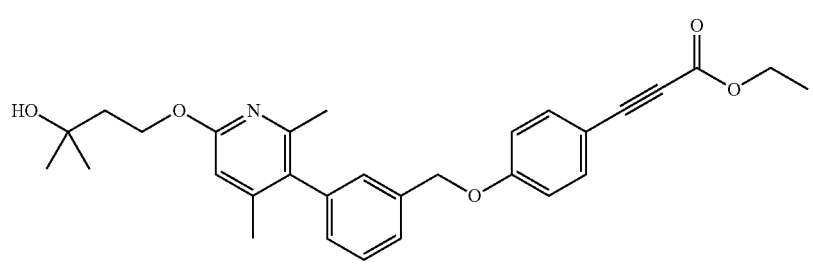
Example 42-1
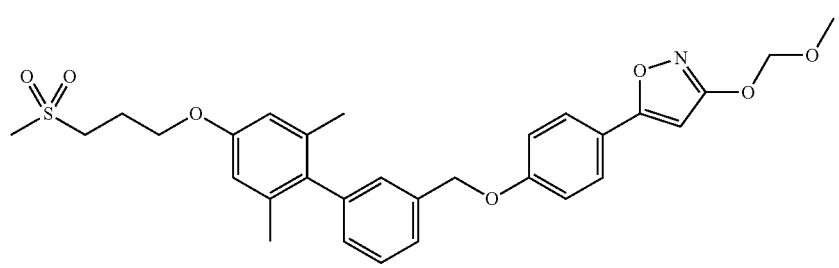
Example 43-1
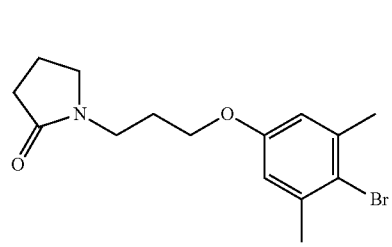
Example 43-2
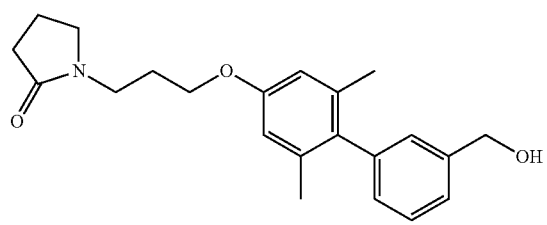
Example 43-3
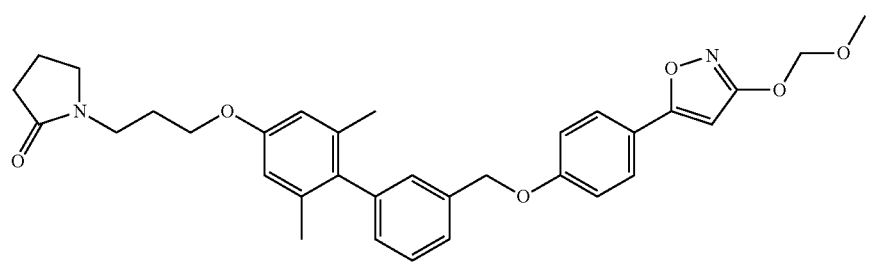
Example 44-1
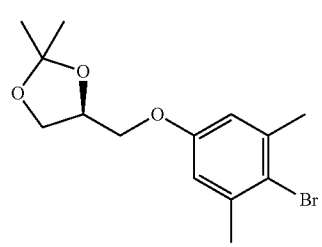
Example 44-2
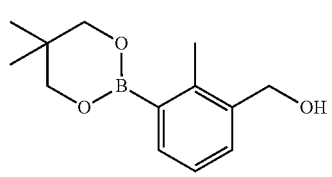

Example 44-3
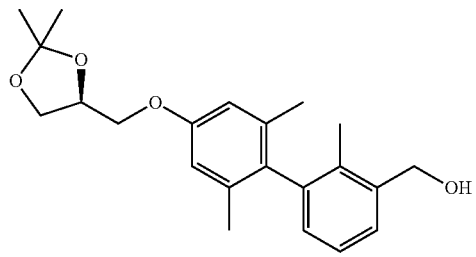
Example 44-4
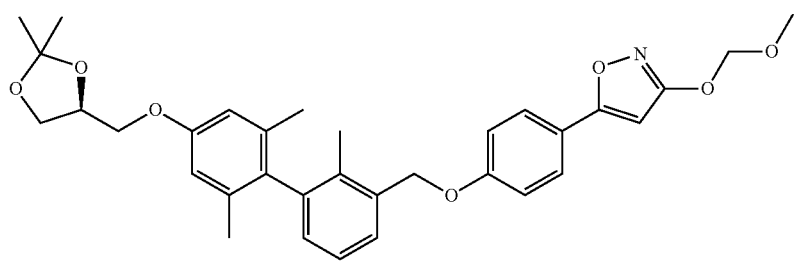
Example 45-1
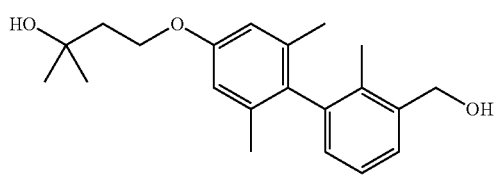
Example 45-2
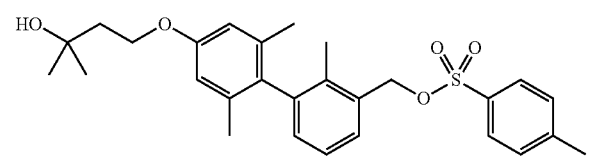
Example 45-3
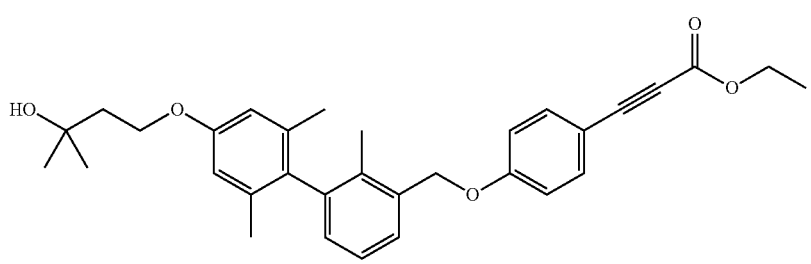
Example 46-1
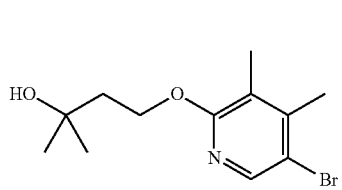
Example 46-2
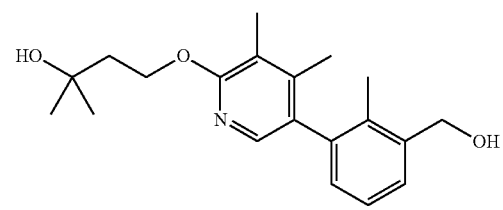
Example 46-3
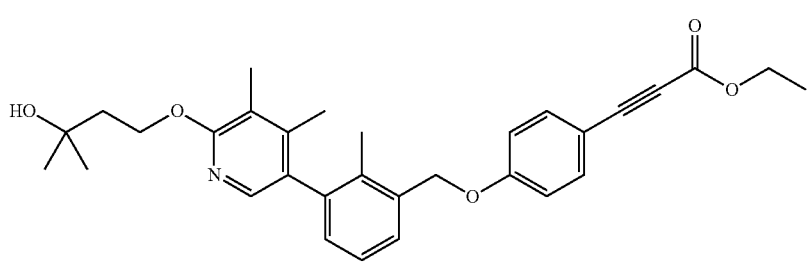

-continued
Example 47-1
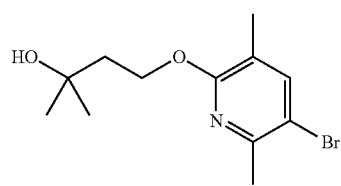
Example 47-2
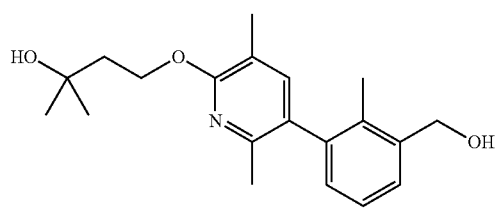
Example 47-3
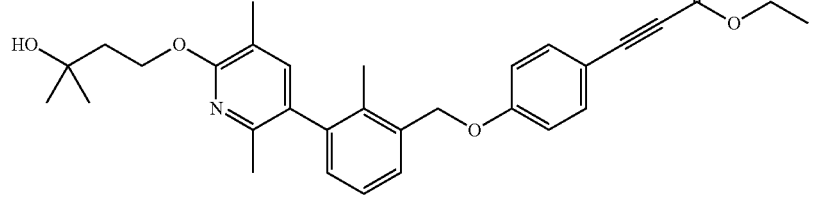
Reference Example 1
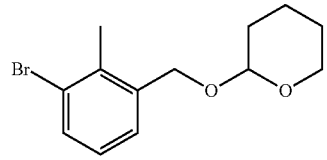
Reference Example 2
Reference Example 3
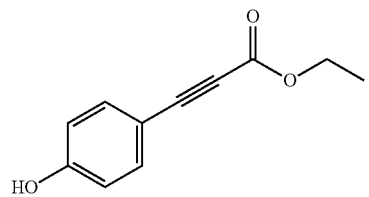
Reference Example 4
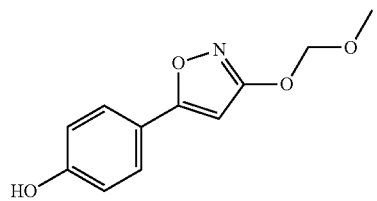
TABLE 2
| Example | MS-ESI (m/z) [M + H]⁺ | Retention Time (Minute) |
|---|---|---|
| 1 | 306* | 6.10 |
| 2 | 294 | 6.10 |
| 3 | 292* | 6.08 |
| 4 | 294* | 5.62 |
| 5 | 322 | 6.30 |
| 6 | 308 | 6.27 |
| 7 | 292* | 5.97 |
| 8 | 292* | 5.97 |
| 9# | 312 | 6.23 |
| 10 | 308 | 6.18 |
| 11 | 326* | 6.32 |
| 12 | 317* | 5.55 |
| 13 | 326* | 6.32 |
| 14 | 370* | 6.37 |
| 15 | 326* | 6.37 |
| 16 | 326* | 6.03 |
| 17 | 326* | 6.28 |
| 18 | 326* | 6.27 |
| 19 | 362 | 6.65 |
| 20 | 398* | 6.38 |
| 21 | 398* | 6.53 |
| 22 | 398* | 6.53 |
| 23 | 401 | 6.12 |
| 24 | 501 | 5.57 |
| 25 | 501 | 5.53 |
| 26 | 386 | 6.55 |
| 27 | 416 | 6.48 |
| 28 | 400 | 6.55 |
| 29 | 468 | 6.75 |
| 30 | 382* | 6.65 |
| 31 | 325* | 6.02 |
| 32 | 294 | 6.07 |
| 33# | 372 | 5.42 |
| 34# | 428 | 6.32 |
| 35# | 409 | 6.20 |
| 36 | 486 | 6.44 |
| 37 | 522** | 6.60 |
| 38 | 475 | 6.25 |
| 39 | 475 | 6.23 |
| 40 | 489 | 6.32 |
| 41 | 475 | 6.22 |
| 43 | 513 | 6.22 |
| 44# | 476 | 5.85 |
| 45# | 488 | 6.47 |
| 46 | 489 | 6.47 |
| 47 | 489 | 6.58 |
| 1-1 | 321 | 6.57 |
| 2-1 | 307 | 6.40 |
| 3-1 | 329** | 6.42 |
| 4-2 | 362** | 5.77 |
| 5-2 | 388** | 6.55 |
| 6-2 | 374** | 6.45 |
| 7-1 | 360** | 6.27 |
| 8-1 | 360** | 6.15 |
| 9-1 | 360** | 6.23 |
| 9-2 | 378** | 6.55 |
| 10-1 | 374** | 6.42 |
| 11-2 | 394** | 6.45 |
| 12-2 | 385** | 5.82 |
| 13-2 | 363** | 6.68 |

TABLE 2-continued

| Example | MS-ESI (m/z) [M + H]+ | Retention Time (Minute) |
|---|---|---|
| 14-2 | 438** | 6.57 |
| 16-2 | 394** | 6.23 |
| 17-1 | 394** | 6.40 |
| 17-2(A) | 394** | 6.40 |
| 17-2(B) | 394** | 6.42 |
| 19-4 | 428** | 6.73 |
| 20-2 | 438** | 6.47 |
| 20-3 | 466** | 6.52 |
| 21-1 | 466** | 6.52 |
| 22-1 | 466** | 6.63 |
| 23-1 | 445 | 6.27 |
| 24-2(C) | 342 | 5.28 |
| 24-2(D) | 342 | 5.47 |
| 24-3# | 545 | 5.90 |
| 25-1# | 545 | 5.85 |
| 26-3 | 490** | 7.08 |
| 26-4 | 352* | 5.63 |
| 26-5 | 452** | 6.60 |
| 27-1 | 482** | 6.55 |
| 28-1 | 466** | 6.64 |
| 29-1 | 534** | 6.75 |
| 30-1 | 450** | 6.68 |
| 31-2 | 205* | 4.83 |
| 31-3 | 249* | 5.07 |
| 31-4 | 243** | 4.17 |
| 31-5 | 393** | 6.28 |
| 32-1 | 189* | 5.12 |
| 32-2 | 360** | 6.23 |
| 33-1# | 416 | 5.82 |
| 34-1# | 472 | 6.62 |
| 35-1# | 453 | 6.42 |
| 36-1 | 295** | 6.12 |
| 36-2 | 337** | 6.46 |
| 36-3 | 319** | 6.40 |
| 36-5 | 475** | 6.76 |
| 36-6 | 391** | 6.02 |
| 36-7 | 563** | 7.02 |
| 37-1 | 309** | 6.22 |
| 37-2 | 447** | 6.63 |
| 37-3 | 363** | 5.82 |
| 37-4 | 544 | 6.62 |
| 38-2 | 296** | 5.72 |
| 38-3 | 338** | 5.32 |
| 38-4 | 488 | 6.55 |
| 39-1 | 296** | 5.77 |
| 39-2 | 338** | 5.28 |
| 39-3 | 488 | 6.53 |
| 40-1 | 330 | 5.35 |
| 40-2 | 502 | 6.60 |
| 40-4 | 533 | 5.78 |
| 41-1 | 316 | 5.23 |
| 41-2 | 488 | 6.52 |
| 42-1 | 574** | 6.15 |
| 44-1 | 315 | 6.38 |
| 44-3 | 379** | 5.93 |
| 44-4# | 560 | 6.72 |
| 45-1 | 351** | 5.80 |
| 45-2 | 505** | 6.33 |
| 45-3 | 523** | 6.72 |
| 46-1 | 310** | 6.05 |
| 46-2 | 352** | 5.68 |
| 46-3 | 502 | 6.63 |
| 47-2 | 330 | 5.77 |
| 47-3 | 502 | 6.75 |
| Reference Example 1 | 307** | 6.37 |
| Reference Example 2 | 310** | 6.02 |
| Reference Example 3 | 189* | 4.98 |
| Reference Example 4 | 220* | 4.55 |

TFA
*[M − H]−
**[M + Na]+

TABLE 3

| Example | NMR data (δ: ppm) |
|---|---|
| 1 | (CDCl3) 7.71 (2H, d, J = 9 Hz), 7.39-7.33 (1H, m), 7.31-7.16 (3H, m), 7.10 (2H, d, J = 9 Hz), 6.11 (1H, s), 5.47 (1H, t, J = 4 Hz), 3.00-2.74 (2H, m), 2.25-1.96 (3H, m), 1.90-1.77 (1H, m) |
| 2 | (DMSO-d6) 11.32 (1H, bs), 7.72 (2H, d, J = 9 Hz), 7.30-7.22 (2H, m), 7.20-7.12 (2H, m), 7.06 (2H, d, J = 9 Hz), 6.40 (1H, s), 5.36-5.27 (1H, m), 3.40 (2H, dd, J = 17, 6 Hz), 3.03 (2H, dd, J = 17, 2 Hz) |
| 3 | (CDCl3) 7.71 (2H, d, J = 9 Hz), 7.45 (1H, d, J = 7 Hz), 7.38-7.24 (3H, m), 7.09 (2H, d, J = 9 Hz), 6.12 (1H, s), 5.85 (1H, dd, J = 7, 4 Hz), 3.25-3.12 (1H, m), 3.03-2.90 (1H, m), 2.69-2.54 (1H, m), 2.31-2.17 (1H, m) |
| 4 | (DMSO-d6) 7.75 (2H, d, J = 9 Hz), 7.48 (1H, d, J = 8 Hz), 7.37-7.30 (1H, m), 7.14 (2H, d, J = 9 Hz), 6.98-6.91 (2H, m), 6.42 (1H, s), 6.19 (1H, dd, J = 6, 2 Hz), 4.75 (1H, dd, J = 11, 6 Hz), 4.53 (1H, dd, J = 11, 2 Hz) |
| 7 | (CDCl3) 7.71 (2H, d, J = 9 Hz), 7.45 (1H, d, J = 7 Hz), 7.38-7.23 (3H, m), 7.09 (2H, d, J = 9 Hz), 6.11 (1H, s), 5.85 (1H, dd, J = 7, 4 Hz), 3.25-3.12 (1H, m), 3.03-2.91 (1H, m), 2.68-2.55 (1H, m), 2.32-2.18 (1H, m) |
| 8 | (CDCl3) 7.71 (2H, d, J = 8 Hz), 7.45 (1H, d, J = 7 Hz), 7.40-7.22 (3H, m), 7.09 (2H, d, J = 9 Hz), 6.11 (1H, s), 5.85 (1H, dd, J = 6, 4 Hz), 3.25-3.13 (1H, m), 3.03-2.90 (1H, m), 2.68-2.55 (1H, m), 2.31-2.18 (1H, m) |
| 9 | (DMSO-d6) 12.49 (1H, bs), 7.68 (2H, d, J = 9 Hz), 7.42 (1H, d, J = 8 Hz), 7.38-7.20 (3H, m), 7.24 (2H, d, J = 9 Hz), 5.96 (1H, dd, J = 7, 4 Hz), 3.12-3.00 (1H, m), 2.97-2.83 (1H, m), 2.67-2.50 (1H, m), 2.12-1.98 (1H, m) |
| 10 | (DMSO-d6) 11.39 (1H, bs), 7.64 (2H, d, J = 9 Hz), 7.42 (1H, d, J = 8 Hz), 7.38-7.18 (3H, m), 7.19 (2H, d, J = 9 Hz), 5.95 (1H, dd, J = 7, 4 Hz), 3.12-3.00 (1H, m), 2.96-2.84 (1H, m), 2.66-2.50 (1H, m), 2.12-2.00 (1H, m), 2.03 (3H, s) |
| 11 | (DMSO-d6) 11.40 (1H, bs), 7.76 (2H, d, J = 9 Hz), 7.43 (1H, d, J = 8 Hz), 7.40 (1H, d, J = 8 Hz), 7.30 (1H, dd, J = 8, 8 Hz), 7.17 (2H, d, J = 9 Hz), 6.41 (1H, s), 6.04 (1H, dd, J = 7, 4 Hz), 3.15-3.02 (1H, m), 3.00-2.88 (1H, m), 2.72-2.59 (1H, m), 2.15-2.03 (1H, m) |
| 13 | (DMSO-d6) 11.34 (1H, bs), 7.76 (2H, d, J = 9 Hz), 7.43 (1H, d, J = 8 Hz), 7.43 (1H, m), 7.30 (1H, dd, J = 8, 2 Hz), 7.17 (2H, d, J = 9 Hz), 6.42 (1H, |

TABLE 3-continued

| Example | NMR data (δ: ppm) |
|---|---|
| | s), 5.94 (1H, dd, J = 7, 4 Hz), 3.14-3.00 (1H, m), 2.99-2.85 (1H, m), 2.68-2.52 (1H, m), 2.13-2.00 (1H, m) |
| 15 | (CDCl₃) 7.70 (2H, d, J = 9 Hz), 7.41 (1H, s), 7.32-7.20 (2H, m), 7.06 (2H, d, J = 9 Hz), 6.11 (1H, s), 5.82-5.75 (1H, m), 3.19-3.04 (1H, m), 2.95-2.79 (1H, m), 2.69-2.55 (1H, m), 2.31-2.16 (1H, m) |
| 16 | (DMSO-d₆) 11.30 (1H, bs), 7.76 (2H, d, J = 9 Hz), 7.45-7.31 (3H, m), 7.15 (2H, d, J = 9 Hz), 6.41 (1H, s), 5.98 (1H, d, J = 5 Hz), 3.24-3.10 (1H, m), 3.05-2.93 (1H, m), 2.62-2.45 (1H, m), 2.20-2.08 (1H, m) |
| 17 | (DMSO-d₆) 11.43 (1H, bs), 7.74 (2H, d, J = 9 Hz), 7.42 (1H, d, J = 8 Hz), 7.41 (1H, s), 7.29 (1H, dd, J = 8, 2 Hz), 7.15 (2H, d, J = 9 Hz), 6.39 (1H, s), 5.93 (1H, dd, J = 7, 4 Hz), 3.12-3.00 (1H, m), 2.97-2.84 (1H, m), 2.67-2.53 (1H, m), 2.12-2.00 (1H, m) |
| 18 | (DMSO-d₆) 11.42 (1H, bs), 7.74 (2H, d, J = 9 Hz), 7.42 (1H, d, J = 8 Hz), 7.41 (1H, s), 7.29 (1H, dd, J = 8, 2 Hz), 7.15 (2H, d, J = 9 Hz), 6.39 (1H, s), 5.93 (1H, dd, J = 7, 4 Hz), 3.12-3.00 (1H, m), 2.97-2.84 (1H, m), 2.67-2.52 (1H, m), 2.12-2.00 (1H, m) |
| 20* | (DMSO-d₆) 7.75 (2H, d, J = 9 Hz), 7.41-7.34 (2H, m), 7.29 (1H, t, J = 7 Hz), 7.23-7.16 (2H, m), 7.18 (2H, d, J = 9 Hz), 7.11 (1H, d, J = 7 Hz), 7.04-6.99 (1H, m), 6.41 (1H, s), 6.02-5.98 (1H, m), 3.75 (3H, s), 2.88-2.73 (1H, m), 2.71-2.60 (1H, m), 2.59-2.48 (1H, m), 2.05-1.93 (1H, m) |
| 23 | (DMSO-d₆) 8.21 (1H, dd, J = 5, 2 Hz), 7.74 (2H, d, J = 9 Hz), 7.66 (1H, dd, J = 7, 2 Hz), 7.43 (1H, d, J = 8 Hz), 7.37-7.29 (1H, m), 7.27 (1H, dd, J = 7, 1 Hz), 7.18 (2H, d, J = 9 Hz), 7.08 (1H, dd, J = 7, 5 Hz), 6.37 (1H, s), 6.04-5.97 (1H, m), 3.86 (3H, s), 2.94-2.79 (1H, m), 2.78-2.44 (2H, m), 2.09-1.93 (1H, m) |
| 24 | (DMSO-d₆) 7.75 (2H, d, J = 9 Hz), 7.47-7.41 (1H, m), 7.36 (1H, t, J = 8 Hz), 7.19 (2H, d, J = 9 Hz), 7.13-7.08 (1H, m), 6.59 (1H, s), 6.37 (1H, s), 6.08-6.01 (1H, m), 4.42-4.31 (3H, m), 2.70-2.43 (3H, m), 2.08-1.97 (1H, m), 2.05 (3H, s), 1.92 (3H, s), 1.88-1.76 (2H, m), 1.19 (6H, s) |
| 25 | (DMSO-d₆) 7.75 (2H, d, J = 9 Hz), 7.45 (1H, t, J = 7 Hz), 7.36 (1H, t, J = 8 Hz), 7.19 (2H, d, J = 9 Hz), 7.13-7.08 (1H, m), 6.59 (1H, s), 6.38 (1H, s), 6.08-6.00 (1H, m), 4.42-4.32 (3H, m), 2.72-2.39 (3H, m), 2.08 (3H, s), 2.07-1.92 (1H, m), 1.89 (3H, s), 1.85 (2H, t, J = 7 Hz), 1.19 (6H, s) |
| 26 | (CDCl₃) 7.70 (2H, d, J = 9 Hz), 7.34 (1H, d, J = 8 Hz), 7.32 (1H, d, J = 8 Hz), 7.28-7.20 (2H, m), 7.13-7.08 (1H, m), 7.08 (2H, d, J = 9 Hz), 6.98 (2H, d, J = 9 Hz), 6.90 (1H, dd, J = 6, 3 Hz), 6.10 (1H, s), 5.86 (1H, dd, J = 7, 4 Hz), 3.12-3.00 (1H, m), 2.92-2.80 (1H, m), 2.69-2.55 (1H, m), 2.29-2.17 (1H, m) |
| 27 | (CDCl₃) 7.70 (2H, d, J = 9 Hz), 7.23-7.13 (2H, m), 7.08 (2H, d, J = 9 Hz), 6.95 (2H, d, J = 9 Hz), 6.87 (2H, d, J = 9 Hz), 6.77 (1H, dd, J = 7, 2 Hz), 6.10 (1H, s), 5.85 (1H, dd, J = 7, 4 Hz), 3.81 (3H, s), 3.17-3.03 (1H, m), 2.97-2.84 (1H, m), 2.69-2.55 (1H, m), 2.30-2.17 (1H, m) |
| 28 | (CDCl₃) 7.69 (2H, d, J = 9 Hz), 7.47-7.28 (5H, m), 7.26-7.17 (1H, m), 7.09 (2H, d, J = 9 Hz), 7.06 (1H, d, J = 8 Hz), 6.87 (1H, d, J = 8 Hz), 6.10 (1H, s), 5.87-5.81 (1H, m), 5.13 (2H, s), 3.22-3.09 (1H, m), 3.02-2.89 (1H, m), 2.68-2.54 (1H, m), 2.30-2.17 (1H, m) |
| 31 | (DMSO-d₆) 11.20 (1H, bs), 7.52 (2H, d, J = 9 Hz), 7.38-7.34 (1H, m), 7.28 (1H, d, J = 8 Hz), 7.24 (1H, dd, J = 8, 2 Hz), 6.80 (2H, d, J = 9 Hz), 6.58 (1H, d, J = 8 Hz), 6.17 (1H, s), 5.10-5.00 (1H, m), 3.04-2.78 (2H, m), 2.62-2.48 (1H, m), 1.92-1.77 (1H, m) |
| 32 | (CDCl₃) 7.46-7.22 (7H, m), 7.13-7.07 (1H, m), 6.20 (1H, s), 5.88-5.80 (1H, m), 3.23-3.10 (1H, m), 3.01-2.90 (1H, m), 2.68-2.55 (1H, m), 2.32-2.16 (1H, m) |
| 36* | (CDCl₃) 7.70 (2H, d, J = 9 Hz), 7.42 (1H, d, J = 7 Hz), 7.32 (1H, t, J = 8 Hz), 7.10 (2H, d, J = 9 Hz), 7.06 (1H, d, J = 7 Hz), 6.68 (2H, s), 6.11 (1H, s), 5.90 (1H, t, J = 5 Hz), 4.23-4.09 (3H, m), 2.76-2.67 (1H, m), 2.63-2.48 (2H, m), 2.20-2.11 (1H, m), 2.01-1.91 (2H, m), 1.99 (3H, s), 1.95 (3H, s), 1.29 (3H, d, J = 6 Hz) |
| 38* | (CDCl₃) 7.89 (1H, s), 7.69 (2H, d, J = 9 Hz), 7.46 (1H, d, J = 8 Hz), 7.32-7.24 (1H, m), 7.15-7.10 (1H, m), 7.08 (2H, d, J = 9 Hz), 6.67 (1H, s), 6.09 (1H, s), 5.14 (2H, s), 4.58-4.51 (2H, m), 2.09 (3H, s), 2.07-2.00 (2H, m), 2.03 (3H, s), 1.33 (6H, s) |
| 39* | (DMSO-d₆) 7.74 (2H, d, J = 9 Hz), 7.47 (1H, d, J = 7 Hz), 7.42-7.37 (1H, m), 7.31-7.25 (1H, m), 7.18 (2H, d, J = 9 Hz), 7.13-7.10 (1H, m), 6.66 (1H, d, J = 8 Hz), 6.40 (1H, s), 5.22 (2H, s), 4.39 (1H, s), 4.37 (2H, t, J = 7 Hz), 2.12 (3H, s), 2.04 (3H, s), 1.85 (2H, t, J = 7 Hz), 1.18 (6H, s) |
| 40* | (DMSO-d₆) 7.75 (2H, d, J = 9 Hz), 7.48 (1H, d, J = 7 Hz), 7.34-7.28 (1H, m), 7.19 (2H, d, J = 9 Hz), 7.06-7.02 (1H, m), 6.59 (1H, s), 6.42 (1H, s), 5.23 (2H, s), 4.38 (1H, s), 4.35 (2H, t, J = 7 Hz), 2.01 (3H, s), 1.96 (3H, s), 1.87-1.81 (2H, m), 1.85 (3H, s), 1.17 (6H, s) |
| 41* | (DMSO-d₆) 11.52 (1H, bs), 7.71 (2H, d, J = 9 Hz), 7.52-7.43 (2H, m), 7.25 (1H, s), 7.17-7.13 (1H, m), 7.13 (2H, d, J = 9 Hz), 6.55 (1H, s), 6.36 (1H, s), 5.23 (2H, s), 4.37 (1H, s), 4.33 (2H, t, J = 7 Hz), 2.07 (3H, s), 1.91 (3H, s), 1.82 (2H, t, J = 7 Hz), 1.16 (6H, s) |
| 42* | (DMSO-d₆) 7.74-7.69 (2H, m), 7.49-7.40 (2H, m), 7.18 (1H, brs), 7.16-7.10 (2H, m), 7.09-7.05 (1H, m), 6.70 (2H, s), 6.40 (1H, s), 5.23 |

TABLE 3-continued

| Example | NMR data (δ: ppm) |
|---|---|
|  | (2H, s), 4.08 (2H, t, J = 6 Hz), 3.30-3.24 (2H, m), 3.03 (3H, s), 2.18-2.09 (2H, m), 1.91 (6H, s) |
| 43* | (DMSO-d$_6$) 7.74-7.68 (2H, m), 7.49-7.39 (2H, m), 7.18 (1H, brs), 7.16-7.10 (2H, m), 7.10-7.04 (1H, m), 6.68 (2H, s), 6.39 (1H, s), 5.23 (2H, s), 3.94 (2H, t, J = 6 Hz), 3.40-3.29 (4H, m), 2.21 (2H, t, J = 8 Hz), 1.98-1.85 (4H, m), 1.91 (6H, s) |
| 45 | (DMSO-d$_6$) 11.25 (1H, s), 7.74 (2H, d, J = 9 Hz), 7.43 (1H, d, J = 8 Hz), 7.27 (1H, t, J = 8 Hz), 7.17 (2H, d, J = 9 Hz), 6.97 (1H, d, J = 7 Hz), 6.71 (2H, s), 6.40 (1H, s), 5.21 (2H, s), 4.36 (1H, s), 4.08 (2H, t, J = 7 Hz), 1.93 (3H, s), 1.90-1.78 (2H, m), 1.85 (6H, s), 1.18 (6H, s) |

<*400 MHz>

TABLE 4

| Example | NMR data (δ: ppm) |
|---|---|
| 2-1 | (CDCl$_3$) 7.54 (2H, d, J = 9 Hz), 7.30-7.18 (4H, m), 6.89 (2H, d, J = 9 Hz), 5.24-5.15 (1H, m), 4.30 (2H, q, J = 7 Hz), 3.41 (2H, dd, J = 17, 6 Hz), 3.19 (2H, dd, J = 17, 3 Hz), 1.37 (3H, t, J = 7 Hz) |
| 4-1 | (CDCl$_3$) 7.45-7.40 (1H, m), 7.31-7.24 (1H, m), 6.95 (1H, ddd, J = 8, 8, 1 Hz), 6.89 (1H, d, J = 8 Hz), 5.40-5.32 (1H, m), 4.55 (1H, dd, J = 11, 7 Hz), 4.45 (1H, dd, J = 11, 2 Hz), 1.87 (1H, d, J = 8 Hz) |
| 4-2 | (CDCl$_3$) 7.71 (2H, d, J = 9 Hz), 7.44 (1H, d, J = 8 Hz), 7.34 (1H, t, J = 8 Hz), 7.04-6.93 (4H, m), 6.15 (1H, s), 5.99 (1H, dd, J = 6, 2 Hz), 5.38 (2H, s), 4.78-4.70 (1H, m), 4.68-4.62 (1H, m), 3.60 (3H, s) |
| 6-1 | (CDCl$_3$) 7.32-7.14 (4H, m), 3.90-3.75 (2H, m), 3.43-3.32 (1H, m), 3.07-2.83 (2H, m), 2.36-2.21 (1H, m), 2.03-1.89 (1H, m), 1.42 (1H, t, J = 6 Hz) |
| 11-2 | (CDCl$_3$) 7.71 (2H, d, J = 9 Hz), 7.37-7.30 (2H, m), 7.26-7.18 (1H, m), 7.06 (2H, d, J = 9 Hz), 6.14 (1H, s), 5.86 (1H, dd, J = 7, 4 Hz), 5.38 (2H, s), 3.59 (3H, s), 3.27-3.14 (1H, m), 3.06-2.93 (1H, m), 2.72-2.58 (1H, m), 2.32-2.20 (1H, m) |
| 12-1 | (CDCl$_3$) 7.65 (1H, d, J = 8 Hz), 7.56 (1H, d, J = 8 Hz), 7.39-7.31 (1H, m), 5.31 (1H, ddd, J = 6, 6, 6 Hz), 3.33-3.19 (1H, m), 3.09-2.92 (1H, m), 2.69-2.53 (1H, m), 2.12-1.98 (1H, m), 1.96 (1H, d, J = 6 Hz) |
| 15-2 | (CDCl$_3$) 7.69 (2H, d, J = 9 Hz), 7.40 (1H, s), 7.32-7.26 (1H, m), 7.23 (1H, d, J = 8 Hz), 7.04 (2H, d, J = 9 Hz), 6.12 (1H, s), 5.80-5.74 (1H, m), 5.36 (2H, s), 3.58 (3H, s), 3.17-3.04 (1H, m), 2.97-2.82 (1H, m), 2.70-2.55 (1H, m), 2.29-2.16 (1H, m) |
| 16-1 | (CDCl$_3$) 7.24-7.12 (3H, m), 5.43 (1H, dd, J = 7, 3 Hz), 3.28-3.10 (1H, m), 2.95-2.78 (1H, m), 2.50-2.34 (1H, m), 2.28 (1H, bs), 2.19-2.04 (1H, m) |
| 17-1 | (CDCl$_3$) 7.69 (2H, d, J = 9 Hz), 7.34 (1H, d, J = 8 Hz), 7.31-7.28 (1H, m), 7.22 (1H, dd, J = 8, 2 Hz), 7.04 (2H, d, J = 9 Hz), 6.12 (1H, s), 5.77 (1H, dd, J = 7, 4 Hz), 5.36 (2H, s), 3.58 (3H, s), 3.21-3.08 (1H, m), 3.00-2.81 (1H, m), 2.68-2.54 (1H, m), 2.31-2.17 (1H, m) |
| 24-1 | (CDCl$_3$) 7.72 (1H, d, J = 8 Hz), 7.47 (1H, d, J = 7 Hz), 7.26-7.19 (1H, m), 5.26-5.15 (1H, m), 3.76 (4H, s), 3.36-3.22 (1H, m), 3.06-2.92 (1H, m), 2.52-2.38 (1H, m), 1.96-1.83 (1H, m), 1.63 (1H, d, J = 7 Hz), 1.02 (6H, s) |
| 24-2(C) | (CDCl$_3$) 7.42 (1H, d, J = 7 Hz), 7.35-7.28 (1H, m), 7.03-6.96 (1H, m), 6.49 (1H, s), 5.38-5.28 (1H, m), 4.60-4.47 (2H, m), 3.22 (1H, bs), 2.68-2.38 (3H, m), 2.09 (3H, s), 2.00 (2H, t, J = 6 Hz), 1.93 (3H, s), 1.92-1.82 (1H, m), 1.31 (6H, s) |
| 24-2(D) | (CDCl$_3$) 7.43 (1H, d, J = 8 Hz), 7.35-7.28 (1H, m), 7.00 (1H, d, J = 7 Hz), 6.48 (1H, s), 5.37-5.27 (1H, m), 4.60-4.47 (2H, m), 3.19 (1H, s), 2.73-2.61 (1H, m), 2.53-2.32 (2H, m), 2.12 (3H, s), 2.00 (2H, t, J = 6 Hz), 1.98-1.86 (1H, m), 1.90 (3H, s), 1.81 (1H, d, J = 7 Hz), 1.31 (6H, s) |
| 26-2 | (CDCl$_3$) 7.17-7.10 (1H, m), 7.03 (1H, d, J = 8 Hz), 6.71 (1H, d, J = 8 Hz), 5.30-5.20 (1H, m), 3.07-2.96 (1H, m), 2.80-2.68 (1H, m), 2.54-2.42 (1H, m), 2.00-1.87 (1H, m), 1.72 (1H, d, J = 7 Hz), 1.02 (9H, s), 0.221 (3H, s), 0.216 (3H, s) |
| 31-4* | (CDCl$_3$) 7.54 (2H, d, J = 9 Hz), 6.71 (2H, d, J = 9 Hz), 6.04 (1H, s), 5.35 (2H, s), 3.95 (2H, bs), 3.58 (3H, s) |
| 32-1 | (CDCl$_3$) 7.29-7.20 (1H, m), 7.20-7.12 (1H, m), 7.08-7.02 (1H, m), 6.97-6.90 (1H, m), 5.28 (1H, s), 4.30 (2H, q, J = 7 Hz), 1.36 (3H, t, J = 7 Hz) |
| 36-4* | (CDCl$_3$) 7.70 (1H, d, J = 7 Hz), 7.53-7.38 (1H, m), 7.24-7.16 (1H, m), 5.32-5.10 (1H, m), 4.89-4.82 (1H, m), 4.07-3.95 (1H, m), 3.77-3.74 (4H, m), 3.62-3.53 (1H, m), 3.34-3.22 (1H, m), 3.03-2.94 (1H, m), 2.42-2.31 (1H, m), 2.16-1.49 (7H, m), 1.04-0.99 (6H, m) |
| 36-6* | (CDCl$_3$) 7.39 (1H, d, J = 7 Hz), 7.29 (1H, t, J = 8 Hz), 6.99 (1H, d, J = 7 Hz), 6.63 (2H, s), 5.31 (1H, t, J = 6 Hz), 5.19-5.10 (1H, m), 4.01 (2H, t, J = 6 Hz), 2.65-2.57 (1H, m), 2.49-2.36 (2H, m), 2.13-1.85 (3H, m), 2.05 (3H, s), 1.94 (3H, s), 1.91 (3H, s), 1.32 (3H, d, J = 6 Hz) |

TABLE 4-continued

| Example | NMR data (δ: ppm) |
|---|---|
| 36-7* | (CDCl$_3$) 7.59-7.54 (2H, m), 7.39 (1H, d, J = 7 Hz), 7.31 (1H, t, J = 8 Hz), 7.06 (1H, d, J = 7 Hz), 7.03-6.98 (2H, m), 6.64 (2H, s), 5.86 (1H, t, J = 5 Hz), 5.20-5.11 (1H, m), 4.29 (2H, q, J = 7 Hz), 4.01 (2H, t, J = 6 Hz), 2.76-2.66 (1H, m), 2.61-2.46 (2H, m), 2.17-1.95 (3H, m), 2.05 (3H, s), 1.97 (3H, s), 1.93 (3H, s), 1.36 (3H, t, J = 7 Hz), 1.33 (3H, d, J = 6 Hz) |
| 37-2 | (CDCl$_3$) 7.50-7.24 (2H, m), 7.00-6.96 (1H, m), 6.68 (2H, s), 5.45-5.21 (1H, m), 4.96-4.86 (1H, m), 4.21 (2H, t, J = 6 Hz), 4.13-3.95 (1H, m), 3.66-3.55 (1H, m), 2.67-2.54 (1H, m), 2.49-2.31 (2H, m), 2.16-1.52 (7H, m), 2.02 (2H, t, J = 6 Hz), 1.97-1.94 (3H, m), 1.93 (3H, s), 1.34 (6H, s) |
| 38-1* | (CDCl$_3$) 7.77-7.62 (1H, m), 7.42 (1H, d, J = 7 Hz), 7.19-7.13 (1H, m), 4.81 (1H, d, J = 12 Hz), 4.71 (1H, t, J = 4 Hz), 4.50 (1H, d, J = 12 Hz), 3.97-3.88 (1H, m), 3.78 (4H, s), 3.59-3.51 (1H, m), 2.50 (3H, s), 1.92-1.48 (6H, m), 1.04 (6H, s) |
| 38-2 | (CDCl$_3$) 8.16 (1H, s), 6.63 (1H, s), 4.45 (2H, t, J = 7 Hz), 2.33 (3H, s), 2.23 (1H, bs), 1.96 (2H, t, J = 7 Hz), 1.29 (6H, s) |
| 38-3* | (CDCl$_3$) 7.84 (1H, s), 7.42 (1H, d, J = 7 Hz), 7.29-7.23 (1H, m), 7.08-7.03 (1H, m), 6.66 (1H, s), 4.77 (2H, d, J = 5 Hz), 4.58-4.48 (2H, m), 2.61 (1H, bs), 2.06 (3H, s), 2.04-1.99 (2H, m), 2.00 (3H, s), 1.72-1.65 (1H, m), 1.33 (6H, s) |
| 39-1 | (CDCl$_3$) 7.61 (1H, d, J = 9 Hz), 6.45 (1H, d, J = 9 Hz), 4.47 (2H, t, J = 7 Hz), 2.54 (3H, s), 2.43 (1H, bs), 1.97 (2H, t, J = 7 Hz), 1.29 (6H, s) |
| 39-2* | (CDCl$_3$) 7.39 (1H, d, J = 7 Hz), 7.30 (1H, d, J = 8 Hz), 7.27-7.21 (1H, m), 7.07-7.03 (1H, m), 6.61 (1H, d, J = 8 Hz), 4.77 (2H, d, J = 5 Hz), 4.61-4.51 (2H, m), 3.02 (1H, bs), 2.19 (3H, s), 2.07 (3H, s), 2.02 (2H, t, J = 6 Hz), 1.62 (1H, t, J = 5 Hz), 1.32 (6H, s) |
| 39-3* | (CDCl$_3$) 7.56 (2H, d, J = 9 Hz), 7.41 (1H, d, J = 7 Hz), 7.35-7.32 (1H, m), 7.28-7.24 (1H, m), 7.13-7.10 (1H, m), 6.99 (2H, d, J = 9 Hz), 6.62 (1H, d, J = 8 Hz), 5.12 (1H, d, J = 11 Hz), 5.08 (1H, d, J = 11 Hz), 4.62-4.51 (2H, m), 4.29 (2H, q, J = 7 Hz), 2.98 (1H, bs), 2.20 (3H, s), 2.07 (3H, s), 2.02 (2H, t, J = 6 Hz), 1.36 (3H, t, J = 7 Hz), 1.32 (6H, s) |
| 40-1 | (CDCl$_3$) 7.40 (1H, d, J = 8 Hz), 7.30-7.21 (1H, m), 7.00-6.94 (1H, m), 6.51 (1H, s), 4.77 (2H, bs), 4.61-4.47 (2H, m), 3.23 (1H, bs), 2.08 (3H, s), 2.05-1.99 (2H, m), 1.99 (3H, s), 1.89 (3H, s), 1.64 (1H, bs), 1.31 (6H, s) |
| 40-2* | (CDCl$_3$) 7.57 (2H, d, J = 9 Hz), 7.43 (1H, d, J = 7 Hz), 7.31-7.25 (1H, m), 7.06-7.02 (1H, m), 6.99 (2H, d, J = 9 Hz), 6.52 (1H, s), 5.11 (2H, s), 4.60-4.49 (2H, m), 4.29 (2H, q, J = 7 Hz), 3.19 (1H, bs), 2.10 (3H, s), 2.04-1.98 (2H, m), 1.99 (3H, s), 1.90 (3H, s), 1.36 (3H, t, J = 7 Hz), 1.32 (6H, s) |
| 40-4 | (CDCl$_3$) 7.70 (2H, d, J = 9 Hz), 7.46 (1H, d, J = 7 Hz), 7.33-7.25 (1H, m), 7.08 (2H, d, J = 9 Hz), 7.07-7.02 (1H, m), 6.53 (1H, s), 6.13 (1H, s), 5.37 (2H, s), 5.15 (2H, s), 4.63-4.48 (2H, m), 3.59 (3H, s), 3.19 (1H, bs), 2.11 (3H, s), 2.06-1.99 (2H, m), 2.02 (3H, s), 1.92 (3H, s), 1.33 (6H, s) |
| 41-1 | (CDCl$_3$) 7.46-7.32 (2H, m), 7.13 (1H, s), 7.06 (1H, d, J = 7 Hz), 6.48 (1H, s), 4.74 (2H, d, J = 6 Hz), 4.53 (2H, t, J = 6 Hz), 3.24 (1H, bs), 2.17 (3H, s), 2.00 (2H, t, J = 6 Hz), 1.97 (3H, s), 1.73 (1H, t, J = 6 Hz), 1.30 (6H, s) |
| 41-2 | (CDCl$_3$) 7.53 (2H, d, J = 9 Hz), 7.48-7.36 (2H, m), 7.17 (1H, s), 7.10 (1H, d, J = 7 Hz), 6.94 (2H, d, J = 9 Hz), 6.48 (1H, s), 5.14 (2H, s), 4.53 (2H, t, J = 6 Hz), 4.29 (2H, q, J = 7 Hz), 3.17 (1H, bs), 2.15 (3H, s), 1.99 (2H, t, J = 6 Hz), 1.95 (3H, s), 1.35 (3H, t, J = 7 Hz), 1.30 (6H, s) |
| 42-1 | (DMSO-d$_6$) 7.78-7.71 (2H, m), 7.50-7.39 (2H, m), 7.20-7.12 (3H, m), 7.10-7.05 (1H, m), 6.74 (1H, s), 6.71 (2H, s), 5.31 (2H, s), 5.24 (2H, s), 4.08 (2H, t, J = 6 Hz), 3.45 (3H, s), 3.32-3.22 (2H, m), 3.03 (3H, s), 2.19-2.08 (2H, m), 1.92 (6H, s) |
| 43-1 | (CDCl$_3$) 6.63 (2H, s), 3.93 (2H, t, J = 6 Hz), 3.46 (2H, t, J = 7 Hz), 3.42 (2H, t, J = 7 Hz), 2.42-2.35 (2H, m), 2.37 (6H, s), 2.07-1.95 (4H, m) |
| 43-2 | (CDCl$_3$) 7.43-7.29 (2H, m), 7.11 (1H, brs), 7.08-7.02 (1H, m), 6.64 (2H, s), 4.73 (2H, d, J = 6 Hz), 3.99 (2H, t, J = 6 Hz), 3.52-3.40 (4H, m), 2.40 (2H, t, J = 8 Hz), 2.10-1.96 (4H, m), 2.00 (6H, s) |
| 43-3 | (DMSO-d$_6$) 7.79-7.71 (2H, m), 7.50-7.39 (2H, m), 7.21-7.04 (4H, m), 6.74 (1H, s), 6.68 (2H, s), 5.31 (2H, s), 5.24 (2H, s), 3.94 (2H, t, J = 6 Hz), 3.45 (3H, s), 3.49-3.38 (4H, m), 2.21 (2H, t, J = 8 Hz), 1.99-1.84 (10H, m) |
| 44-2* | (CDCl$_3$) 7.64 (1H, dd, J = 8, 1 Hz), 7.41-7.36 (1H, m), 7.21-7.15 (1H, m), 4.71 (2H, s), 3.78 (4H, s), 2.52 (3H, s), 1.05 (6H, s) |
| 45-1* | (CDCl$_3$) 7.36 (1H, d, J = 7 Hz), 7.27-7.21 (1H, m), 6.97 (1H, dd, J = 7, 1 Hz), 6.68 (2H, s), 4.76 (2H, s), 4.21 (2H, t, J = 6 Hz), 2.01 (2H, t, J = 6 Hz), 1.97 (3H, s), 1.90 (6H, s), 1.33 (6H, s) |
| 45-3* | (CDCl$_3$) 7.56 (2H, d, J = 9 Hz), 7.39 (1H, d, J = 6 Hz), 7.29-7.23 (1H, m), 7.05-7.01 (1H, m), 6.99 (2H, d, J = 9 Hz), 6.69 (2H, s), 5.11 (2H, s), 4.29 (2H, q, J = 7 Hz), 4.21 (2H, t, J = 6 Hz), 2.47 (1H, s), 2.02 (2H, t, J = 6 Hz), 1.97 (3H, s), 1.92 (6H, s), 1.35 (3H, t, J = 7 Hz), 1.34 (6H, s) |
| 47-1* | (CDCl$_3$) 7.46 (1H, s), 4.50 (2H, t, J = 6 Hz), 2.67 (2H, s), 2.49 (3H, s), 2.12 (3H, s), 1.98 (2H, t, J = 6 Hz), 1.30 (6H, s). |
| Reference Example 1 | (CDCl$_3$) 7.50 (1H, d, J = 8 Hz), 7.34 (1H, d, J = 8 Hz), 7.04 (1H, dd, J = 8, 8 Hz), 4.82 (1H, d, J = 12 Hz), 4.71 (1H, t, J = 3 Hz), 4.51 (1H, d, J = 12 Hz), 3.97-3.82 (1H, m), 3.62-3.53 (1H, m), 2.43 (3H, s), 1.95-1.50 (6H, m) |

TABLE 4-continued

| Example | NMR data (δ: ppm) |
|---|---|
| Reference Example 2* | (CDCl₃) 6.47 (1H, s), 4.47 (2H, t, J = 6 Hz), 2.62 (1H, bs), 2.57 (3H, s), 2.35 (3H, s), 1.97 (2H, t, J = 6 Hz), 1.30 (6H, s) |
| Reference Example 3 | (CDCl₃) 7.50 (2H, d, J = 9 Hz), 6.83 (2H, d, J = 9 Hz), 5.22 (1H, bs), 4.30 (2H, q, J = 7 Hz), 1.37 (3H, t, J = 7 Hz) |
| Reference Example 4 | (CDCl₃) 7.64 (2H, d, J = 9 Hz), 6.92 (2H, d, J = 9 Hz), 6.12 (1H, s), 5.58 (1H, bs), 5.37 (2H, s), 3.59 (3H, s) |

<*400 MHz>

The invention claimed is:

1. A compound of Formula (I):

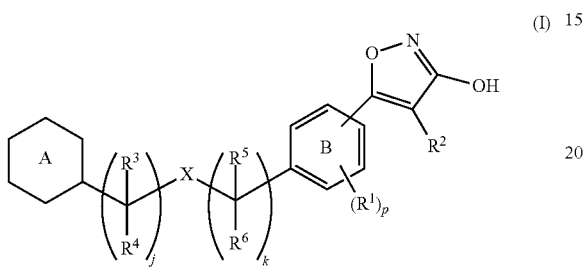

(wherein p is an integer of 0 to 4; j is an integer of 0 to 3; k is an integer of 0 to 2);

a ring B is a benzene ring, a pyridine ring, or a pyrimidine ring;

X is —$CH_2$—, an oxygen atom, —$S(O)_i$— (i is an integer of 0 to 2) or —$NR^7$— (with a proviso that X is not —$CH_2$— when a ring A is Formula (A) mentioned below);

$R^1$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a group: —$S(O)_iR^a$ (i is an integer of 0 to 2) or a group: —$NR^bR^c$;

$R^2$ is a group arbitrarily selected from a hydrogen atom, a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

$R^3$, $R^4$, $R^5$, $R^6$, and $R^7$ are independently a group arbitrarily selected from a hydrogen atom, a $C_{1-6}$ alkyl group, a halogenated $C_{1-6}$ alkyl group, a $C_{2-6}$ alkenyl group or a $C_{2-6}$ alkynyl group;

a ring A is Formula (A):

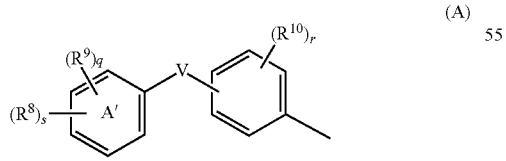

(wherein q and r are independently an integer of 0 to 4; s is an integer of 1 to 2); a ring A' is a benzene ring, a pyridine ring, or a pyrimidine ring; V is a single bond or an oxygen atom;

$R^8$s are independently a group arbitrarily selected from a $C_{1-6}$ alkoxy group which is substituted with 1 to 5 substituent(s) L, a $C_{2-6}$ alkenyloxy group which is substituted with 1 to 5 substituent(s) L, a $C_{2-6}$ alkynyloxy group which is substituted with 1 to 5 substituent(s) L, or a non-aromatic heterocyclic oxy group;

the substituents L are independently a group arbitrarily selected from a halogen atom, —OH, a $C_{1-6}$ alkoxy group, a non-aromatic heterocyclic group (the heterocyclic group is optionally substituted with —OH or a $C_{1-6}$ alkyl group), a group: —$S(O)_iR^a$ (i is an integer of 0 to 2), a group: —$CO_2R^f$, a group: —$SO_2NR^dR^e$, a group: —$CONR^dR^e$, or a group: —$NR^bR^c$;

$R^9$ and $R^{10}$ are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI); or a ring A is Formula (AA):

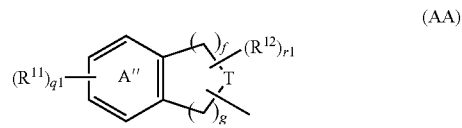

(wherein f is an integer of 0 to 2; g is an integer of 1 to 4; q1 is an integer of 0 to 4; r1 is an integer of 0 to 2);

a ring A" is a benzene ring, or a pyridine ring;

T is —$CH_2$—, an oxygen atom, —$S(O)_i$— (i is an integer of 0 to 2) or —$NR^7$—;

$R^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —$S(O)_iR^a$ (i is an integer of 0 to 2), or a group: —$NR^bR^c$;

$R^{12}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a C$_{1-6}$ alkoxy group which is optionally substituted with 1 to 5 substituent(s) RI, —SH, a group: —S(O)$_i$R$^c$ (i is an integer of 0 to 2), or a group: —NR$^b$R$^c$);

the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$) or a non-aromatic heterocyclic oxy group;

the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$);

the above-mentioned substituent R$^a$ is a group arbitrarily selected from a C$_{1-6}$ alkyl group or a halogenated C$_{1-6}$ alkyl group;

the above-mentioned substituents R$^b$ and R$^c$ are independently a group arbitrarily selected from a hydrogen atom, a C$_{1-6}$ alkyl group, a halogenated C$_{1-6}$ alkyl group, a C$_{2-6}$ alkenyl group, a C$_{2-6}$ alkynyl group, a C$_{2-7}$ alkanoyl group, a C$_{1-6}$ alkylsulfonyl group, an arylcarbonyl group, or a heterocyclic carbonyl group, or R$^b$ and R$^c$ optionally form together with a nitrogen atom to which R$^b$ and R$^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a C$_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents R$^{b1}$ and R$^{c1}$ are independently a group arbitrarily selected from a hydrogen atom, a C$_{1-6}$ alkyl group, a C$_{2-7}$ alkanoyl group or a C$_{1-6}$ alkylsulfonyl group, the above-mentioned substituents R$^d$, R$^e$ and R$^f$ are independently a group arbitrarily selected from a hydrogen atom or a C$_{1-6}$ alkyl group), a salt of the compound, or a solvate of the salt or the compound.

2. A compound of Formula (Ia):

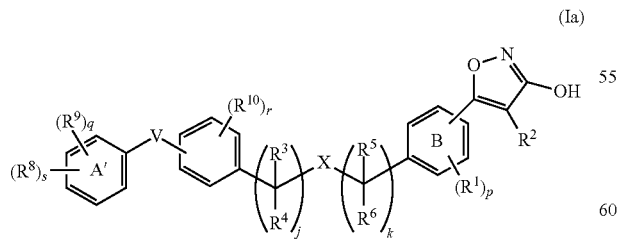

(Ia)

(wherein s is an integer of 1 to 2; q, r, and p are independently an integer of 0 to 4; j is an integer of 0 to 3; k is an integer of 0 to 2);

a ring A' is a benzene ring, a pyridine ring, or a pyrimidine ring;

a ring B is a benzene ring, a pyridine ring, or a pyrimidine ring;

X is an oxygen atom, —S(O)$_i$— (i is an integer of 0 to 2) or —NR$^7$—;

V is a single bond or an oxygen atom;

R$^8$s are independently a group arbitrarily selected from a C$_{1-6}$ alkoxy group which is substituted with 1 to 5 substituent(s) L, a C$_{2-6}$ alkenyloxy group which is substituted with 1 to 5 substituent(s) L, a C$_{2-6}$ alkynyloxy group which is substituted with 1 to 5 substituent(s) L, or a non-aromatic heterocyclic oxy group;

the substituents L are independently a group arbitrarily selected from a halogen atom, —OH, a C$_{1-6}$ alkoxy group, a non-aromatic heterocyclic group (the heterocyclic group is optionally substituted with —OH or a C$_{1-6}$ alkyl group), a group: —S(O)$_i$R$^a$ (i is an integer of 0 to 2), a group: —CO$_2$R$^f$, a group: —SO$_2$NR$^d$R$^e$, a group: —CONR$^d$R$^e$ or a group: —NR$^b$R$^c$;

R$^9$ and R$^{10}$ are independently a group arbitrarily selected from a halogen atom, a C$_{1-6}$ alkyl group which is optionally substituted with 1 to 5 substituent(s) RI, a C$_{2-6}$ alkenyl group which is optionally substituted with 1 to 5 substituent(s) RI, or a C$_{2-6}$ alkynyl group which is optionally substituted with 1 to 5 substituent(s) RI;

R$^1$s are independently a group arbitrarily selected from a halogen atom, —OH, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, a C$_{2-6}$ alkynyl group which is optionally substituted with 1 to 5 substituent(s) RI, a C$_{1-6}$ alkoxy group which is optionally substituted with 1 to 5 substituent(s) RI, —SH, a group: —S(O)$_i$R$^a$ (i is an integer of 0 to 2) or a group: —NR$^b$R$^c$;

R$^2$ is a group arbitrarily selected from a hydrogen atom, a halogen atom, a cyano group, a C$_{1-6}$ alkyl group which is optionally substituted with 1 to 5 substituent(s) RI, a C$_{2-6}$ alkenyl group which is optionally substituted with 1 to 5 substituent(s) RI, or a C$_{2-6}$ alkynyl group which is optionally substituted with 1 to 5 substituent(s) RI;

R$^3$, R$^4$, R$^5$, R$^6$, and R$^7$ are independently a group arbitrarily selected from a hydrogen atom, a C$_{1-6}$ alkyl group, a halogenated C$_{1-6}$ alkyl group, a C$_{2-6}$ alkenyl group or a C$_{2-6}$ alkynyl group;

the above-mentioned substituents RI are the same as or different from each other and are each a group arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with —OH or a C$_{1-6}$ alkyl group), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$) or a non-aromatic heterocyclic oxy group;

the above-mentioned substituents RII are the same as or different from each other and are each a group arbitrarily selected from the above-mentioned substituent RI, or a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s) or 1 to 5 group(s): —NR$^{b1}$R$^{c1}$);

the above-mentioned substituent R$^a$ is a group arbitrarily selected from a C$_{1-6}$ alkyl group or a halogenated C$_{1-6}$ alkyl group;

the above-mentioned substituents R$^f$, R$^d$ and R$^e$ are independently a group arbitrarily selected from a hydrogen atom or a C$_{1-6}$ alkyl group;

the above-mentioned substituents R$^b$ and R$^c$ are independently a group arbitrarily selected from a hydrogen atom, a C$_{1-6}$ alkyl group, a halogenated C$_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or $R^b$ and $R^c$ optionally form together with a nitrogen atom to which $R^b$ and $R^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents $R^{b1}$ and $R^{c1}$ are independently a group arbitrarily selected from a hydrogen atom, a $C_{1-6}$ alkyl group, a $C_{2-7}$ alkanoyl group or a $C_{1-6}$ alkylsulfonyl group), a salt of the compound, or a solvate of the salt or the compound.

3. A compound of Formula (Ib):

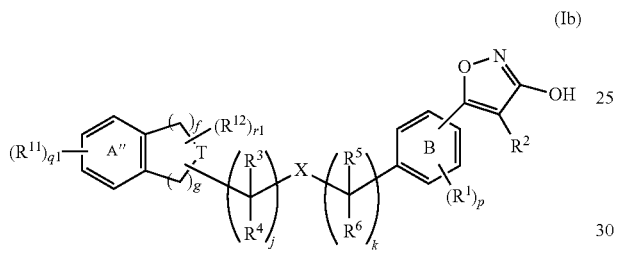

(Ib)

(wherein f is an integer of 0 to 2; g is an integer of 1 to 4; q1 and p are independently an integer of 0 to 4; j is an integer of 0 to 3; r1 and k are independently an integer of 0 to 2);

a ring A" is a benzene ring or a pyridine ring;

a ring B is a benzene ring, a pyridine ring, or a pyrimidine ring;

X and T are independently —$CH_2$—, an oxygen atom, —$S(O)_i$— (i is an integer of 0 to 2) or —$NR^7$—;

$R^{11}$s are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a group: —$S(O)_iR^a$ (i is an integer of 0 to 2), or a group: —$NR^bR^c$ group;

$R^1$ and $R^{12}$ are independently a group arbitrarily selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a group: —$S(O)_iR^a$ (i is an integer of 0 to 2), or a group: —$NR^bR^c$;

$R^2$ is a group arbitrarily selected from a hydrogen atom, a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, or a $C_{2-6}$ alkynyl group which is optionally substituted with 1 to 5 substituent(s) RI;

$R^3$, $R^4$, $R^5$, $R^6$, and $R^7$ are independently a group arbitrarily selected from a hydrogen atom, a $C_{1-6}$ alkyl group, a halogenated $C_{1-6}$ alkyl group, a $C_{2-6}$ alkenyl group or a $C_{2-6}$ alkynyl group;

the above-mentioned substituents RI are the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with —OH or a $C_{1-6}$ alkyl group), 1 to 5 group(s): —$S(O)_iR^a$ (i is an integer of 0 to 2), 1 to 5 group(s): —$SO_2NR^dR^e$, 1 to 5 group(s): —$CONR^dR^e$ or 1 to 5 group(s): —$NR^{b1}R^{c1}$) or a non-aromatic heterocyclic oxy group;

the above-mentioned substituents RII are the same as or different from each other and are each a group arbitrarily selected from the above-mentioned substituent RI, or a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s) or 1 to 5 group(s): —$NR^{b1}R^{c1}$);

the above-mentioned substituent $R^a$ is a group arbitrarily selected from a $C_{1-6}$ alkyl group or a halogenated $C_{1-6}$ alkyl group;

the above-mentioned substituents $R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group, a $C_{1-6}$ alkylsulfonyl group, an arylcarbonyl group or a heterocyclic carbonyl group, or $R^b$ and $R^c$ optionally form together with a nitrogen atom to which $R^b$ and $R^c$ are bonded, a 3- to 8-membered cyclic group, where in the cyclic group, one carbon atom is optionally substituted with an atom arbitrarily selected from an oxygen atom, a sulfur atom or a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

the above-mentioned substituents $R^{b1}$ and $R^{c1}$ are independently a group arbitrarily selected from a hydrogen atom, a $C_{1-6}$ alkyl group, a $C_{2-7}$ alkanoyl group or a $C_{1-6}$ alkylsulfonyl group;

the above-mentioned substituents $R^d$ and $R^e$ are independently a group arbitrarily selected from a hydrogen atom or a $C_{1-6}$ alkyl group), a salt of the compound, or a solvate of the salt or the compound.

* * * * *